(12) United States Patent
Blau et al.

(10) Patent No.: US 11,738,031 B2
(45) Date of Patent: Aug. 29, 2023

(54) COMPOSITIONS AND METHODS FOR PREVENTING OR TREATING MUSCLE CONDITIONS

(71) Applicant: The Board of Trustees of the Leland Stanford Junior University, Stanford, CA (US)

(72) Inventors: Helen M. Blau, Stanford, CA (US); Adelaida R. Palla, Stanford, CA (US); Andrew Tri Van Ho, Paris (FR)

(73) Assignee: THE BOARD OF TRUSTEES OF THE LELAND STANFORD JUNIOR UNIVERSITY, Stanford, CA (US)

( * ) Notice: Subject to any disclaimer, the term of this patent is extended or adjusted under 35 U.S.C. 154(b) by 0 days.

(21) Appl. No.: 17/399,490

(22) Filed: Aug. 11, 2021

(65) Prior Publication Data
US 2022/0265677 A1  Aug. 25, 2022

Related U.S. Application Data

(63) Continuation of application No. 16/148,976, filed on Oct. 1, 2018, now abandoned, which is a continuation of application No. PCT/US2018/036727, filed on Jun. 8, 2018.
(Continued)

(51) Int. Cl.
*A61K 31/00*  (2006.01)
*A61K 31/5575*  (2006.01)
(Continued)

(52) U.S. Cl.
CPC ........ *A61K 31/5575* (2013.01); *A61K 9/0019* (2013.01); *A61K 31/167* (2013.01);
(Continued)

(58) Field of Classification Search
CPC .................................................... A61K 31/00
See application file for complete search history.

(56) References Cited

U.S. PATENT DOCUMENTS

| 3,927,213 A | 12/1975 | Lippmann |
| 5,466,676 A | 11/1995 | Booth et al. |
(Continued)

FOREIGN PATENT DOCUMENTS

| CN | 101495623 A | 7/2009 |
| CN | 102014921 A | 4/2011 |
(Continued)

OTHER PUBLICATIONS

Kim et al., "Clinical report of Oriental medicine treatment with bee venom therapy of progressive muscle atrophy 1 patient," J of Korean Institute of Herbal Acupuncture, 3(1):3, 2000.*
(Continued)

*Primary Examiner* — Rosanne Kosson
(74) *Attorney, Agent, or Firm* — Kilpatrick Townsend & Stockton LLP

(57) ABSTRACT

Provided herein are compositions for preventing or treating muscle conditions such as muscle damage, injury, or atrophy. In some embodiments, the compositions comprise a prostaglandin E2 (PGE2) compound and a myotoxin. In some embodiments, the muscle damage, injury, or atrophy is the result of a nerve injury, a surgical procedure, or a traumatic injury. Methods of promoting muscle regeneration and methods of increasing muscle mass are also provided herein.

9 Claims, 51 Drawing Sheets

Specification includes a Sequence Listing.

Related U.S. Application Data

(60) Provisional application No. 62/517,758, filed on Jun. 9, 2017.

(51) Int. Cl.
| | | |
|---|---|---|
| A61K 45/06 | (2006.01) | |
| A61K 38/17 | (2006.01) | |
| A61K 35/64 | (2015.01) | |
| A61K 35/583 | (2015.01) | |
| A61P 21/06 | (2006.01) | |
| A61K 31/167 | (2006.01) | |
| A61K 31/245 | (2006.01) | |
| A61K 31/46 | (2006.01) | |
| A61K 31/47 | (2006.01) | |
| A61K 33/00 | (2006.01) | |
| A61K 33/06 | (2006.01) | |
| A61K 33/24 | (2019.01) | |
| A61K 33/32 | (2006.01) | |
| A61K 38/46 | (2006.01) | |
| A61P 21/00 | (2006.01) | |
| A61K 9/00 | (2006.01) | |
| A61K 31/445 | (2006.01) | |

(52) U.S. Cl.
CPC .......... *A61K 31/245* (2013.01); *A61K 31/445* (2013.01); *A61K 31/46* (2013.01); *A61K 31/47* (2013.01); *A61K 33/00* (2013.01); *A61K 33/06* (2013.01); *A61K 33/24* (2013.01); *A61K 33/32* (2013.01); *A61K 35/583* (2013.01); *A61K 35/64* (2013.01); *A61K 38/1703* (2013.01); *A61K 38/465* (2013.01); *A61K 45/06* (2013.01); *A61P 21/00* (2018.01); *A61P 21/06* (2018.01)

(56) References Cited

U.S. PATENT DOCUMENTS

| | | | |
|---|---|---|---|
| 5,599,561 A * | 2/1997 | Gonzalez, Jr. | A61K 36/00 514/557 |
| 5,736,396 A | 4/1998 | Bruder et al. | |
| 5,833,978 A | 11/1998 | Tremblay | |
| 5,942,225 A | 8/1999 | Bruder et al. | |
| 5,962,528 A | 10/1999 | Scott | |
| 6,841,573 B2 | 1/2005 | Llewellyn | |
| 7,632,848 B1 | 12/2009 | Scott | |
| 7,772,433 B2 | 8/2010 | Dalton et al. | |
| 8,193,220 B1 | 6/2012 | Scott | |
| 8,227,466 B2 | 7/2012 | Schuster et al. | |
| 8,436,026 B2 | 5/2013 | Sakai et al. | |
| 9,248,185 B2 | 2/2016 | Rubin et al. | |
| 9,649,350 B2 | 5/2017 | Choi et al. | |
| 9,660,998 B1 | 5/2017 | Sethi | |
| 9,782,417 B2 | 10/2017 | Rubin et al. | |
| 9,918,994 B2 | 3/2018 | Blau et al. | |
| 10,449,205 B2 | 10/2019 | Blau et al. | |
| 2011/0004589 A1 | 1/2011 | Rischar et al. | |
| 2012/0282242 A1 | 11/2012 | Abreu | |
| 2013/0236433 A1 | 9/2013 | Webster | |
| 2013/0331389 A1 | 12/2013 | Hsieh et al. | |
| 2014/0348802 A1 | 11/2014 | Shoemaker et al. | |
| 2015/0072998 A1 | 3/2015 | Markowitz et al. | |
| 2017/0252354 A1 | 9/2017 | Blau et al. | |
| 2018/0177799 A1 | 6/2018 | Blau et al. | |
| 2018/0200264 A1 | 7/2018 | Blau et al. | |
| 2019/0167695 A1 | 6/2019 | Blau et al. | |
| 2020/0147103 A1 | 5/2020 | Blau et al. | |

FOREIGN PATENT DOCUMENTS

| | | |
|---|---|---|
| WO | 9628541 A1 | 9/1996 |
| WO | 2008157753 A1 | 12/2008 |
| WO | 2015065716 A1 | 5/2015 |
| WO | 2016123117 A1 | 8/2016 |
| WO | 2017152044 A1 | 9/2017 |
| WO | 2018227134 A1 | 12/2018 |
| WO | 2018227138 A1 | 12/2018 |

OTHER PUBLICATIONS

U.S. Appl. No. 16/548,531, Final Office Action, dated Nov. 22, 2022, 9 pages.

Cho, H. and H.-H. Tai, "Inhibition of $NAD^+$-dependent 15-hydroxyprostaglandin dehydrogenase (15-PGDH) by cyclooxygenase inhibitors and chemopreventive agents," Prostaglandins, Leukotrienes and Essential Fatty Acids, 67(6):461-465, 2002.

Palla et al., "Inhibition of prostaglandin-degrading enzyme 15-PGDH rejuvenates aged muscle mass and strength," Science, 371, eabc8059, Jan. 29, 2021, 13 pages.

U.S. Appl. No. 16/548,531, Non-Final Office Action, dated Jun. 8, 2022, 9 pages.

Arnold et al., "Inflammatory monocytes recruited after skeletal muscle injury switch into antiinflammatory macrophages to support myogenesis," The Journal of Experimental Medicine, 204(5):1057-1069, 2007.

Baracos et al., "Stimulation of muscle protein degradation and prostaglandin E2 release by leukocytic pyrogen (interleukin-1). A mechanism for the increased degradation of muscle proteins during fever," N. Engl. J. Med., 308(10):553-8, 1983.

Beaulieu et al., "Abnormal prostaglandin E2 production blocks myogenic differentiation in myotonic dystrophy," Neurobiology of Disease, 45:122-129, 2012.

Bernet et al., "p38 MAPK signaling underlies a cell-autonomous loss of stem cell self-renewal in skeletal muscle of aged mice," Nature Medicine, 20(3):265-271, 2014.

Burkholder et al., "Relationship between muscle fiber types and sizes and muscle architectural properties in the mouse hindlimb," Journal of Morphology, 221:177-190, 1994.

Carlson et al., "A histological study of local anesthetic-induced muscle degeneration and regeneration in the monkey," J. Orthop. Res., 8:485-494, 1990.

Chakkalakal et al., "The aged niche disrupts muscle stem cell quiescence," Nature, 490:355-360, 2012.

Chazaud et al., "Inflammation during skeletal muscle regeneration and tissue remodeling: application to exercise-induced muscle damage management," Immunol Cell Biology, 94:140-145, 2016.

Chenouard et al., "Objective comparison of particle tracking methods," Nature Methods, 11:281-289, 2014.

Cherng et al., "Intramuscular bupivacaine injection dose-dependently increases glutamate release and muscle injury in rats," Taiwan Society of Anesthesiologists, 48(1):8-14, 2010.

Cosgrove et al., "Rejuvenation of the muscle stem cell population restores strength to injured aged muscles," Nature Medicine, 20:255-264, 2014.

Costamagna et al., "Adult stem cells and skeletal muscle regeneration," Current Gene Therapy, 15(4):348-363, 2015.

Crameri et al., "Changes in satellite cells in human skeletal muscle after a single bout of high intensity exercise," The Journal of Physiology, 558:333-340, 2004.

Darr et al., "Exercise-Induced Satellite Cell Activation in Growing and Mature Skeletal Muscle," Journal of Applied Physiology, vol. 63, 1987, pp. 1816-1821.

Debert et al., "Pharmacologic injection treatment of comitant strabismus," J AAPOS, 20(2):106-111, 2016, Author Manuscript, retrieved online at <https://www.ncbi.nlm.nih.gov/pmc/articles/PMC4833878/>, 14 pages.

Dingfelder et al., "The thermogenic activity of exogenous E and F prostaglandins in humans," Acta Obstet Gynecol Scand, 57(1)35-40, 1978.

Dolkart et al., "Statins enhance rotator cuff healing by stimulating the COX2/PGE2/EP4 pathway," The American Journal of Sports Medicine, 42(12):2869-2876, 2014.

(56) References Cited

OTHER PUBLICATIONS

Dreyer et al., "Satellite cell numbers in young and older men 24 hours after eccentric exercise," Muscle & Nerve, 33:242-253 2006.
European Patent Application No. 17760893.2, Extended European Search Report, dated Aug. 2, 2019, 10 pages.
European Patent Application No. 18813514.9, Extended European Search Report, dated May 12, 2021, 10 pages.
European Patent Application No. 18813514.9, Partial Supplementary European Search Report, dated Feb. 10, 2021, 11 pages.
Ferry et al., "Effect of prostaglandin E2 injection on the structural properties of the rat patellar tendon," Sports Medicine, Arthroscopy, Rehabilitation, Therapy & Technology, 4(2):1-9 2012.
Gilbert, "Substrate elasticity regulates skeletal muscle stem cell self-renewal in culture," Science, 329:1078-1081 2010.
Gupta et al., "Salts of therapeutic agents: chemical, physicochemical, and biological considerations," Molecules, MDPI, vol. 23, No. 7, Jul. 14, 2018, 15 pages.
Han et al., "Persistent diplopia after retrobulbar anesthesia," J Cataract Refract Surg, 30:1248-1253, 2004.
Ho et al., "Prostaglandin E2 is essential for efficacious skeletal muscle stem-cell function, augmenting regeneration and strength," Proc Natl Acad Sci USA, 114(26):6675-84, 2017.
International Patent Application No. PCT/US2017/020650, International Preliminary Report on Patentability, dated Sep. 4, 2018, 10 pages.
International Patent Application No. PCT/US2017/020650, International Search Report, dated Jun. 19, 2017, 3 pages.
International Patent Application No. PCT/US2017/020650, Written Opinion, dated Jun. 19, 2017, 9 pages.
International Patent Application No. PCT/US2018/036727, International Preliminary Report on Patentability, dated Dec. 19, 2019, 17 pages.
International Patent Application No. PCT/US2018/036727, International Search Report and Written Opinion, dated Oct. 19, 2018, 13 pages.
International Patent Application No. PCT/US2018/036727, Invitation to Pay Add'l Fees and Partial Search Report, dated Aug. 24, 2018, 2 pages.
International Patent Application No. PCT/US2018/036731, International Preliminary Report on Patentability, dated Dec. 19, 2019, 7 pages.
International Patent Application No. PCT/US2018/036731, International Search Report and Written Opinion, dated Sep. 7, 2018, 9 pages.
Joe et al., "Muscle injury activates resident fibro/adipogenic progenitors that facilitate myogenesis," Nature Cell Biology, 12:153-163, 2010.
Johnson et al., "Local anesthetics as antimicrobial agents: a review," Surgical Infections, 9(2):205-213, 2008.
Khan et al., "Repeated exposure of tendon to prostaglandin-E2 leads to localized tendon degeneration," Clin J Sport Med, 15(1):27-33, 2005.
Korotkova et al., "The skeletal muscle arachidonic acid cascade in health and inflammatory disease," Nature Reviews, Rheumatology, 10:295-303, 2014.
Kuang, "Niche regulation of muscle satellite cell self-renewal and differentiation," Cell Stem Cell, 2(1):22-31, 2007.
Mackey et al., "The influence of anti-inflammatory medication on exercise-induced myogenic precursor cell responses in humans," Journal of Applied Physiology, 103:425-431, 2007.
Magnusson et al., "Global linking of cell tracks using the Viterbi algorithm," IEEE Transactions on Medical Imaging, 34:911-929, 2015.
Maska et al., "A benchmark for comparison of cell tracking algorithms," Bioinformatics, 30:1609-1617, 2014.
Mauro et al., "Satellite cell of skeletal muscle fibers," J Biophys Biochem Cytol, 9:493-495, 1961.
Miller et al., "Bupivacaine injection remodels extraocular muscles and corrects comitant strabismus," Ophthalmology, 120(12):2733-2740, 2013.
Mo et al., "Prostaglandin E2 promotes proliferation of skeletal muscle myoblasts via Ep4 receptor activation," Cell Cycle, 14:1507-1516, 2015.
Mo et al., "Prostaglandin E2: from clinical applications to its potential role in bone-muscle crosstalk and myogenic differentiation," Recent Patents on Biotechnology, 6(3):223-229, 2012.
Monaco et al., "Prevalence of sarcopenia and its association with osteoporosis in 313 older women following a hip fracture," Archives of Gerontology and Geriatrics, 52:71-74, 2010.
Montarras et al., "Direct isolation of satellite cells for skeletal muscle regeneration," Science, 309:2064-2067, 2005.
Murphy et al., "Satellite cells, connective tissue fibroblasts and their interactions are crucial for muscle regeneration," Development, 138:3625-3637, 2011.
Murray, "An approach to some aspects of strabismus from ocular and orbital trauma," Middle East African Journal of Ophthalmology, 22(3):312-319, 2015.
National Library of Medicine, "11-deoxy-16, 16-dimethyl-PGE2," PubChem, 2006, retrieved online at <https://pubchem.ncbi.nlm.nih.gov/compound/5283063#section=Top>, 14 pages.
National Library of Medicine, "Bupivacaine Versus Lidocaine Local Anesthesia," ClinicalTrials.gov, University of British Columbia, Dec. 14, 2015, retrieved online at <https://clinicaltrials.gov/ct2/show/study/NCT01751347>, 5 pages.
National Library of Medicine, "Dinoprostone," PubChem, 2004, retrieved online at <https://pubchem.ncbi.nlm.nih.gov/compound/5280360#section=Top>, 42 pages.
National Library of Medicine, "Ono-AE3-208," PubChem, 2006, retrieved online at <https://pubchem.ncbi.nlm.nih.gov/compound/ono-ae3-208#section=Top>, 17 pages.
National Library of Medicine, "Prostaglandin E2 Sodium Salt," PubChem, 2008, retrieved online at <https://pubchem.ncbi.nlm.nih.gov/compound/23667543>, 11 pages.
National Library of Medicine, "Sulprostone," PubChem, 2005, retrieved online at <https://pubchem.ncbi.nlm.nih.gov/compound/5312153#section=Top> on Oct. 15, 2018, 26 pages.
North et al., "Prostaglandin E2 regulates vertebrate haematopoietic stem cell homeostasis," Nature, 447:1007-1011, 2007.
Ohno et al., "Studies on 15-hydroxyprostaglandin dehydrogenase with various prostaglandin analogues," Journal of Biochemistry, 84(6):1485-1494, 1978.
Otis et al., "Stretch-induced myoblast proliferation is dependent on the COX2 pathway," Experimental Cell Research, 310(2): 417-425, 2005.
Papapetrou et al., "Genomic safe harbors permit high beta-globin transgene expression in thalassemia induced pluripotent stem cells," Nature Biotechnology, 29(1):73-78, 2011.
Paulsen et al., "Leucocytes, cytokines and satellite cells: what role do they play in muscle damage and regeneration following eccentric exercise?" Exercise Immunology Review, 18:42-97, 2012.
Pawlikowski, "Pervasive satellite cell contribution to uninjured adult muscle fibers," Skeletal Muscle, vol. 5, No. 42, 2015, 13 pages.
Prasain, "Prostaglandin extraction and analysis in Caenorhabditis elegans," J. Vis. Exp., 76:50447, 2013, 8 pages.
Price et al., "Inhibition of JAK-STAT signaling stimulates adult satellite cell function," Nature Medicine, 20(10):1174-1181, 2014.
Ricciotti et al., "Prostaglandins and inflammation," Arteriosclerosis, Thrombosis, and Vascular Biology, 31(5):986-1000, 2011.
Rodemann et al., "Arachidonic acid, prostaglandin E2 and F2 alpha influence rates of protein turnover in skeletal and cardiac muscle," J. Biol. Chem., 257(4):1632-8, 1982.
Rosa et al., "Clinical effectiveness of lidocaine and benzocaine for topical anesthesia," Anesthesia Progress, 46(3):97-99, 1999.
Ruiz et al., "Association between muscular strength and mortality in men: prospective cohort study," British Medical Journal, 337:92-95, 2008.
Sacco et al., "Self-renewal and expansion of single transplanted muscle stem cells," Nature, 456:502-506, 2008.
Sacco et al., "Short telomeres and stem cell exhaustion model Duchenne muscular dystrophy in mdx/mTR mice," Cell, 143:1059-1071, 2010.

(56) References Cited

OTHER PUBLICATIONS

Safran et al., "Mouse reporter strain for noninvasive bioluminescent imaging of cells that have undergone Cre-mediated recombination," Molecular Imaging, 2(4):297-302, 2003.
Schlondorff et al., "Prostaglandins and other arachidonic acid metabolites in the kidney," Kidney International, 29(1):108-119, 1986.
Schneider et al., "Generation of a conditional allele of the mouse prostaglandin EP4 receptor," Genesis, 40:7-14, 2004.
Schumert et al., "Effects of 16,16-dimethyl prostaglandin E2 and indomethacin on leukotriene B4 and inflammation in rabbit colitis," Prostaglandins, 36(4):565-577, 1988.
Scott et al., "Bupivacaine injection of eye muscles to treat strabismus," Br. J. Ophthalmol., 91:146-148, 2007.
Scott et al., "Bupivacaine injection of the lateral rectus muscle to treat esotropia," J AAPOS, 13(2):119-22, 2009.
Shen et al., "Inhibited skeletal muscle healing in cyclooxygenase-2 gene-deficient mice; the role of PGE2 and PGF2alpha," Journal of Applied Physiology, 101(4):1215-1221, 2006.
Shi, "Muscle stem cells in development, regeneration, and disease," Genes & Development, 20:1692-1708, 2006.
Smethurst et al., "Levels of prostaglandin E and prostaglandin F in samples of commercial serum used for tissue culture," Prostaglandins, 13:719-722, 1977.
Sousa et al., "Geriatric muscle stem cells switch reversible quiescence into senescence," Nature, 506:316-321, 2014.
Thomas et al., "Vaginal prostaglandin (PGE2 and PGF2a) for induction of labour at term," Cochrane Database of Systematic Reviews, 6:1-398, , 2014.
Tidball et al., "Mechanisms of muscle injury, repair, and regeneration," Comprehensive Physiology, 2011, pp. 2029-2062.
Tierney et al., "STAT3 signaling controls satellite cell expansion and skeletal muscle repair," Nature Medicine, 20(10):1182-1186, 2014.
Tocris Bioscience, "ONO AE3 208," Datasheet [online], 2018, retrieved online at <https://www.tocris.com/products/ono-ae3-208_3565> on Oct. 15, 2018, 6 pages.
Tocris Bioscience, "Sulprostone," Datasheet [online], 2018, retrieved online at <https://www.tocris.com/products/sulprostone_3049> on Oct. 15, 2018, 6 pages.
U.S. Appl. No. 15/498,293, Non-Final Office Action, dated Jul. 19, 2017, 10 pages.
U.S. Appl. No. 15/498,293, Notice of Allowance, dated Jan. 12, 2018, 8 pages.
U.S. Appl. No. 15/891,278, Corrected Notice of Allowability, dated Oct. 8, 2019, 5 pages.
U.S. Appl. No. 15/891,278, Corrected Notice of Allowability, dated Sep. 17, 2019, 3 pages.
U.S. Appl. No. 15/891,278, Final Office Action, dated Oct. 16, 2018, 11 pages.
U.S. Appl. No. 15/891,278, First Action Interview Office Action Summary, dated Jul. 27, 2018, 5 pages.
U.S. Appl. No. 15/891,278, First Action Interview Pilot Program Pre-Interview Communication, dated Jun. 19, 2018, 4 pages.
U.S. Appl. No. 15/891,278, Non-Final Office Action, dated Apr. 24, 2019, 6 pages.
U.S. Appl. No. 15/891,278, Notice of Allowance, dated Jun. 10, 2019, 6 pages.
U.S. Appl. No. 15/916,779, Final Office Action, dated Oct. 18, 2018, 14 pages.
U.S. Appl. No. 15/916,779, Final Office Action, dated Oct. 24, 2019, 8 pages.
U.S. Appl. No. 15/916,779, First Action Interview Office Action Summary, dated Jul. 27, 2018, 5 pages.
U.S. Appl. No. 15/916,779, First Action Interview Pilot Program Pre-Interview Communication, dated Jun. 19, 2018, 4 pages.
U.S. Appl. No. 15/916,779, Non-Final Office Action, dated May 7, 2019, 15 pages.
U.S. Appl. No. 16/148,976, Final Office Action, dated Feb. 12, 2021, 26 pages.
U.S. Appl. No. 16/148,976, Final Office Action, dated Nov. 4, 2019, 16 pages.
U.S. Appl. No. 16/148,976, Non-Final Office Action, dated May 15, 2019, 15 pages.
U.S. Appl. No. 16/148,976, Non-Final Office Action, dated Jul. 9, 2020, 18 pages.
Ulmsten et al., "Intracervical application of prostaglandin gel for induction of term labor," Obstetrics & Gynecology, 59(3):336-339, 1982.
Zhang et al., "Inhibition of the prostaglandin-degrading enzyme 15-PGDH potentiates tissue regeneration," Science, vol. 348, No. 6240, 2015, 10 pages.
Ziboh et al., "Effects of prostaglandin E2 on rat skin: inhibition of sterol ester biosynthesis and clearing of scaly lesions in essential fatty acid deficiency," J. Lipid Res., 13:458-467, 1972.

* cited by examiner

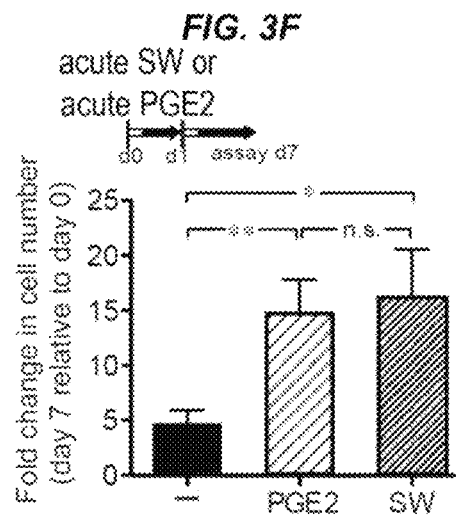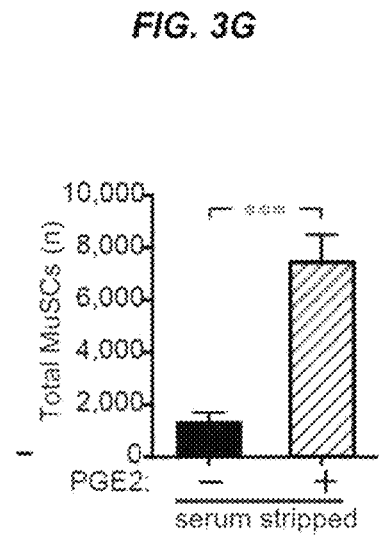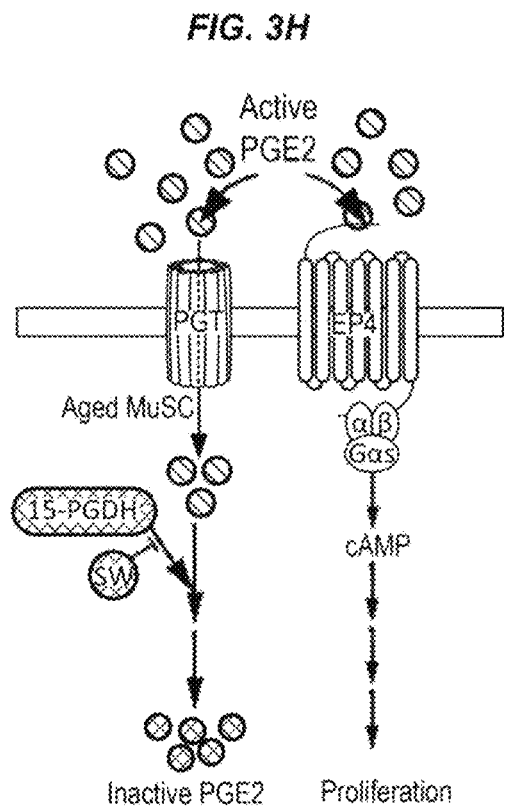

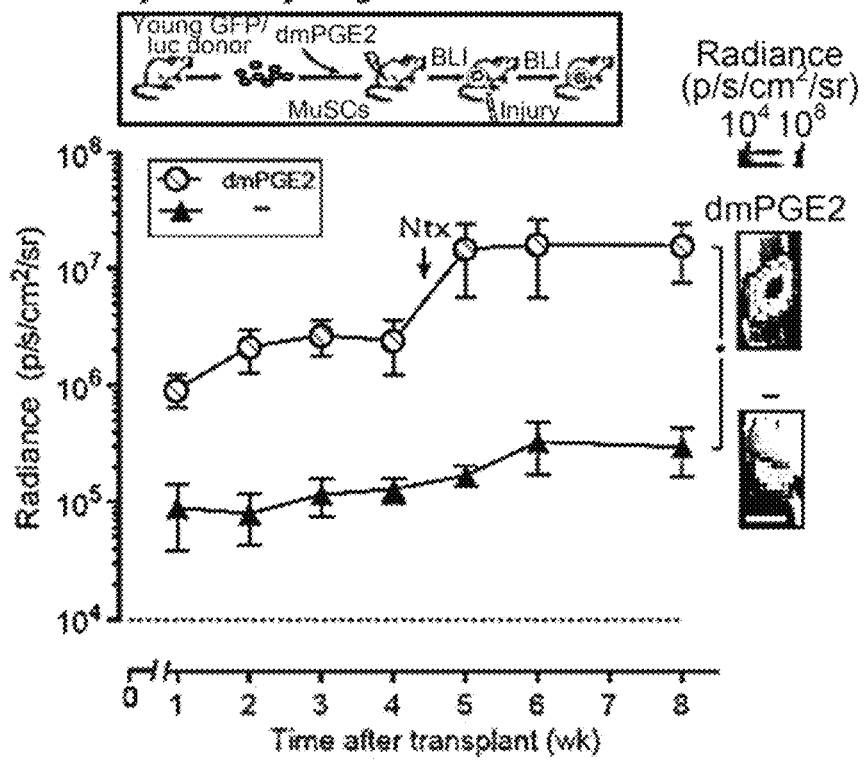
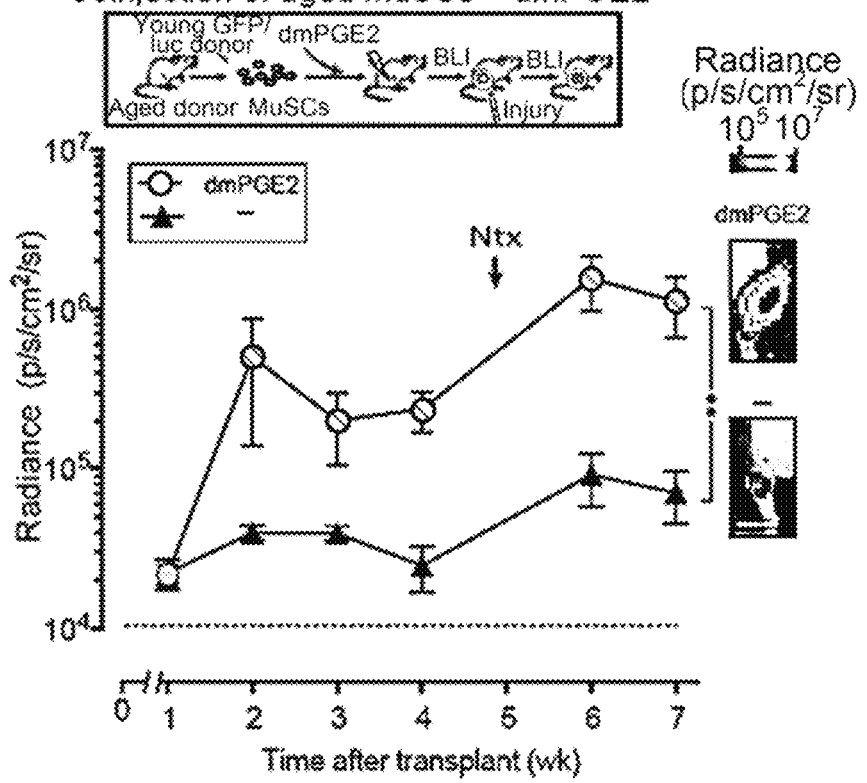

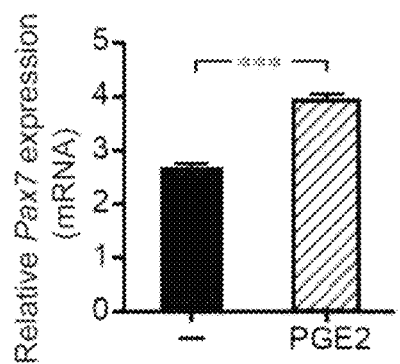
FIG. 6G
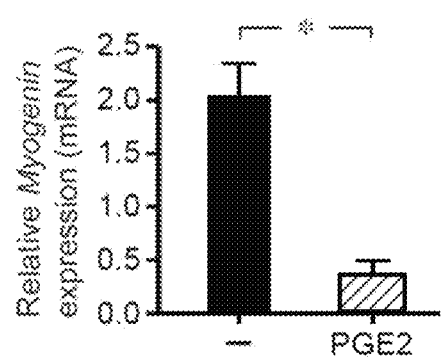
FIG. 6H
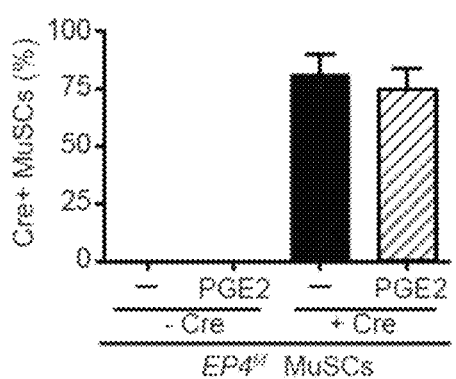
FIG. 6I
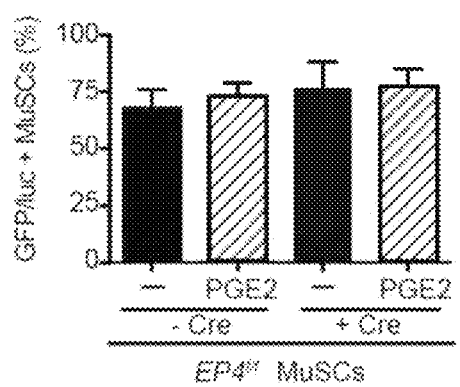
FIG. 6J
FIG. 6K
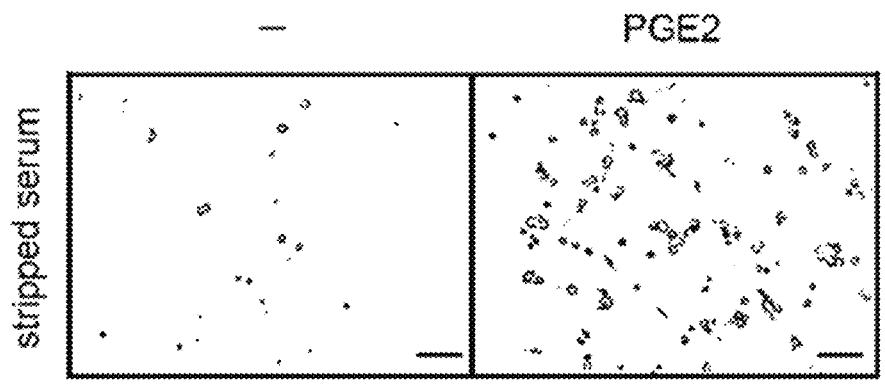

Immunofluorescent staining of myofibers in TA cross-section

Myofiber segmentation for quantification of cross sectional area (CSA)

In vivo force measurement

Immunofluorescent staining of myofibers in TA cross-section

Myofiber segmentation for quantification of cross sectional area (CSA)

FIG. 21A

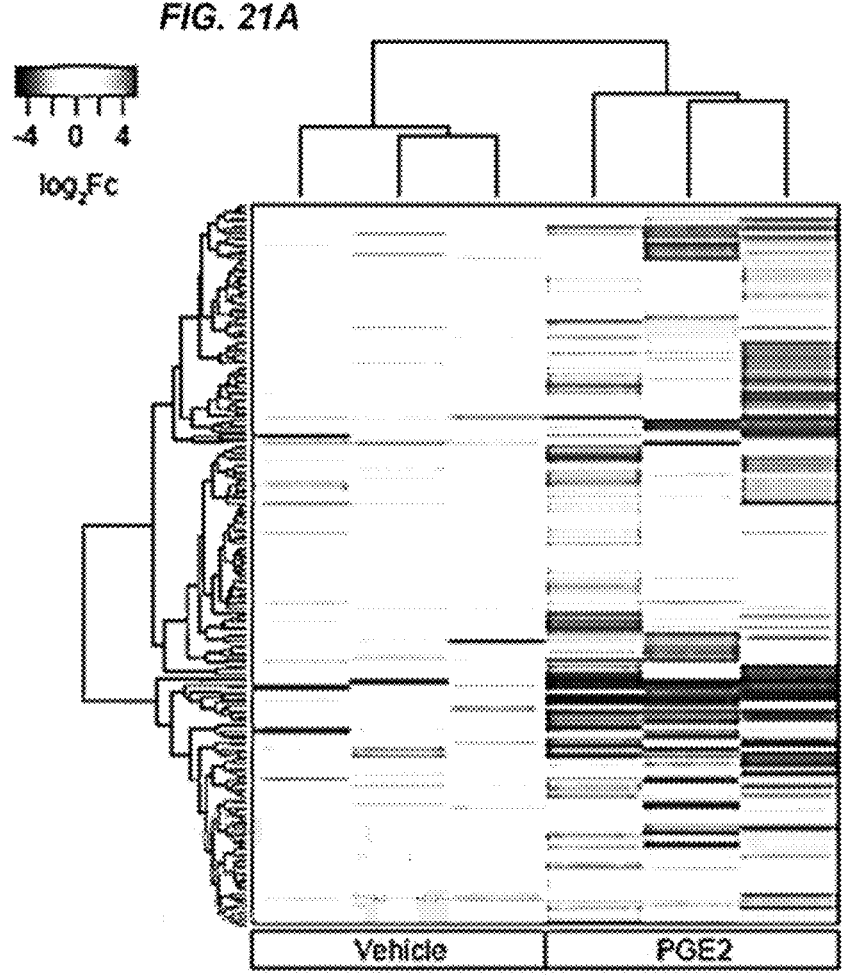

FIG. 21B

| Molecular and cellular functions | p-value |
|---|---|
| Cell morphology | 4.22E-05 |
| Lipid metabolism | 4.45E-04 |
| Molecular transport | 4.45E-04 |
| Small molecule biochemistry | 4.45E-04 |
| Cell-to-cell signaling and interaction | 4.83E-04 |

FIG. 21C

| Pathway Enrichment | p-value |
|---|---|
| Nociceptin receptor signaling | 6.591E-03 |
| PGE2 pathways | 2.649E-03 |
| Signaling via Cyclic AMP | 2.255E-03 |
| Metabolite transport | 2.014E-03 |
| Oxidative stress regulation | 1.664E-03 |
| Cell cycle regulation | 1.214E-03 |
| Regulation of G1/S checkpoint | 1.128E-02 |
| Regulation of G2/M checkpoint | 1.128E-02 |

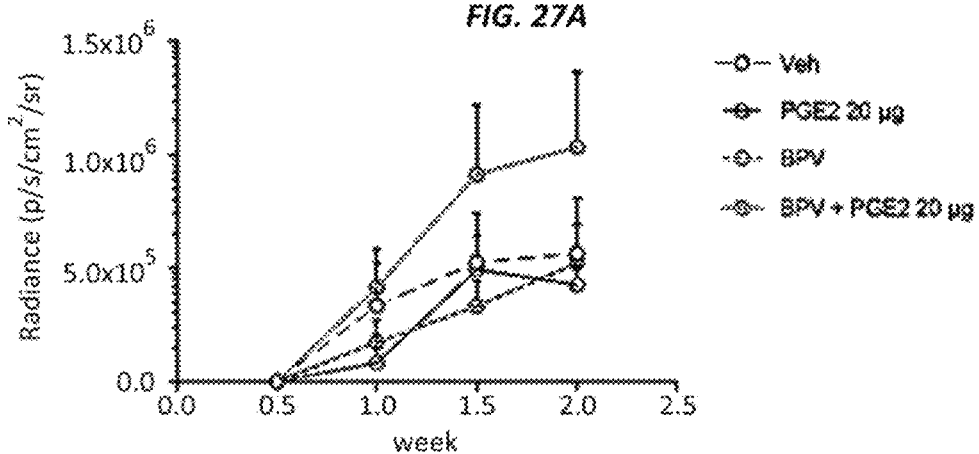
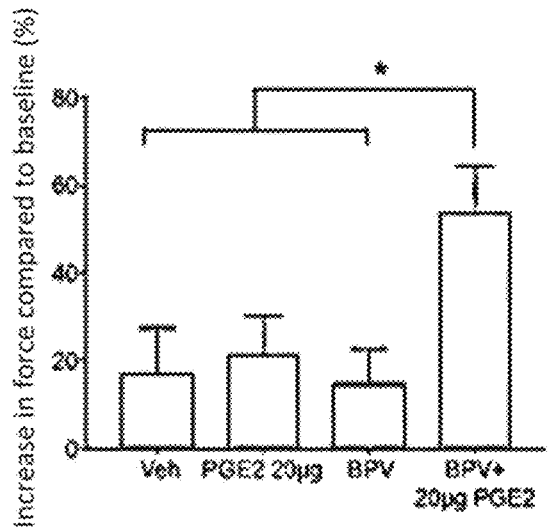
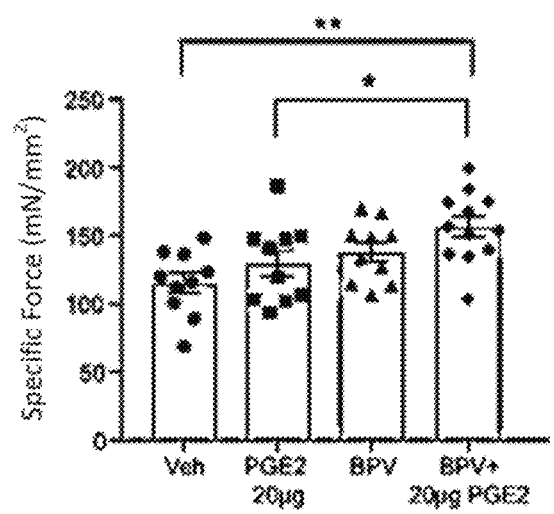

SEQUENCE LISTING

<160> NUMBER OF SEQ ID NOS: 12

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 1
ttcaccacca tggagaaggc                                              20

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: Synthetic primer

```
<400> SEQUENCE: 2 ccctttggc tccaccct                                                  18

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
tccagtgtga tgtggctgac                                               20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
attgttcacg cctgcattgt                                               20

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gctgtcatca caggccaga                                                19

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ctccacatct gggtcactcc                                               20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ctcctacagg aaagtgccca                                               20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 8
accaggtagg tcttgagggc                                              20

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gtggtgtcgt gcatctgct                                               19

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ccgctgcagg gagttagagt                                              20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
accttcgcca tatgctcctt                                              20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ggaccggtgg cctaagtatg                                              20
```

COMPOSITIONS AND METHODS FOR PREVENTING OR TREATING MUSCLE CONDITIONS

CROSS-REFERENCE TO RELATED APPLICATIONS

This application is a continuation of U.S. patent application Ser. No. 16/148,976, filed Oct. 1, 2018, which is a continuation of PCT Application No. PCT/US2018/036727, filed Jun. 8, 2018, which claims priority to U.S. Provisional Application No. 62/517,758, filed Jun. 9, 2017, the disclosures of which are hereby incorporated by reference in their entireties for all purposes.

STATEMENT AS TO RIGHTS TO INVENTIONS MADE UNDER FEDERALLY SPONSORED RESEARCH AND DEVELOPMENT

This invention was made with government support under Grant No. AG020961, awarded by the National Institutes of Health. The government has certain rights in the invention.

SEQUENCE LISTING

The instant application contains a Sequence Listing which has been filed electronically in ASCII format and is hereby incorporated by reference in its entirety. Said ASCII copy, created Aug. 10, 2021, is named 079445-001530US-1263929_SL.txt and is 3,030 bytes in size.

BACKGROUND OF THE INVENTION

Muscle injuries are an extremely common phenomenon which range from being relatively mild to extremely severe and can take many forms. In addition, muscle injuries arise from any number of causes. For example, muscles are often incidentally injured during surgical procedures (e.g., surgical treatments). This is especially apparent in the context of surgical procedures such as Caesarean sections and joint replacement surgeries (e.g., knee and hip replacement surgeries). Furthermore, many muscle injuries are the result of trauma and accidental events that produce cutting, compression, and/or crushing of muscle tissue. In addition, many muscle injuries are the consequence of immobilization (e.g., limb immobilization) and/or nerve injuries (e.g., peripheral nerve injuries).

Peripheral nerve injuries (PNI) are a common result of trauma or immobilization due to illness and can produce severe motor deficits that ultimately impact the physical, psychological, and social well-being of those affected. In particular, peripheral nerves are prevalently injured in combat from high velocity gunshot wounds and explosive fragments. Furthermore, combat PNIs are increasingly common because improvements in body armor and rapid evacuations allow more soldiers to survive severe extremity trauma. PNIs occurred in 8% of UK combat casualties from the Iraq and Afghanistan conflicts. Of those with combat PNIs, only about 9% return to full duty.

Compression PNIs (such as carpal tunnel syndrome (CTS)) are a category of nerve injury caused by constriction of the nerve. Compression PNIs are especially common in the military veteran population. For example, in 2007-2008 120,000 veterans received a diagnosis of CTS and 10,000 of them underwent carpal tunnel release.

A primary morbidity after PNI (either due to combat or compression) is muscle atrophy that occurs when a muscle is denervated. Recovery of denervated muscle is a complex process that is not fully understood; however intrinsic regenerative factors of the muscle are known to be critical and can be influenced by factors such as age. For those with severe CTS, the denervated muscle is the abductor pollicis brevis (APB), which brings the thumb out of the plane of the palm and is integral to many fine motor activities (FIG. 1). To date, the only means of medical intervention is by surgery to release the band constricting the median nerve. This allows for regeneration of the motor nerve and potential recovery of the muscle. Unfortunately, many of those with severe CTS have poor functional recovery even after the nerve has been released.

There is a need for new therapies that improve the recovery of muscle function following muscle and nerve injuries. The present invention satisfies this need, and provides related advantages as well.

BRIEF SUMMARY OF THE INVENTION

In a first aspect, provided herein is a composition for preventing or treating a muscle condition. In some embodiments, the composition comprises a prostaglandin E2 (PGE2) compound and a myotoxin.

In a second aspect, provided herein is a pharmaceutical composition. In some embodiments, the pharmaceutical composition comprises a composition described herein that comprises a PGE2 compound and a myotoxin.

In a third aspect, provided herein is a method for promoting muscle regeneration and/or increasing muscle mass in a subject in need thereof. In some embodiments, the method comprises administering a combination of a PGE2 compound and a myotoxin to the subject.

In a fourth aspect, provided herein is a method for preventing or treating a muscle condition in a subject in need thereof. In some embodiments, the method comprises administering a combination of a PGE2 compound and a myotoxin to the subject. In other embodiments, the method comprises administering a PGE2 receptor agonist and a myotoxin to the subject.

In fifth aspect, provided herein is a kit for promoting muscle regeneration, increasing muscle strength, and/or increasing muscle mass in a subject in need thereof, or for preventing or treating a muscle condition in a subject in need thereof. In some embodiments, the kit comprises a composition described herein that comprises a combination of a PGE2 compound and a myotoxin. In other embodiments, the kit comprises a pharmaceutical composition described herein.

Described herein is a composition for preventing or treating a muscle condition, the composition comprising a prostaglandin E2 (PGE2) compound and a myotoxin. In some embodiments, the PGE2 compound is selected from the group consisting of PGE2, a PGE2 prodrug, a PGE2 receptor agonist, a compound that attenuates PGE2 catabolism, a compound that neutralizes PGE2 inhibition, a derivative thereof, an analog thereof, and a combination thereof. In some embodiments, the PGE2 receptor agonist comprises a compound of Formula (I), a derivative thereof, a pharmaceutically acceptable salt thereof, a solvate thereof, a stereoisomer thereof, or a combination thereof, Formula (I)

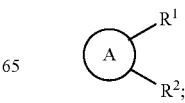

wherein ring A is a substituted 4- to 6-membered cycloalkyl ring or a substituted 4- to 6-membered cycloalkenyl ring that comprises substituents $R^1$ and $R^2$ that are independently selected from the group consisting of substituted $C_1$-$C_{10}$ alkyl and substituted $C_2$-$C_{10}$ alkenyl, and ring A further comprises one or more additional substituents.

In some cases, ring A is a substituted cyclopentyl ring or a substituted cyclopentenyl ring. In some cases, the one or more additional substituents on ring A are selected from the group consisting of deuterium, hydroxy, amino, oxo, $C_1$-$C_6$ alkyl, and halogen. In some cases, the one or more additional substituents on ring A are hydroxy or oxo. In some embodiments, ring A has two additional substituents that are taken together to form a covalent bond to form a heterocycloalkyl ring. In some embodiments, ring A is selected from the group consisting of

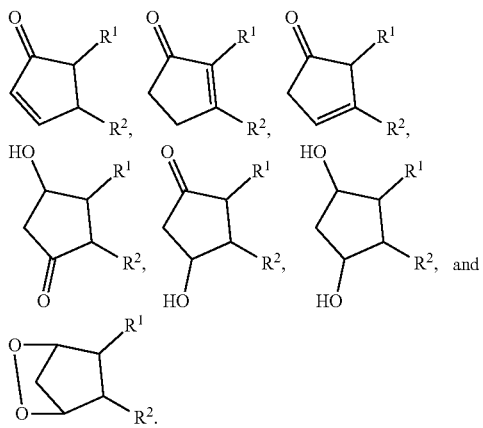

In some embodiments, ring A is selected from the group consisting of

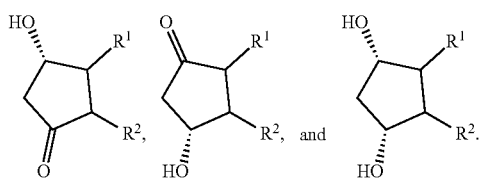

In some embodiments, ring A is

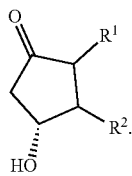

In some embodiments, $R^1$ is substituted $C_1$-$C_{10}$ alkyl. In some embodiments, $R^1$ is substituted $C_2$-$C_{10}$ alkenyl. In some embodiments, the substituent on $R^1$ is selected from the group consisting of deuterium, hydroxy, oxo, $C_1$-$C_6$ alkyl, —COOR$^3$, and halogen, wherein $R^3$ is hydrogen or $C_1$-$C_6$ alkyl. In some embodiments, $R^1$ is selected from the group consisting of

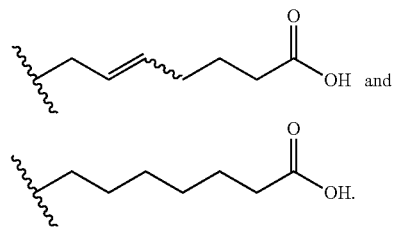

In some embodiments, $R^1$ is selected from the group consisting of

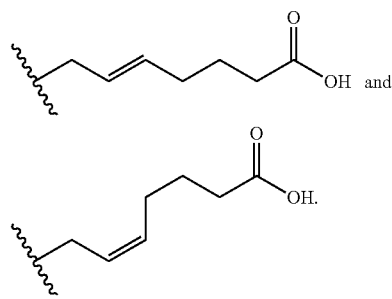

In some embodiments, $R^1$ is

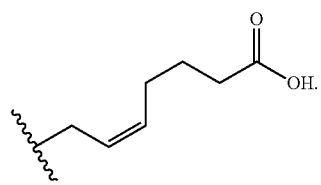 [SMILES: *C/C=C\CCCC(=O)O]

In some embodiments, $R^2$ is substituted $C_1$-$C_{10}$ alkyl. In some embodiments, $R^2$ is substituted $C_2$-$C_{10}$ alkenyl. In some embodiments, the substituent on $R^2$ is selected from the group consisting of deuterium, hydroxy, oxo, $C_1$-$C_6$ alkyl, —COOR$^3$, and halogen, wherein $R^3$ is hydrogen or $C_1$-$C_6$ alkyl. In some embodiments, $R^2$ is selected from the group consisting of

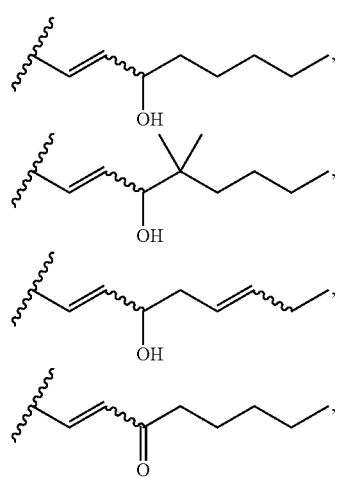

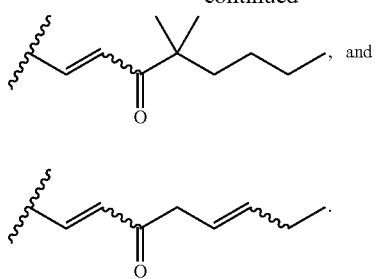

In some embodiments, R² is selected from the group consisting of

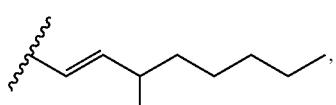
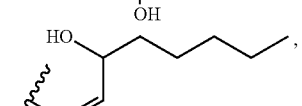
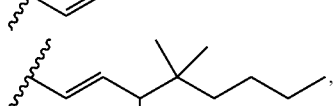
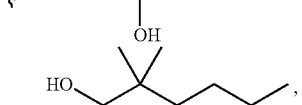
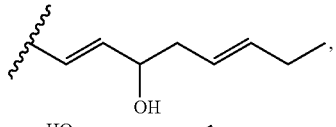
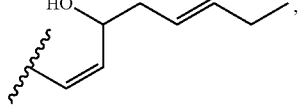
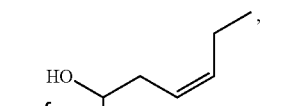
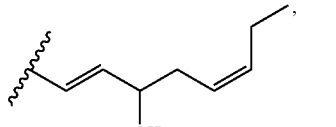
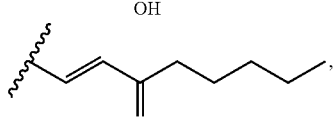

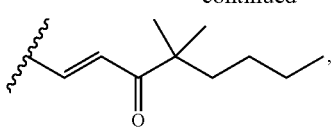
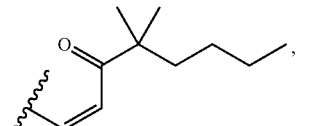
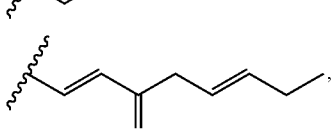
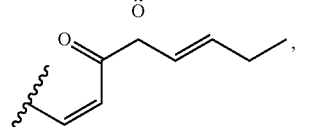
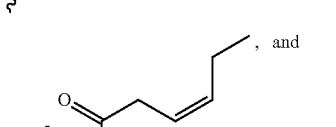
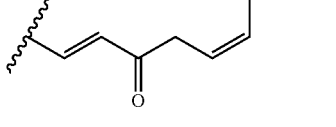

In some embodiments, R² is

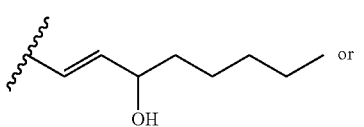
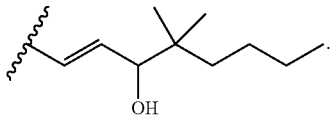

In some embodiments, the compound of Formula (I), the pharmaceutically acceptable salt thereof, the solvate thereof, or the stereoisomer thereof is a compound of Formula (Ia), Formula (Ib), Formula (Ic), or Formula (Id), or a pharmaceutically acceptable salt, solvate, or stereoisomer thereof:

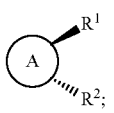

Formula (Ia)

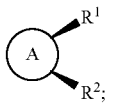

Formula (Ib)

-continued

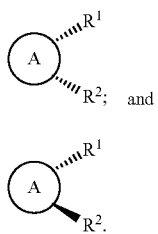

Formula (Ic)

and

Formula (Id)

In some embodiments, the compound of Formula (I), the pharmaceutically acceptable salt thereof, the solvate thereof, or the stereoisomer thereof is a compound of Formula (Id), or a pharmaceutically acceptable salt, solvate, or stereoisomer thereof.

In some embodiments, the PGE2 derivative comprises 16,16-dimethyl prostaglandin E2. In some embodiments, the compound that attenuates PGE2 catabolism comprises a compound, neutralizing peptide, or neutralizing antibody that inactivates or blocks 15-hydroxyprostaglandin dehydrogenase (15-PGDH) or inactivates or blocks a prostaglandin transporter (PGT or SLCO2A1). In some embodiments, the PGE2 compound is PGE2.

In some embodiments, the myotoxin is selected from the group consisting of an anesthetic, a divalent cation, snake venom, lizard venom, bee venom, and a combination thereof. In some embodiments, the anesthetic is selected from the group consisting of an amino-amide anesthetic, an amino-ester anesthetic, and a combination thereof. In some embodiments, the amino-amide anesthetic is selected from the group consisting of bupivacaine, levobupivacaine, articaine, ropivacaine, butanilicaine, carticaine, dibucaine, etidocaine, lidocaine, mepivacaine, prilocaine, trimecaine, and a combination thereof. In some embodiments, the amino-ester anesthetic is selected from the group consisting of an aminobenzoic acid ester anesthetic, a benzoic acid ester anesthetic, and a combination thereof. In some embodiments, the aminobenzoic acid ester anesthetic is selected from the group consisting of benzocaine, butacaine, butamben, chloroprocaine, dimethocaine, lucaine, meprylcaine, metabutethamine, metabutoxycaine, nitracaine, orthocaine, propoxycaine, procaine, proxymetacaine, risocaine, tetracaine, and a combination thereof. In some embodiments, the benzoic acid ester anesthetic is selected from the group consisting of amylocaine, cocaine, cyclomethycaine, α-eucaine, β-eucaine, hexylcaine, isobucaine, piperocaine, and a combination thereof. In some embodiments, the snake venom or the lizard venom is selected from the group consisting of notexin, cardiotoxin, bungarotoxin, and a combination thereof. In some embodiments, the divalent cation is selected from the group consisting of $Ba^{2+}$, $Sr^{2+}$, $Mg^{2+}$, $Ca^{2+}$, $Mn^{2+}$, $Ni^{2+}$, $Co^{2+}$, a salt thereof, and a combination thereof.

In some embodiments, PGE2 compound is PGE2 and/or 16,16-dimethyl prostaglandin E2 and the myotoxin is bupivacaine.

In some embodiments, PGE2 compound is PGE2 and/or 16,16-dimethyl prostaglandin E2 and the myotoxin is bupivacaine. In some embodiments, the muscle condition is associated with muscle damage, injury, or atrophy.

Described herein is a pharmaceutical composition comprising the composition described herein and a pharmaceutically acceptable carrier. In some embodiments, the pharmaceutically acceptable carrier comprises an aqueous base. In some embodiments, the pharmaceutically acceptable carrier comprises a low viscosity compound. In some embodiments, the low viscosity compound comprises gelatin. In some embodiments, the low viscosity compound comprises a hydrogel.

Described herein is a method for promoting muscle regeneration and/or increasing muscle mass in a subject in need thereof, the method comprising administering a combination of a PGE2 compound and a myotoxin to the subject. In some embodiments, the PGE2 compound is selected from the group consisting of PGE2, a PGE2 prodrug, a PGE2 receptor agonist, a compound that attenuates PGE2 catabolism, a compound that neutralizes PGE2 inhibition, a derivative thereof, an analog thereof, and a combination thereof. In some embodiments, the PGE2 derivative comprises 16,16-dimethyl prostaglandin E2. In some embodiments, the compound that attenuates PGE2 catabolism comprises a compound, neutralizing peptide, or neutralizing antibody that inactivates or blocks 15-hydroxyprostaglandin dehydrogenase (15-PGDH) or inactivates or blocks a prostaglandin transporter (PGT or SLCO2A1). In some embodiments, the PGE2 compound is PGE2.

In some embodiments, the myotoxin is selected from the group consisting of an anesthetic, a divalent cation, snake venom, lizard venom, bee venom, and a combination thereof. In some embodiments, the anesthetic is selected from the group consisting of an amino-amide anesthetic, an amino-ester anesthetic, and a combination thereof. In some embodiments, the amino-amide anesthetic is selected from the group consisting of bupivacaine, levobupivacaine, articaine, ropivacaine, butanilicaine, carticaine, dibucaine, etidocaine, lidocaine, mepivacaine, prilocaine, trimecaine, and a combination thereof. In some embodiments, the amino-ester anesthetic is selected from the group consisting of an aminobenzoic acid ester anesthetic, a benzoic acid ester anesthetic, and a combination thereof. In some embodiments, the aminobenzoic acid ester anesthetic is selected from the group consisting of benzocaine, butacaine, butamben, chloroprocaine, dimethocaine, lucaine, meprylcaine, metabutethamine, metabutoxycaine, nitracaine, orthocaine, propoxycaine, procaine, proxymetacaine, risocaine, tetracaine, and a combination thereof. In some embodiments, the benzoic acid ester anesthetic is selected from the group consisting of amylocaine, cocaine, cyclomethycaine, α-eucaine, β-eucaine, hexylcaine, isobucaine, piperocaine, and a combination thereof. In some embodiments, the snake venom or the lizard venom is selected from the group consisting of notexin, cardiotoxin, bungarotoxin, and a combination thereof. In some embodiments, the divalent cation is selected from the group consisting of $Ba^{2+}$, $Sr^{2+}$, $Mg^{2+}$, $Ca^{2+}$, $Mn^{2+}$, $Ni^{2+}$, $Co^{2+}$, a salt thereof, and a combination thereof.

In some embodiments, PGE2 compound is PGE2 and/or 16,16-dimethyl prostaglandin E2 and the myotoxin is bupivacaine. In some embodiments, the PGE2 compound and the myotoxin are administered concomitantly. In some embodiments, the PGE2 compound and the myotoxin are administered sequentially. In some embodiments, the PGE2 compound is administered before the myotoxin. In some embodiments, the PGE2 compound is administered after the myotoxin.

In some embodiments, administering the PGE2 compound, the myotoxin, or both, comprises topical, oral, intraperitoneal, intramuscular, intra-arterial, intradermal, subcutaneous, intravenous, or intracardiac administration. In some embodiments, administering comprises intramuscular administration. In some embodiments, a dose of the PGE2 compound, the myotoxin, or both, is determined based upon a target muscle size. In some embodiments, the target muscle is an abductor pollicis brevis muscle and the dose of the PGE2 compound, the myotoxin, or both, is about 10 µg.

In some embodiments, the method further comprises subjecting a target muscle to mechanical injury. In some embodiments, the mechanical injury comprises cutting, burning, freezing, needle puncture, exercise, a surgical procedure, traumatic injury, or a combination thereof. In some embodiments, the method further comprises administering a population of isolated muscle cells to the subject. In some embodiments, the population of isolated muscle cells is autologous to the subject. In some embodiments, the population of isolated muscle cells is allogeneic to the subject. In some embodiments, the population of isolated muscle cells is purified. In some embodiments, population of isolated muscle cells is cultured with the PGE2 compound, the myotoxin, or both, prior to being administered to the subject. In some embodiments, culturing the population of isolated muscle cells with the PGE2 compound, the myotoxin, or both, comprises acute, intermittent, or continuous exposure of the population of isolated muscle cells to the PGE2 compound, the myotoxin, or both. In some embodiments, wherein administering the population of isolated muscle cells comprises injecting or transplanting the cells into the subject. In some embodiments, wherein administration of the population of isolated muscle cells and administration of the PGE2 compound and the myotoxin are performed concomitantly. In some embodiments, administration of the population of isolated muscle cells and administration of the PGE2 compound and the myotoxin are performed sequentially. In some embodiments, the subject has a muscle condition.

In some embodiments, the muscle condition is associated with muscle damage, injury, atrophy, or any combination thereof. In some embodiments, the muscle condition is selected from the group consisting of traumatic injury, acute muscle injury, acute nerve injury, chronic nerve injury, soft tissue hand injury, carpal tunnel syndrome (CTS), Duchenne muscular dystrophy (DMD), Becker muscular dystrophy, limb girdle muscular dystrophy, amyotrophic lateral sclerosis (ALS), distal muscular dystrophy (DD), inherited myopathies, myotonic muscular dystrophy (MDD), mitochondrial myopathies, myotubular myopathy (MM), myasthenia gravis (MG), congestive heart failure, periodic paralysis, polymyositis, rhabdomyolysis, dermatomyositis, cancer cachexia, AIDS cachexia, cardiac cachexia, stress induced urinary incontinence, sarcopenia, spinal muscular atrophy, fecal sphincter dysfunction, Bell's palsy, rotator cuff injury, spinal cord injury, hip replacement, knee replacement, wrist fracture, and diabetic neuropathy.

In some embodiments, the PGE2 compound and the myotoxin are administered immediately after the traumatic injury. In some embodiments, the subject receives a surgical procedure. In some embodiments, the surgical procedure is for the prevention of a nerve injury, reduction of a nerve injury, repair of a nerve injury, or any combination thereof. In some embodiments, the surgical procedure comprises cutting a muscle, repairing a muscle, or both. In some embodiments, the subject receives the surgical procedure before administration of the PGE2 compound and the myotoxin. In some embodiments, the subject receives the surgical procedure at the same time as administration of the PGE2 compound and the myotoxin. In some embodiments, the subject receives the surgical procedure after administration of the PGE2 compound and the myotoxin. In some embodiments, the nerve injury is a peripheral nerve injury.

In some embodiments, the surgical procedure comprises a carpal tunnel release procedure.

Described herein is a method for preventing or treating a muscle condition in a subject in need thereof, the method comprising administering a combination of a PGE2 compound and a myotoxin to the subject. In some embodiments, the PGE2 compound is selected from the group consisting of PGE2, a PGE2 prodrug, a PGE2 receptor agonist, a compound that attenuates PGE2 catabolism, a compound that neutralizes PGE2 inhibition, a derivative thereof, an analog thereof, and a combination thereof. In some embodiments, the PGE2 derivative comprises 16,16-dimethyl prostaglandin E2. In some embodiments, the compound that attenuates PGE2 catabolism comprises a compound, neutralizing peptide, or neutralizing antibody that inactivates or blocks 15-hydroxyprostaglandin dehydrogenase (15-PGDH) or inactivates or blocks a prostaglandin transporter (PGT or SLCO2A1). In some embodiments, wherein the PGE2 compound is PGE2. In some embodiments, the myotoxin is selected from the group consisting of an anesthetic, a divalent cation, snake venom, lizard venom, bee venom, and a combination thereof. In some embodiments, the anesthetic is selected from the group consisting of an amino-amide anesthetic, an amino-ester anesthetic, and a combination thereof. In some embodiments, the amino-amide anesthetic is selected from the group consisting of bupivacaine, levobupivacaine, articaine, ropivacaine, butanilicaine, carticaine, dibucaine, etidocaine, lidocaine, mepivacaine, prilocaine, trimecaine, and a combination thereof. In some embodiments, the amino-ester anesthetic is selected from the group consisting of an aminobenzoic acid ester anesthetic, a benzoic acid ester anesthetic, and a combination thereof. In some embodiments, the aminobenzoic acid ester anesthetic is selected from the group consisting of benzocaine, butacaine, butamben, chloroprocaine, dimethocaine, lucaine, meprylcaine, metabutethamine, metabutoxycaine, nitracaine, orthocaine, propoxycaine, procaine, proxymetacaine, risocaine, tetracaine, and a combination thereof. In some embodiments, the benzoic acid ester anesthetic is selected from the group consisting of amylocaine, cocaine, cyclomethycaine, α-eucaine, β-eucaine, hexylcaine, isobucaine, piperocaine, and a combination thereof. In some embodiments, the snake venom or the lizard venom is selected from the group consisting of notexin, cardiotoxin, bungarotoxin, and a combination thereof. In some embodiments, the divalent cation is selected from the group consisting of $Ba^{2+}$, $Sr^{2+}$, $Mg^{2+}$, $Ca^{2+}$, $Mn^{2+}$, $Ni^{2+}$, $Co^{2+}$, a salt thereof, and a combination thereof.

In some embodiments, the PGE2 compound is PGE2 and the myotoxin is bupivacaine. In some embodiments, the PGE2 compound and the myotoxin are administered concomitantly. In some embodiments, the PGE2 compound and the myotoxin are administered sequentially. In some embodiments, the PGE2 compound is administered before the myotoxin. In some embodiments, the PGE2 compound is administered after the myotoxin. In some embodiments, administering the PGE2 compound, the myotoxin, or both, comprises topical, oral, intraperitoneal, intramuscular, intraarterial, intradermal, subcutaneous, intravenous, or intracardiac administration. In some embodiments, administering comprises intramuscular administration. In some embodiments, a dose of the PGE2 compound, the myotoxin, or both, is determined based upon a target muscle size. In some embodiments, the target muscle is an abductor pollicis brevis muscle and the dose of the PGE2 compound, the myotoxin, or both, is about 10 µg.

In some embodiments, the method further comprises subjecting a target muscle to mechanical injury. In some embodiments, the mechanical injury comprises cutting, burning, freezing, needle puncture, exercise, a surgical procedure, traumatic injury, or a combination thereof.

In some embodiments, the method further comprises administering a population of isolated muscle cells to the subject. In some embodiments, the population of isolated muscle cells is autologous to the subject. In some embodiments, the population of isolated muscle cells is allogeneic to the subject. In some embodiments, the population of isolated muscle cells is purified. In some embodiments, the population of isolated muscle cells is cultured with the PGE2 compound, the myotoxin, or both, prior to being administered to the subject. In some embodiments, culturing the population of isolated muscle cells with the PGE2 compound, the myotoxin, or both, comprises acute, intermittent, or continuous exposure of the population of isolated muscle cells to the PGE2 compound, the myotoxin, or both. In some embodiments, the population of isolated muscle cells comprises injecting or transplanting the cells into the subject. In some embodiments, administration of the population of isolated muscle cells and administration of the PGE2 compound and the myotoxin are performed concomitantly. In some embodiments, administration of the population of isolated muscle cells and administration of the PGE2 compound and the myotoxin are performed sequentially.

In some embodiments, the muscle condition is associated with muscle damage, injury, atrophy, or any combination thereof. In some embodiments, the muscle condition is selected from the group consisting of traumatic injury, acute muscle injury, acute nerve injury, chronic nerve injury, soft tissue hand injury, carpal tunnel syndrome (CTS), Duchenne muscular dystrophy (DMD), Becker muscular dystrophy, limb girdle muscular dystrophy, amyotrophic lateral sclerosis (ALS), distal muscular dystrophy (DD), inherited myopathies, myotonic muscular dystrophy (MDD), mitochondrial myopathies, myotubular myopathy (MM), myasthenia gravis (MG), congestive heart failure, periodic paralysis, polymyositis, rhabdomyolysis, dermatomyositis, cancer cachexia, AIDS cachexia, cardiac cachexia, stress induced urinary incontinence, sarcopenia, spinal muscular atrophy, fecal sphincter dysfunction, Bell's palsy, rotator cuff injury, spinal cord injury, hip replacement, knee replacement, wrist fracture, and diabetic neuropathy.

In some embodiments, the PGE2 receptor agonist and the myotoxin are administered immediately after the traumatic injury. In some embodiments, the subject receives a surgical procedure. In some embodiments, the surgical procedure is for the prevention of a nerve injury, reduction of a nerve injury, repair of a nerve injury, or any combination thereof. In some embodiments, the surgical procedure comprises cutting a muscle, repairing a muscle, or both. In some embodiments, the subject receives the surgical procedure before administration of the PGE2 compound and the myotoxin. In some embodiments, the subject receives the surgical procedure at the same time as administration of the PGE2 compound and the myotoxin. In some embodiments, the subject receives the surgical procedure after administration of the PGE2 compound and the myotoxin. In some embodiments, the nerve injury is a peripheral nerve injury. In some embodiments, the surgical procedure comprises a carpal tunnel release procedure. In some embodiments, treating the subject results in an improvement in muscle strength, muscle coordination, or both, in the subject.

Described herein is a method for preventing or treating a muscle condition in a subject in need thereof, the method comprising administering a prostaglandin E2 (PGE2) receptor agonist to the subject. In some embodiments, the PGE2 receptor agonist comprises a compound of Formula (I), a derivative thereof, a pharmaceutically acceptable salt thereof, a solvate thereof, a stereoisomer thereof, or a combination thereof,

Formula (I)

wherein ring A is a substituted 4- to 6-membered cycloalkyl ring or a substituted 4- to 6-membered cycloalkenyl ring that comprises substituents $R^1$ and $R^2$ that are independently selected from the group consisting of substituted $C_1$-$C_{10}$ alkyl and substituted $C_2$-$C_{10}$ alkenyl, and ring A further comprises one or more additional substituents.

In some embodiments, A is a substituted cyclopentyl ring or a substituted cyclopentenyl ring. In some embodiments, the one or more additional substituents on ring A are selected from the group consisting of deuterium, hydroxy, amino, oxo, $C_1$-$C_6$ alkyl, and halogen. In some embodiments, the one or more additional substituents on ring A are hydroxy or oxo. In some embodiments, ring A has two additional substituents that are taken together to form a covalent bond to form a heterocycloalkyl ring.

In some embodiments, ring A is selected from the group consisting of

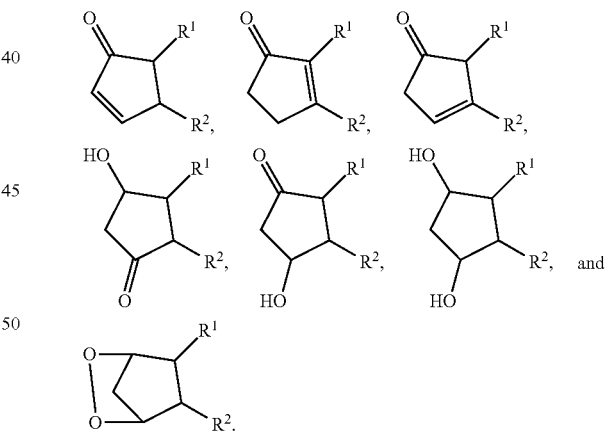

In some embodiments, ring A is selected from the group consisting of

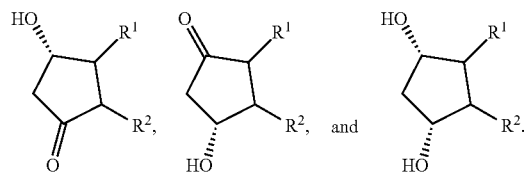

In some embodiments, ring A is

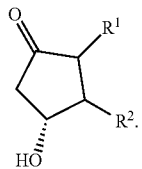

In some embodiments, $R^1$ is substituted $C_1$-$C_{10}$ alkyl.

In some embodiments, $R^1$ is substituted $C_2$-$C_{10}$ alkenyl.

In some embodiments, the substituent on $R^1$ is selected from the group consisting of deuterium, hydroxy, oxo, $C_1$-$C_6$ alkyl, —COOR$^3$, and halogen, wherein $R^3$ is hydrogen or $C_1$-$C_6$ alkyl.

In some embodiments, $R^1$ is selected from the group consisting of

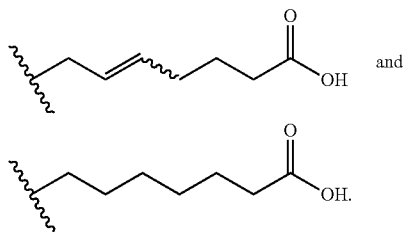

In some embodiments, $R^1$ is selected from the group consisting of

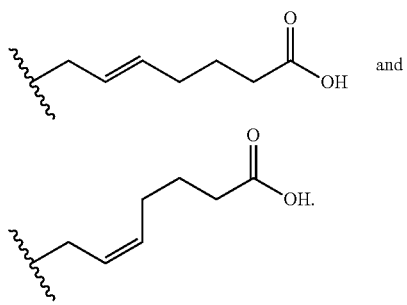

In some embodiments, $R^1$ is

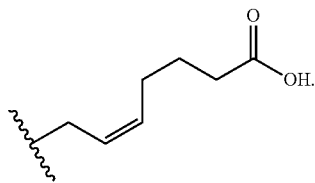

In some embodiments, $R^2$ is substituted $C_1$-$C_{10}$ alkyl. In some embodiments, $R^2$ is substituted $C_2$-$C_{10}$ alkenyl. In some embodiments, the substituent on $R^2$ is selected from the group consisting of deuterium, hydroxy, oxo, $C_1$-$C_6$ alkyl, —COOR$^3$, and halogen, wherein $R^3$ is hydrogen or $C_1$-$C_6$ alkyl. In some embodiments, $R^2$ is selected from the group consisting of

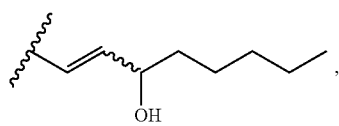

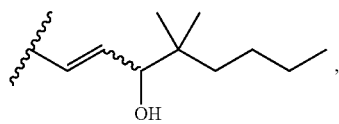

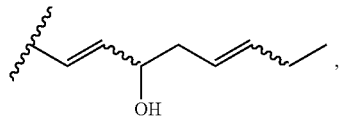

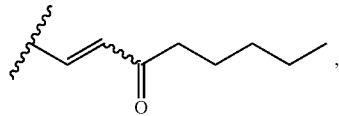

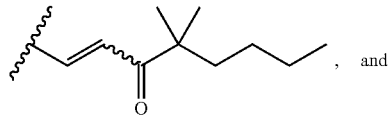

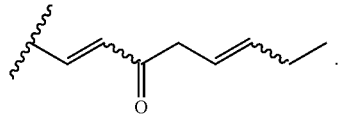

In some embodiments, $R^2$ is selected from the group consisting of

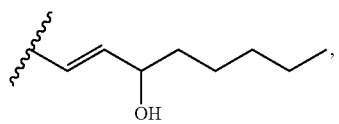

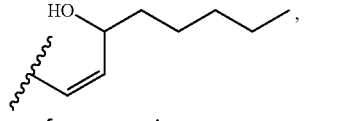

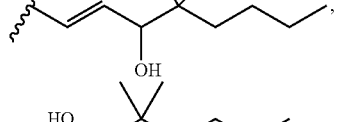

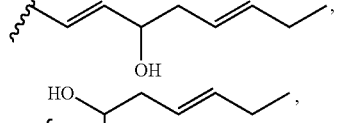

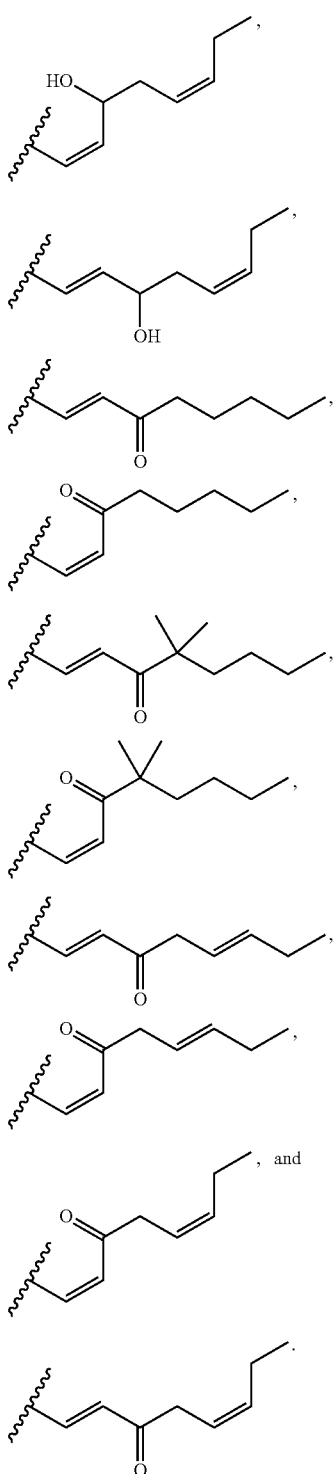

In some embodiments, R² is

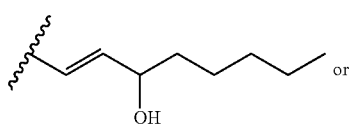

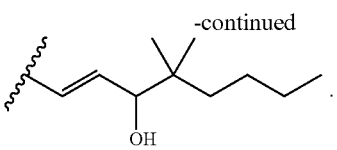

In some embodiments, the compound of Formula (I), the pharmaceutically acceptable salt thereof, the solvate thereof, or the stereoisomer thereof is a compound of Formula (Ia), Formula (Ib), Formula (Ic), or Formula (Id), or a pharmaceutically acceptable salt, solvate, or stereoisomer thereof:

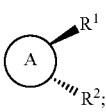

Formula (Ia)

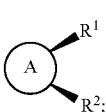

Formula (Ib)

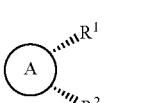

Formula (Ic)

and

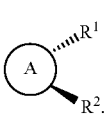

Formula (Id)

In some embodiments, the compound of Formula (I), the pharmaceutically acceptable salt thereof, the solvate thereof, or the stereoisomer thereof is a compound of Formula (Id), or a pharmaceutically acceptable salt, solvate, or stereoisomer thereof.

In some embodiments, the PGE2 receptor agonist comprises PGE2, 16,16-dimethyl prostaglandin E2, or both.

In some embodiments, the method further comprises administering a myotoxin to the subject. In some embodiments, the myotoxin is selected from the group consisting of an anesthetic, a divalent cation, snake venom, lizard venom, bee venom, and a combination thereof. In some embodiments, the anesthetic is selected from the group consisting of an amino-amide anesthetic, an amino-ester anesthetic, and a combination thereof. In some embodiments, the amino-amide anesthetic is selected from the group consisting of bupivacaine, levobupivacaine, articaine, ropivacaine, butanilicaine, carticaine, dibucaine, etidocaine, lidocaine, mepivacaine, prilocaine, trimecaine, and a combination thereof. In some embodiments, the amino-ester anesthetic is selected from the group consisting of an aminobenzoic acid ester anesthetic, a benzoic acid ester anesthetic, and a combination thereof. In some embodiments, the aminobenzoic acid ester anesthetic is selected from the group consisting of benzocaine, butacaine, butamben, chloroprocaine, dimethocaine, lucaine, meprylcaine, metabutethamine, metabutoxycaine, nitracaine, orthocaine, propoxycaine, procaine, proxymetacaine, risocaine, tetracaine, and a combination thereof. In some embodiments, the benzoic acid ester anesthetic is selected from the group consisting of amylocaine, cocaine, cyclomethycaine, α-eucaine, β-eucaine, hexylcaine, isobucaine, piperocaine, and a combination thereof. In some embodiments, the snake venom or the lizard venom is selected from the group consisting of notexin, cardiotoxin, bungarotoxin, and a combination thereof. In some embodiments, the divalent cation is selected from the group consisting of $Ba^{2+}$, $Sr^{2+}$, $Mg^{2+}$, $Ca^{2+}$, $Mn^{2+}$, $Ni^{2+}$, $Co^{2+}$, a salt thereof, and a combination thereof. In some embodiments, the PGE2 receptor agonist is PGE2, 16,16-dimethyl prostaglandin E2, or both, and the myotoxin is bupivacaine.

In some embodiments, the method further comprises subjecting a target muscle to mechanical injury. In some embodiments, the mechanical injury comprises cutting, burning, freezing, needle puncture, exercise, a surgical procedure, traumatic injury, or a combination thereof.

In some embodiments, the method further comprises administering a population of isolated muscle cells to the subject. In some embodiments, the population of isolated muscle cells is autologous to the subject. In some embodiments, the population of isolated muscle cells is allogeneic to the subject. In some embodiments, the population of isolated muscle cells is purified. In some embodiments, the population of isolated muscle cells is cultured with the PGE2 receptor agonist prior to being administered to the subject. In some embodiments, culturing the population of isolated muscle cells with the PGE2 compound comprises acute, intermittent, or continuous exposure of the population of isolated muscle cells to the PGE2 compound. In some embodiments, administering the population of isolated muscle cells comprises injecting or transplanting the cells into the subject. In some embodiments, administration of the population of isolated muscle cells and administration of the PGE2 receptor agonist are performed concomitantly. In some embodiments, administration of the population of isolated muscle cells and administration of the PGE2 receptor agonist are performed sequentially.

In some embodiments, the muscle condition is associated with muscle damage, injury, atrophy, or any combination thereof. In some embodiments, the muscle condition is selected from the group consisting of traumatic injury, acute muscle, acute nerve injury, chronic nerve injury, soft tissue hand injury, carpal tunnel syndrome (CTS), Duchenne muscular dystrophy (DMD), Becker muscular dystrophy, limb girdle muscular dystrophy, amyotrophic lateral sclerosis (ALS), distal muscular dystrophy (DD), inherited myopathies, myotonic muscular dystrophy (MDD), mitochondrial myopathies, myotubular myopathy (MM), myasthenia gravis (MG), congestive heart failure, periodic paralysis, polymyositis, rhabdomyolysis, dermatomyositis, cancer cachexia, AIDS cachexia, cardiac cachexia, stress induced urinary incontinence, sarcopenia, spinal muscular atrophy, fecal sphincter dysfunction, Bell's palsy, rotator cuff injury, spinal cord injury, hip replacement, knee replacement, wrist fracture, and diabetic neuropathy.

In some embodiments, the PGE2 receptor agonist is administered immediately after the traumatic injury.

In some embodiments, the subject receives a surgical procedure. In some embodiments, the surgical procedure is for the prevention of a nerve injury, reduction of a nerve injury, repair of a nerve injury, or any combination thereof. In some embodiments, the surgical procedure comprises cutting a muscle, repairing a muscle, or both. In some embodiments, the subject receives the surgical procedure before administration of the PGE2 receptor agonist. In some embodiments, the subject receives the surgical procedure at the same time as administration of the PGE2 receptor agonist. In some embodiments, the subject receives the surgical procedure after administration of the PGE2 receptor agonist. In some embodiments, the nerve injury is a peripheral nerve injury. In some embodiments, the surgical procedure comprises a carpal tunnel release procedure. In some embodiments, no anesthetic is administered to the subject.

Described herein is a kit for promoting muscle regeneration in a subject in need thereof, increasing muscle mass in a subject in need thereof, or both, or for preventing or treating a muscle condition in a subject in need thereof, the kit comprising a composition described herein or a pharmaceutical composition described herein. In some embodiments, the subject has a muscle condition. In some embodiments, the muscle condition is associated with muscle damage, injury, atrophy, or any combination thereof. In some embodiments, muscle condition is selected from the group consisting of traumatic injury (e.g., acute muscle trauma, acute nerve trauma), acute muscle injury, acute nerve injury, chronic nerve injury, soft tissue hand injury, carpal tunnel syndrome (CTS), Duchenne muscular dystrophy (DMD), Becker muscular dystrophy, limb girdle muscular dystrophy, amyotrophic lateral sclerosis (ALS), distal muscular dystrophy (DD), inherited myopathies, myotonic muscular dystrophy (MDD), mitochondrial myopathies, myotubular myopathy (MM), myasthenia gravis (MG), congestive heart failure, periodic paralysis, polymyositis, rhabdomyolysis, dermatomyositis, cancer cachexia, AIDS cachexia, cardiac cachexia, stress induced urinary incontinence, sarcopenia, spinal muscular atrophy, fecal sphincter dysfunction, Bell's palsy, rotator cuff injury, spinal cord injury, hip replacement, knee replacement, wrist fracture, and diabetic neuropathy.

In some embodiments, the kit further comprises isolated muscle cells. In some embodiments, the kit further comprises instructions for use. In some embodiments, the kit further comprises one or more reagents. In some embodiments, the kit further comprises a delivery device for administering the composition, pharmaceutical composition, isolated muscle cells, or any combination thereof, to the subject.

Described herein is a method for treating a pelvic floor disorder in a subject in need thereof, the method comprising administering a combination of a PGE2 compound and a myotoxin to the subject. In some embodiments, the administering comprises administering the combination of a PGE2 compound and a myotoxin to a pelvic floor muscle of the subject. In some embodiments, the pelvic floor muscle is the levator ani, the coccygeus muscle, or both. In some embodiments, the levator ani comprises the pubococcygeus muscle, the iliococcygeus muscle, the puborectalis muscle, or a combination thereof. In some embodiments, the pelvic floor disorder is selected from the group consisting of stress urinary incontinence, overactive bladder/urinary urgency incontinence, mixed urinary incontinence, pelvic organ prolapse, and fecal incontinence. In some embodiments, the method further comprises administering a therapy suitable to treat, prevent, or ameliorate symptoms associated with pelvic floor disorders to the subject. In some embodiments, the additional therapy is selected from the group consisting of muscle training/biofeedback, neuromodulation, pharmacotherapy, surgery, and a combination thereof.

Described herein is a method for treating an ocular disease or disorder in a subject in need thereof, the method comprising administering a combination of a PGE2 compound and a myotoxin to the subject. In some embodiments, the ocular disease or disorder comprises impaired eyelid function. In some embodiments, the administering comprises administering the combination of a PGE2 compound and a myotoxin to an eyelid muscle of the subject. In some embodiments, the eyelid muscle is selected from the group consisting of Muller's muscle, ocipitofrontalis muscle, temporoparietalis muscle, procerus muscle, nasalis muscle, depressor septi nasi muscle, orbicularis oculi muscle, corrugator supercilii muscle, depressor supercilii muscle, anterior auricular muscles, superior auricular muscle, posterior auricular muscle, orbicularis oris muscle, depressor anguli oris muscle, risorius, zygomaticus major muscle, zygomaticus minor muscle, levator labii superioris, levator labii superioris alaeque nasi muscle, depressor labii inferioris muscle, levator anguli oris, buccinator muscle, mentalis, frontalis muscle, and a combination thereof. In some embodiments, the impaired eyelid function is selected from the group consisting of eyelid drooping, ptosis, dermatochalasis, and a combination thereof. In some embodiments, the method further comprises, prior to, during, or after the administering, performing eyelift surgery on the subject. In some embodiments, the impaired eyelid function is associated with irregular astigmatism. In some embodiments, the ocular disease or disorder is selected from the group consisting of impaired blinking, wet eye syndrome, dry eye syndrome, lacrimal gland atrophy, $7^{th}$ facial nerve palsy, recurring styes, and a combination thereof. In some embodiments, the administering comprises administering the combination of a PGE2 compound and a myotoxin to an eye muscle of the subject. In some embodiments, the eye muscle is selected from the group consisting of muscle of Riolan, Homer's muscle, frontalis muscle, ocipitofrontalis muscle, temporoparietalis muscle, procerus muscle, nasalis muscle, depressor septi nasi muscle, orbicularis oculi muscle, corrugator supercilii muscle, depressor supercilii muscle, anterior auricular muscles, superior auricular muscle, posterior auricular muscle, orbicularis oris muscle, depressor anguli oris muscle, risorius, zygomaticus major muscle, zygomaticus minor muscle, levator labii superioris, levator labii superioris alaeque nasi muscle, depressor labii inferioris muscle, levator anguli oris, buccinator muscle, mentalis, and a combination thereof. In some embodiments, the ocular disease or disorder is ectropion or entropion. In some embodiments, the administering comprises administering the combination of a PGE2 compound and a myotoxin to an eye muscle of the subject. In some embodiments, the eye muscle is selected from the group consisting of frontalis muscle, ocipitofrontalis muscle, temporoparietalis muscle, procerus muscle, nasalis muscle, depressor septi nasi muscle, orbicularis oculi muscle, corrugator supercilii muscle, depressor supercilii muscle, anterior auricular muscles, superior auricular muscle, posterior auricular muscle, orbicularis oris muscle, depressor anguli oris muscle, risorius, zygomaticus major muscle, zygomaticus minor muscle, levator labii superioris, levator labii superioris alaeque nasi muscle, depressor labii inferioris muscle, levator anguli oris, buccinator muscle, mentalis, and a combination thereof. In some embodiments, the method further comprises, prior to, during, or after the administering, performing eyelid surgery on the subject. In some embodiments, the eyelid surgery is a lateral tarsal strip procedure. In some embodiments, the ocular disease or disorder is strabismus or nystagmus. In some embodiments, the administering comprises administering the combination of a PGE2 compound and a myotoxin to an extraocular muscle of the subject. In some embodiments, the extraocular muscle is selected from the group consisting of lateral rectus, medial rectus, superior rectus, inferior rectus, superior oblique, inferior oblique, and a combination thereof. In some embodiments, the strabismus is associated with any one of the following Apert syndrome, cerebral palsy, congenital rubella, hemangioma, Incontinentia Pigmenti, Noonan syndrome, Prader-Willi syndrome, retinopathy of prematurity, retinoblastoma, traumatic brain injury, trisomy-18, botulism, diabetes mellitus, Graves' disease, Guillain-Barre syndrome, injury to an eye, shellfish poisoning, stroke, and vision loss from an eye disease or injury. In some embodiments, the nystagmus is associated with any one of the following infantile nystagmus syndrome, intake of drugs or medications, excessive alcohol consumption, sedating medicine that impairs a function of the labyrinth, head injury, an inner ear disorder, stroke, thiamine or vitamin B12 deficiency, and Parkinson's disease. In some embodiments, the method further comprises, prior to, during, or after the administering, performing eye surgery on the subject. In some embodiments, the ocular disease or disorder is associated with impaired iris function. In some embodiments, the administering comprises administering the combination of a PGE2 compound and a myotoxin to an iris sphincter muscle or an iris dilator muscle of the subject. In some embodiments, the ocular disease or disorder is presbyopia. In some embodiments, the administering comprises administering the combination of a PGE2 compound and a myotoxin to a ciliary muscle of the subject. In some embodiments, the ocular disease or disorder is myopia. In some embodiments, the administering comprises administering the combination of a PGE2 compound and a myotoxin to a ciliary muscle, a muscle in the sclera, a muscle around the sclera, an intraocular muscle, or a combination thereof, of the subject.

Described herein is a method for treating a musculoskeletal disorder of a subject in need thereof, the method comprising administering a combination of a PGE2 compound and a myotoxin to the subject. In some embodiments, the musculoskeletal disorder comprises impaired hand function. In some embodiments, the administering comprises administering the combination of a PGE2 compound and a myotoxin to a hand muscle of the subject. In some embodiments, the hand muscle is selected from the group consisting of abductor pollicis brevis, flexor pollicis brevis, opponens pollicis, abductor digiti minimi, flexor digiti minimi brevis, opponens digiti minimi, a dorsal interossei muscle, a volar interossei muscle, a lumbrical muscle, palmaris brevis, adductor pollicis, abductor pollicis longus, extensor pollicis brevis, flexor pollicis longus, flexor carpi radialis, flexor digitorum profundus, flexor digitorum superficialis, flexor carpi ulnaris, extensor carpi radialis longus, extensor carpi radialis brevis, extensor indicis, extensor digitorum communis, extensor digiti minimi, extensor carpi ulnaris, and a combination thereof.

In some embodiments, the method further comprises, prior to, during, or after the administering, performing hand surgery on the subject. In some embodiments, the musculoskeletal disorder comprises impaired thumb function. In some embodiments, the administering comprises administering the combination of a PGE2 compound and a myotoxin to a hand muscle of the subject. In some embodiments, the hand muscle is selected from the group consisting of abductor pollicis brevis, opponens pollicis, flexor pollicis brevis, and a combination thereof. In some embodiments, the impaired thumb function is due to thenar atrophy.

In some embodiments, the method further comprises, prior to, during, or after the administering, performing hand surgery on the subject. In some embodiments, the hand surgery is carpal tunnel syndrome surgery. In some embodiments, the impaired thumb function is associated with cubital tunnel syndrome or thoracic outlet syndrome.

In some embodiments, the musculoskeletal disorder comprises impaired foot function. In some embodiments, the administering comprises administering the combination of a PGE2 compound and a myotoxin to a foot muscle of the subject. In some embodiments, the foot muscle is selected from the group consisting of flexor digitorum brevis, abductor hallucis, abductor digiti minimi, quadratus plantae, lumbricals, flexor digitorum longus, adductor hallucis, flexor hallucis brevis, flexor hallucis longus, flexor digiti minimi brevis, dorsal interossei, plantar interossei, flexor hallucis medialis, flexor hallucis brevis lateralis, adductor hallucis transverse, adductor hallucis oblique, and a combination thereof. In some embodiments, the impaired foot function is due to plantar fasciitis. In some embodiments, the impaired foot function is foot drop. In some embodiments, the administering comprises administering the combination of a PGE2 compound and a myotoxin to a foot muscle or a lower leg muscle of the subject. In some embodiments, the foot muscle or lower leg muscle is selected from the group consisting of anterior tibialis muscle, fibularis tertius, extensor digitorum longus, extensor hallucis longus, and a combination thereof.

In some embodiments, the method further comprises, prior to, during, or after the administering, performing surgery on the subject. In some embodiments, the foot drop is associated with any one of the following: compression of a peroneal nerve; a nerve root injury; muscular dystrophy; amyotrophic lateral sclerosis; multiple sclerosis; or stroke. In some embodiments, the musculoskeletal disorder is disuse-induced muscle atrophy. In some embodiments, the disuse-induced muscle atrophy is caused by a distal radius fracture. In some embodiments, the administering comprises administering the combination of a PGE2 compound and a myotoxin to a hand muscle or lower arm muscle of the subject. In some embodiments, the hand muscle or lower arm muscle is selected from the group consisting of flexor carpi radialis, flexor pollicis longus, flexor digitorum superficialis, flexor digitorum profundus, flexor carpi ulnaris, extensor carpi radialis brevis, extensor carpi radialis longus, extensor pollicis longus, extensor digitorum communis, extensor carpi ulnaris, and a combination thereof.

In some embodiments, the method further comprises prior to, during, or after the administering, performing surgery on the subject. In some embodiments, the surgery is wrist arthroscopy. In some embodiments, the disuse-induced muscle atrophy is caused by a hip fracture. In some embodiments, the administering comprises administering the combination of a PGE2 compounds and a myotoxin to a hip muscle of the subject. In some embodiments, the hip muscles is selected from the group consisting of iliacus, psoas major, gluteus maximus, gluteus medius, gluteus minimus, tensor fasciae latae, superior gemellus, inferior gemellus, obturator internus, obturator externus, quadratus femoris, piriformis, adductor magnus, adductor longus, adductor brevis, adductor minimus, pectineus, rectus femoris, vastus lateralis, vastus medialis, vastus intermedius, quadriceps femoris, Sartorius, biceps femoris, semitendinosus, semimembranosus, psoas minor, iliopsoas, gracilis, and a combination thereof.

In some embodiments, the method further comprises, prior to, during, or after the administering, performing surgery on the subject. In some embodiments, the surgery is joint arthroplasty. In some embodiments, the disuse-induced muscle atrophy is caused by a rotator cuff injury. In some embodiments, the administering comprises administering the combination of a PGE2 compound and a myotoxin to a rotator cuff muscle of the subject. In some embodiments, the rotator cuff muscle is selected from the group consisting of supraspinatus, infraspinatus, subscapularis, teres minor, and a combination thereof.

Described herein is a method for treating gastroesophageal reflux disease (GERD) in a subject in need thereof, the method comprising administering a combination of a PGE2 compound and a myotoxin to the subject. In some embodiments, the administering comprises administering the combination of a PGE2 compounds and a myotoxin to a crural diaphragm of the subject.

Described herein is a method for treating obstructive sleep apnea in a subject in need thereof, the method comprising administering a combination of a PGE2 compound and a myotoxin to the subject. In some embodiments, the administering comprises administering the combination of a PGE2 compound and a myotoxin to an upper airway muscle of the subject. In some embodiments, the upper airway muscle is selected from the group consisting of genioglossus, tensor palatine, a geniohyoid muscle, and a combination thereof.

Described herein is a method for treating oculopharyngeal muscular dystrophy in a subject in need thereof, the method comprising administering a combination of a PGE2 compound and a myotoxin to the subject. In some embodiments, the administering comprises administering the combination of a PGE2 compound and a myotoxin to a muscle of the upper eyelid or a muscle of the throat.

Described herein is a method for treating diabetic neuropathy in a subject in need thereof, the method comprising administering a combination of a PGE2 compound and a myotoxin to the subject. In some embodiments, the administering comprises administering the combination of a PGE2 compound and a myotoxin to a small muscle of a foot, a lower leg muscle, or an intrinsic muscle of a foot. In some embodiments, the PGE2 compound is selected from the group consisting of PGE2, a PGE2 prodrug, a PGE2 receptor agonist, a compound that attenuates PGE2 catabolism, a compound that neutralizes PGE2 inhibition, a derivative thereof, an analog thereof, and a combination thereof. In some embodiments, the PGE2 derivative comprises 16,16-dimethyl prostaglandin E2. In some embodiments, the compound that attenuates PGE2 catabolism comprises a compound, neutralizing peptide, or neutralizing antibody that inactivates or blocks 15-hydroxyprostaglandin dehydrogenase (15-PGDH) or inactivates or blocks a prostaglandin transporter (PGT or SLCO2A1). In some embodiments, the PGE2 compound is PGE2. In some embodiments, the myotoxin is selected from the group consisting of an anesthetic, a divalent cation, snake venom, lizard venom, bee venom, and a combination thereof. In some embodiments, the anesthetic is selected from the group consisting of an amino-amide anesthetic, an amino-ester anesthetic, and a combination thereof. In some embodiments, the amino-amide anesthetic is selected from the group consisting of bupivacaine, levobupivacaine, articaine, ropivacaine, butanilicaine, carticaine, dibucaine, etidocaine, lidocaine, mepivacaine, prilocaine, trimecaine, and a combination thereof. In some embodiments, the amino-ester anesthetic is selected from the group consisting of an aminobenzoic acid ester anesthetic, a benzoic acid ester anesthetic, and a combination thereof. In some embodiments, the aminobenzoic acid ester anesthetic is selected from the group consisting of benzocaine, butacaine, butamben, chloroprocaine, dimethocaine, lucaine, meprylcaine, metabutethamine, metabutoxycaine, nitracaine, orthocaine, propoxycaine, procaine, proxymetacaine, risocaine, tetracaine, and a combination thereof. In some embodiments, the benzoic acid ester anesthetic is selected from the group consisting of amylocaine, cocaine, cyclomethycaine, α-eucaine, β-eucaine, hexylcaine, isobucaine, piperocaine, and a combination thereof. In some embodiments, the snake venom or the lizard venom is selected from the group consisting of notexin, cardiotoxin, bungarotoxin, and a combination thereof. In some embodiments, the divalent cation is selected from the group consisting of $Ba^{2+}$, $Sr^{2+}$, $Mg^{2+}$, $Ca^{2+}$, $Mn^{2+}$, $Ni^{2+}$, $Co^{2+}$, a salt thereof, and a combination thereof. In some embodiments, the PGE2 compound is PGE2 and/or 16,16-dimethyl prostaglandin E2 and the myotoxin is bupivacaine. In some embodiments, the PGE2 compound and the myotoxin are administered concomitantly. In some embodiments, the PGE2 compound and the myotoxin are administered sequentially. In some embodiments, the PGE2 compound is administered before the myotoxin. In some embodiments, the PGE2 compound is administered after the myotoxin. In some embodiments, administering the PGE2 compound, the myotoxin, or both, comprises topical, oral, intraperitoneal, intramuscular, intra-arterial, intradermal, subcutaneous, intravenous, or intracardiac administration. In some embodiments, administering comprises intramuscular administration. In some embodiments, wherein a dose of the PGE2 compound, the myotoxin, or both, is determined based upon a target muscle size. In some embodiments, the target muscle is an abductor pollicis brevis muscle and the dose of the PGE2 compound, the myotoxin, or both, is about 10 µg.

In some embodiments, the method further comprises subjecting a target muscle to mechanical injury. In some embodiments, the mechanical injury comprises cutting, burning, freezing, needle puncture, exercise, a surgical procedure, traumatic injury, or a combination thereof. In some embodiments, the method further comprises administering a population of isolated muscle cells to the subject. In some embodiments, the population of isolated muscle cells is autologous to the subject. In some embodiments, the population of isolated muscle cells is allogeneic to the subject. In some embodiments, the population of isolated muscle cells is purified. In some embodiments, the population of isolated muscle cells is cultured with the PGE2 compound, the myotoxin, or both, prior to being administered to the subject. In some embodiments, culturing the population of isolated muscle cells with the PGE2 compound, the myotoxin, or both, comprises acute, intermittent, or continuous exposure of the population of isolated muscle cells to the PGE2 compound, the myotoxin, or both. In some embodiments, administering the population of isolated muscle cells comprises injecting or transplanting the cells into the subject. In some embodiments, administration of the population of isolated muscle cells and administration of the PGE2 compound and the myotoxin are performed concomitantly. In some embodiments, administration of the population of isolated muscle cells and administration of the PGE2 compound and the myotoxin are performed sequentially.

Other objects, features, and advantages of the present invention will be apparent to one of skill in the art from the following detailed description and figures.

BRIEF DESCRIPTION OF THE DRAWINGS

FIG. 2A: PGE2 levels after young tibialis anterior (TA) muscle injury (notexin, NTX); controls are uninjured contralateral TAs assayed by ELISA; (n=4 mice per time point). FIG. 2B: Expression of PGE2 synthesizing enzymes (Ptges2 and Ptges) by MuSCs after notexin injury by RT-qPCR, (n=3 mice per time point). FIG. 2C: Increase in MuSC numbers after 24 hr treatment with vehicle (−) or PGE2 (10 ng/ml), and subsequent culture on hydrogel until day 7 (acute treatment); (n=12 mice in 4 independent experiments). FIG. 2D: Increase in MuSC numbers after transient 24 hr treatment with vehicle (−) or PGE2 (10 ng/ml) in absence or presence of EP4 antagonist (ONO-AE3-208, 1 µM); (n=9 mice assayed in 3 independent experiments). FIGS. 2E-2G: Proliferation of EP4 null MuSCs. $EP4^{f/f}$ (null) MuSCs were transduced with a lentiviral vector encoding GFP/luciferase and treated with lentiviral vector encoding Cre (+Cre) or without (−Cre; empty vector) to delete EP4 alleles. Subsequently MuSCs were treated with vehicle (−) or PGE2 (10 ng/ml) for 24 hr and cultured on hydrogels for three days. FIG. 2E: Scheme depicting EP4-null MuSC analysis. FIG. 2F: EP4 null MuSC numbers; (n=6 mice in 2 independent experiments). FIG. 2G: Representative image. Bar=40 m; GFP, green; mCherry, red. FIG. 2H: MuSC numbers after culture in charcoal stripped medium treated with vehicle (−) or PGE2 (10 ng/ml) every two days for 7 days on hydrogels; (n=3 mice with 3 technical replicates). *P<0.05, P<0.001, *P<0.0005****P<0.0001. ANOVA test with Bonferroni correction for multiple comparisons (FIGS. 2A, 2B, 2D, and 2F); paired t-test (FIG. 2C); Mann-Whitney test (FIG. 2H). Means+s.e.m. n.s., non-significant.

FIGS. 3A-3J show an aberrant response of aged MuSCs to PGE2. FIG. 3A: PGE2 levels after aged TA injury (notexin, NTX); controls are uninjured contralateral TAs assayed by ELISA; (n=4 mice per time point). FIG. 3B: PGE2 levels in TAs of uninjured young (n=7 mice) and aged (n=5 mice) mice assayed by ELISA. FIG. 3C: Scheme showing PGE2 catabolism via degrading enzyme 15-PGDH to its inactive PGE metabolite, 13,14-dihydro-15-keto PGE2 (PGEM). FIG. 3D: Levels of PGEM quantified by mass spectrometry; (n=4 mice per age group). FIG. 3E: Expression of PGE2 degrading enzyme 15-PGDH (Hpgd); (n=3 mice with 2 technical replicates). FIG. 3F: Increase in aged MuSC numbers after acute 24 hr treatment with vehicle (−), PGE2 (10 ng/ml) or the 15-PGDH inhibitor, SW033291 (1 µM; SW) assayed at day 7; (n=15 mice in 5 independent experiments). FIG. 3G: Aged MuSC numbers after culture in charcoal stripped medium treated with vehicle (−) or PGE2 (10 ng/ml) every two days for 7 days on hydrogels; (n=3 mice with 3 technical replicates). FIG. 3H: Scheme depicting PGE2 effects on MuSCs. PGE2 acts through the EP4 receptor/cAMP (cyclic AMP) signaling pathway to promote proliferation. In aged MuSCs, following intracellular transport by PGT (prostaglandin transporter), PGE2 catabolism is mediated by 15-PGDH to the inactive form, PGEM. FIG. 3I: Trajectories from a clone of aged MuSCs tracked by time-lapse microscopy for 48 h in a microwell for control (left) and after acute treatment with PGE2 (right). The trajectory of the original cell and each of its newborn progeny are represented by a different color. FIG. 3J: Change in aged MuSC live cell counts (numbers) in clones tracked by time-lapse microscopy for control (left, n=32 clones) and after acute treatment with PGE2 (right, n=45 clones). The proportion of live cells in each generation (G1-G6) at all timepoints is shown as cell number normalized to a starting population of 100 single MuSCs. The percent increase in live cell count was 4.0% (control) and 5.4% (PGE2-treated) (top panels). Change in aged MuSC dead cell counts (numbers) in clones tracked by time-lapse microscopy for control (left) and after acute treatment with PGE2 (right). The proportion of dead cells in each generation (G1-G6) at all timepoints is shown as cell number normalized to a starting population of 100 single MuSCs. The percent increase in dead cell count was 1.0% (control) and 0.1% (PGE2-treated)

Figure 3A:
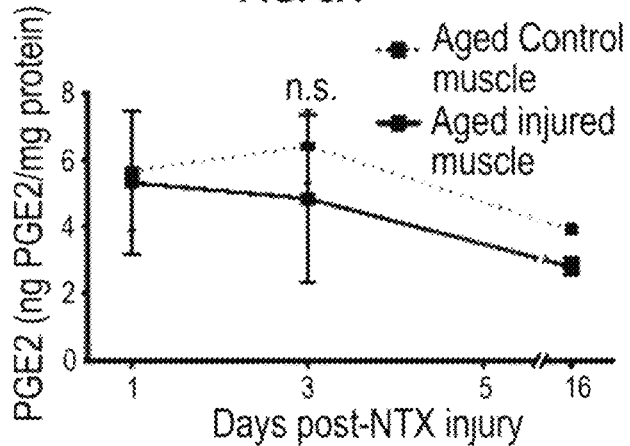

(bottom panels). *P<0.05, P<0.001, *P<0.0005. ANOVA test with Bonferroni correction for multiple comparisons (FIGS. 3A and 3F); Mann-Whitney test (FIGS. 3B, 3D, 3E, and 3G). Means±s.e.m. n.s., non-significant.

Figure 4A:
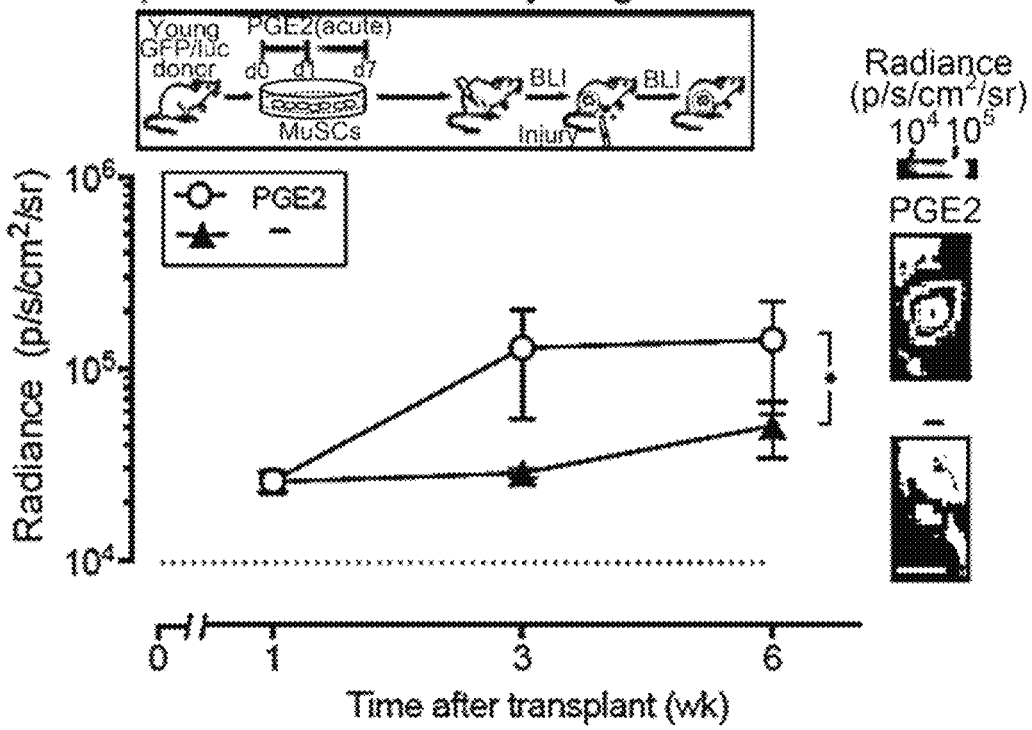
Figure 4B:
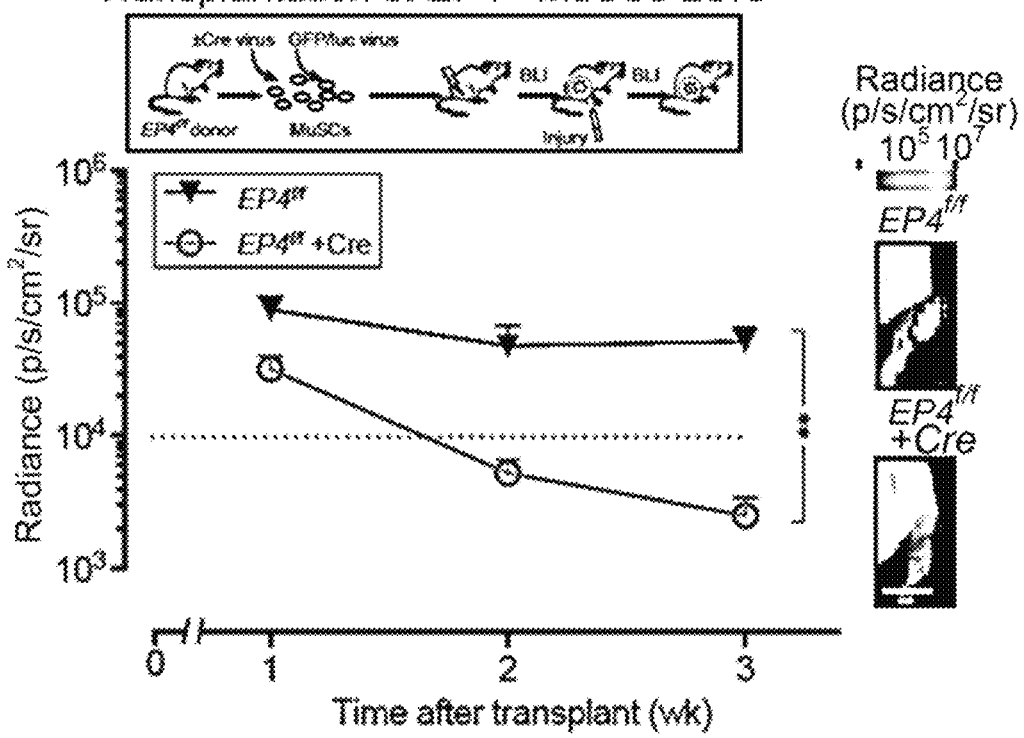

FIGS. 4A-4D show that acute PGE2 treatment promotes MuSC engraftment and regeneration in vivo. FIG. 4A: Engraftment of cultured GFP/luc-labeled young MuSCs (250 cells) isolated from transgenic mice after acute treatment with vehicle (−) or PGE2 as described in FIG. 2C. Transplant scheme (top). Non-invasive bioluminescence imaging (BLI) signal measured as radiance for each TA; (n=5 mice per condition) (bottom). FIG. 4B: Engraftment of GFP/luc-labeled EP4$^{f/f}$ MuSCs (1,000 cells) treated with Cre (+Cre) or without (−Cre; empty vector) in culture to delete EP4 alleles. EP4$^{f/f}$ MuSCs were transduced with a lentiviral vector encoding GFP/luciferase for BLI. Transplant scheme (top). BLI signals post-transplant (n=5 mice per condition (bottom). FIG. 4C: Engraftment of freshly sorted GFP/luc-labeled young MuSCs (250 cells) coinjected with vehicle (−) or dmPGE2. Transplant scheme (top). BLI signals post-transplant; (n=4 and n=5 mice for vehicle and dmPGE2 treated, respectively). FIG. 4D: Engraftment of GFP/luc-labeled aged MuSCs (250 cells) coinjected with vehicle (−) or dmPGE2; (n=3 mice per condition) (bottom). Aged MuSCs were transduced with a lentiviral vector encoding GFP/luciferase for BLI. Transplant scheme (top). BLI signals post-transplant expressed as average radiance (p s$^{-1}$ cm$^{-2}$ sr$^{-1}$). Representative BLI images for each condition. Bar=5 mm (FIGS. 4A-4D). Data are representative of two independent experiments. *P<0.05, P<0.001 and *P<0.0005. ANOVA test for group comparisons and significant difference for endpoints by Fisher's test. Means+s.e.m.

Figure 5A:
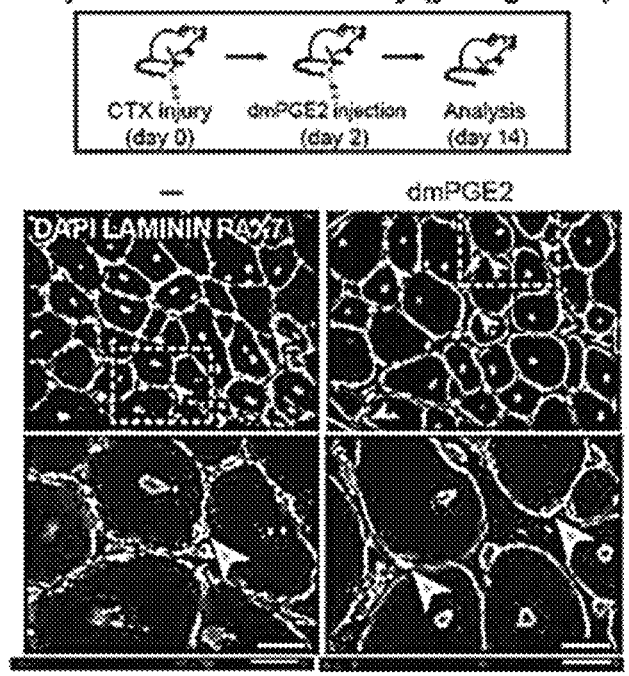
Figure 5B:
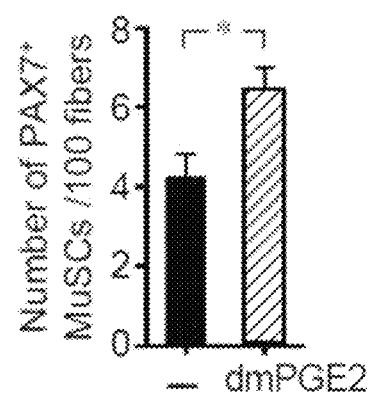
Figure 5C:
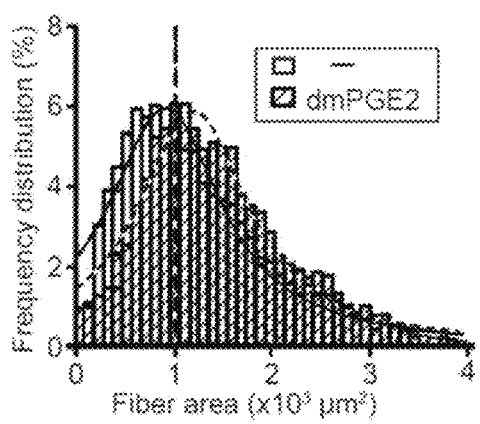
Figure 5D:
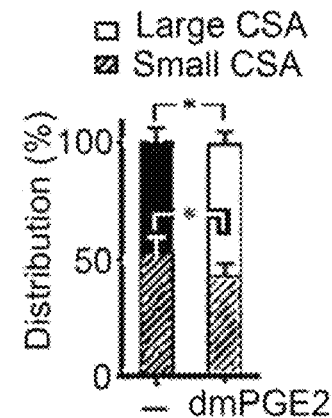
Figure 5E:
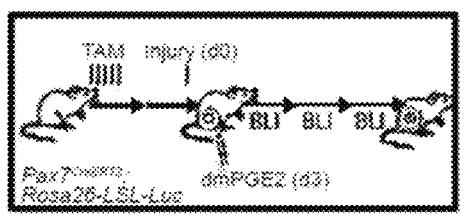
Figure 5F:
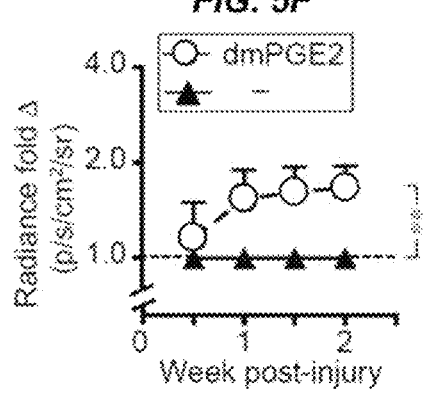
Figure 5G:
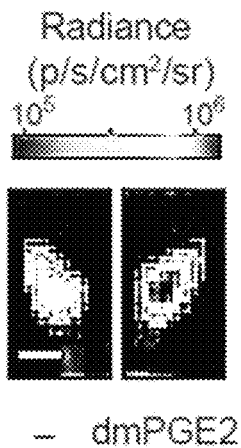
Figure 5H:
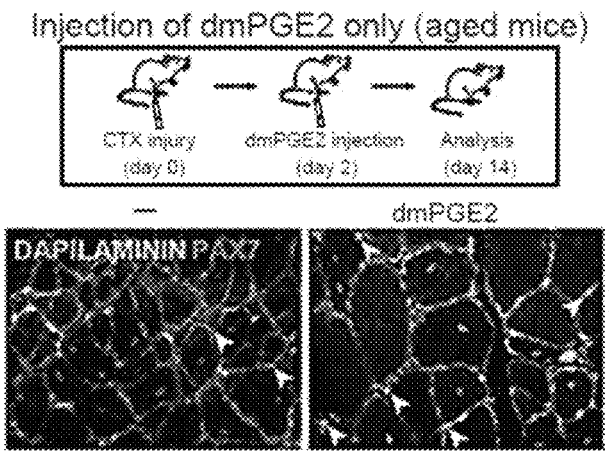
Figure 5I:
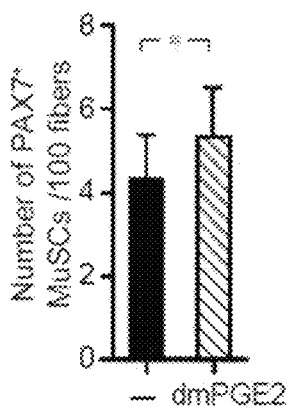
Figure 5J:
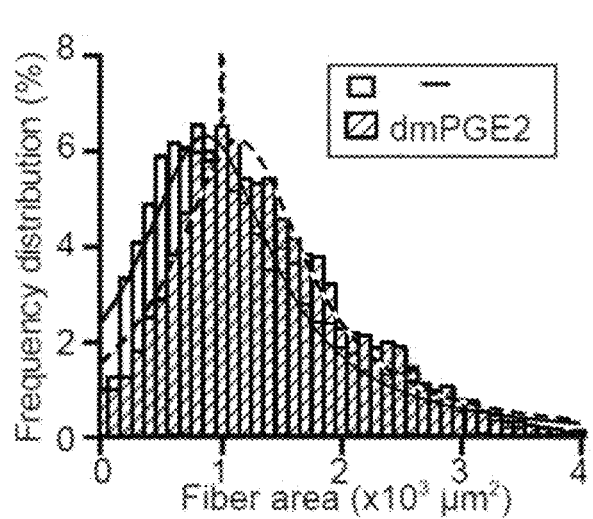
Figure 5K:
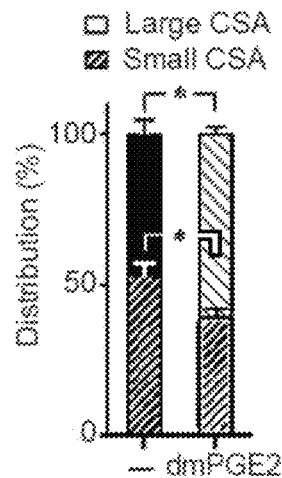
Figure 5L:
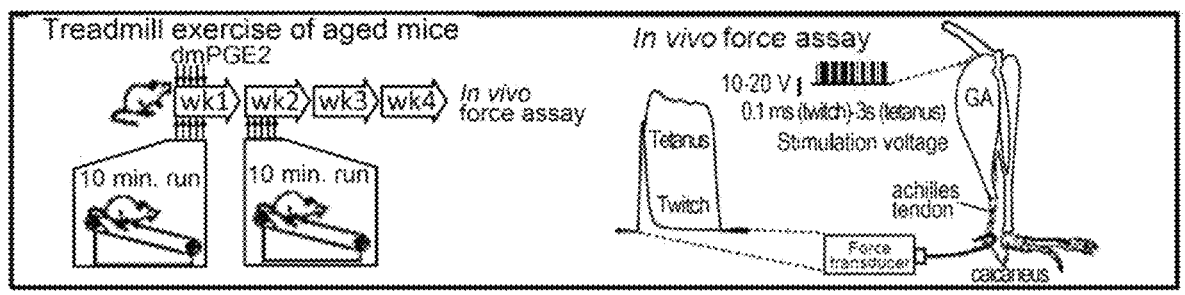
Figure 5M:
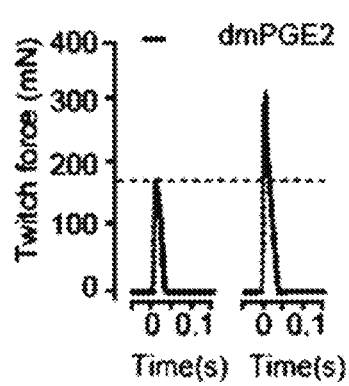
Figure 5N:
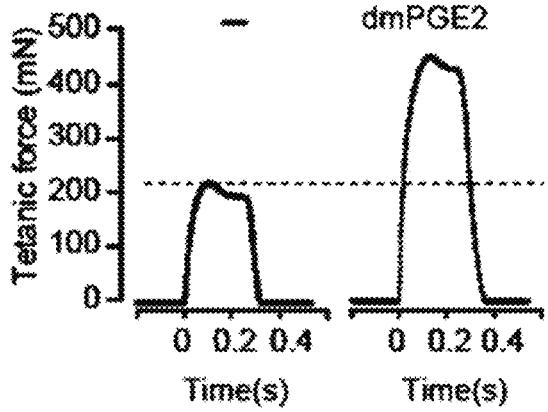
Figure 5O:
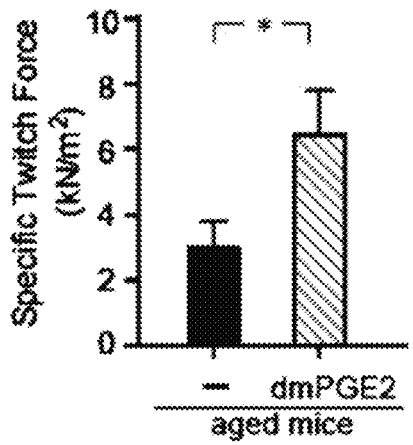
Figure 5P:
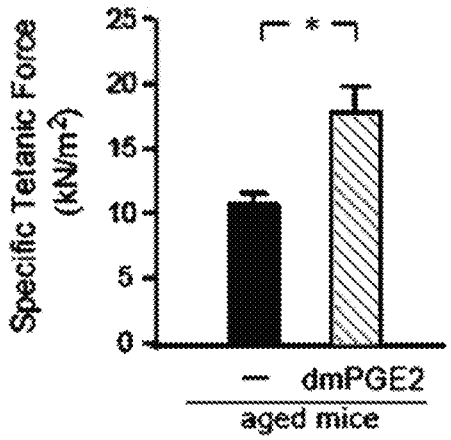
Figure 5Q:
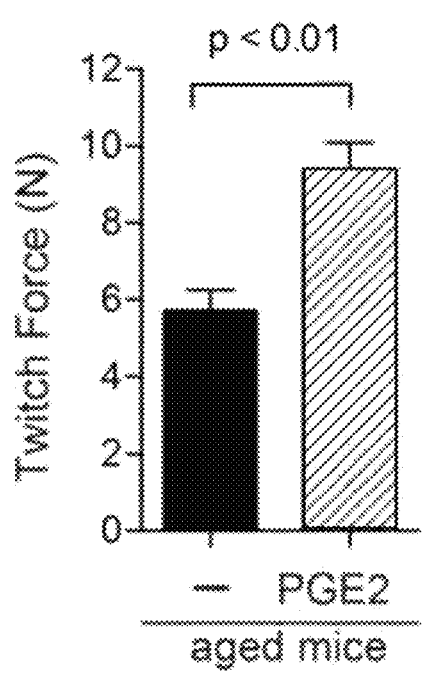
Figure 5R:
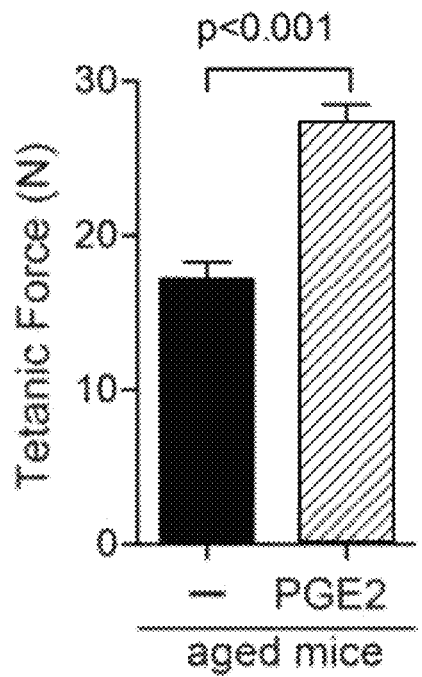

FIGS. 5A-5R show that intramuscular injection of PGE2 alone promotes MuSC expansion, improves regeneration, and increases force. Young: (FIGS. 5A-5D) TA muscles of young mice were injected with vehicle (−) or dmPGE2 48 hr post-cardiotoxin (CTX) injury; (n=3 mice per condition). FIG. 5A: Scheme of experimental procedure (top). Representative TA cross-section (bottom) with nuclei (DAPI; blue), LAMININ (green) and PAX7 (red) staining 14 days after cardiotoxin injury. Arrowheads indicate PAX7$^+$ MuSCs. Bar=40 μm. FIG. 5B: Increase in endogenous MuSCs by immunofluorescence of PAX7 expressing satellite cells per 100 fibers in cross-sections of TAs from young mice. FIG. 5C: Myofiber cross-sectional areas (CSA) in vehicle (−, open white bar) and dmPGE2 treated (filled blue bar) young TAs quantified using the Baxter Algorithms for Myofiber Analysis. FIG. 5D: Distribution of small (<1,000 μm$^2$ CSA) and large (>1,000 μm$^2$ CSA) myofibers. (FIGS. 5E-5G) Increase in endogenous MuSCs assayed by Pax7-luciferase. Pax7$^{CreERT2}$;Rosa26-LSL-Luc mice were treated intraperitoneally with tamoxifen (TAM), TAs subjected to cardiotoxin (CTX) injury, injected with vehicle (−) or dmPGE2 3 days later and monitored by BLI; (n=3 mice per condition). FIG. 5E: Scheme of experimental procedure. FIG. 5F: BLI (n=3 mice per condition). FIG. 5G: Representative BLI image. Bar=5 mm. Aged: (FIGS. 5H-5K) TAs of aged mice were treated in vivo with vehicle (−) or dmPGE2 treatment 48 hr post-cardiotoxin (CTX) injury; (n=3 mice per condition). FIG. 5H: Scheme of experimental procedure (top). Representative TA cross-section (bottom) with nuclei (DAPI; blue), LAMININ (green) and PAX7 (red) staining 14 days after cardiotoxin injury. Arrowheads indicate PAX7$^+$ muscle stem cells. Bar=40 μm. FIG. 5I: Increase in endogenous MuSCs as in FIG. 5B for aged mice. FIG. 5J: Myofiber cross-sectional area (CSA) as in FIG. 5C for aged TAs. FIG. 5K: Distribution of CSA as in FIG. 5D for aged TAs. (FIGS. 5L-5P) Increase in strength in aged mice measured in vivo as muscle contractile force after downhill treadmill run. Mice were subject to a 200 downhill treadmill run for 2 consecutive weeks and force was assayed at week 5. During the first week, medial and lateral gastrocnemius (GA) of aged mice were injected either with vehicle (−) or dmPGE2. n=10 or 8 biological replicates for vehicle (−) treated or dmPGE2 treated, respectively, with 5 technical replicates each. FIG. 5L: Experimental scheme. Representative twitch force (FIG. 5M) and tetanic force (FIG. 5N). Specific muscle twitch forces (FIG. 5O) and specific muscle tetanic force (FIG. 5P) were calculated by normalizing force to physiological cross sectional areas (PCSA). Paired t-test (FIGS. 5B, 5D, 5I and 5K); ANOVA test for group comparison and significant difference for the endpoint by Fisher's test (FIG. 5F); Mann-Whitney test (FIGS. 5O and 5P). *P<0.05, P<0.001 and **P<0.0001. Means+s.e.m. FIG. 5Q: Muscle twitch forces in aged mice that were administered PGE2 or vehicle only. FIG. 5R: Muscle tetanic force in mice that were administered PGE2 or vehicle only.

Figure 6A:
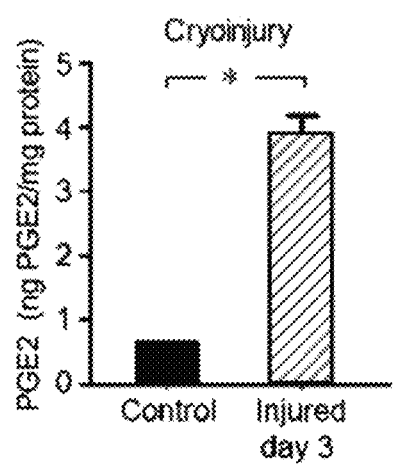
Figure 6B:
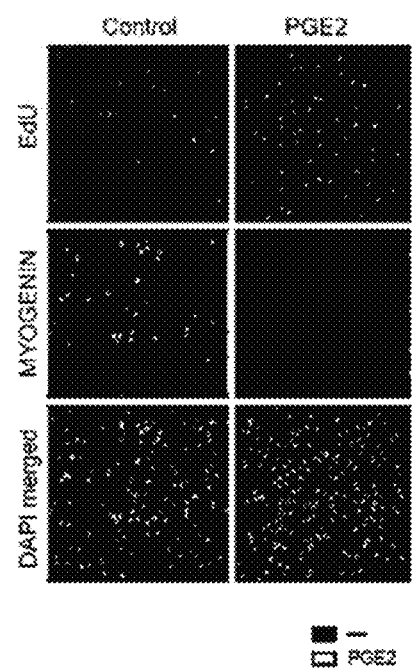
Figure 6C:
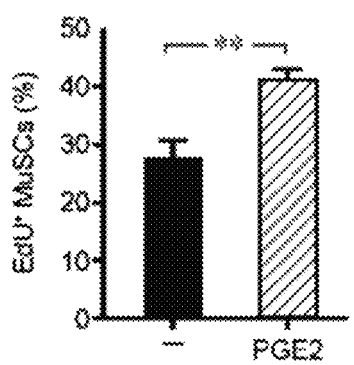
Figure 6D:
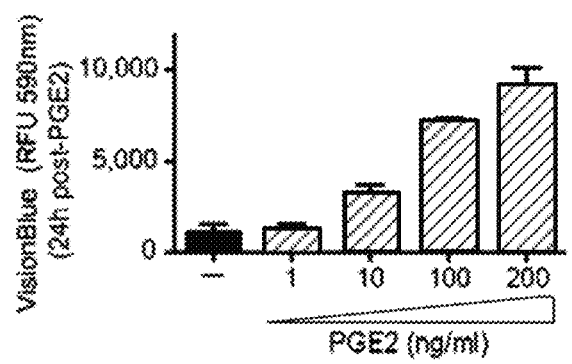
Figure 6E:
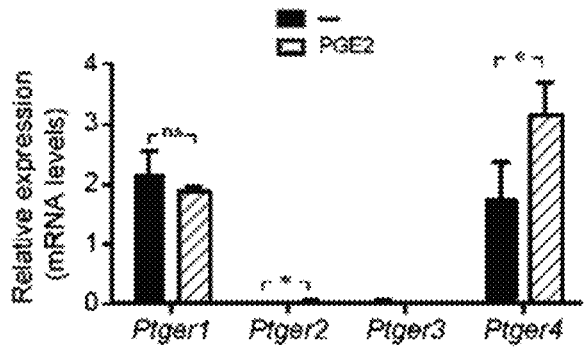
Figure 6F:
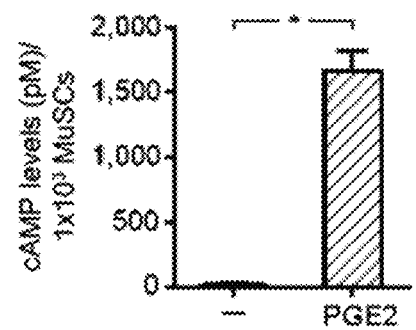

FIGS. 6A-6K show that PGE2 promotes MuSC expansion. FIG. 6A: PGE2 levels day 3 after cryoinjury for tibialis anterior (TA) hindlimb muscles of young mice compared to contralateral uninjured controls as assayed by ELISA; (n=4 mice per time point per condition). FIG. 6B: Representative image of dividing muscle stem cells (MuSCs) labelled with EdU (red) during 1 hr after treatment with PGE2 (10 ng/ml) for 24 h (d0 to d1) or vehicle (−), and stained for MYOGENIN (green). Bar represents 40 μm. FIG. 6C: Percentage of dividing MuSCs labeled with EDU as in (b); (n=6 mice with 3 technical replicates in two independent experiments). FIG. 6D: Increase in proliferation measured by the metabolic viability assay VisionBlue after treatment with vehicle (−) or indicated doses of PGE2 (1-200 ng/ml); (n=6 mice with 3 technical replicates in two independent experiments). FIG. 6E: Expression of prostaglandin receptors (Ptger 1-4) by MuSCs after 24 hr treatment with vehicle (−) or PGE2; (n=3 mice with 2 technical replicates). FIG. 6F: Increase in cAMP levels in MuSCs after 1 hr PGE2 treatment relative to untreated controls (−); (n=6 mice with 3 technical replicates assayed in 2 independent experiments). FIGS. 6G-6H: Expression of Pax7 (FIG. 6G) and Myogenin (FIG. 6H) by MuSCs after 24 hr treatment with vehicle (−) or PGE2; (n=3 mice with 2 technical replicates). FIGS. 6I-6J: EP4$^{f/f}$ MuSCs were transduced with a lentiviral vector encoding GFP/luciferase and treated with lentiviral vector encoding Cre (+Cre) or without (−Cre; empty vector) to delete EP4 alleles. Bar graphs show percentage of +Cre MuSCs (FIG. 6I) and GFP/Luc$^+$ MuSCs (FIG. 6J). FIG. 6K: Representative image of MuSCs in hydrogel culture after 7 days in myoblast medium containing charcoal stripped fetal bovine supplemented with vehicle (−) or PGE2 (10 ng/ml) every two days. Bar represents 40 μm. *P<0.05, P<0.001, *P<0.0005. Paired t-test (FIGS. 6A, 6E, 6G, and 6H); Mann-Whitney test (FIG. 6C). Means+s.e.m. n.s., non-significant.

Figure 7A:
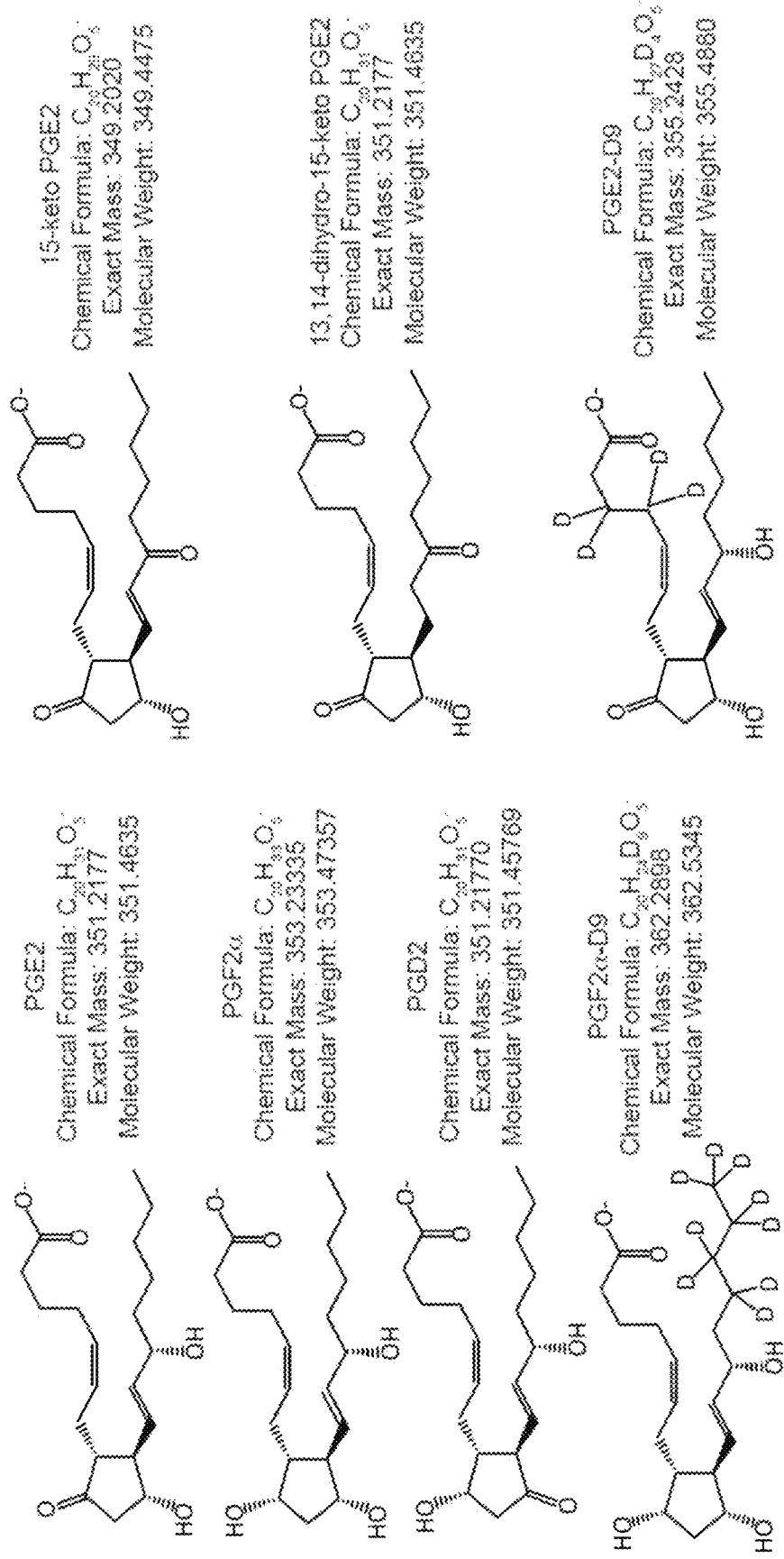
Figure 7B:
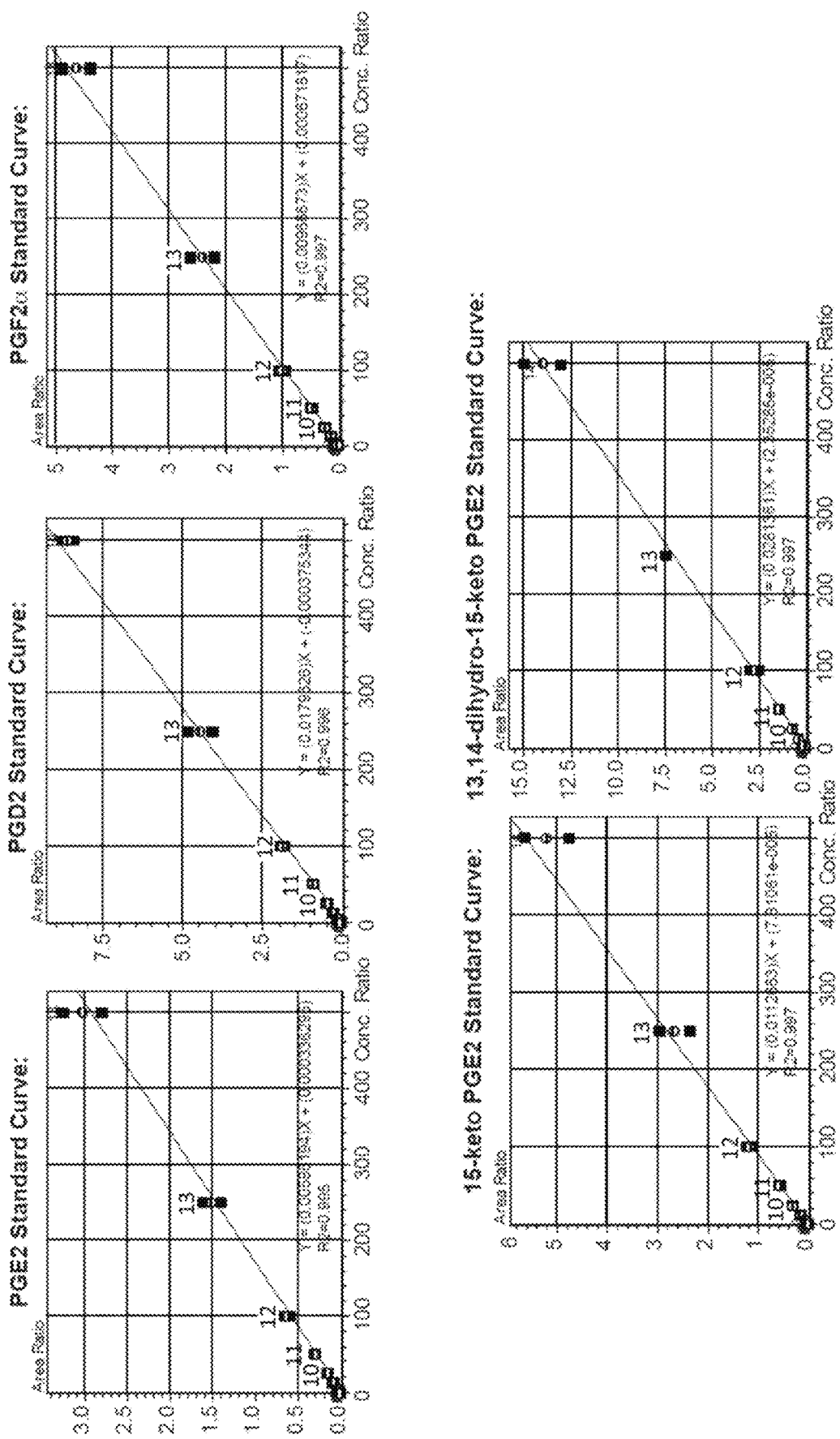
Figure 7C:
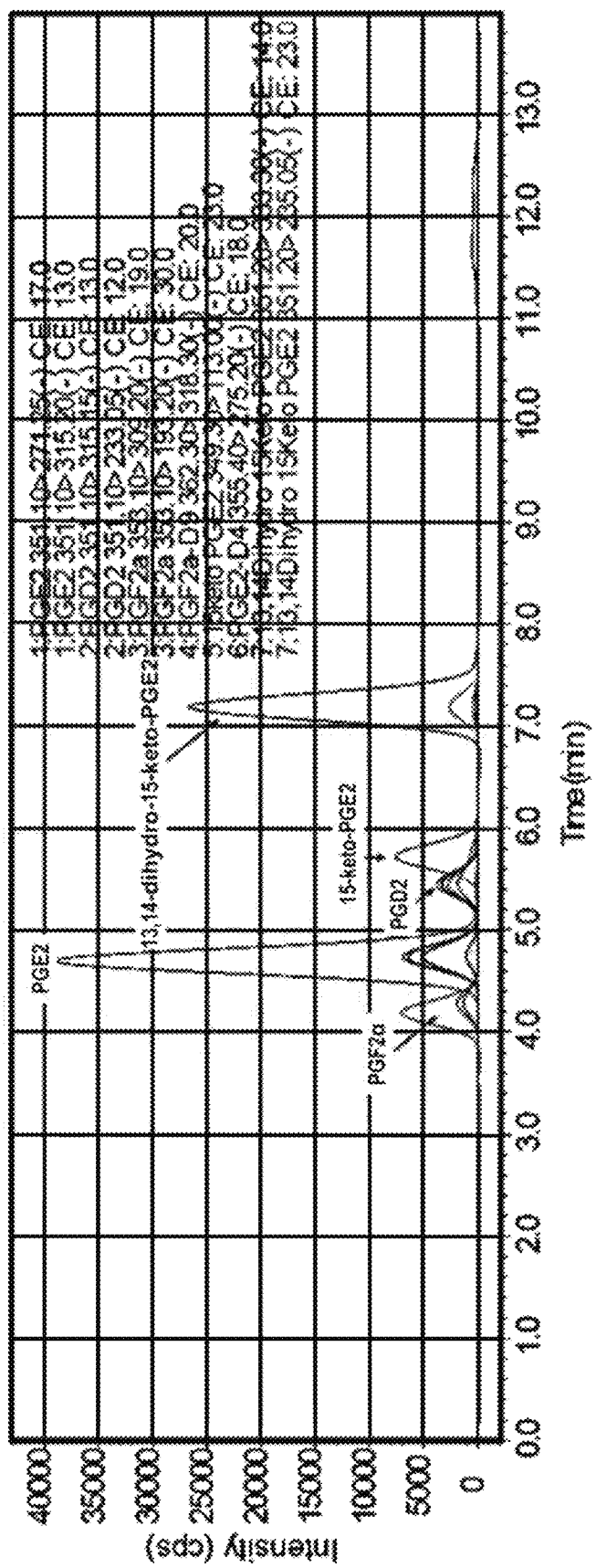

FIGS. 7A-7C show mass spectrometry analysis of young and aged muscle to detect prostaglandins and PGE2 metabolites. FIG. 7A: Chemical structures, chemical formula, exact mass and molecular weight of analyzed prostaglandins (PGE2, PGF2α and PGD2) and PGE2 metabolites (15-keto PGE2 and 13,14-dihydro-15-keto PGE2). The internal standards PGF2α-D9 and PGE2-D9 were added to all composite standards. FIG. 7B: Calibration lines for liquid chromatography-electrospray ionization-tandem mass spectrometry (LC-ESI-MS/MS) analysis were prepared by diluting stock solutions to final concentrations of 0.1 ng/ml to 500 ng/ml.

Standard curve equations and correlation coefficients are shown for each standard. FIG. 7C: Representative chromatogram. The separate peaks show excellent chromatographic resolution of the analyzed prostaglandins and their metabolites. cps, counts per second.

Figure 8A:
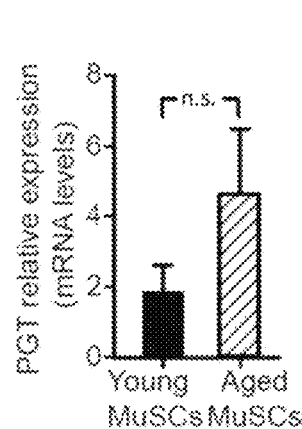
Figure 8B:
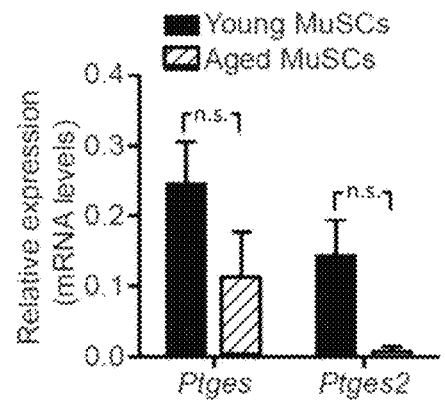
Figure 8C:
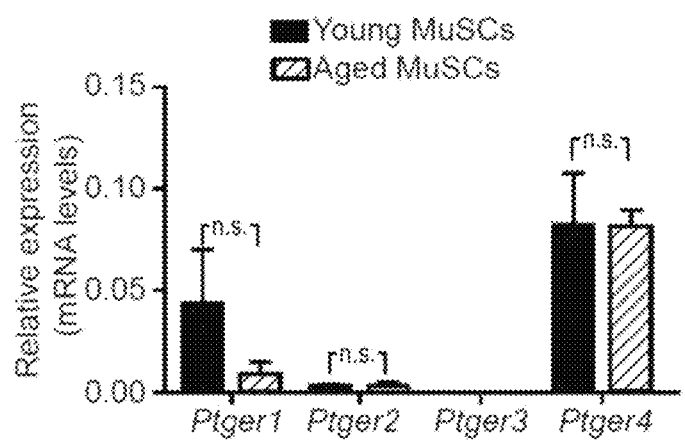
Figure 8D:
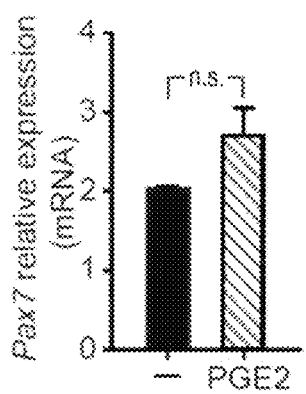
Figure 8E:
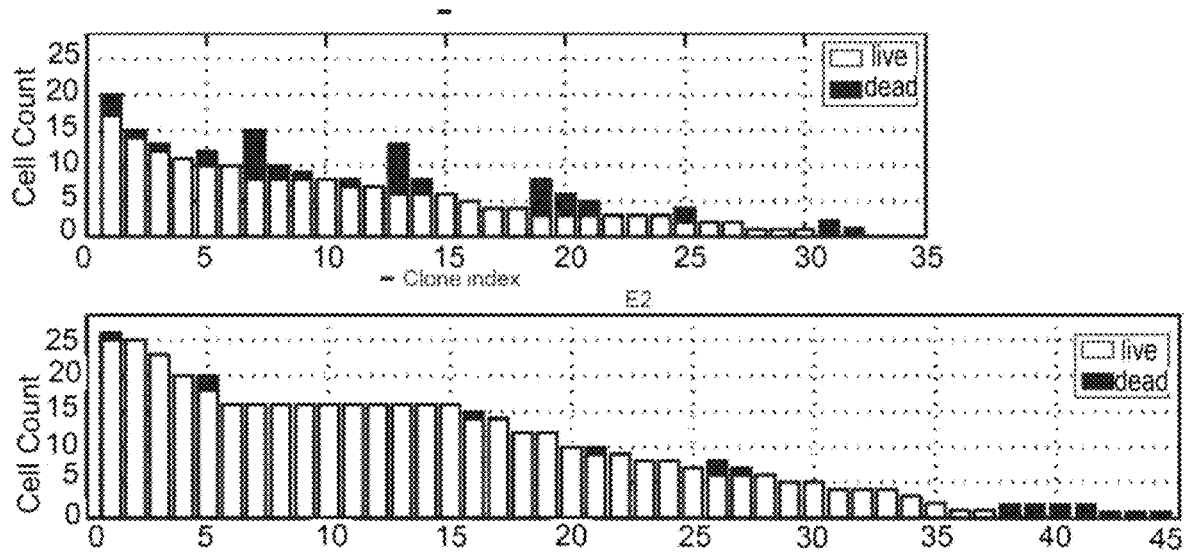
Figure 8F:
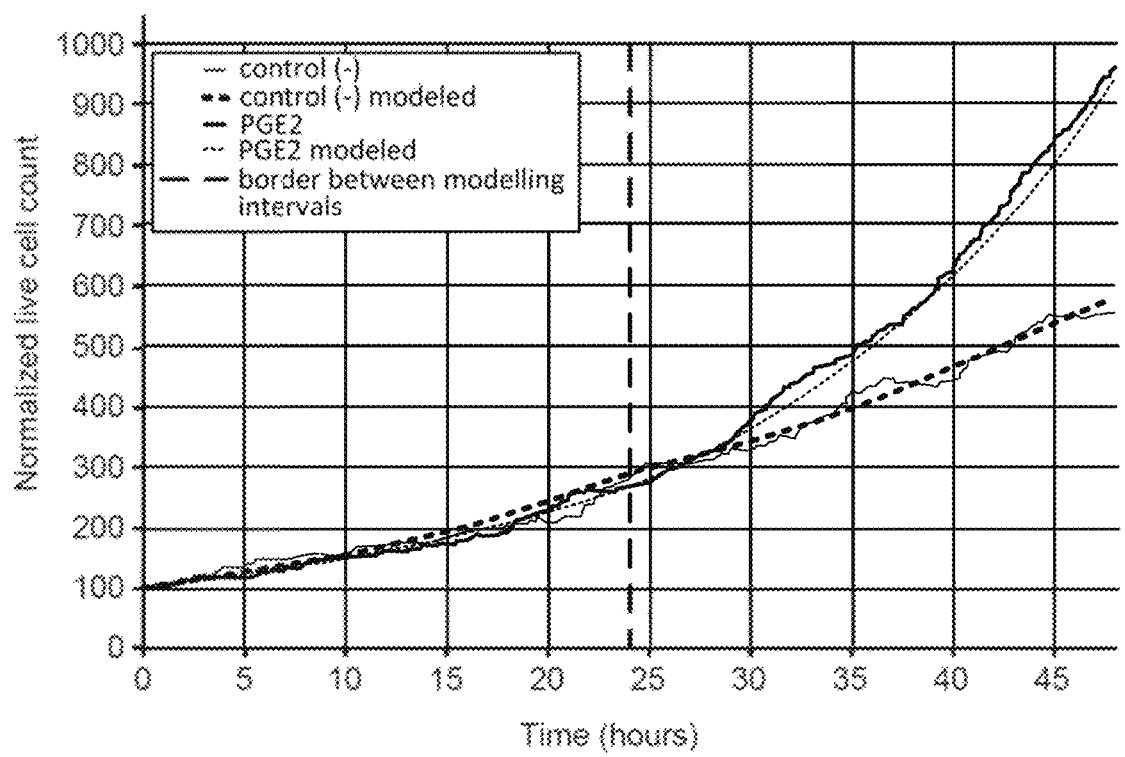
Figure 8G:
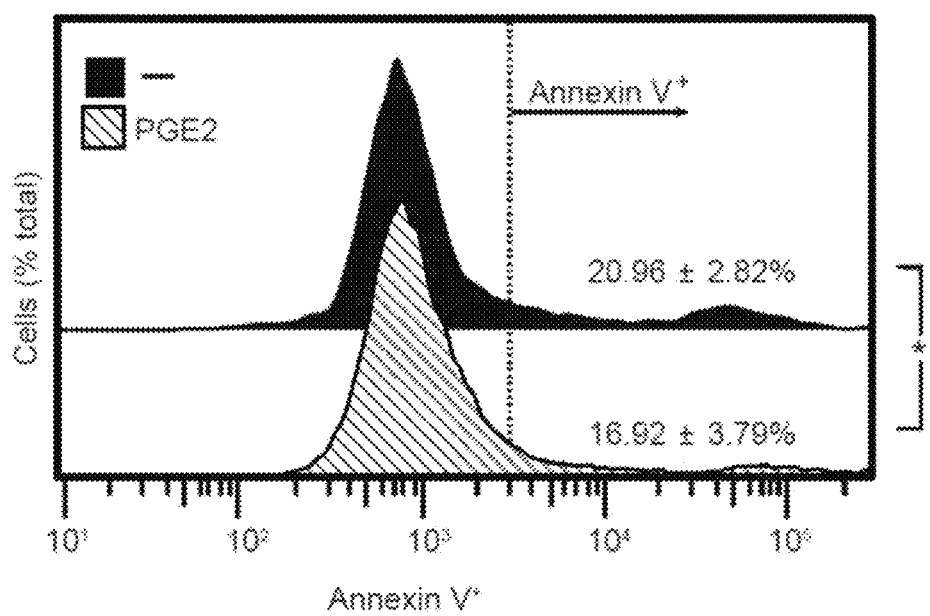

FIGS. 8A-8G show that aged MuSCs increase proliferation and cell survival in response to PGE2 treatment. FIGS. 8A-8C: mRNA levels measured by qRT-PCR were normalized to Gapdh for young and aged MuSCs; (n=3 mice with 2 technical replicates). FIG. 8A: Prostaglandin transporter (PGT) encoded by the Slco2a1 gene. FIG. 8B: PGE2 synthesizing enzymes, Ptges and Ptges2. FIG. 8C: EP1-4 receptors encoded by the genes Ptger1-4. FIG. 8D: Pax7 mRNA levels in MuSCs after 24 hr treatment with vehicle (−) or PGE2 treatment; (n=3 mice with 2 technical replicates). FIG. 8E: Single aged MuSC clones tracked by time-lapse microscopy after acute treatment with vehicle (−; top) or PGE2 (bottom). For each clone the resulting number of live (open bar) and dead (black bar) cells after 48 h timelapse tracking is shown. FIG. 8F: Proliferation curve of tracked live aged MuSCs assessed by time-lapse microscopy for vehicle (−) or transient PGE2 treatment during 48 h. FIG. 8G: Flow cytometry analysis of apoptotic Annexin $V^+$ on aged MuSCs after 24 hr treatment with vehicle (−) or PGE2 and analyzed 7 days later after growth on hydrogels; (n=9 mice in 3 independent experiments). Mann-Whitney test (FIGS. 8A-8D) and paired t-test (FIG. 8G) at α=0.05. Means+s.e.m. n.s., non-significant.

Figure 9A:
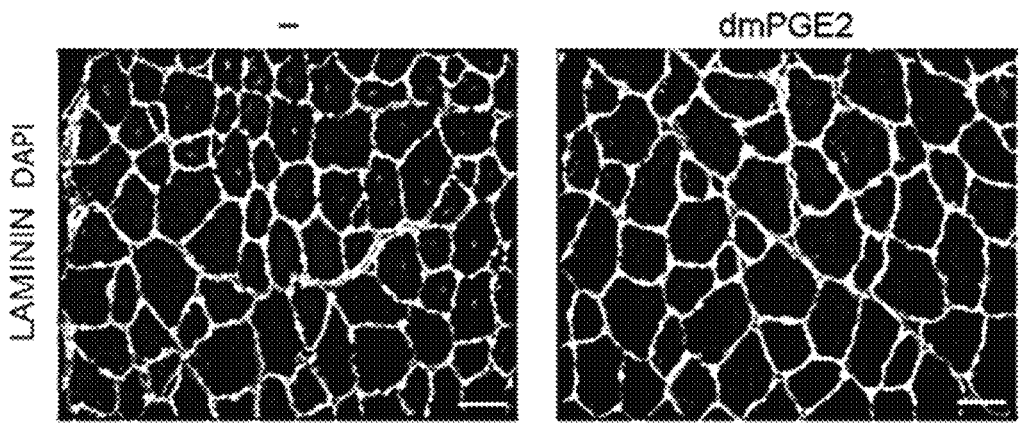
Figure 9B:
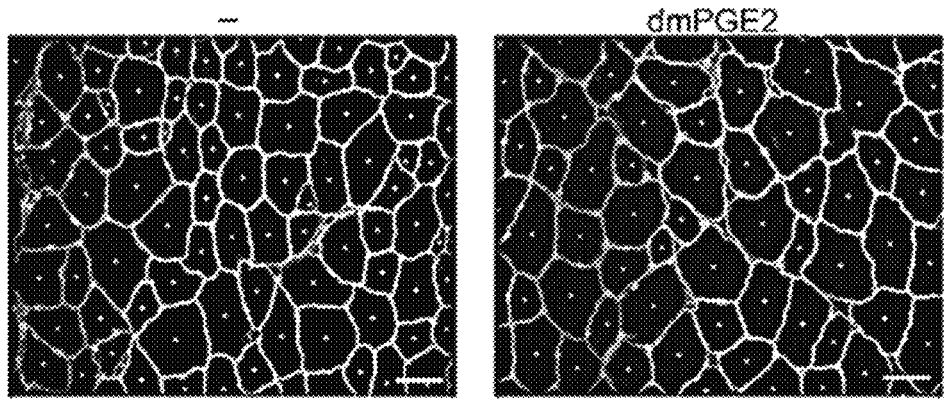

FIGS. 9A-9B show Baxter Algorithms for Myofiber Analysis of muscle cross-sectional area. FIG. 9A: Representative cross-sectional images of tibialis anterior myofibers of young mice treated in vivo with vehicle (−) or PGE2 48 hr post-cardiotoxin (CTX) injury. Images show staining with LAMININ, green and DAPI, blue. FIG. 9B: The corresponding segmentation images from FIG. 9A analyzed by the Baxter Algorithms for Myofiber Analysis to determine the cross sectional area (CSA) of transverse sections of myofibers (bottom) at day 14 post-injury. Bar represents 40 μm.

Figure 10A:
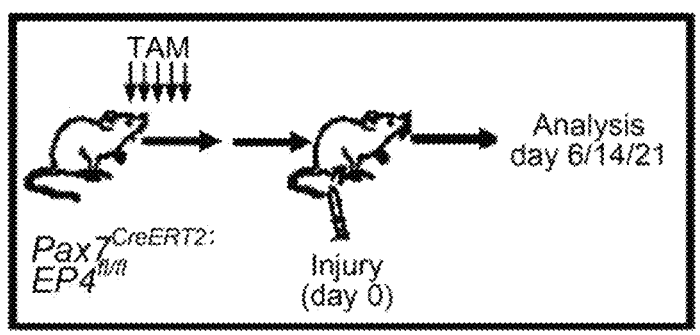
Figure 10B:
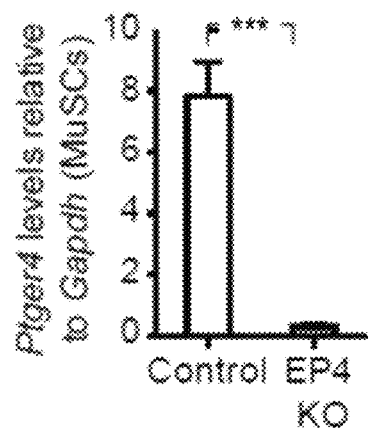
Figure 10C:
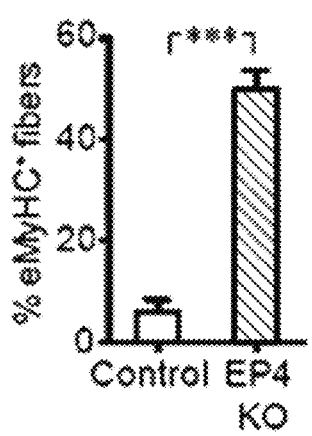
Figure 10D:
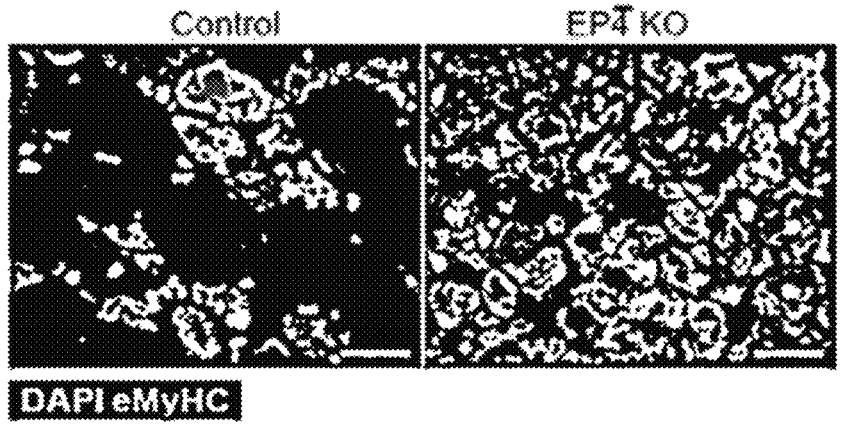
Figure 10E:
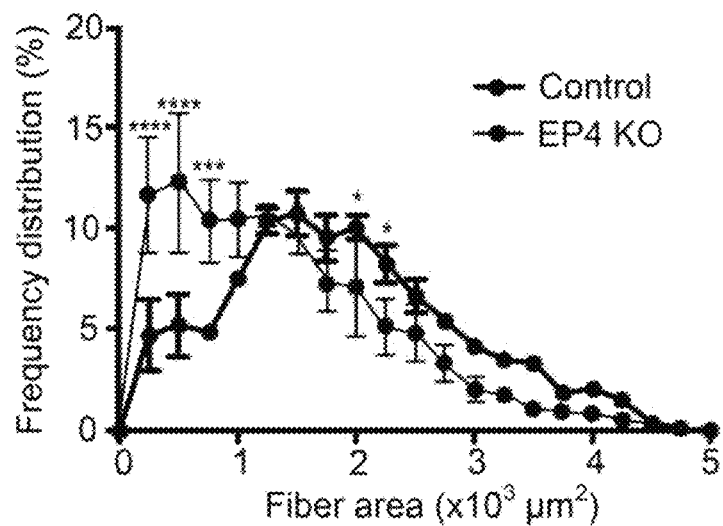
Figure 10F:
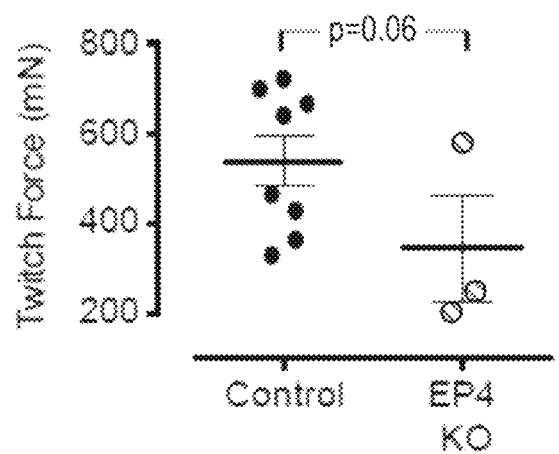

FIGS. 10A-10G show that deletion of PGE2 receptor EP4 in MuSCs decreases regeneration and force of skeletal muscle after injury. Tibialis anteriors (TAs) of Pax7-specific EP4 conditional knockout mice (Pax7$^{CreERT2}$;EP4$^{fl/fl}$) treated with tamoxifen were assayed at 6 (FIGS. 10C-10D), 21 (FIGS. 10B and 10E), and 14 (FIGS. 10F and 10G) days post-notexin injury; (n=3 mice per condition). FIG. 10A: Experimental scheme. FIG. 10B: Expression of Ptger4 (EP4 receptor) in sorted MuSCs ($\alpha^{7+}$ CD34$^+$ lin$^-$) from control or EP4 KO mice post-injury. FIG. 10C: Representative TA cross-section. DAPI, blue; Embryonic Myosin Heavy Chain (eMyHC), red. Bar=40 μm. FIG. 10D: Percentage of eMyHC$^+$ fibers. FIG. 10E: Myofiber cross-sectional areas (CSA) in control and Pax7-specific EP4 knockout TAs. FIG. 10F: Muscle twitch forces and (FIG. 10G) muscle tetanic force at day 14 post-notexin injury. Mann-Whitney test (FIGS. 10B, 10C, 10F, and 10G); ANOVA test for group comparison and significant difference for each bin by Fisher's test (FIG. 10E). *P<0.05, *P<0.0005, and **P<0.0001 Means+s.e.m.

Figure 11A:
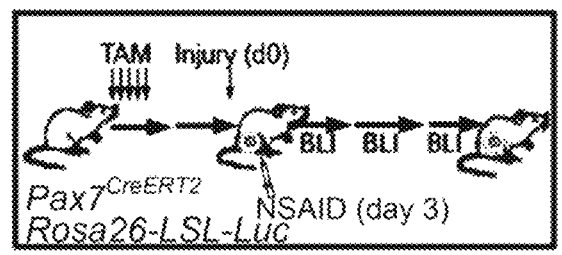
Figure 11B:
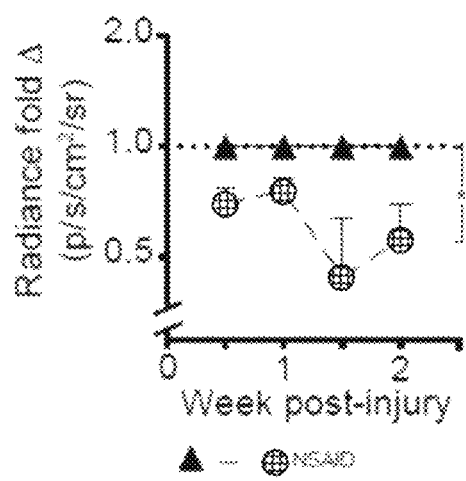
Figure 11C:
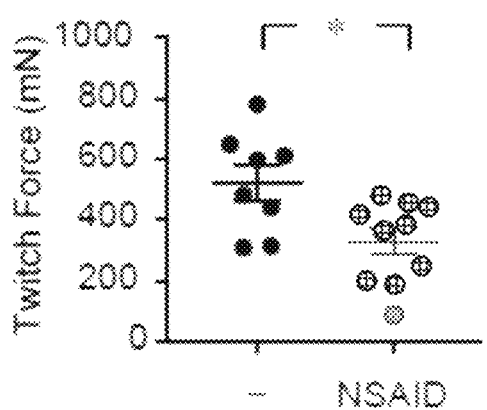

FIGS. 11A-11C show that blockage of endogenous PGE2 signaling in muscle at an early time point of regeneration reduces regeneration and force. Endogenous MuSCs assayed in Pax7$^{CreERT2}$;Rosa26-LSL-Luc mice treated with tamoxifen (TAM) by non-invasive bioluminescence imaging (BLI) after injection with vehicle (−) or NSAID (Indomethacin) post-cardiotoxin injury into the Tibialis anterior (TA); (n=3 mice per condition). FIG. 11A: Experimental scheme. FIG. 11B: BLI; (n=3 mice per condition). FIG. 11C: Muscle twitch forces at day 14 post-notexin injury (n=8 for vehicle-treated and 10 for NSAID-treated). ANOVA test for group comparison and significant difference for the endpoint by Fisher's test (FIG. 11B). Mann-Whitney test (FIG. 11C). *P<0.05, P<0.001, *P<0.0005, and ****P<0.0001. Means+s.e.m.

Figure 12A:
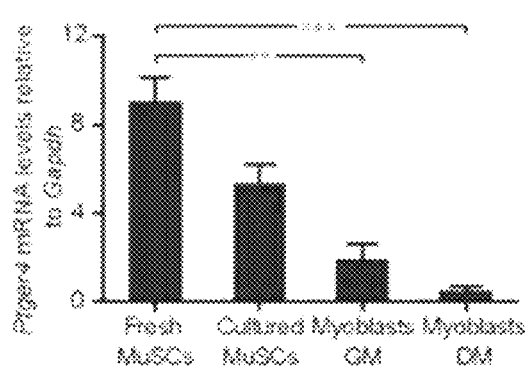
Figure 12B:
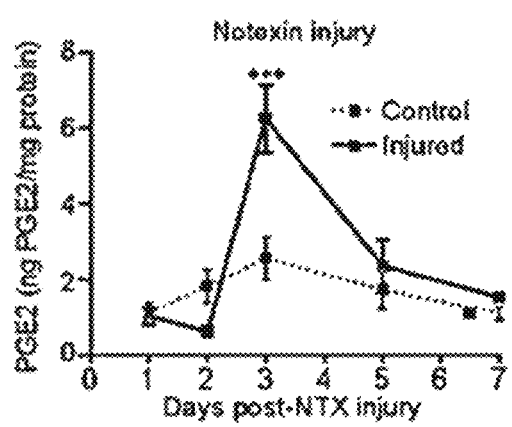
Figure 12C:
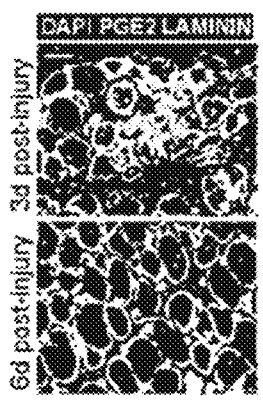
Figure 12D:
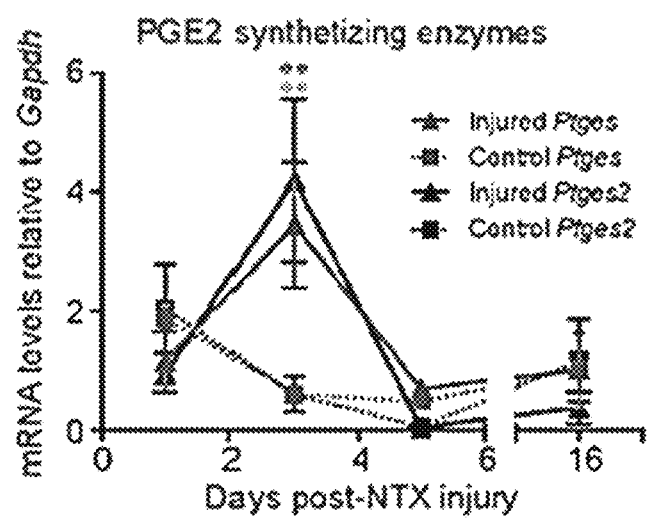
Figure 12E:
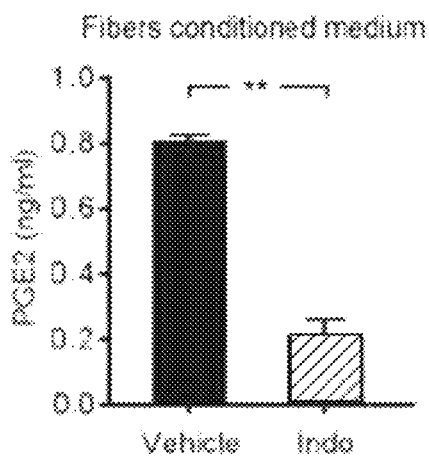
Figure 12F:
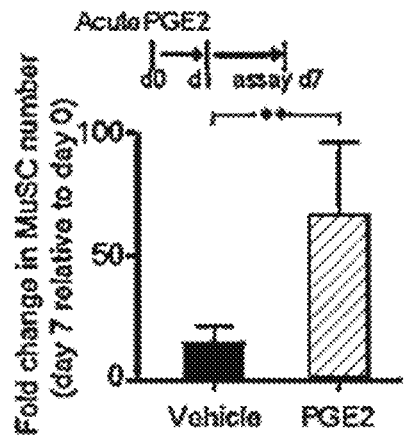
Figure 12G:
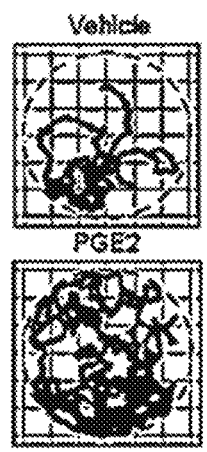
Figure 12H:
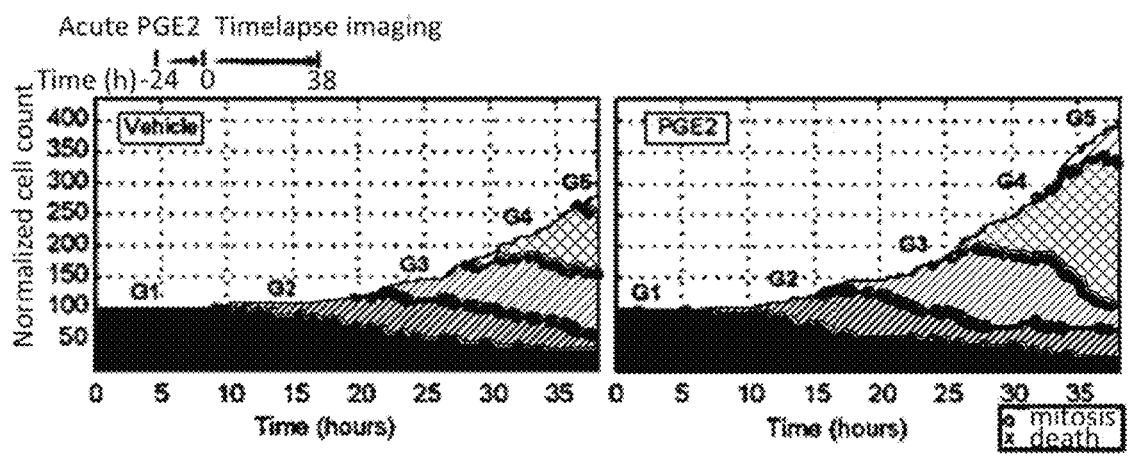
Figure 12I:
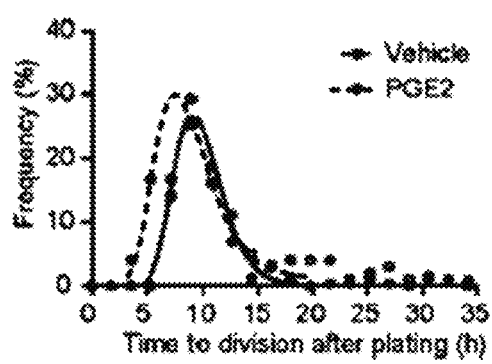
Figure 12J:
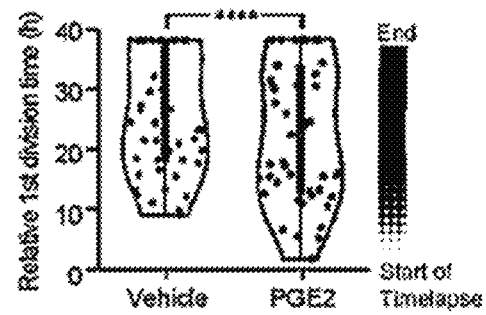
Figure 12K:
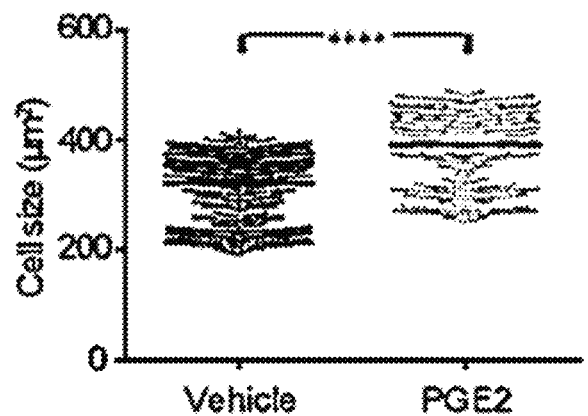

FIGS. 12A-12K show that a transient increase in PGE2 in damaged muscle tissues accelerates MuSC proliferation. FIG. 12A: Expression of Ptger4 in freshly isolated muscle stem cells (MuSCs) from uninjured mouse hindlimbs (Fresh MuSCs), MuSCs cultured for two days on hydrogels (Cultured MuSCs), primary myoblasts cultured in growth medium (Myoblasts GM) and differentiating primary myoblasts cultured in differentiation medium for 24 hr (Myoblasts DM) (n=3 biological replicates per condition). FIG. 12B: PGE2 levels assayed by ELISA after tibialis anterior (TA) muscle injury with notexin; (n=4 mice per condition measured). Control refers to the contralateral uninjured leg. FIG. 12C: Representative TA cross-sections of 3 and 6 days post-notexin injury. DAPI, blue; LAMININ, white; PGE2, green. Bar=40 μm. FIG. 12D: Expression of prostaglandin synthetizing enzymes, Ptges and Ptges2 after TA muscle injury (notexin) (n=3 mice with 2 technical replicates). Control refers to the contralateral uninjured leg. FIG. 12E: PGE2 levels of conditioned medium from isolated fibers in the presence or absence of indomethacin (Indo) assayed by ELISA; (n=3 mice per condition). FIG. 12F: MuSC numbers after 24 hr treatment with vehicle or PGE2 (10 ng/ml), and subsequent culture on hydrogel until day 7; (n=12 mice in 4 independent experiments). FIG. 12G: Trajectories of a MuSC clone treated with vehicle (top) or PGE2 (bottom) by time-lapse microscopy for 38 hr. FIG. 12H: Change in MuSC cell counts (numbers) in clones tracked by time-lapse microscopy after vehicle (left, n=40 clones) and PGE2 treatment (right, n=44 clones). FIG. 12I: Plot of time to division after plating for each MuSC clone treated with vehicle or PGE2. Clones showing a 38 hr time to division refers to clones that never divided during the recorded time-lapse. The lines represent the non-linear regression curve from Gaussian lognormal fit with R$^2$=0.9 (control) and 0.97 (PGE2). FIG. 12J: Violin plot of time to division post-plating in MuSC clones treated with vehicle or PGE2. FIG. 12K: Cell sizes of tracked MuSCs treated with vehicle or PGE2. *P<0.05, P<0.001, *P<0.0005****P<0.0001. Mann-Whitney test (FIG. 12A, 12E, 12J, 12K); ANOVA test with Bonferroni correction for multiple comparisons (FIG. 12B, 12D); Paired t-test (FIG. 12F). Means+s.e.m.

Figure 13A:
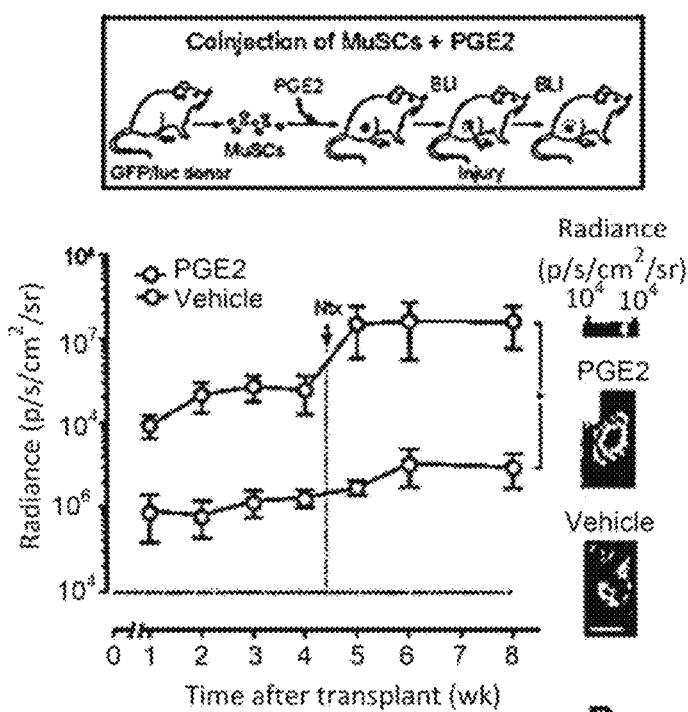
Figure 13C:
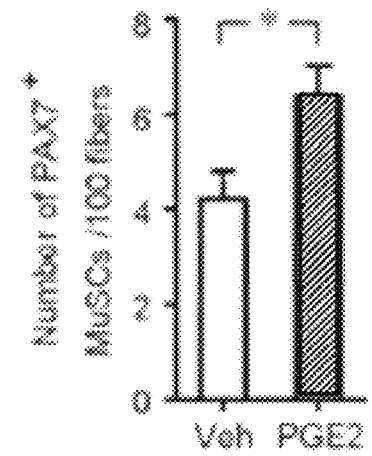
Figure 13B:
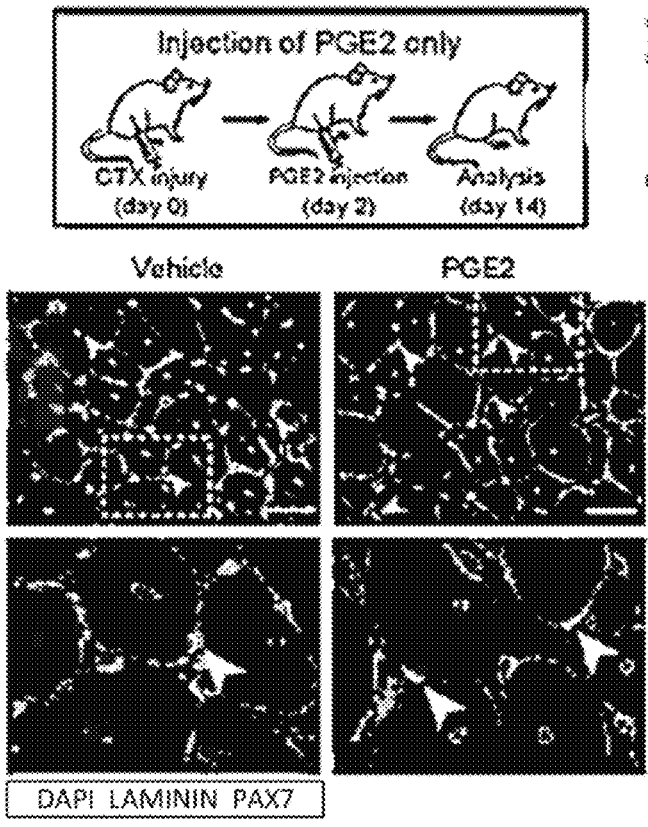
Figure 13D:
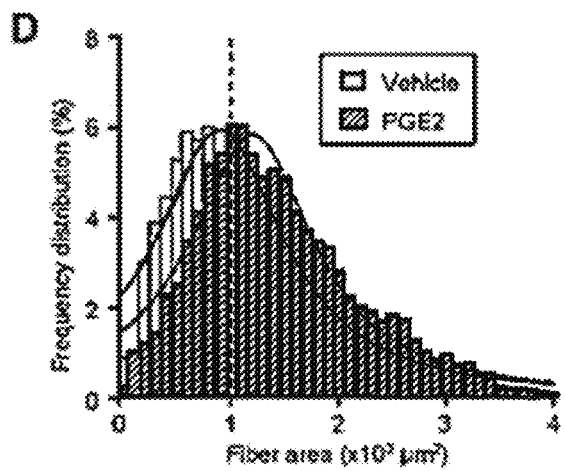
Figure 13E:
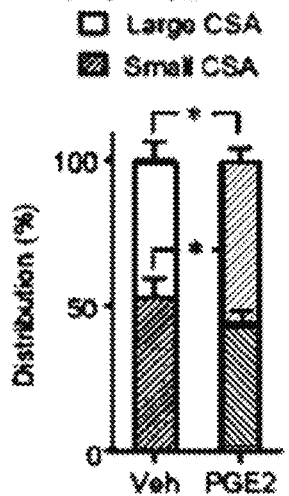
Figure 13F:
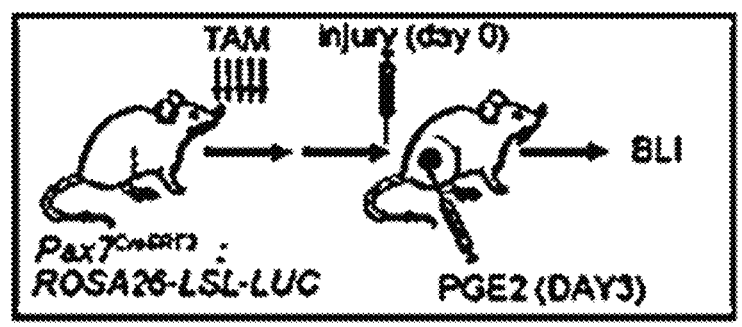
Figure 13G:
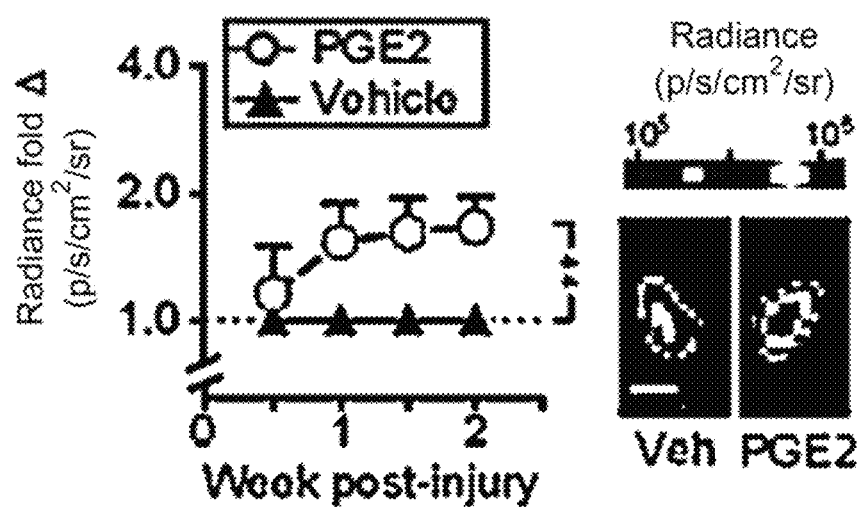

FIGS. 13A-13G show that PGE2 treatment augments muscle regeneration. FIG. 13A: Engraftment of freshly sorted GFP/luc-labeled MuSCs (250 cells) coinjected with vehicle or PGE2. Transplant scheme (top). Bioluminescence imaging (BLI) signals post-transplant expressed as average radiance (p s$^{-1}$ cm$^{-2}$ sr$^{-1}$); (n=4 and n=5 mice for vehicle and PGE2 treated respectively, bottom). At 4 weeks post-transplant, recipient mice were reinjured with Notexin. FIGS. 13B-13E: TAs of mice were injected with vehicle or PGE2 post-cardiotoxin (CTX) injury; (n=3 mice per condition, vehicle-treated is the contralateral leg). FIG. 13B: Experimental scheme (top). Representative TA cross-section (bottom). DAPI, blue; LAMININ, green; PAX7, red. Arrowheads indicate PAX7$^+$ MuSCs. Bar=40 μm. FIG. 13C: Quantification of PAX7$^+$ satellite cells per 100 fibers. FIG. 13D: Representative myofiber cross-sectional areas (CSA) in vehicle (open white bar) and PGE2 treated (filled blue bar) TAs. FIG. 13E Distribution of small (<1,000 μm$^2$ CSA) and large (>1,000 μm$^2$ CSA) myofibers. FIGS. 13F and 13G:

Endogenous MuSCs assayed in Pax7$^{CreERT2}$;Rosa26-LSL-Luc mice treated with tamoxifen (TAM) by BLI; (n=3 mice per condition). FIG. 13F: Experimental scheme. FIG. 13G BLI (left); (n=3 mice per condition). Representative BLI image (right). Bar=5 mm. *P<0.05, P<0.001. ANOVA test for group comparisons and significant difference for endpoint by Fisher's test (FIG. 13A, 13G); Paired t-test (FIG. 13C, 13E**). Means+s.e.m.

Figure 14A:
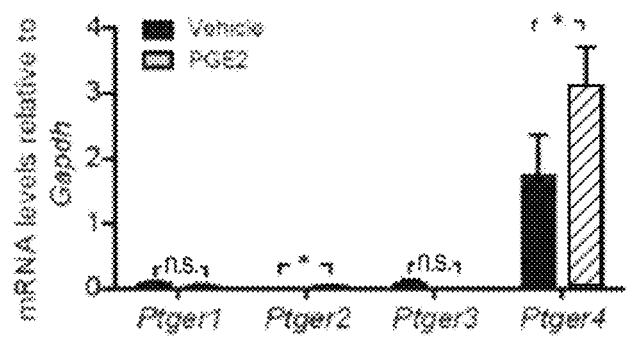
Figure 14B:
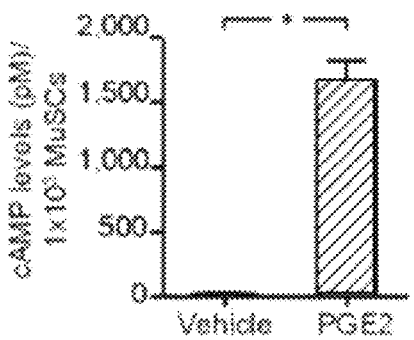
Figure 14C:
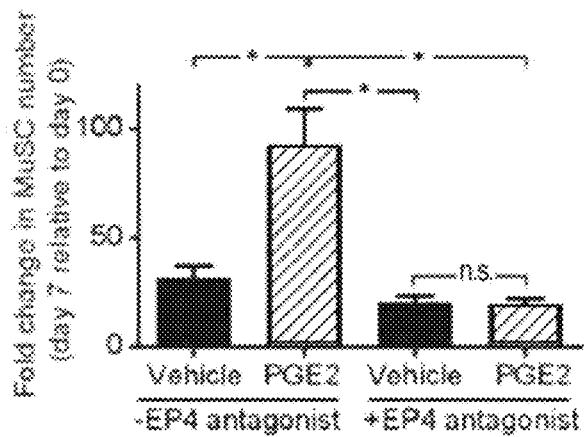
Figure 14D:
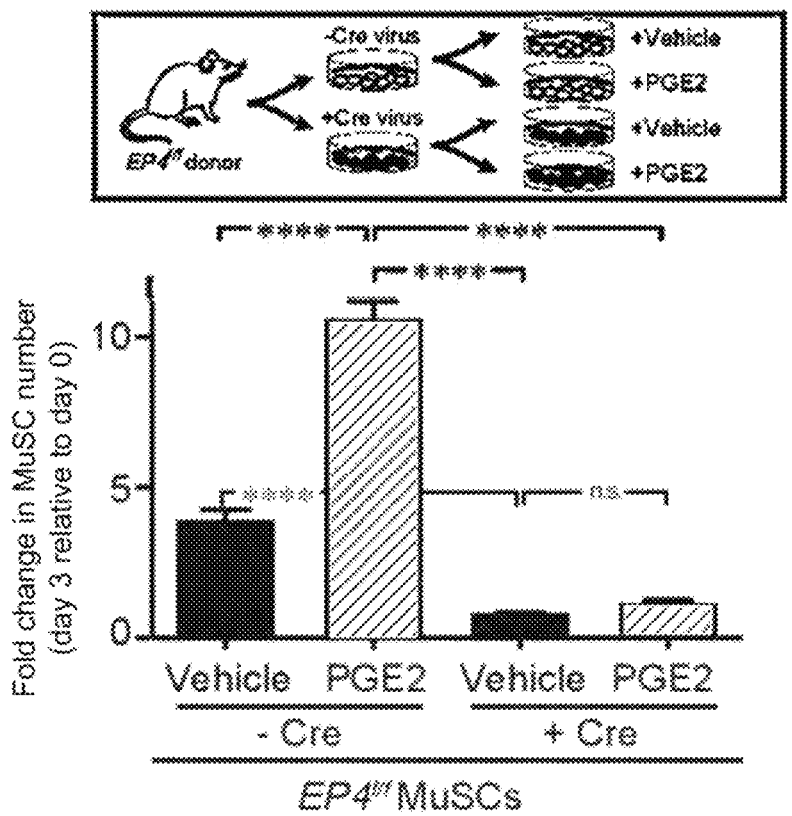
Figure 14E:
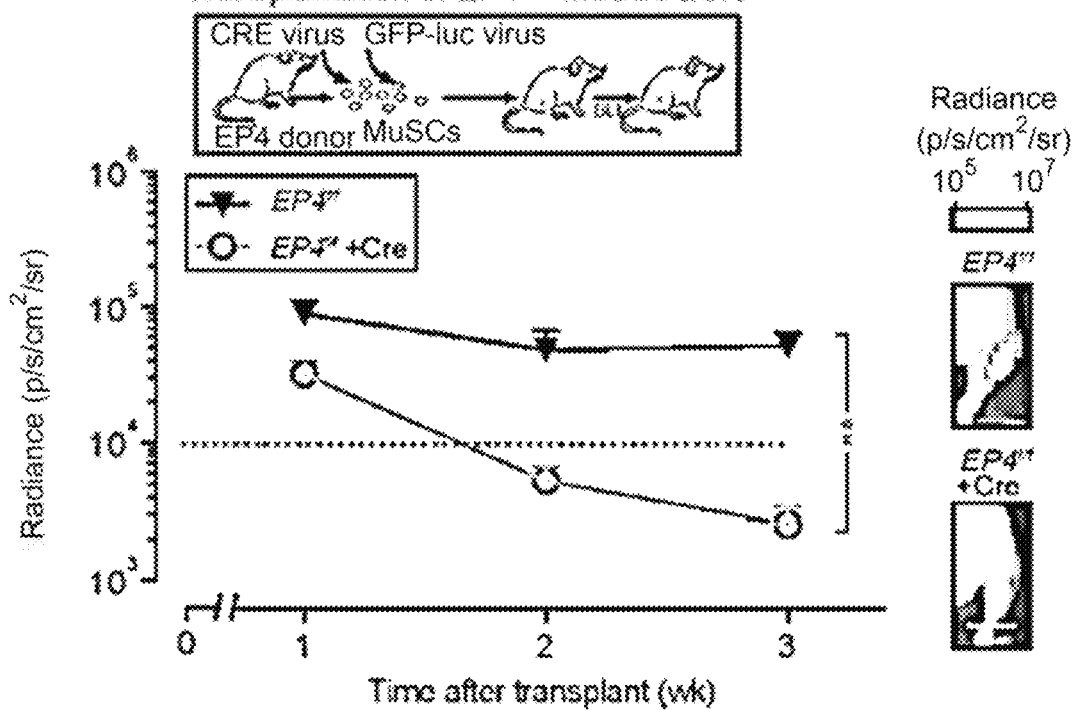

FIGS. 14A-14E show that EP4 mediates PGE2 signaling in MuSCs. FIG. 14A: Expression of prostaglandin receptors (Ptger 1-4) by MuSCs after 24 hr treatment with vehicle or PGE2; (n=3 mice with 2 technical replicates). FIG. 14B: cAMP levels in MuSCs after 1 hr PGE2 treatment; (n=6 mice with 3 technical replicates assayed in 2 independent experiments). FIG. 14C: MuSC numbers after 24 hr treatment with vehicle or PGE2 in the absence or presence of EP4 antagonist (ONO-AE3-208, 1 μM). FIG. 14D: Proliferation of EP4 null MuSCs treated with vehicle or PGE2. EP4$^{f/f}$ MuSCs were treated with lentiviral vector encoding Cre (+Cre, EP4-null) or without (−Cre; control) to delete EP4 alleles. Scheme depicting EP4-null and control MuSC analysis (top). EP4-null and control MuSC numbers; (n=6 mice in 2 independent experiments) (bottom). FIG. 14E: Engraftment of GFP/luc-labeled EP4$^{f/f}$ MuSCs (1,000 cells) treated with Cre (+Cre) or without (−Cre; empty vector) in culture to delete EP4 alleles. EP4$^{f/f}$ MuSCs were transduced with a lentiviral vector encoding GFP/luciferase for BLI. Transplant scheme (top). BLI signals post transplant (n=5 mice per condition) (bottom left). Representative BLI image (bottom right). Bar=5 mm. *P<0.05, P<0.001, P<0.0001. Mann-Whitney test (FIG. 14A, 14B); ANOVA test with Bonferroni correction for multiple comparisons (FIG. 14C, 14D); ANOVA test for group comparisons and significant difference for endpoint by Fisher's test (FIG. 14E**). Means+s.e.m. n.s., non significant.

Figure 15A:
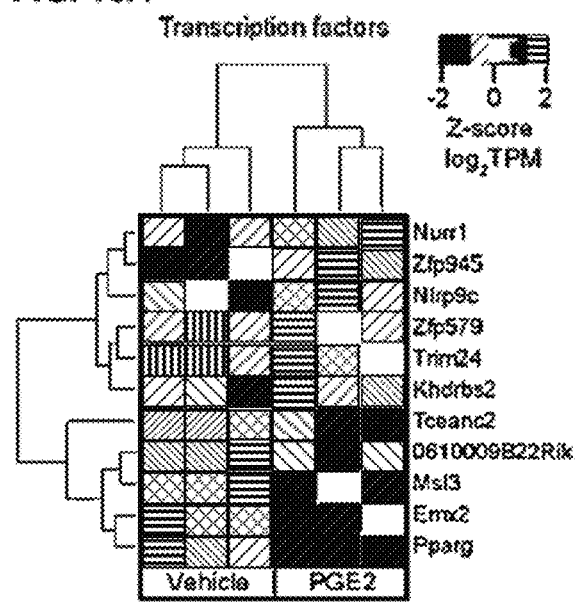
Figure 15B:
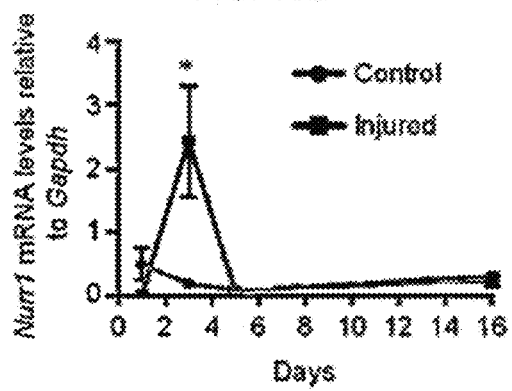
Figure 15C:
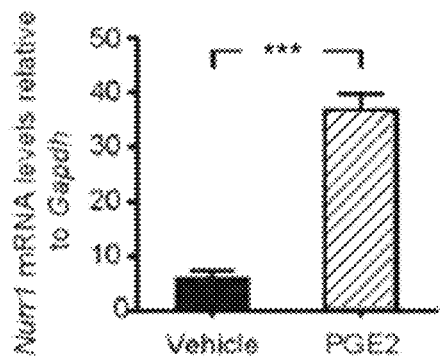
Figure 15D:
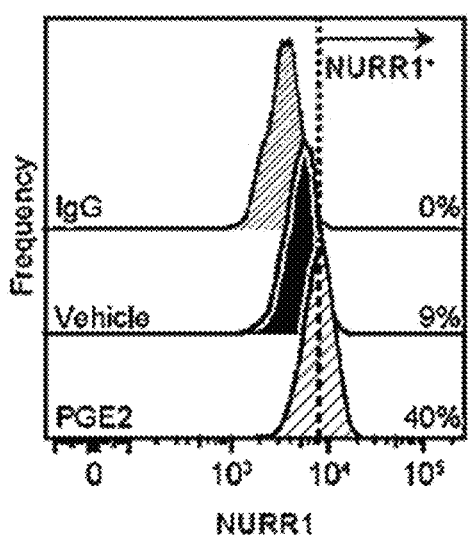
Figure 15E:
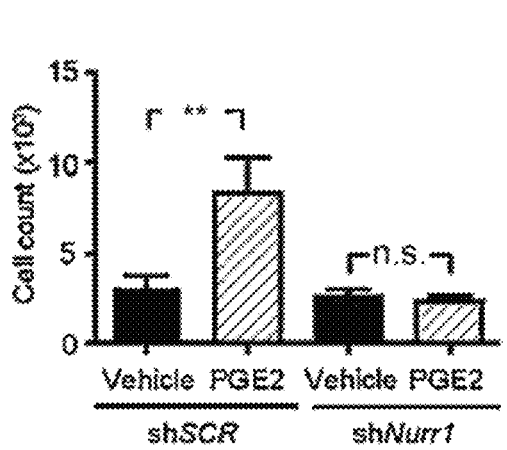
Figure 15F:
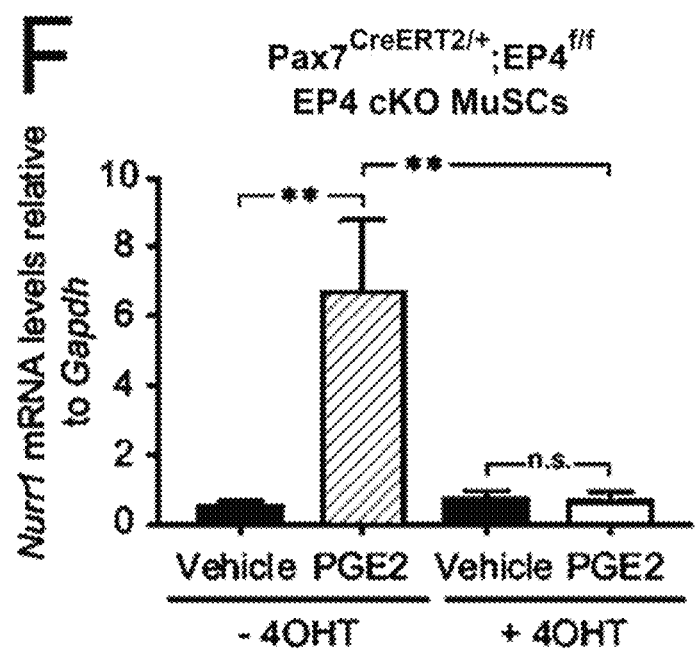
Figure 15G:
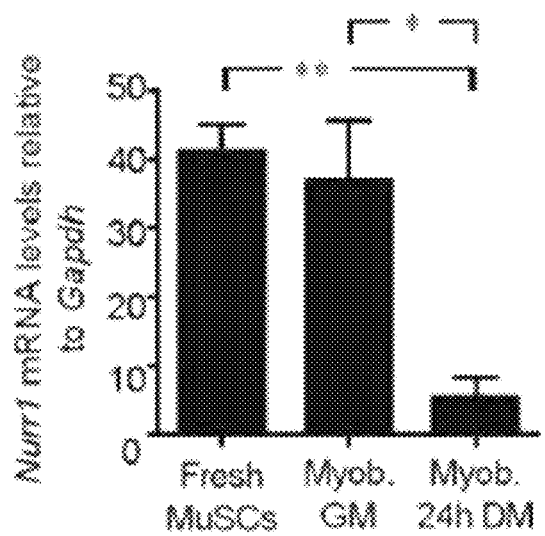

FIGS. 15A-15G show that Nurr1 is a downstream effector of PGE2/EP4 signaling in MuSCs. FIG. 15A: Heat map of differentially expressed transcription factors in vehicle or PGE2 treated MuSCs after 24 hr. FIG. 15B: Expression of Nurr1 after TA muscle injury (notexin) (n=3 mice per timepoint). FIG. 15C: Expression of Nurr1 by MuSCs after 24 hr treatment with vehicle or PGE2; (n=3 mice, performed in 3 independent experiments). FIG. 15D: Flow cytometric analysis of NURR1 or IgG control in myogenic progenitors treated with vehicle or PGE2 for 24 hr. FIG. 15E: MuSC numbers after 24 hr treatment of PGE2 or vehicle and subsequent culture on hydrogel until day 7 of shSCR or shNurr1 transfected cells (n=6 mice performed 2 independent experiments). FIG. 15F: Expression of Nurr1 in Pax7$^{CreERT2}$:EP4$^{f/f}$ (EP4 cKO) MuSCs treated with or without 4-hydroxytamoxifen (4OHT) in vitro and subsequently exposed to vehicle or PGE2 for 24 hr; (n=3 mice). FIG. 15G: Expression of Nurr1 in MuSCs, primary myoblasts cultured in growth medium (Myob. GM) and differentiating primary myoblasts cultured in differentiation medium for 24 hr (Myob. DM) (n=3 biological replicates per condition). *P<0.05, P<0.001, *P<0.0005. ANOVA test with Bonferroni correction for multiple comparisons (FIG. 15B, 15E, 15F, 15G); Mann-Whitney test (FIG. 15C). Means+s.e.m. n.s., non significant.

Figure 16A:
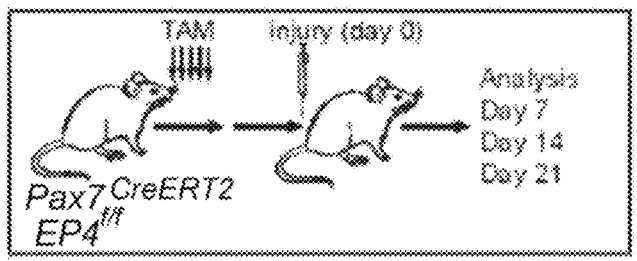
Figure 16B:
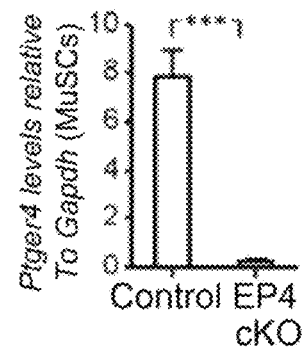
Figure 16C:
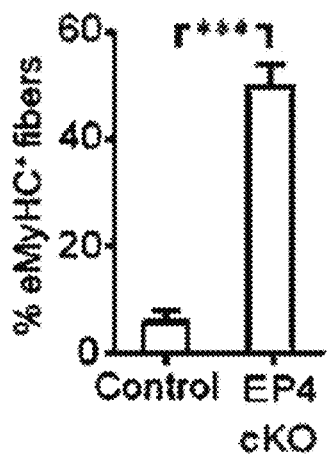
Figure 16D:
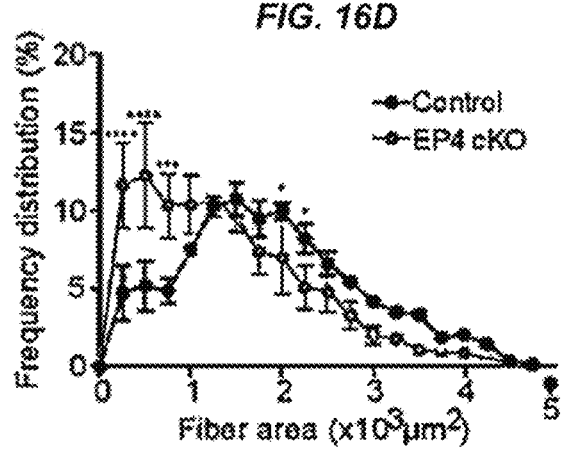
Figure 16E:
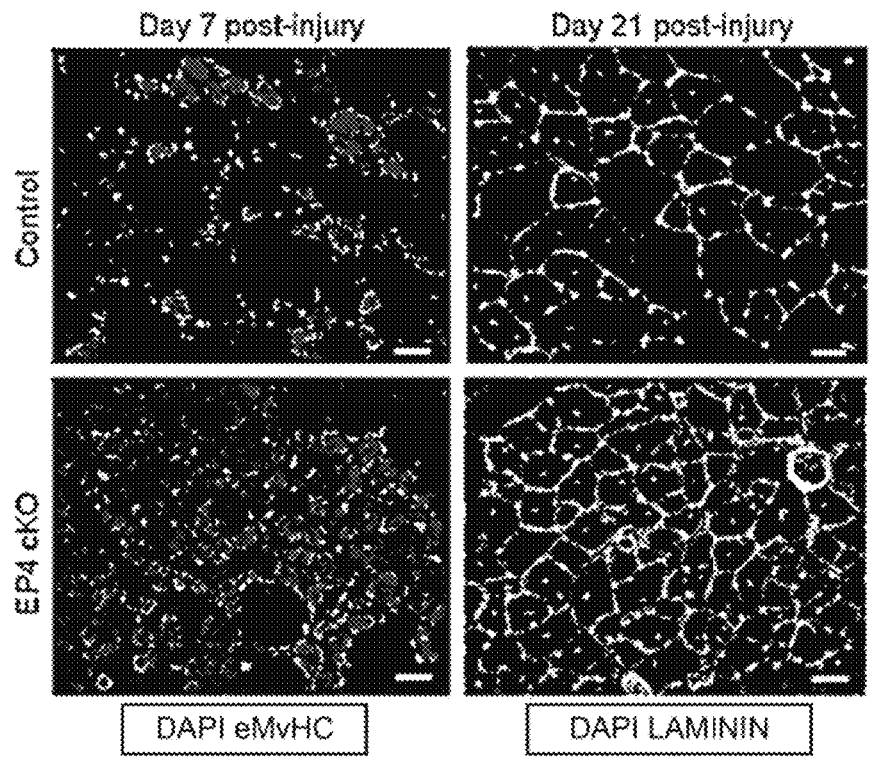
Figure 16F:
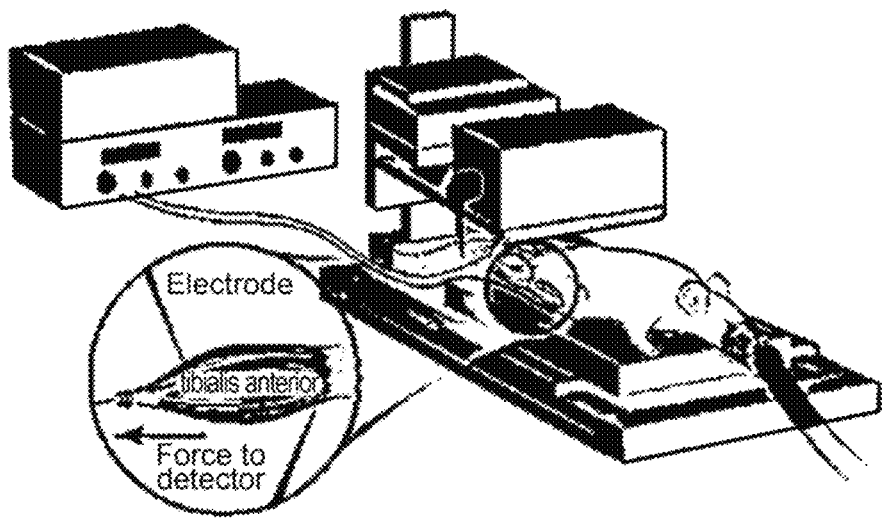
Figure 16G:
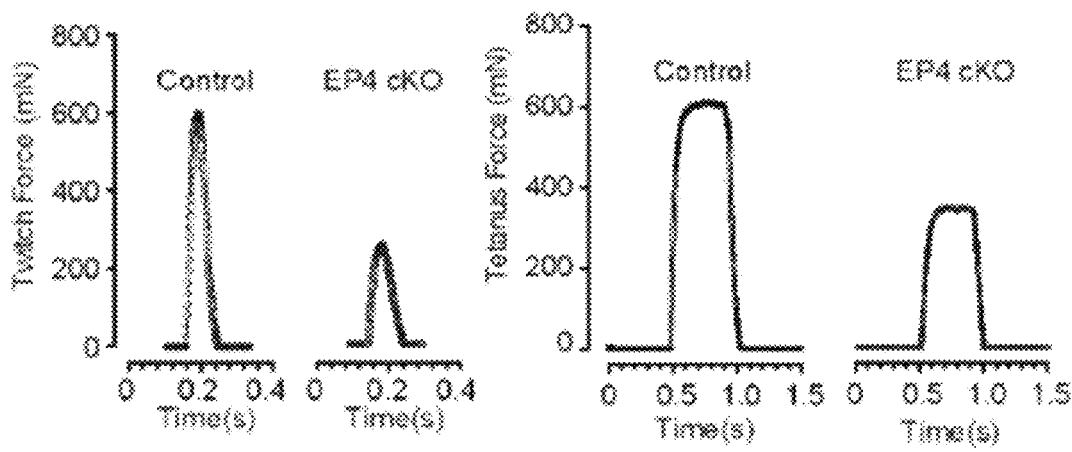
Figure 16H:
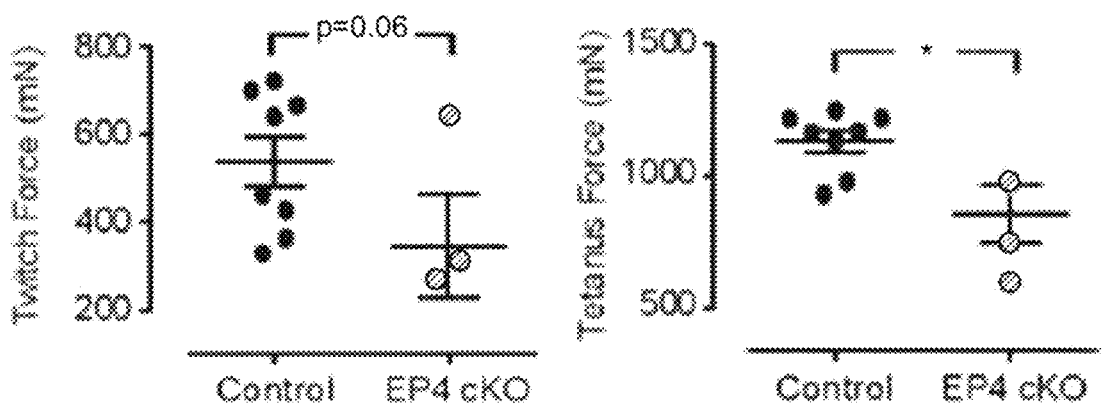
Figure 16I:
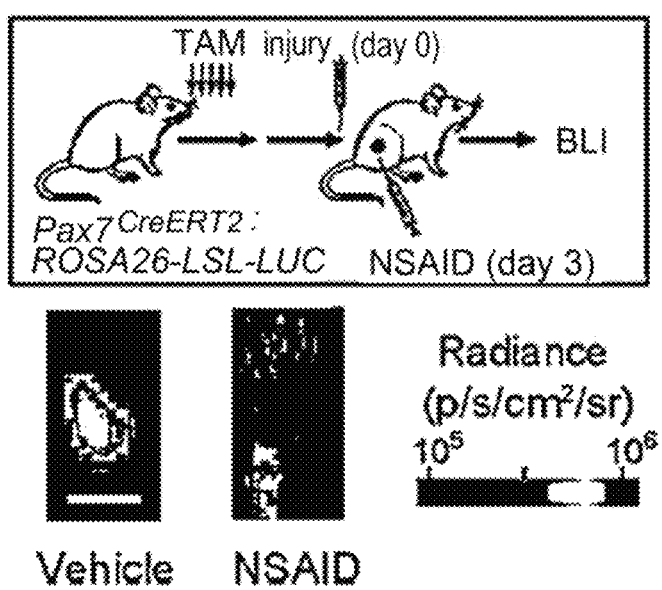
Figure 16J:
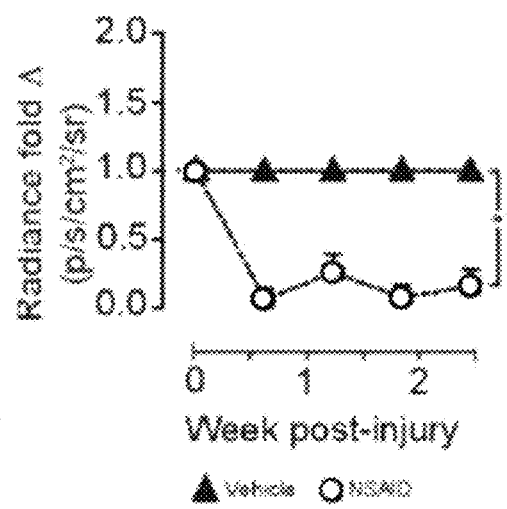
Figure 16K:
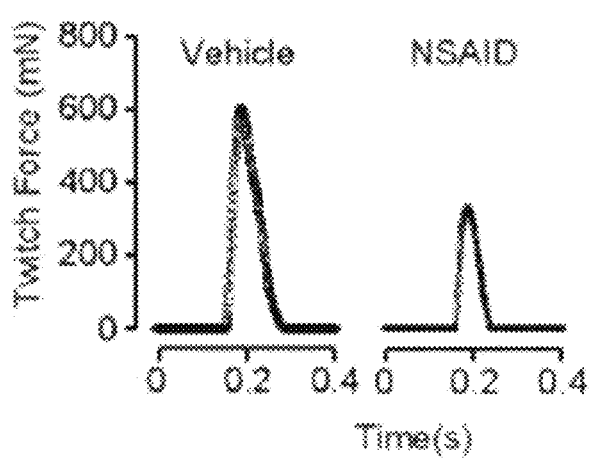
Figure 16L:
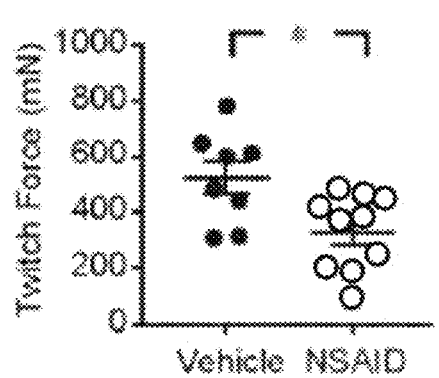

FIGS. 16A-16L show that loss of function of PGE2 signaling in MuSCs impairs muscle regeneration and strength. FIGS. 16A-16H: Tibialis anteriors (TAs) of Pax7-specific EP4 conditional knockout mice (Pax7$^{CreERT2}$;EP4$^{f/f}$, EP4 cKO) treated with tamoxifen (TAM) were assayed at 7 (FIG. 16C, 16E), 14 (FIGS. 16G, 16H) and 21 (FIG. 16B, 16D) days post-notexin injury; (n=3 mice per condition for all timepoints). FIG. 16A: Experimental scheme. FIG. 16B: Expression of Ptger4 (EP4 receptor) in sorted MuSCs (α$^{7+}$ CD34$^+$ lin$^−$) from control or EP4 cKO mice 21 days post-injury. FIG. 16C: Percentage of embryonic Myosin Heavy Chain (eMyHC) positive fibers 7 days post-injury. FIG. 16D: Myofiber cross-sectional areas (CSA) in control and EP4 cKO TAs 21 days post-injury. FIG. 16E: Representative TA cross-section at 7 days post-injury, DAPI, blue; eMyHC, red (left); and at 21 days post-injury, DAPI, blue, LAMININ, green (right). Bar=40 μm. FIG. 16F: In vivo muscle contractile force assay scheme. FIG. 16G: Representative twitch force (left) and tetanic force (right) at day 14 post-notexin injury. FIG. 16H: Quantification of muscle twitch forces (left) and tetanic forces (right). (n=8 for control and 3 for EP4 cKO). (FIG. 16I, 16J) Endogenous muscle stem cells (MuSCs) assayed in Pax7$^{CreERT2}$;Rosa26-LSL-Luc mice treated with tamoxifen (TAM) by non-invasive bioluminescence imaging (BLI) after injection with vehicle or NSAID (Indomethacin) post-cardiotoxin injury into the TA. FIG. 16I: Experimental scheme (top). Representative BLI image (bottom). Bar=5 mm. FIG. 16J: BLI; (n=3 mice per condition performed in 2 independent experiments; figure is representative of one experiment). (FIG. 16K, 16L) Muscle force was measured after vehicle or NSAID (Indomethacin) at day 14 post-cardiotoxin in C57Bl/6 mice (2-4 month old). FIG. 16K: Representative twitch force. FIG. 16L: Quantification of muscle twitch forces (n=8 for vehicle-treated and 10 for NSAID-treated). *P<0.05, *P<0.0005 and P<0.0001. Mann-Whitney test (FIG. 16B, 16C, 16H, 16L); ANOVA test for group comparison and significant difference for each bin by Fisher's test FIG. 16D, ANOVA test for group comparisons and significant difference for endpoint by Fisher's test FIG. 16J**. Means+s.e.m.

Figure 17:
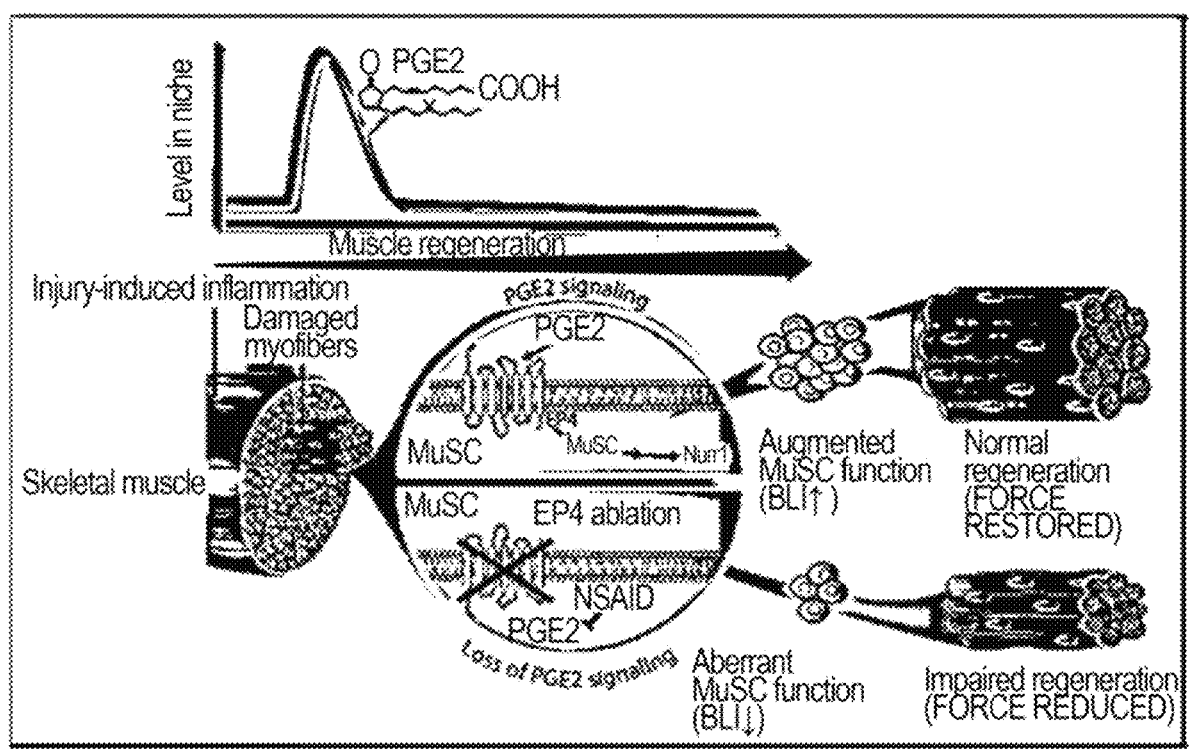

FIG. 17 shows a model for PGE2 signaling to expand MuSC function in regeneration. Shown is a schematic of the role of PGE2 in MuSCs. After injury, PGE2 released into the muscle niche acts on the EP4 receptor, which signals through cAMP/phospho-CREB leading to the expression of Nurr1 proliferation-inducing transcription factor. This promotes MuSC expansion for efficient muscle regeneration. Loss of PGE2/EP4 signaling by NSAID treatment or specific loss of EP4 receptor leads to aberrant MuSC function and impaired muscle regeneration and strength recovery.

Figure 18A:
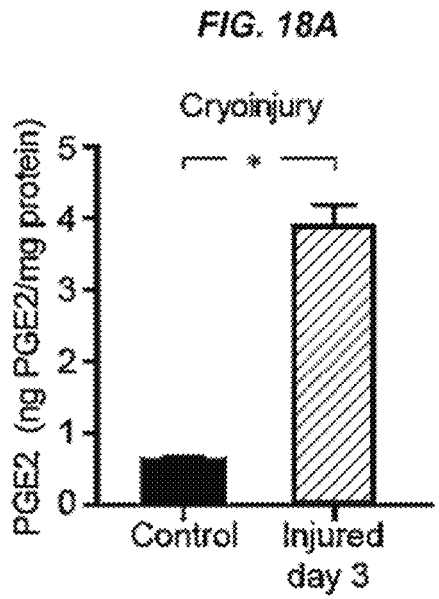
Figure 18C:
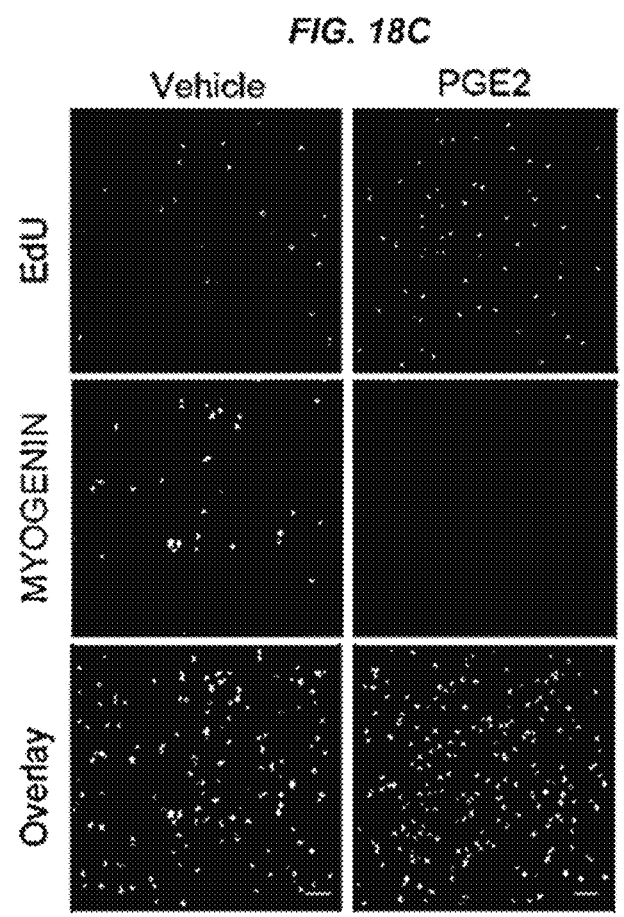
Figure 18B:
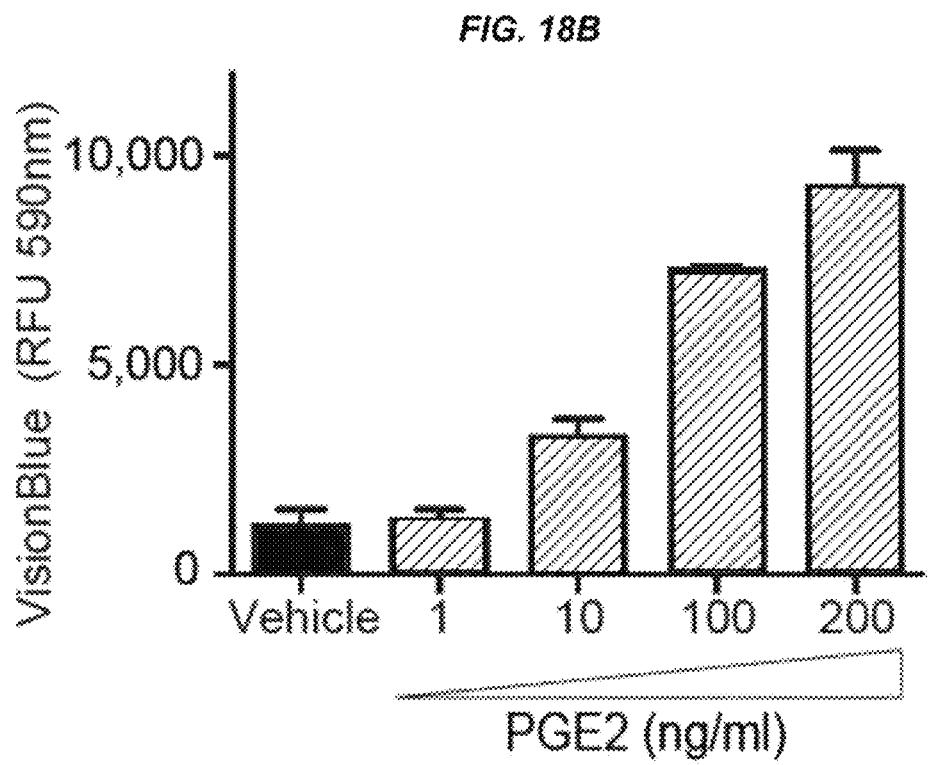
Figure 18D:
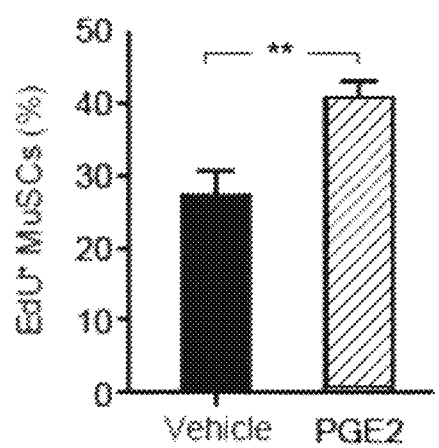
Figure 18E:
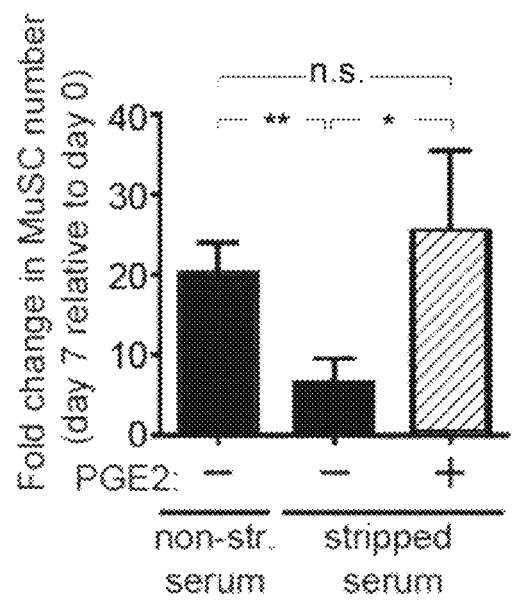
Figure 18F:
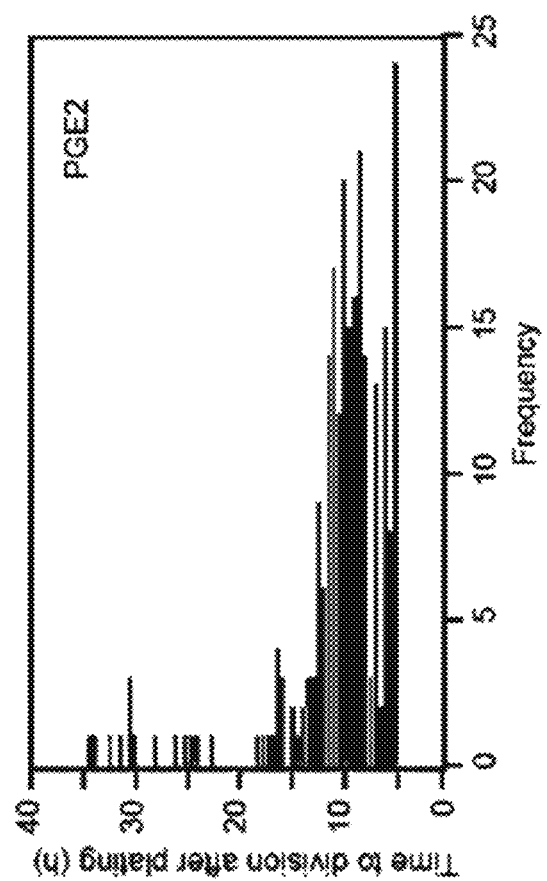
Figure 18F:
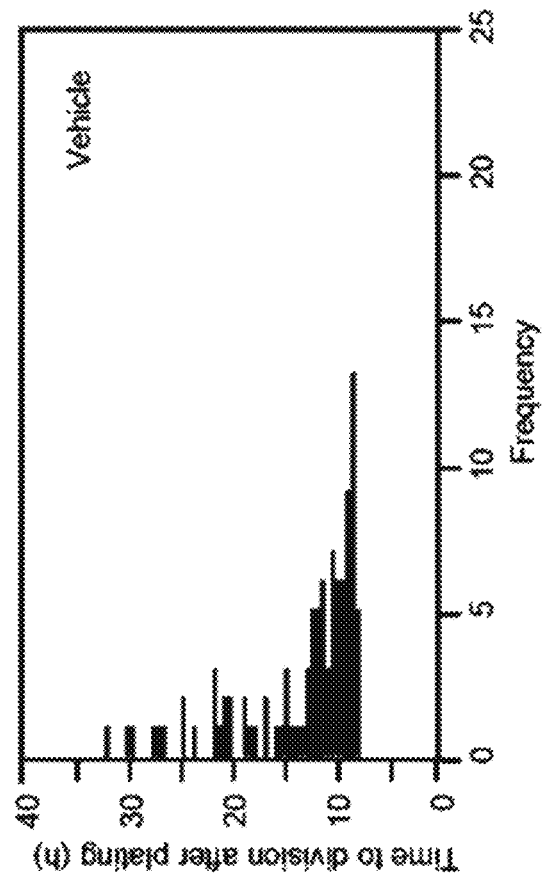
Figure 18G:
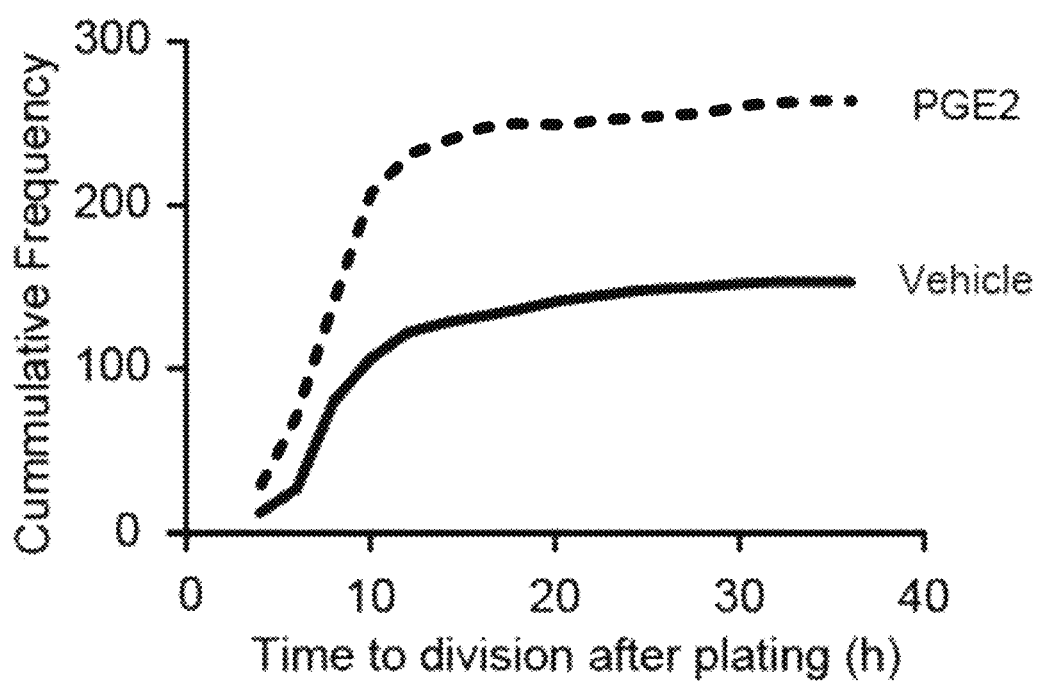

FIGS. 18A-18G show that PGE2 promotes MuSC proliferation. FIG. 18A: PGE2 levels assayed by ELISA after cryoinjury for tibialis anterior (TA); (n=3 mice per condition). Control refers to the contralateral uninjured leg. FIG. 18B: Proliferation measured by the metabolic viability assay VisionBlue after treatment with vehicle or indicated doses of PGE2 (1-200 ng/ml); (n=6 mice with 3 technical replicates in two independent experiments). FIG. 18C: Representative image of MuSCs labeled with EdU during 1 hr (red) and costained with MYOGENIN (green) after treatment with PGE2 (10 ng/ml) for 24 h or vehicle. Bar represents 40 μm. FIG. 18D: Percentage of dividing MuSCs labeled with EdU in FIG. 18C; (n=6 mice with 3 technical replicates in two independent experiments). FIG. 18E: MuSC numbers after culture in growth medium with normal serum (non-str. Serum) or charcoal stripped medium (stripped-serum) treated daily with vehicle or PGE2 for 7 days; (n=6 mice in 3 independent experiments). FIG. 18F: Time to first division after plating for each individual MuSC clone analyzed by time-lapse after vehicle (left) or PGE2 (right) treatment. FIG. 18G: Cumulative Frequency of the time to division after plating of all tracked MuSC clones throughout the entire timelapse duration (38 hr).*P<0.05, P<0.001. Mann-Whitney test (FIG. 18A, 18D**). ANOVA test with Bonferroni correction for multiple comparisons (FIG. 18E). Means+s.e.m. n.s., non significant.

Figure 19A:
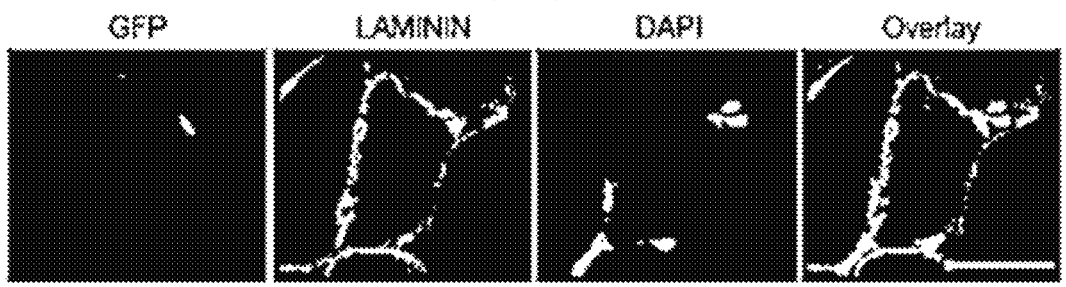
Figure 19B:
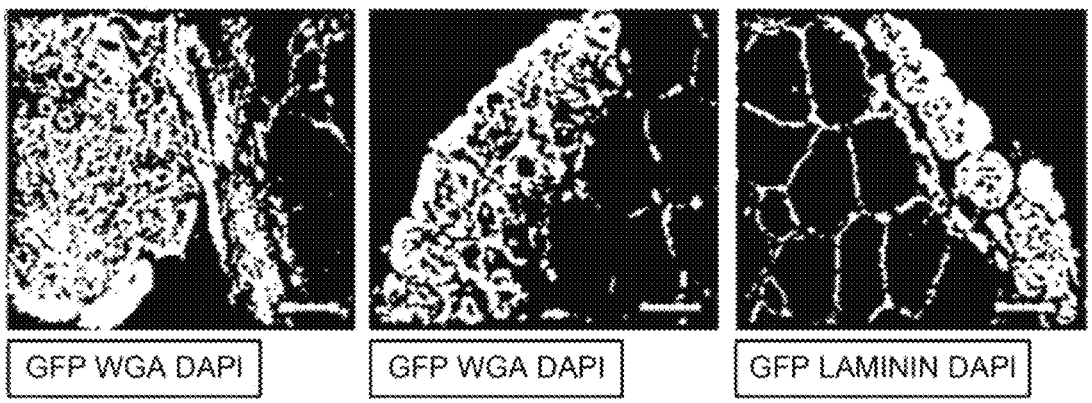
Figure 19C:
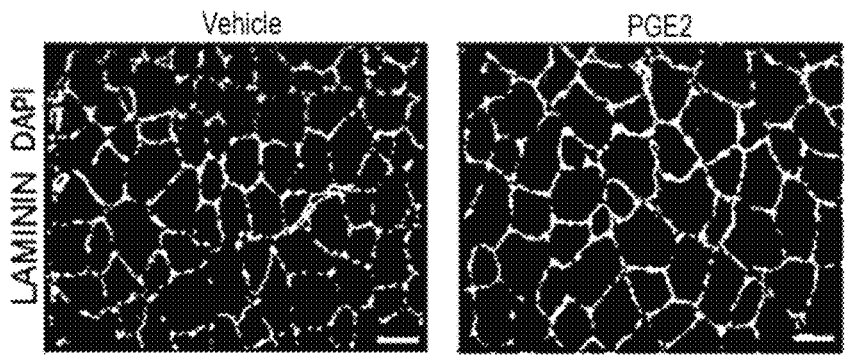
Figure 19D:
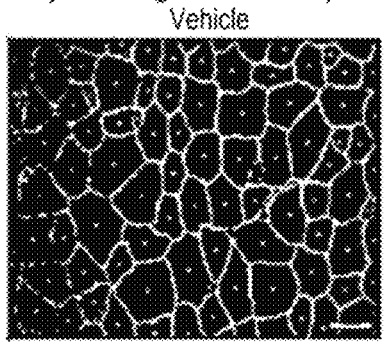
Figure 19D:
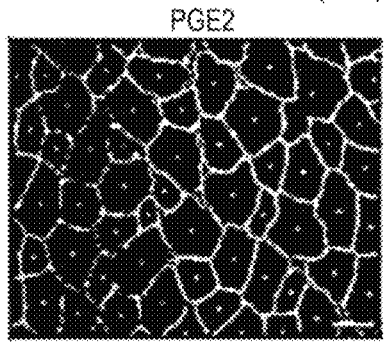
Figure 19E:
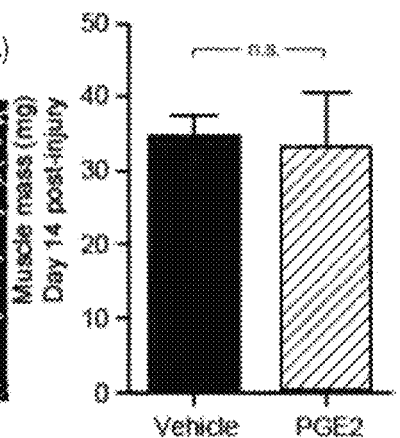

FIGS. 19A-19E show that PGE2 direct injection augments muscle regeneration without promoting hypertrophy. FIG. 19A: Representative cross-sectional images of the TA showing a GFP⁺ MuSC after engraftment of freshly sorted GFP/luc-labeled MuSCs (250 cells) coinjected with PGE2 at 8 weeks post-engraftment. Images show staining with GFP, green, LAMININ, red and DAPI, blue. Bar represents 40 µm. FIG. 19B: Representative cross-sectional images of the TA showing GFP⁺ myofibers after engraftment of freshly sorted GFP/luc-labeled MuSCs (250 cells) coinjected with PGE2 at 8 weeks post-engraftment. Images show staining with GFP, green, wheat germ agglutinin (WGA) or LAMININ, red and DAPI, blue. Bar represents 40 µm. FIG. 19C: Representative cross-sectional images of TA myofibers of C57Bl/6 mice at day 14 post-cardiotoxin (CTX) injury treated in vivo with vehicle or PGE2 48 hr post-injury. Images show staining with LAMININ, green and DAPI, blue. Bar represents 40 µm. FIG. 19D: The corresponding segmentation images from (A) analyzed by the Baxter Algorithms for Myofiber Analysis to determine the cross sectional area (CSA) of transverse sections of myofibers (bottom) at day 14 post-injury. Bar represents 40 µm. FIG. 19E: Mass of vehicle or PGE2-treated TAs at day 14 post-injury. Mann-Whitney test (FIG. 19E). Means+s.e.m. n.s., non-significant.

Figure 20A:
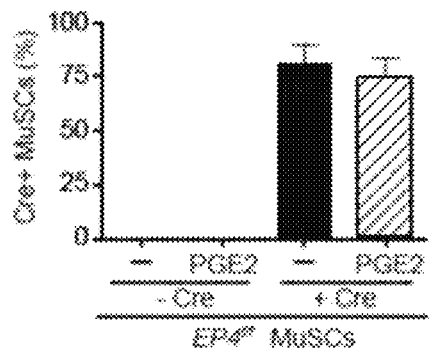
Figure 20B:
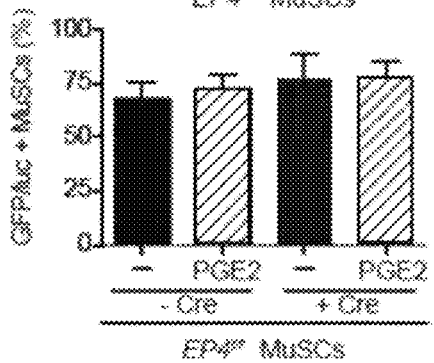
Figure 20C:
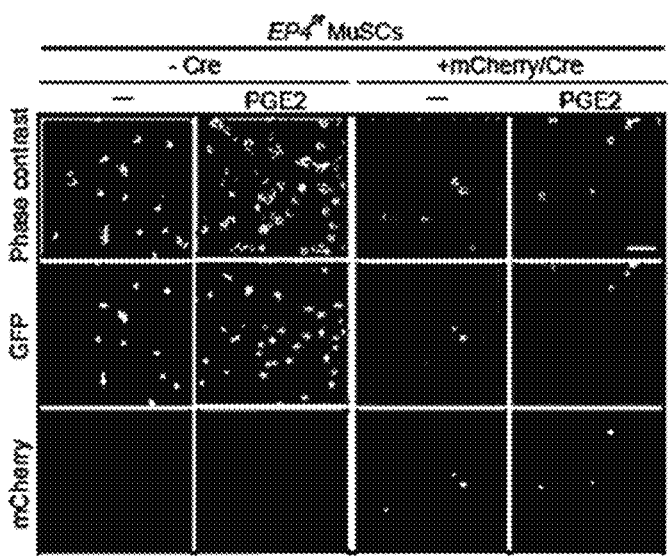
Figure 20D:
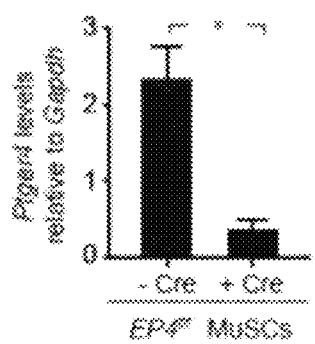
Figure 20E:
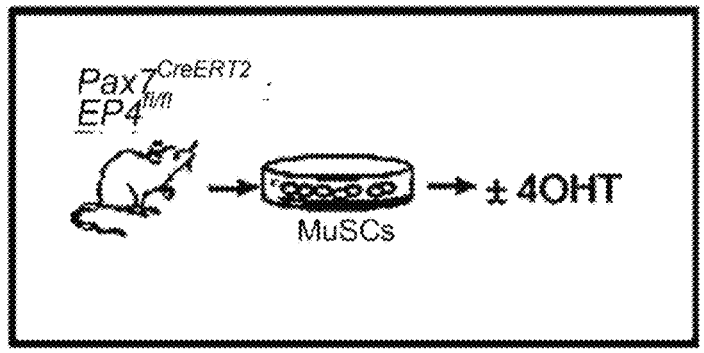
Figure 20F:
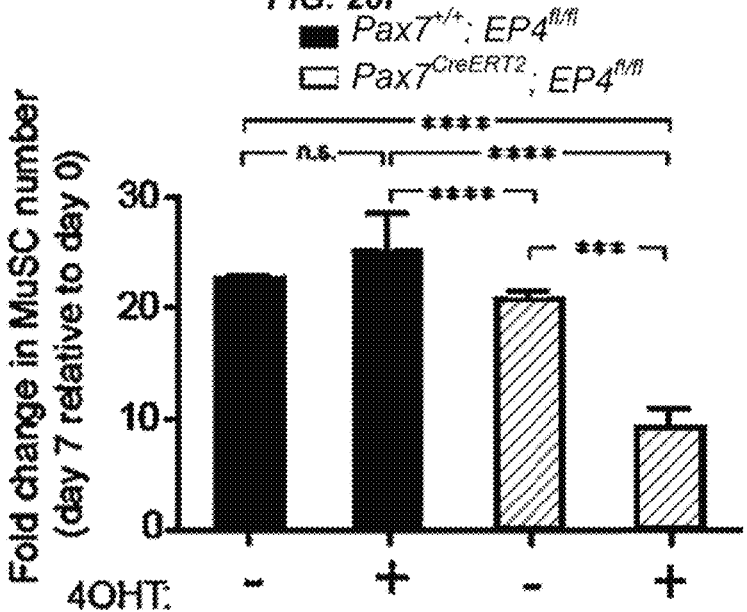
Figure 20G:
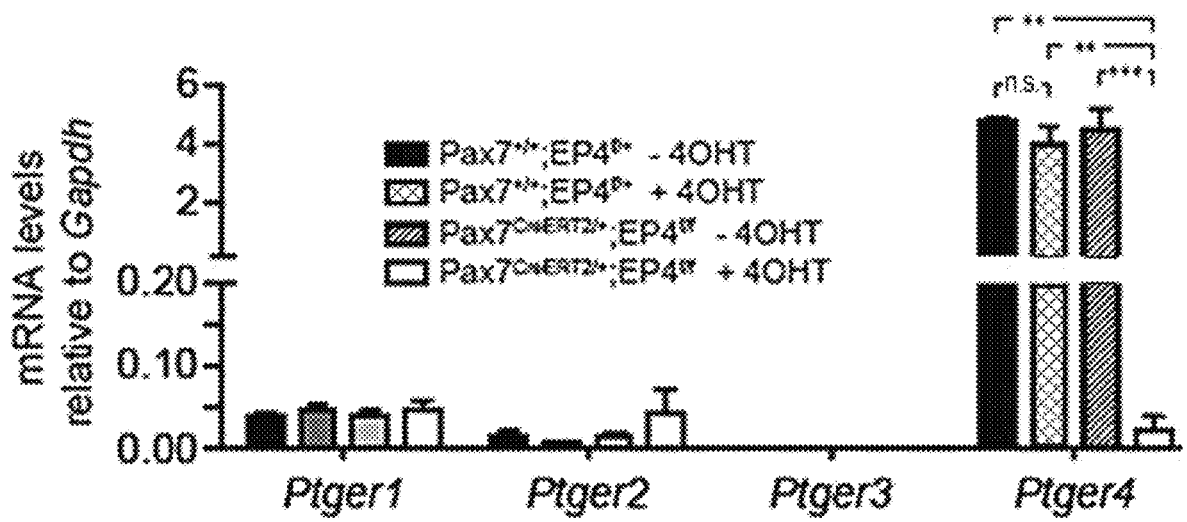

FIGS. 20A-20G show that EP4 loss of function in MuSC leads to decreased proliferation. FIGS. 20A-20D: EP4$^{f/f}$ MuSCs treated with lentiviral vector encoding mCherry/Cre (+Cre) or without (−Cre; empty vector) to delete EP4 alleles. Bar graphs show percentage of Cre⁺ MuSCs (FIG. 20A) and GFP/Luc⁺ MuSCs (FIG. 20B). FIG. 20C: Representative image. Bar=40 µm; GFP, green; mCherry, red. FIG. 20D: Expression of Ptger4 by EP4$^{f/f}$ MuSCs±Cre. FIGS. 20E-20G: Pax7 specific EP4 knockout MuSCs isolated from Pax7$^{CreERT2}$;EP4$^{f/f}$ or control Pax7$^{+/+}$;EP4$^{f/+}$ mice treated with 4-hydroxytamoxifen (4OHT) in vitro (n=3 mice per condition). FIG. 20E: Experimental scheme. FIG. 20F: MuSC numbers after 7 days of culture. FIG. 20G: Expression of prostaglandin receptors (Ptger 1-4) by qRT-PCR. *P<0.05, P<0.001, *P<0.0005, ****P<0.0001. Mann-Whitney test (FIG. 20D); ANOVA test with Bonferroni correction for multiple comparisons (FIG. 20F, 20G). Means+s.e.m. n.s., non-significant.

Figure 21D:
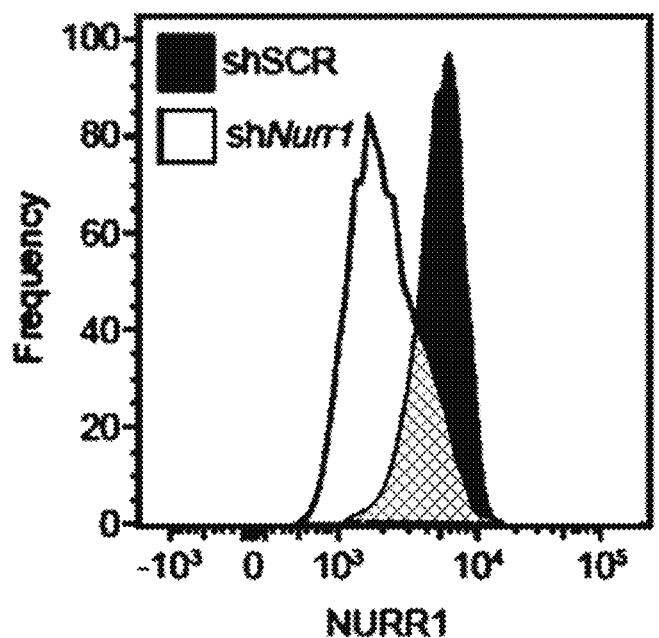
Figure 21E:
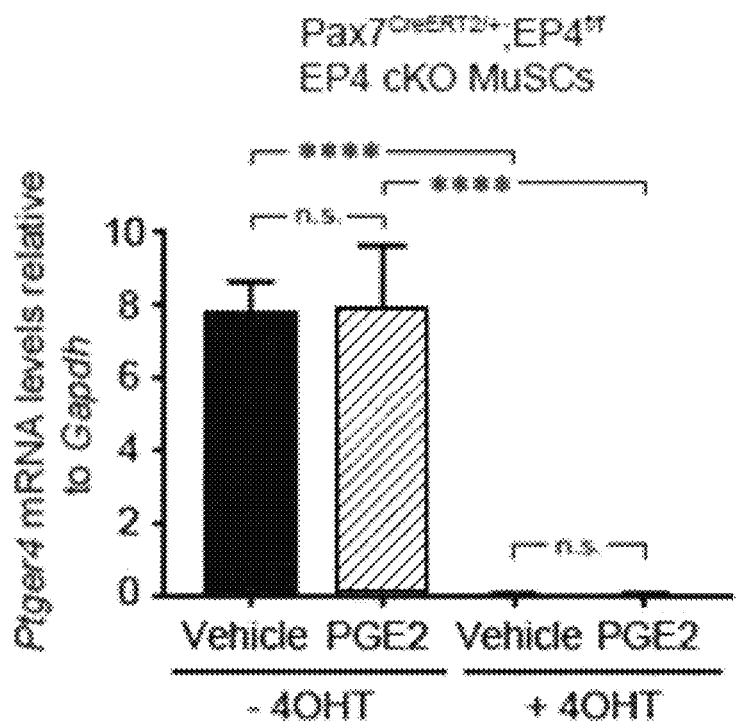

FIGS. 21A-21E show transcriptome analysis of PGE2-treated MuSCs. FIG. 21A: Heat map of the transcriptome of vehicle or PGE2 treated MuSCs after 24 hr shown as expression fold-change over vehicle-treated MuSCs. FIG. 21B: Enriched molecular and cellular function pathways of the differentially expressed upregulated genes in the PGE2-treated MuSCs indicated by Ingenuity Pathway Analysis. FIG. 21C: Enriched pathway maps of the differentially expressed upregulated genes in the PGE2-treated MuSCs indicated by Metacore Analysis. FIG. 21D: Flow cytometric analysis of NURR1 in shSCR (control) or shNurr1 transfected cells. FIG. 21E: Expression of Ptger4 (EP4 receptor) in Pax7$^{CreERT2}$;EP4$^{f/f}$ MuSCs treated with or without 4-hydroxytamoxifen (4OHT) in vitro and and subsequently exposed to vehicle or PGE2 for 24 hr; (n=3 mice). ****P<0.0001. ANOVA test with Bonferroni correction for multiple comparisons (FIG. 21E). Means+s.e.m. n.s., non-significant.

Figure 22A:
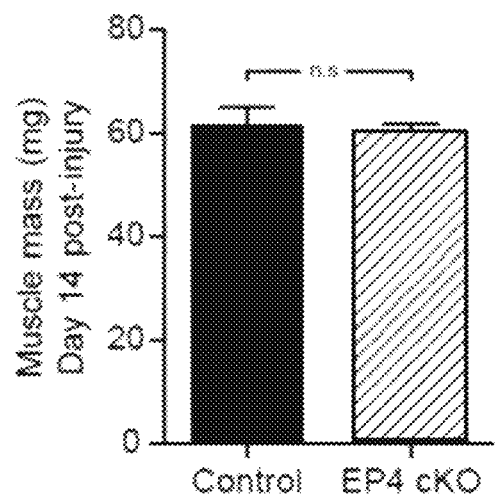
Figure 22B:
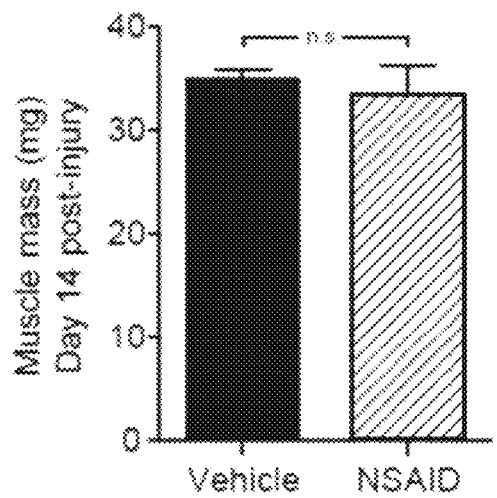

FIGS. 22A and 22B show that muscle mass is not altered after PGE2 loss of function post-injury. FIG. 22A: Mass of TAs of control or MuSC-specific EP4 conditional knockout mice at day 14 post-injury. FIG. 22B: Mass of vehicle or NSAID-treated TAs at day 14 post-injury. Mann-Whitney test. Means+s.e.m. n.s., non significant.

Figure 23A:
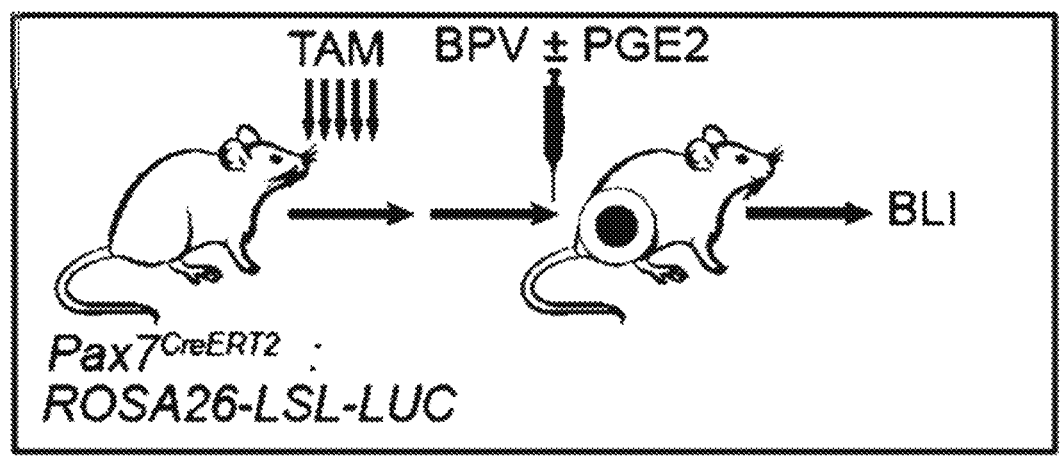
Figure 23B:
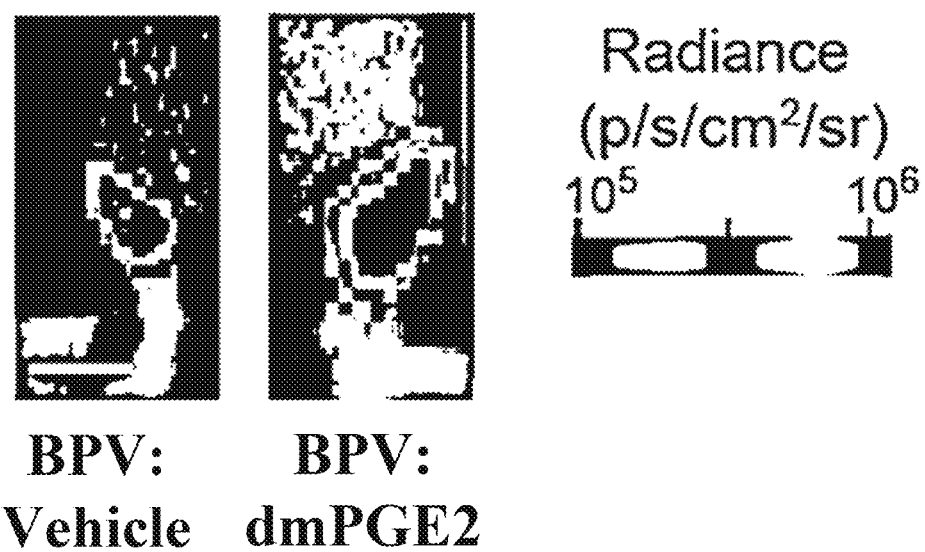
Figure 23C:
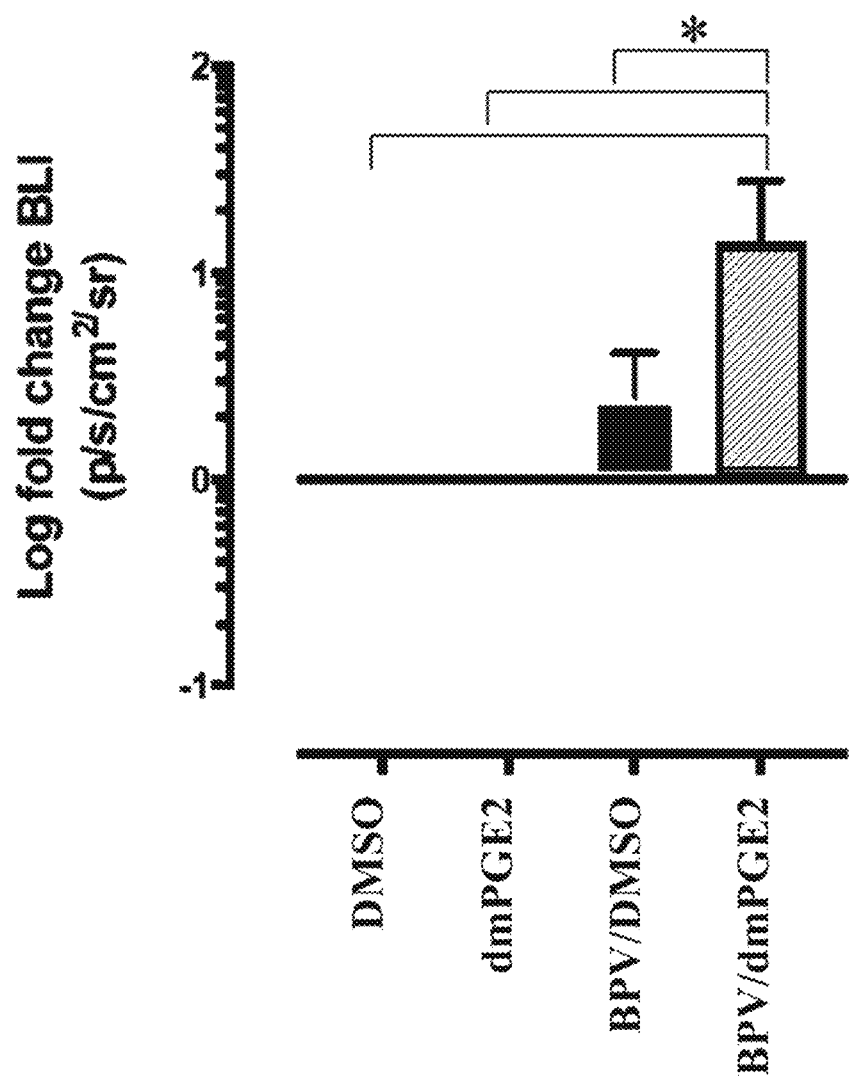

FIGS. 23A-23C show that a composition comprising a combination of a PGE2 derivative (16,16-dimethyl prostaglandin E2; dmPGE2) and bupivacaine (BPV) enhances muscle stem cell expansion during regeneration. FIG. 23A shows a scheme illustrating experimental procedures for the in vivo analysis of endogenous muscle stem cell (MuSC) expansion during regeneration in Pax7$^{CreERT2}$;Rosa26-LSL-Luc mice treated with tamoxifen (TAM) via bioluminescent imaging (BLI). FIG. 23B shows representative BLI images of control (BPV/vehicle) and experimental (BPV/dmPGE2) mouse limb 2-week post-injury. Bar=5 mm. FIG. 23C shows log-fold changes of BLI signals between control and experimental groups at week 2 post-injury. Data are shown as the mean±s.e.m. (n=6). The asterisk (*) indicates statistical significant difference with p<0.05.

Figure 24:
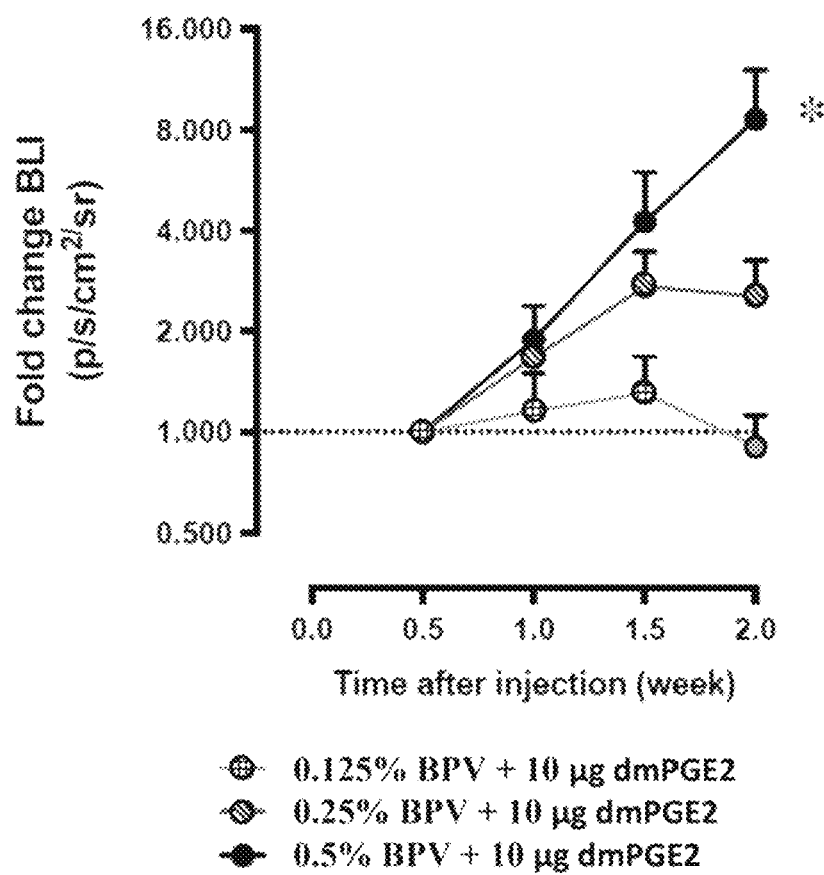

FIG. 24 shows a dose-dependent effect of bupivacaine, when administered in combination with dmPGE2, in inducing muscle stem cell expansion during regeneration. The graph shows the relative endogenous mouse muscle stem cell expansion in Pax7$^{CreERT2}$;Rosa26-LSL-Luc mice as measured by the radiance fold change of bioluminescent imaging (BLI) from day 3 post-injection. Statistical significance for the difference between the control vs. treatment group was determined by one-way ANOVA test with Bonferroni's multiple comparison correction. Error bar represents s.e.m. and n>3 per condition.

Figure 25A:
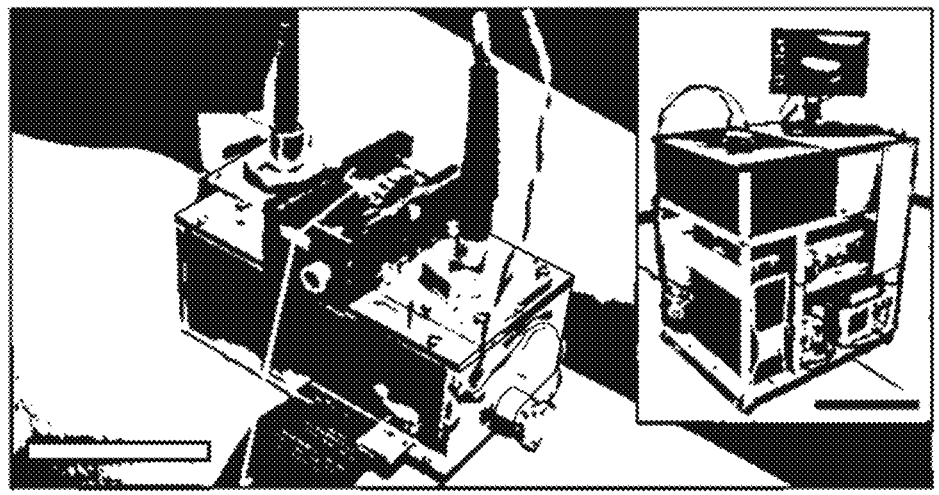
Figure 25B:
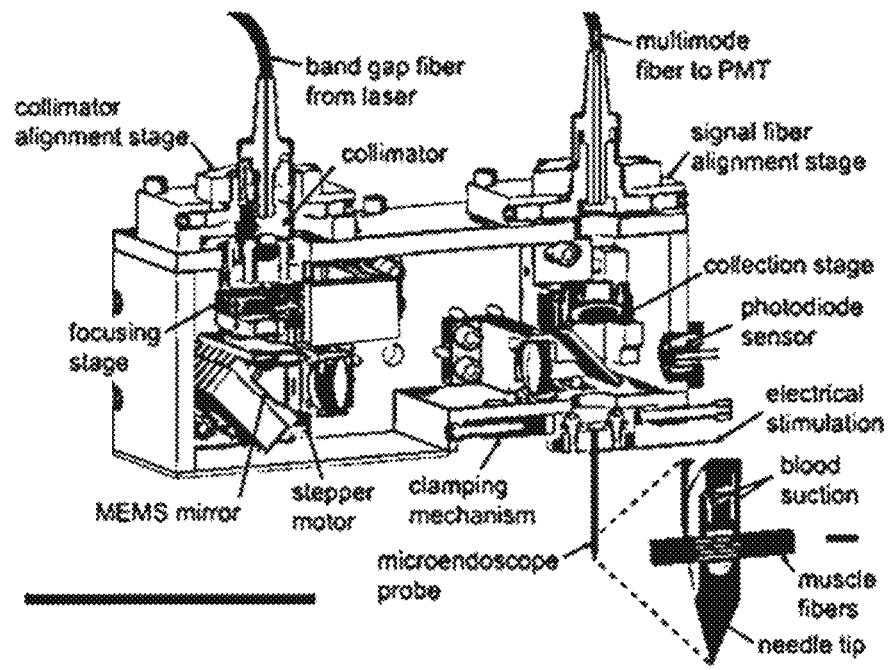
Figure 25C:
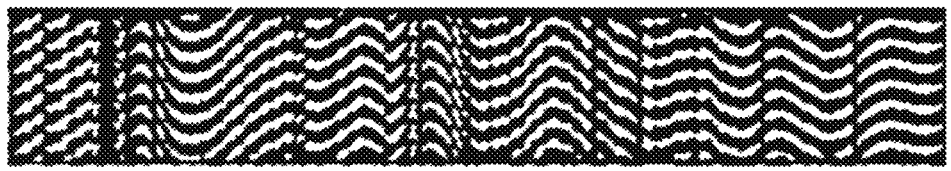
Figure 25D:
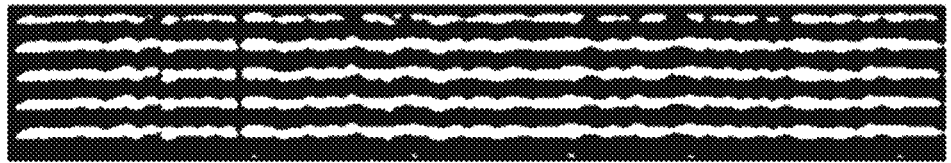

FIGS. 25A-25D describe a handheld microendoscope for use in assessing the benefits of compositions and methods of the present invention. FIG. 25A shows photographs of the microendoscope and associated workstation. FIG. 25B shows a schematic of the microendoscope. FIG. 25C shows an exemplary image generated by the microendoscope. FIG. 25D shows a more highly magnified exemplary image generated by the microendoscope.

Figure 26:
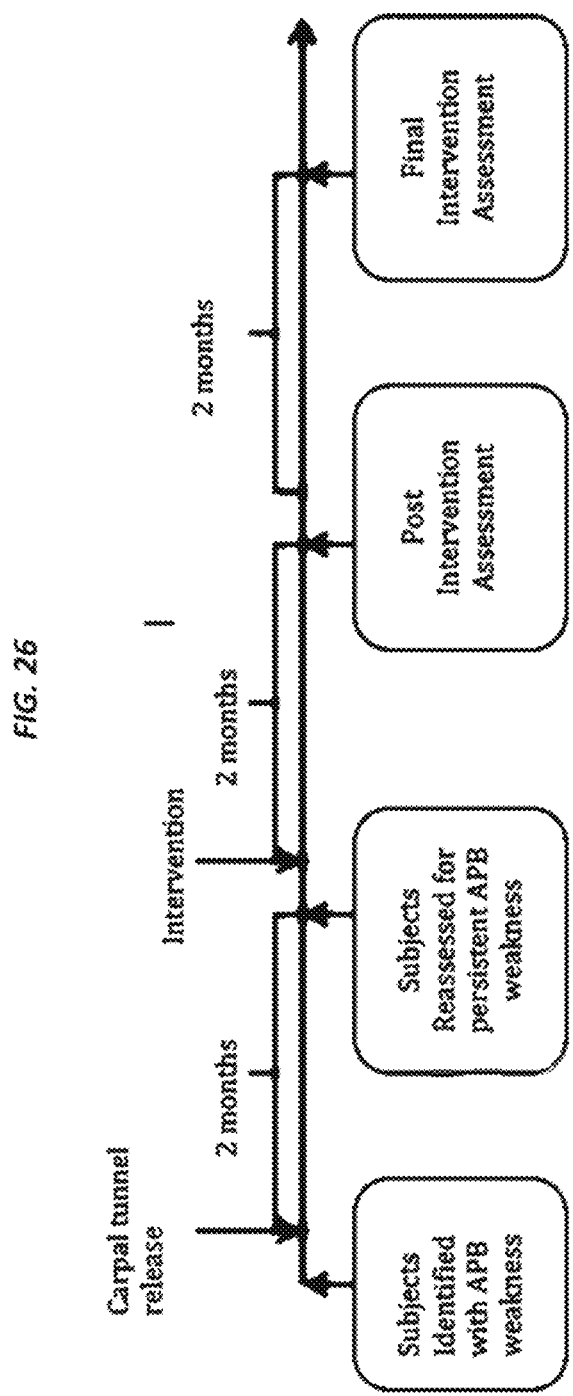

FIG. 26 shows an exemplary timeline for a clinical trial.

FIGS. 27A-27C show the synergistic effect of combining a PGE2 compound and a myotoxin to induce muscle regeneration and improve muscle function. Pax7-CreERT2; Rosa-LSL-Luciferase mice (2-4 months old) were treated with tamoxifen for five consecutive days in order to obtain Pax7 promoter expressing luciferase mice in vivo. One week later, baseline tetanic force of the tibialis anterior was measured using a foot plate force measurement instrument before injection of drugs (timepoint day 0). Mice were subsequently injected with 50 µl of vehicle (saline), the muscle stem cell activator prostaglandin E2 (PGE2, 20 µg), the muscle stem cell expansion agent bupivacaine (BPV, 0.25%) or the combination drug (bupivacaine 0.25% together with PGE2 20 µg) into the Tibialis anterior (TA) muscle. FIG. 27A shows bioluminescence (BLI, measured as radiance) measured every 3 days for 2 weeks to measure muscle stem cell expansion. FIG. 27B shows the resulting tetanic force measured at week 4 from the same mice, where the percent difference to baseline force was calculated. FIG. 27C: at 4 weeks (endpoint) the TA was isolated, and the specific force (mN/mm²) was obtained based on the physiological cross-sectional area (PCSA) calculated by the muscle length, weight and pennation angle. The specific force and the percent difference of tetanic force were significantly increased for the combination drug compared to the vehicle and both of the small molecules injected alone. *P<0.05, **P<0.001. ANOVA test for group comparisons and significant difference for endpoint by Fisher's test (FIG. 27A).

ANOVA test with Bonferroni correction for multiple comparisons (FIG. 27B, FIG. 27C). Data are shown as means±SEM.

DETAILED DESCRIPTION OF THE INVENTION

I. Introduction

Recent studies have shown the importance of muscle stem cells (MuSCs) in stimulating neuromuscular junctions in denervated muscles, although until recently improving the recovery of muscle function following denervation remained an unsolved problem. A solution to this problem lies in the ability to reverse or prevent denervation atrophy by stimulating and augmenting MuSCs that are already present in the muscles or by stimulating and augmenting MuSCs from muscle transplantation.

The present invention is based, in part, on the discovery that a combination of prostaglandin E2 (PGE2) compounds and myotoxins such as bupivacaine invoke dormant MuSCs to engage in muscle regeneration and restore strength. In some cases, the addition of a myotoxin induces muscle regeneration. In those cases, the addition of a myotoxin to a PGE2 compound improves muscle regeneration, better than muscle regeneration induced by a PGE2 compound alone. As such, in certain aspects, the compositions and methods of the present invention are particularly useful for promoting regeneration of atrophic abductor pollicis brevis (APB) muscle post nerve release surgery to promote neuromuscular junction establishment and restoration of muscle contractile function and volume.

Recent studies have shown the importance of muscle stem cells (MuSCs) in stimulating neuromuscular junctions in denervated muscles (Liu et al., 2015), although until recently improving the recovery of muscle function following denervation remained an unsolved problem. A solution to this problem lies in the ability to reverse or prevent denervation atrophy by stimulating and augmenting MuSCs that are already present in the muscles.

II. Definitions

As used herein, the following terms have the meanings ascribed to them unless specified otherwise.

The terms "a," "an," or "the" as used herein not only include aspects with one member, but also include aspects with more than one member. For instance, the singular forms "a," "an," and "the" include plural referents unless the context clearly dictates otherwise. Thus, for example, reference to "a cell" includes a plurality of such cells and reference to "the agent" includes reference to one or more agents known to those skilled in the art, and so forth.

The term "prostaglandin E2" or "PGE2" refers to prostaglandin that can be synthesized via arachidonic acid via cyclooxygenase (COX) enzymes and terminal prostaglandin E synthases (PGES). PGE2 plays a role in a number of biological functions including vasodilation, inflammation, and modulation of sleep/wake cycles.

The term "prostaglandin E2 receptor agonist" or "PGE2 receptor agonist" refers to a chemical compound, small molecule, polypeptide, biological product, etc. that can bind to and activate any PGE2 receptor, thereby stimulating the PGE2 signaling pathway.

The term "compound that attenuates PGE2 catabolism" refers to a chemical compound, small molecule, polypeptide, biological product, etc. that can reduce or decrease the breakdown of PGE2.

The term "compound that neutralizes PGE2 inhibition" refers to a chemical compound, small molecule, polypeptide, biological product, etc. that can block or impede an inhibitor of PGE2 synthesis, activity, secretion, function, and the like.

The term "compound that attenuates PGE2 catabolism" refers to a physical process that attenuates the transport of PGE2 via a transporter for the breakdown of PGE2 intracellularly. This process can be the physical block of a prostaglandin transporter, which transports PGE2 inside cells for catabolism by 15-PGDH. The prostaglandin transporter is also known as 2310021C19Rik, MATR1, Matrin F/Q, OATP2A1, PGT, PHOAR2, SLC21A2, solute carrier organic anion transporter family member 2A1, and SLCO2A1.

The term "derivative," in the context of a compound, includes but is not limited to, amide, ether, ester, amino, carboxyl, acetyl, and/or alcohol derivatives of a given compound.

The term "treating" or "treatment" refers to any one of the following: ameliorating one or more symptoms of disease; preventing the manifestation of such symptoms before they occur; slowing down or completely preventing the progression of the disease (as may be evident by longer periods between reoccurrence episodes, slowing down or prevention of the deterioration of symptoms, etc.); enhancing the onset of a remission period; slowing down the irreversible damage caused in the progressive-chronic stage of the disease (both in the primary and secondary stages); delaying the onset of said progressive stage; or any combination thereof.

The term "administer," "administering," or "administration" refers to the methods that may be used to enable delivery of agents or compositions such as the compounds and cells described herein to a desired site of biological action. These methods include, but are not limited to, parenteral administration (e.g., intravenous, subcutaneous, intraperitoneal, intramuscular, intra-arterial, intravascular, intracardiac, intrathecal, intranasal, intradermal, intravitreal, and the like), transmucosal injection, oral administration, administration as a suppository, and topical administration. One skilled in the art will know of additional methods for administering a therapeutically effective amount of the compounds and/or cells described herein for preventing or relieving one or more symptoms associated with a disease or condition.

The term "therapeutically effective amount" or "therapeutically effective dose" or "effective amount" refers to an amount of a compound, therapeutic agent (e.g., cells), and/or pharmaceutical drug that is sufficient to bring about a beneficial or desired clinical effect. A therapeutically effective amount or dose may be based on factors individual to each patient, including, but not limited to, the patient's age, size, type or extent of disease, stage of the disease, route of administration of the regenerative cells, the type or extent of supplemental therapy used, ongoing disease process and type of treatment desired (e.g., aggressive vs. conventional treatment). Therapeutically effective amounts of a pharmaceutical compound or compositions, as described herein, can be estimated initially from cell culture and animal models. For example, $IC_{50}$ values determined in cell culture methods can serve as a starting point in animal models, while $IC_{50}$ values determined in animal models can be used to find a therapeutically effective dose in humans.

The term "pharmaceutically acceptable carrier" refers to a carrier or a diluent that does not cause significant irritation to an organism and does not abrogate the biological activity and properties of the administered compound.

The terms "subject," "individual," and "patient" are used interchangeably herein to refer to a vertebrate, preferably a mammal, more preferably a human. Mammals include, but are not limited to, murines, rats, simians, humans, farm animals, sport animals, and pets.

The term "mechanical injury" refers to myotoxic effects that are induced by physical processes, non-limiting examples including cutting, burning, freezing, needle puncture, and exercise. In some instances, mechanical injury occurs as the result of a surgical procedure (e.g., a surgical procedure or treatment that comprises cutting, incising, suturing, and/or repairing a muscle) or a traumatic injury (e.g., accidental trauma or injury), non-limiting examples being blunt and/or crush injuries (e.g., involving limbs or appendages such as the arms, legs, hand, feet, and digits).

The term "myotoxin" means a compound that induces damage or death in muscle cells. In some embodiments, the toxic effects produced in muscle cells (e.g., muscle cell damage, muscle cell death) by the myotoxin may trigger, either directly or indirectly, the subsequent activation of muscle stem cells, muscle regeneration, or both. Non-limiting examples of myotoxins include anesthetics (e.g., bupivacaine), divalent cations, snake venom, lizard venom, bee venom, and compounds contained within (e.g., notexin, cardiotoxin, and bungarotoxin).

In some cases, the myotoxin is a mild myotoxin. A mild myotoxin as used herein means that muscle tissue is subjected to minor damage assessed by histology. A mild myotoxin as used herein may include any compound that causes transient but reversible muscle damage or cell death. Myotoxicity of excipients administered intramuscularly can be assessed by monitoring recruitment of inflammatory cells (leucocytes, macrophages and other monocytes), induction of transient cytokine levels, growth factors and inflammatory metabolites. Histologically, myotoxicity could be assessed by disruption of myofiner architecture and the encompassing matrix, induction of acute cell death and necrosis, induction of acute muscle resident cell proliferation (including muscle stem cells), induction of embryonic myosin heavy chain (eMHC) expression, and presence of central nuclei position within myofibers. Systemically, myotoxicity can also be detected by muscle creatin kinase level. Functionally, myotoxicity can be detected by reduction in muscle force and disruption in neuromuscular junction.

Reversibility of the myotoxicity can be assessed by restoration in the damaged myofiber histology in a short duration (for example, in about 21 days in a mouse model), lack of fibrosis in the tissue (lack of excess collagen deposition or other matrix constituents) and lack of lipid deposition (adipocyte transdifferentiation).

Non-limiting examples of mild myotoxins may include anesthetics, such as, e.g., bupivacaine or lidocaine.

The term "acute exposure," in the context of administration of a compound, refers to a temporary or brief application of a compound to a subject, e.g., human subject, or cells. In some embodiments, an acute exposure includes a single administration of a compound over the course of treatment or over an extended period of time.

The term "intermittent exposure," in the context of administration of a compound, refers to a repeated application of a compound to a subject, e.g., human subject, or cells, wherein a desired period of time lapses between applications.

The term "acute regimen," in the context of administration of a compound, refers to a temporary or brief application of a compound to a subject, e.g., human subject, or to a repeated application of a compound to a subject, e.g., human subject, wherein a desired period of time (e.g., 1 day) lapses between applications. In some embodiments, an acute regimen includes an acute exposure (e.g., a single dose) of a compound to a subject over the course of treatment or over an extended period of time. In other embodiments, an acute regimen includes intermittent exposure (e.g., repeated doses) of a compound to a subject in which a desired period of time lapses between each exposure.

The term "continuous exposure," in the context of administration of a compound, refers to a repeated, chronic application of a compound to a subject, e.g., human subject, or cells, over an extended period of time.

The term "chronic regimen," in the context of administration of a compound, refers to a repeated, chronic application of a compound to a subject, e.g., human subject, over an extended period of time such that the amount or level of the compound is substantially constant over a selected time period. In some embodiments, a chronic regimen includes a continuous exposure of a compound to a subject over an extended period of time.

III. Detailed Description of the Embodiments

A. Compositions and Pharmaceutical Compositions

In one aspect of the present invention, provided herein is a composition for preventing or treating a muscle condition. In some embodiments, the composition comprises a prostaglandin E2 (PGE2) compound and a myotoxin. In some embodiments, the PGE2 compound is selected from the group consisting of PGE2, a PGE2 prodrug, a PGE2 receptor agonist, a compound that attenuates PGE2 catabolism, a compound that neutralizes PGE2 inhibition, a derivative thereof, an analog thereof, and a combination thereof. A prodrug of PGE2 can be metabolized into a pharmacologically active PGE2 drug, for example, at the site of administration or muscle regeneration, or when the prodrug is exposed to muscle cells.

In particular embodiments, the PGE2 compound is a PGE2 derivative or analog that contains one or more modifications to PGE2 that increase its stability, activity, resistance to degradation, transport into muscle cells (e.g., promote cellular uptake), and/or retention in muscle cells (e.g., reduce secretion from muscle cells after uptake).

Without limitation, examples of PGE2 derivatives and analogs include 2,2-difluoro-16-phenoxy-PGE2 compounds, 2-decarboxy-2-hydroxymethyl-16-fluoro-PGE2 compounds, 2-decarboxy-2-hydroxymethyl-11-deoxy-PGE2 compounds, 19(R)-hydroxy PGE2, 16,16-dimethyl PGE2, 16,16-dimethyl PGE2 p-(p-acetamidobenzamido) phenyl ester, 11-deoxy-16,16-dimethyl PGE2 (dmPGE2), 9-deoxy-9-methylene-16,16-dimethyl PGE2, 9-deoxy-9-methylene PGE2, butaprost, sulprostone, enprostil, PGE2 serinol amide, PGE2 methyl ester, 16-phenyl tetranor PGE2, 5-trans-PGE2, 15(S)-15-methyl PGE2, and 15(R)-15-methyl PGE2. Additional PGE2 derivatives and analogs are set forth, e.g., in U.S. Pat. No. 5,409,911.

Additional non-limiting examples of PGE2 derivatives and analogs include hydantoin derivatives of PGE2, the more stable PGE2 analogs described in Zhao et al. (*Bioorganic & Medicinal Chemistry Letters*, 17:6572-5 (2007)) in which the hydroxy cyclopentanone ring is replaced by heterocyclic rings and the unsaturated alpha-alkenyl chain is substituted with a phenethyl chain, the PGE2 analogs described in Ungrin et al. (*Mol. Pharmacol.*, 59:1446-56 (2001)), the 13-dehydro derivatives of PGE2 described in Tanami et al. (*Bioorg. Med. Chem. Lett.*, 8:1507-10 (1998)), and the substituted cyclopentanes described in U.S. Pat. Nos. 8,546,603 and 8,158,676.

In some embodiments, the PGE2 compound is an agonist of a PGE2 receptor, e.g., EP1 receptor, EP2 receptor, EP3 receptor, and EP4 receptor. Non-limiting examples of PGE2 receptor agonists include ONO-DI-004, ONO-AE1-259, ONO-AE-248, ONO-AE1-329, ONO-4819CD (Ono Pharmaceutical Co., Japan), L-902688 (Cayman Chemical), CAY10598 (Cayman Chemical), and CP-533536 (Pfizer). Additional PGE2 receptor agonists are described, e.g., in U.S. Pat. Nos. 6,410,591; 6,610,719; 6,747,037; 7,696,235; 7,662,839; 7,652,063; 7,622,475; and 7,608,637.

In particular embodiments, the PGE2 receptor agonist comprises a compound of Formula (I), a derivative thereof, a pharmaceutically acceptable salt thereof, a solvate thereof, a stereoisomer thereof, or a combination thereof,

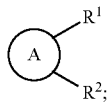

Formula (I)

wherein ring A is a substituted 4- to 6-membered cycloalkyl ring or a substituted 4- to 6-membered cycloalkenyl ring that comprises substituents $R^1$ and $R^2$ that are independently selected from the group consisting of substituted $C_1$-$C_{10}$ alkyl and substituted $C_2$-$C_{10}$ alkenyl, and ring A further comprises one or more additional substituents. In some embodiments, ring A is a substituted cyclopentyl ring or a substituted cyclopentenyl ring. In particular embodiments, the one or more additional substituents on ring A are selected from the group consisting of deuterium, hydroxy, amino, oxo, $C_1$-$C_6$ alkyl, and halogen. In some instances, the one or more additional substituents on ring A are hydroxy or oxo. In some embodiments, ring A has two additional substituents that are taken together to form a covalent bond to form a heterocycloalkyl ring.

In some embodiments, ring A is selected from the consisting of

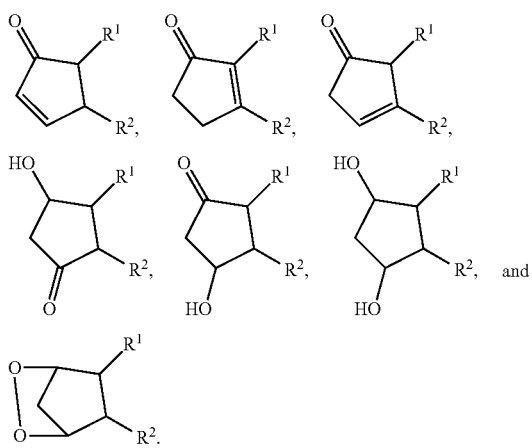

In particular embodiments, ring A is selected from the group consisting of from the group consisting of

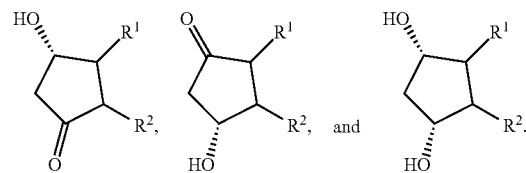

In some instances, ring A is

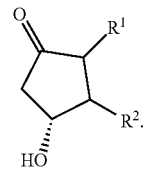

In some embodiments, $R^1$ is substituted $C_1$-$C_{10}$ alkyl. In other embodiments, $R^1$ is substituted $C_2$-$C_{10}$ alkenyl. In some embodiments, $R^1$ is selected from the group consisting of deuterium, hydroxy, oxo, $C_1$-$C_6$ alkyl, —COOR$^3$, and halogen, wherein $R^3$ is hydrogen or $C_1$-$C_6$ alkyl.

In some embodiments, $R^1$ is selected from the group consisting of

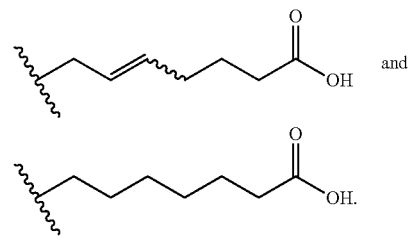

In other embodiments, $R^1$ is selected from the group consisting of

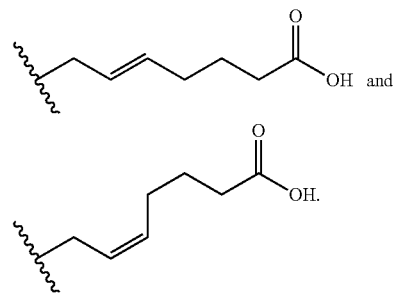

In some instances, $R^1$ is

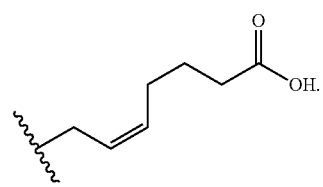 [SMILES: *C/C=C\CCCC(=O)O]

In some embodiments, $R^2$ is substituted $C_1$-$C_{10}$ alkyl. In other embodiments, $R^2$ is substituted $C_2$-$C_{10}$ alkenyl. In some embodiments, the substituent on $R^2$ is selected from the group consisting of deuterium, hydroxy, oxo, $C_1$-$C_6$ alkyl, —COOR$^3$, and halogen, wherein $R^3$ is hydrogen or $C_1$-$C_6$ alkyl.
In some embodiments $R^2$ is selected from the group consisting of
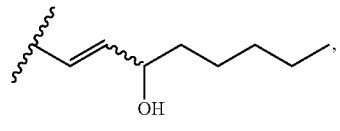
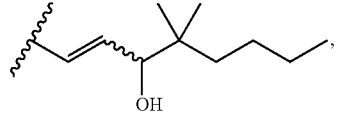
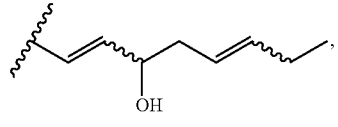
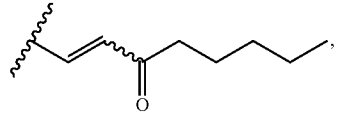
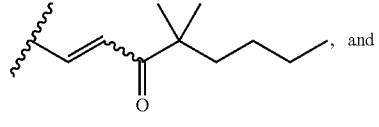, and
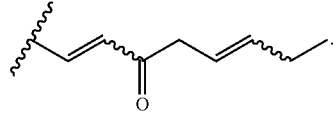.
In some embodiments, $R^2$ is selected from the group consisting of
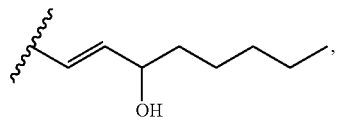
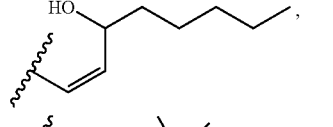
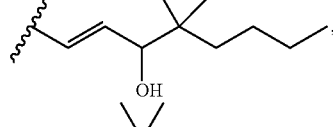
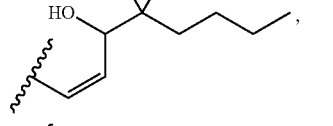
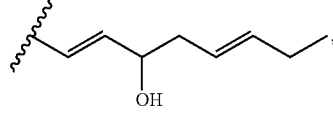
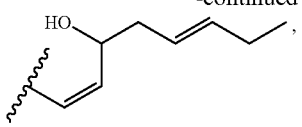
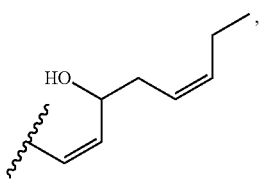
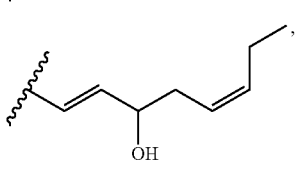
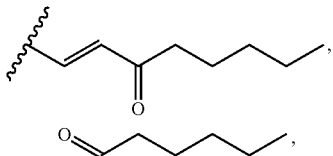
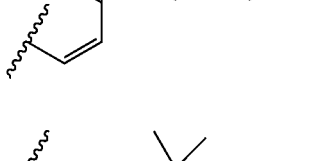
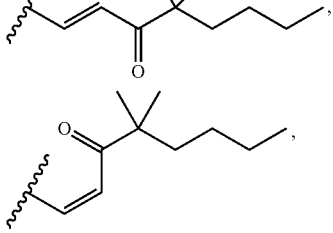
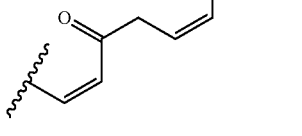, and
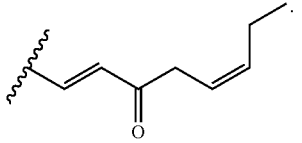.

In some instances, $R^2$ is

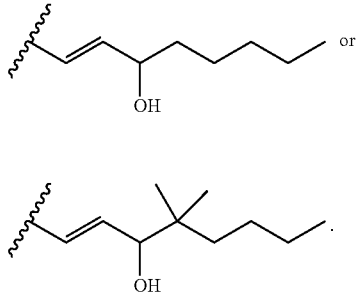

or

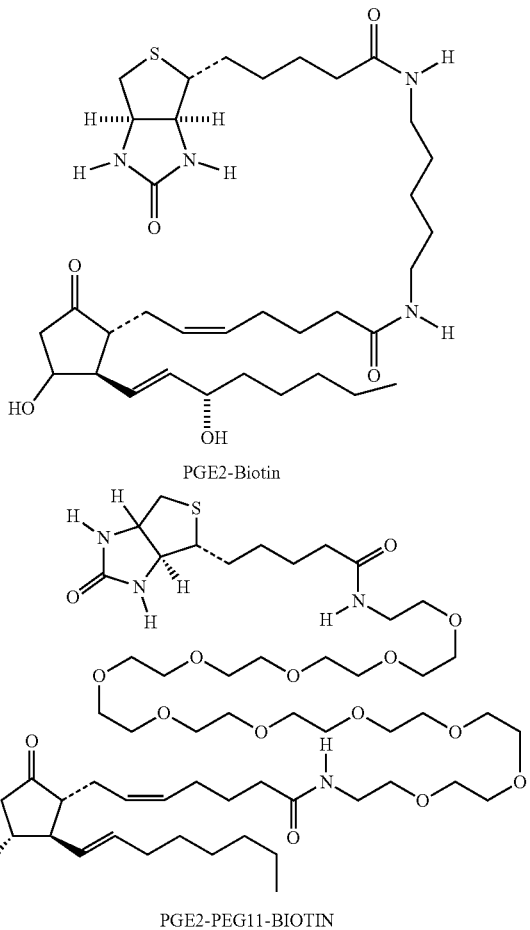

PGE2-Biotin

PGE2-PEG11-BIOTIN

In some embodiments, the compound of Formula (I), the pharmaceutically acceptable salt thereof, the solvate thereof, or the stereoisomer thereof is a compound of Formula (Ia), Formula (Ib), Formula (Ic), or Formula (Id), or is a pharmaceutically acceptable salt thereof, a solvate thereof, or a stereoisomer thereof:

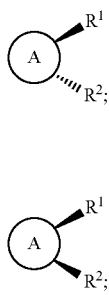

Formula (Ia)

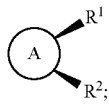

Formula (Ib)

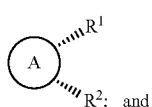

Formula (Ic)

and

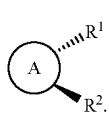

Formula (Id)

In some instances, the compound is of Formula (Id).

In some embodiments, the PGE2 compound is PGE2. In other embodiments, the PGE2 compound is a derivative of PGE2. In some instances, the derivative is 16,16-dimethyl prostaglandin E2 (dmPGE2). In particular embodiments, the PGE2 compound is PGE2 and/or dmPGE2.

In other embodiments, the PGE2 compound is a derivative of PGE2. In some instances, the derivative is PGE2 conjugated to a moiety. In particular embodiments, the PGE2 compound is PGE2-Biotin or PGE2-PEG (Polyethylene glycol) hydrogel. Exemplary embodiments are shown below.

In some embodiments, the PGE2 derivative comprises a PGE2 compound conjugated to a molecular probe. In some cases, the molecular probe is a peptide sequence, a fragment antigen-binding (Fab), a heavy-chain only antibody (HcAbs), a full-length antibody (Ab), a single-domain antibody/nanobody (Nb), or a nanoparticle, or a combination. In some cases, the molecular probe is capable of homing to and targeting muscle tissue via systemic delivery.

In those embodiments, a PGE2 derivative comprising a PGE2 compound conjugated to a molecular probe may increase the half-life of the PGE2 compound, increase the specificity of the PGE compound, and reduce adverse off-target effects of the PGE2 compound. Non-limiting examples of PGE2 conjugated to a molecular probe include PGE2-Integrin-alpha7 antibody or nanobody; PGE2-M-cadherin antibody or nanobody; and PGE2-anti PGE2 antibody. In some cases, a PGE2 derivative comprising a PGE2 compound conjugated to a molecular probe may be used to treat sarcopenia or cachexia.

In some embodiments, the PGE2 compound is a compound that attenuates PGE2 catabolism. In some cases, a compound that attenuates PGE2 catabolism can be a compound, a neutralizing peptide, or a neutralizing antibody that inactivates or blocks 15-hydroxyprostaglandin dehydrogenase (15-PGDH) or inactivates or blocks a prostaglandin transporter, which transports PGE2 inside cells for catabolism by 15-PGDH. The prostaglandin transporter is also known as 2310021C19Rik, MATR1, Matrin F/Q, OATP2A1, PGT, PHOAR2, SLC21A2, solute carrier organic anion transporter family member 2A1, and SLCO2A1.

In some embodiments, the composition may include a stem-cell inducing molecule. In some cases, the stem-cell inducing molecule is a PGE2 compound as described herein. In some cases, the composition includes a stem-cell inducing molecule in combination with a myotoxin. Other non-limiting examples of stem-cell inducing molecules that may be used herein include oxytocin, beta integrin activating antibody, rapamycin, SetD7 inhibitors, p38 MAPK inhibitors (such as SB202190 and SB203580), neuregulin, nerve growth factor (NGF), Hif2alpha inhibitors, basic fibroblast growth factor (bFGF), fibroblast growth factor 4 (FGF4), epidermal growth factor (EGF), Interleukin-1α, Interleukin-13, TNFα, LIF, IL6, interferon gamma, oncostatin M (OSM), ghrelin, and apelin.

In some embodiments, the myotoxin is selected from the group consisting of an anesthetic, a divalent cation, venom from snakes, venom from lizards, venom from bees, and a combination thereof. Suitable divalent cations include but are not limited to $Ba^{2+}$, $Sr^{2+}$, $Mg^{2+}$, $Ca^{2+}$, $Mn^{2+}$, $Ni^{2+}$, $Co^{2+}$, salts thereof, and combinations thereof. In some embodiments, the snake or lizard venom is selected from the group consisting of notexin, cardiotoxin, bungarotoxin, and a combination thereof.

In some embodiments, the anesthetic is selected from the group consisting of an amino-amide anesthetic, an amino-ester anesthetic, and a combination thereof. In some cases, the anesthetic is a mild myotoxin. Non-limiting examples of amino-amide anesthetics include bupivacaine, levobupivacaine, articaine, ropivacaine, butanilicaine, carticaine, dibucaine, etidocaine, lidocaine, mepivacaine, prilocaine, and trimecaine. In some embodiments, the composition comprises a combination of amino-amide anesthetics.

In some embodiments, the anesthetic is an amino-ester anesthetic. In particular embodiments, the amino-ester anesthetic is an aminobenzoic acid ester anesthetic, a benzoic acid ester anesthetic, or a combination thereof. Non-limiting examples of aminobenzoic acid ester anesthetics include benzocaine, butacaine, butamben, chloroprocaine, dimethocaine, lucaine, meprylcaine, metabutethamine, metabutoxycaine, nitracaine, orthocaine, propoxycaine, procaine, proxymetacaine, risocaine, and tetracaine. Non-limiting examples of benzoic acid anesthetics include amylocaine, cocaine, cyclomethycaine, α-eucaine, β-eucaine, hexylcaine, isobucaine, and piperocaine. In particular embodiments, the composition comprises a combination of one or more aminobenzoic acid ester anesthetics and/or one or more benzoic acid ester anesthetics.

Other non-limiting examples of anesthetics that may have mild myotoxic effects include benzonatate, diperodon, fomocaine, fotocaine, hydroxyprocaine, oxetacaine, oxybuprocaine, paraethoxycaine, phenacaine, piridocaine, pramocaine, primacaine, procainamide, proparacaine, pyrrocaine, quinisocaine, tolycaine, and tropacocaine.

In some embodiments, the composition comprises a PGE2 compound that comprises PGE2 and/or dmPGE2 and a myotoxin that is bupivacaine.

Compositions of the present invention may be suitable for treating any number of muscle conditions, including but not limited to muscle conditions that are associated with muscle damage, injury, or atrophy. The compositions are also useful for promoting muscle regeneration in a subject in need thereof, for increasing muscle mass in a subject in need thereof, or both. Non-limiting examples of suitable conditions for prevention or treatment with compositions of the present invention include traumatic injury (e.g., acute muscle trauma, acute nerve trauma), acute muscle injury, acute nerve injury, chronic nerve injury, soft tissue hand injury, carpal tunnel syndrome (CTS), Duchenne muscular dystrophy (DMD), Becker muscular dystrophy, limb girdle muscular dystrophy, amyotrophic lateral sclerosis (ALS), distal muscular dystrophy (DD), inherited myopathies, myotonic muscular dystrophy (MDD), mitochondrial myopathies, myotubular myopathy (MM), myasthenia gravis (MG), congestive heart failure, periodic paralysis, polymyositis, rhabdomyolysis, dermatomyositis, cancer cachexia, AIDS cachexia, cardiac cachexia, stress induced urinary incontinence, sarcopenia, spinal muscular atrophy, fecal sphincter dysfunction, Bell's palsy, rotator cuff injury, spinal cord injury, hip replacement, knee replacement, wrist fracture, diabetic neuropathy, gastroesophageal reflux disease (GERD), obstructive sleep apnea (OSA), pelvic floor disorders (e.g., stress urinary incontinence, overactive bladder/urinary urgency incontinence, mixed urinary incontinence, pelvic organ prolapse, fecal incontinence), musculoskeletal disorders (e.g., impaired hand function, impaired thumb function, impaired foot function), plantar fasciitis, foot drop, disuse-induced muscle atrophy, impaired eyelid function (e.g., eyelid drooping, impaired blinking, entropion, ectropion), strabismus, nystagmus, and presbyopia. Additional examples of suitable conditions for prevention or treatment with compositions of the present invention may include muscle disorders that affect small isolated muscles that can be regenerated with localized transplantation of small numbers of cells, including: atrophy and muscle dysfunction in the face or hand after nerve injury or direct trauma that does not recover after reinnervation; extraocular muscle injury causing inability to move the eye and dipoplia seen in Graves' disease, traumatic injury, and progressive external ophthalmoplegia; and urinary and fecal incontinence.

In another aspect of the present invention, provided herein is a pharmaceutical composition. In some embodiments, the pharmaceutical composition comprises a pharmaceutically acceptable carrier and a composition described herein that comprises a PGE2 compound and a myotoxin. In certain aspects, pharmaceutically acceptable carriers are determined in part by the particular composition being administered, as well as by the particular method used to administer the composition. Accordingly, there is a wide variety of suitable formulations of pharmaceutical compositions of the present invention (see, e.g., *Remington's Pharmaceutical Sciences*, 18th Ed., Mack Publishing Co., Easton, Pa. (1990)).

As used herein, "pharmaceutically acceptable carrier" comprises any of standard pharmaceutically accepted carriers known to those of ordinary skill in the art in formulating pharmaceutical compositions. Thus, the cells or compounds, by themselves, such as being present as pharmaceutically acceptable salts, or as conjugates, may be prepared as formulations in pharmaceutically acceptable diluents; for example, saline, phosphate buffer saline (PBS), aqueous ethanol, or solutions of glucose, mannitol, dextran, propylene glycol, oils (e.g., vegetable oils, animal oils, synthetic oils, etc.), microcrystalline cellulose, carboxymethyl cellulose, hydroxylpropyl methyl cellulose, magnesium stearate, calcium phosphate, gelatin, polysorbate 80 or the like, or as solid formulations in appropriate excipients.

The pharmaceutical compositions will often further comprise one or more buffers (e.g., neutral buffered saline or phosphate buffered saline), carbohydrates (e.g., glucose, mannose, sucrose or dextrans), mannitol, proteins, polypeptides or amino acids such as glycine, antioxidants (e.g., ascorbic acid, sodium metabisulfite, butylated hydroxytoluene, butylated hydroxyanisole, etc.), bacteriostats, chelating agents such as EDTA or glutathione, solutes that render the formulation isotonic, hypotonic or weakly hypertonic with the blood of a recipient, suspending agents, thickening agents, preservatives, flavoring agents, sweetening agents, and coloring compounds as appropriate.

The pharmaceutical compositions of the invention may be administered in a manner compatible with the dosage formulation, and in such amount as will be therapeutically effective. The quantity to be administered may depend on a variety of factors including, e.g., the age, body weight, physical activity, and diet of the individual, the condition or disease to be treated, and the stage or severity of the condition or disease. In certain embodiments, the size of the dose may also be determined by the existence, nature, and extent of any adverse side effects that accompany the administration of a therapeutic agent(s) in a particular individual.

It will be understood, however, that the specific dose level and frequency of dosage for any particular patient may be varied and may depend upon a variety of factors including the activity of the specific compound employed, the metabolic stability and length of action of that compound, the age, body weight, hereditary characteristics, general health, sex, diet, mode and time of administration, rate of excretion, drug combination, the severity of the particular condition, and the host undergoing therapy.

In certain embodiments, the dose of the compound may take the form of solid, semi-solid, lyophilized powder, or liquid dosage forms, such as, for example, tablets, pills, pellets, capsules, powders, solutions, suspensions, emulsions, suppositories, retention enemas, creams, ointments, lotions, gels, aerosols, foams, or the like, preferably in unit dosage forms suitable for simple administration of precise dosages.

As used herein, the term "unit dosage form" refers to physically discrete units suitable as unitary dosages for humans and other mammals, each unit containing a predetermined quantity of a therapeutic agent calculated to produce the desired onset, tolerability, and/or therapeutic effects, in association with a suitable pharmaceutical excipient (e.g., an ampoule). In addition, more concentrated dosage forms may be prepared, from which the more dilute unit dosage forms may then be produced. The more concentrated dosage forms thus may contain substantially more than, e.g., at least 1, 2, 3, 4, 5, 6, 7, 8, 9, 10, or more times the amount of the therapeutic compound.

Methods for preparing such dosage forms are known to those skilled in the art (see, e.g., *Remington's Pharmaceutical Sciences*, supra). The dosage forms typically include a conventional pharmaceutical carrier or excipient and may additionally include other medicinal agents, carriers, adjuvants, diluents, tissue permeation enhancers, solubilizers, and the like. Appropriate excipients can be tailored to the particular dosage form and route of administration by methods well known in the art (see, e.g., *Remington's Pharmaceutical Sciences*, supra).

Examples of suitable excipients include, but are not limited to, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, saline, syrup, methylcellulose, ethylcellulose, hydroxypropylmethylcellulose, and polyacrylic acids such as Carbopols, e.g., Carbopol 941, Carbopol 980, Carbopol 981, etc. The dosage forms can additionally include lubricating agents such as talc, magnesium stearate, and mineral oil; wetting agents; emulsifying agents; suspending agents; preserving agents such as methyl-, ethyl-, and propyl-hydroxy-benzoates (i.e., the parabens); pH adjusting agents such as inorganic and organic acids and bases; sweetening agents; and flavoring agents. The dosage forms may also comprise biodegradable polymer beads, dextran, hydrogels, and cyclodextrin inclusion complexes.

For oral administration, the therapeutically effective dose can be in the form of tablets, capsules, emulsions, suspensions, solutions, syrups, sprays, lozenges, powders, and sustained-release formulations. Suitable excipients for oral administration include pharmaceutical grades of mannitol, lactose, starch, magnesium stearate, sodium saccharine, talcum, cellulose, glucose, gelatin, sucrose, magnesium carbonate, and the like.

The therapeutically effective dose can also be provided in a lyophilized form. Such dosage forms may include a buffer, e.g., bicarbonate, for reconstitution prior to administration, or the buffer may be included in the lyophilized dosage form for reconstitution with, e.g., water. The lyophilized dosage form may further comprise a suitable vasoconstrictor, e.g., epinephrine. The lyophilized dosage form can be provided in a syringe, optionally packaged in combination with the buffer for reconstitution, such that the reconstituted dosage form can be immediately administered to an individual.

In some embodiments, a pharmaceutical composition of the present invention comprises a pharmaceutically acceptable carrier that comprises an aqueous base. In other embodiments, the pharmaceutically acceptable carrier comprises a low viscosity compound. In some instances, the low viscosity compound comprises gelatin. In other instances, the low viscosity compound comprises a hydrogel.

B. Methods for Promoting Muscle Regeneration and Preventing or Treating Muscle Conditions In another aspect of the present invention, provided herein is a method for promoting muscle regeneration in a subject in need thereof, increasing muscle mass in a subject in need thereof, or both. In some embodiments, the method comprises administering a combination of a PGE2 compound and a myotoxin to the subject. In some embodiments, a pharmaceutical composition comprising a pharmaceutically acceptable carrier and combination of a PGE2 compound and a myotoxin is administered to the subject. In some embodiments, a therapeutically effective amount of the PGE2 compound is administered to the subject. In other embodiments, a therapeutically effective amount of the myotoxin is administered to the subject. In particular embodiments, a therapeutically effective amount of the PGE2 compound and the myotoxin are administered to the subject.

In yet another aspect of the present invention, provided herein is a method for preventing or treating a muscle condition in a subject in need thereof. In some embodiments, the method comprises administering a combination of a PGE2 compound and a myotoxin to the subject. In some embodiments, a pharmaceutical composition comprising a pharmaceutically acceptable carrier and combination of a PGE2 compound and a myotoxin is administered to the subject. In some embodiments, a therapeutically effective amount of the PGE2 compound is administered to the subject. In other embodiments, a therapeutically effective amount of the myotoxin is administered to the subject. In particular embodiments, a therapeutically effective amount of the PGE2 compound and the myotoxin are administered to the subject.

In still another aspect of the present invention, provided herein is a method for preventing or treating a muscle condition in a subject in need thereof. In some embodiments, the method comprises administering a PGE2 receptor agonist to the subject. In other embodiments, the method further comprises administering a myotoxin to the subject. In some embodiments, a pharmaceutical composition comprising a pharmaceutically acceptable carrier, a PGE2 receptor agonist, and optionally a myotoxin is administered to the subject. In some embodiments, a therapeutically effective amount of the PGE2 receptor agonist is administered to the subject. In other embodiments, a therapeutically effective amount of the myotoxin is administered to the subject. In particular embodiments, a therapeutically effective amount of the PGE2 receptor agonist and the myotoxin are administered to the subject.

In some embodiments, the methods comprise administering a PGE2 compound that is selected from the group consisting of PGE2, a PGE2 prodrug (e.g. PGE2 coupled to neural cadherin (NCAD) that targets NCAD receptor), a PGE2 receptor agonist, a compound that attenuates PGE2 catabolism, a compound that neutralizes PGE2 inhibition, a derivative thereof, an analog thereof, and a combination thereof. A prodrug of PGE2 can be metabolized into a pharmacologically active PGE2 drug, for example, at the site of administration or muscle regeneration, or when the prodrug is exposed to muscle cells. In some cases, the PGE2 compound is a biotinylated drug or other modification that retains PGE2 receptor engagement and signaling but prevents internalization—leading to prolonged activity and overcoming the degradative pathway.

In particular embodiments, the PGE2 compound that is administered is a PGE2 derivative or analog that contains one or more modifications to PGE2 that increase its stability, activity, resistance to degradation, transport into muscle cells (e.g., promote cellular uptake), and/or retention in muscle cells (e.g., reduce secretion from muscle cells after uptake).

Without limitation, examples of PGE2 derivatives and analogs that are suitable for administration according to methods of the present invention include 2,2-difluoro-16-phenoxy-PGE2 compounds, 2-decarboxy-2-hydroxymethyl-16-fluoro-PGE2 compounds, 2-decarboxy-2-hydroxymethyl-11-deoxy-PGE2 compounds, 19(R)-hydroxy PGE2, 16,16-dimethyl PGE2, 16,16-dimethyl PGE2 p-(p-acetamidobenzamido) phenyl ester, 11-deoxy-16,16-dimethyl PGE2 (dmPGE2), 9-deoxy-9-methylene-16,16-dimethyl PGE2, 9-deoxy-9-methylene PGE2, butaprost, sulprostone, enprostil, PGE2 serinol amide, PGE2 methyl ester, 16-phenyl tetranor PGE2, 5-trans-PGE2, 15(S)-15-methyl PGE2, and 15(R)-15-methyl PGE2, and PGE2-Biotin or PGE2-PEG (Polyethylene glycol) hydrogel. Additional PGE2 derivatives and analogs are set forth, e.g., in U.S. Pat. No. 5,409,911.

Additional non-limiting examples of PGE2 derivatives and analogs for administration include hydantoin derivatives of PGE2, the more stable PGE2 analogs described in Zhao et al. (*Bioorganic & Medicinal Chemistry Letters*, 17:6572-5 (2007)) in which the hydroxy cyclopentanone ring is replaced by heterocyclic rings and the unsaturated alpha-alkenyl chain is substituted with a phenethyl chain, the PGE2 analogs described in Ungrin et al. (*Mol. Pharmacol.*, 59:1446-56 (2001)), the 13-dehydro derivatives of PGE2 described in Tanami et al. (*Bioorg. Med. Chem. Lett.*, 8:1507-10 (1998)), and the substituted cyclopentanes described in U.S. Pat. Nos. 8,546,603 and 8,158,676.

In some embodiments, a PGE2 compound that is an agonist of a PGE2 receptor is administered, e.g., EP1 receptor, EP2 receptor, EP3 receptor, and EP4 receptor. Non-limiting examples of PGE2 receptor agonists include ONO-DI-004, ONO-AE1-259, ONO-AE-248, ONO-AE1-329, ONO-4819CD (Ono Pharmaceutical Co., Japan), L-902688 (Cayman Chemical), CAY10598 (Cayman Chemical), and CP-533536 (Pfizer). Additional PGE2 receptor agonists are described, e.g., in U.S. Pat. Nos. 6,410,591; 6,610,719; 6,747,037; 7,696,235; 7,662,839; 7,652,063; 7,622,475; and 7,608,637.

In particular embodiments, the PGE2 receptor agonist that is administered per methods of the present invention comprises a compound of Formula (I), a derivative thereof, a pharmaceutically acceptable salt thereof, a solvate thereof, a stereoisomer thereof, or a combination thereof,

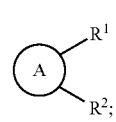

Formula (I)

wherein ring A is a substituted 4- to 6-membered cycloalkyl ring or a substituted 4- to 6-membered cycloalkenyl ring that comprises substituents $R^1$ and $R^2$ that are independently selected from the group consisting of substituted $C_1$-$C_{10}$ alkyl and substituted $C_2$-$C_{10}$ alkenyl, and ring A further comprises one or more additional substituents. In some embodiments, ring A is a substituted cyclopentyl ring or a substituted cyclopentenyl ring. In particular embodiments, the one or more additional substituents on ring A are selected from the group consisting of deuterium, hydroxy, amino, oxo, $C_1$-$C_6$ alkyl, and halogen. In some instances, the one or more additional substituents on ring A are hydroxy or oxo. In some embodiments, ring A has two additional substituents that are taken together to form a covalent bond to form a heterocycloalkyl ring.

In some embodiments, ring A is selected from the consisting of

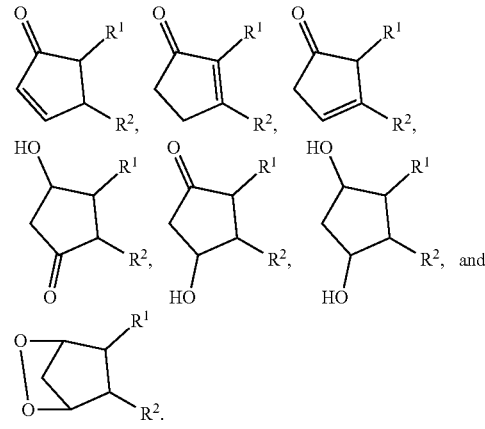

In particular embodiments, ring A is selected from the group consisting of from the group consisting of

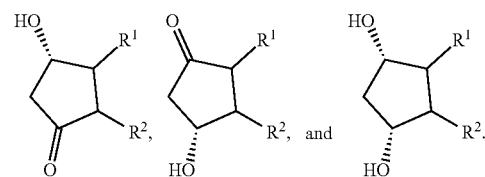

In some instances, ring A is

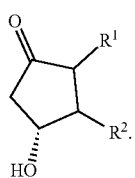

In some embodiments, $R^1$ is substituted $C_1$-$C_{10}$ alkyl. In other embodiments, $R^1$ is substituted $C_2$-$C_{10}$ alkenyl. In some embodiments, $R^1$ is selected from the group consisting of deuterium, hydroxy, oxo, $C_1$-$C_6$ alkyl, —COOR$^3$, and halogen, wherein $R^3$ is hydrogen or $C_1$-$C_6$ alkyl.

In some embodiments, $R^1$ is selected from the group consisting of

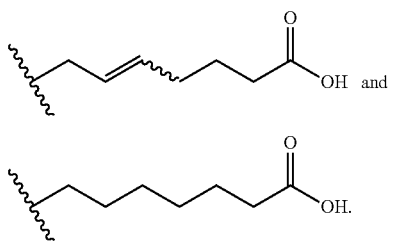

In other embodiments, $R^1$ is selected from the group consisting of

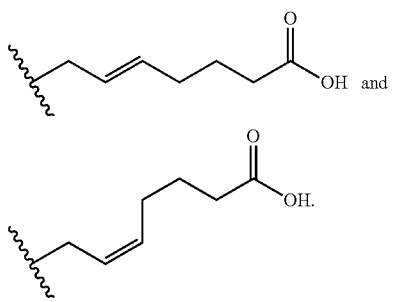

In some instances, $R^1$ is

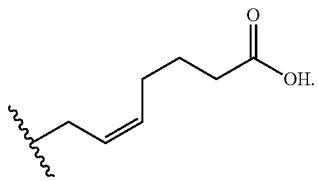 [SMILES: *C/C=C\CCCC(=O)O]

In some embodiments, $R^2$ is substituted $C_1$-$C_{10}$ alkyl. In other embodiments, $R^2$ is substituted $C_2$-$C_{10}$ alkenyl. In some embodiments, the substituent on $R^2$ is selected from the group consisting of deuterium, hydroxy, oxo, $C_1$-$C_6$ alkyl, —COOR$^3$, and halogen, wherein $R^3$ is hydrogen or $C_1$-$C_6$ alkyl.

In some embodiments, $R^2$ is selected from the group consisting of

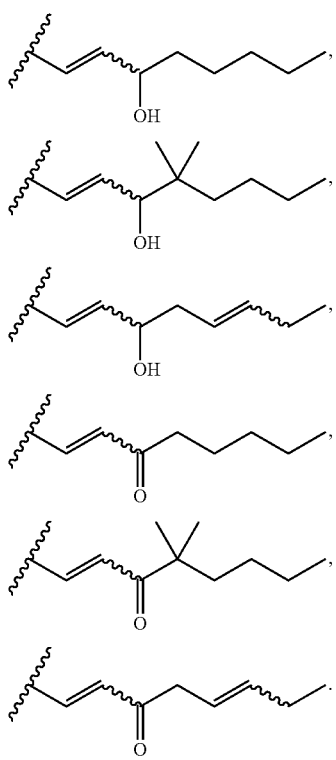

In some embodiments, $R^2$ is selected from the group consisting of

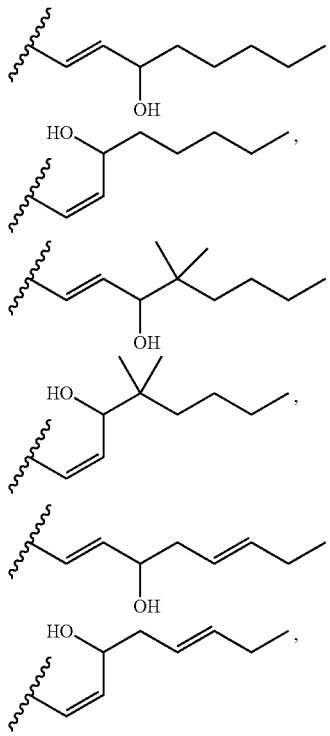

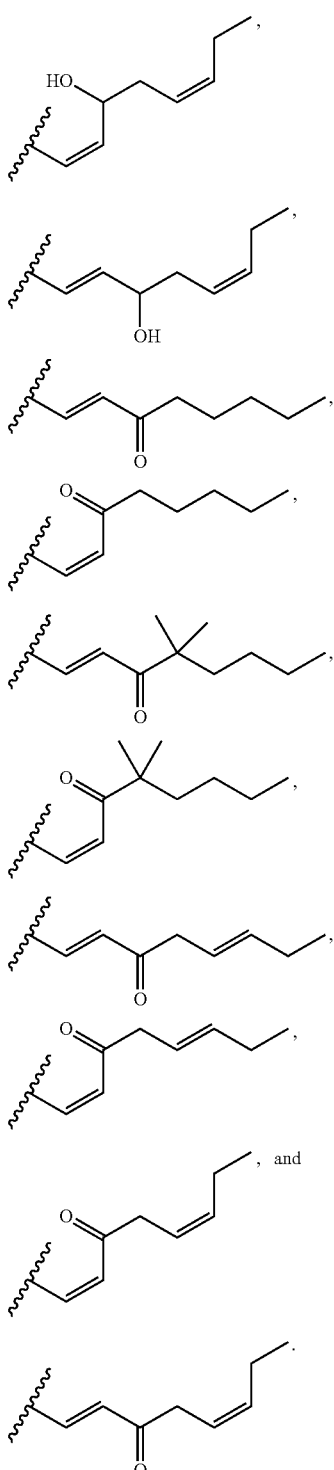

In some instances, R² is

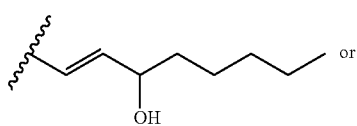

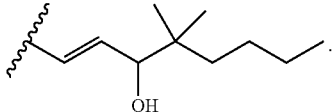

In some embodiments, the compound of Formula (I), the pharmaceutically acceptable salt thereof, the solvate thereof, or the stereoisomer thereof is a compound of Formula (Ia), Formula (Ib), Formula (Ic), or Formula (Id), or is a pharmaceutically acceptable salt thereof, a solvate thereof, or a stereoisomer thereof:

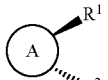

Formula (Ia)

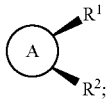

Formula (Ib)

Formula (Ic)

Formula (Id)

In some instances, the compound is of Formula (Id).

In some embodiments, the PGE2 compound that is administered according to the methods of the present invention comprises PGE2. In other embodiments, the PGE2 compound that is administered comprises a derivative of PGE2. In some instances, the derivative is 16,16-dimethyl prostaglandin E2 (dmPGE2). In particular embodiments, the PGE2 compound that is administered comprises PGE2 and/or dmPGE2.

In some embodiments, the PGE2 compound that is administered is a compound that attenuates PGE2 catabolism. In some cases, a compound that attenuates PGE2 catabolism can be a compound, a neutralizing peptide, or a neutralizing antibody that inactivates or blocks 15-hydroxy-prostaglandin dehydrogenase (15-PGDH) or inactivates or blocks a prostaglandin transporter, which transports PGE2 inside cells for catabolism by 15-PGDH. The prostaglandin transporter is also known as 2310021C19Rik, MATR1, Matrin F/Q, OATP2A1, PGT, PHOAR2, SLC21A2, solute carrier organic anion transporter family member 2A1, and SLCO2A1.

In some embodiments, the composition that is administered according to the methods of the present invention may include a stem-cell inducing molecule. In some cases, the stem-cell inducing molecule is a PGE2 compound as described herein. Other non-limiting examples of stem-cell inducing molecules that may be used herein include oxytocin, beta integrin activating antibody, rapamycin, SetD7 inhibitors, p38 MAPK inhibitors (such as SB202190 and SB203580), neuregulin, nerve growth factor (NGF), Hif2alpha inhibitors, basic fibroblast growth factor (bFGF), fibroblast growth factor 4 (FGF4), epidermal growth factor (EGF), Interleukin-1α, Interleukin-13, TNFα, LIF, IL6, interferon gamma, oncostatin M (OSM), ghrelin, and apelin.

In some embodiments, the myotoxin that is administered according to methods of the present invention is selected from the group consisting of an anesthetic, a divalent cation, venom from snakes, venom from lizards, venom from bees, and a combination thereof. Suitable divalent cations include but are not limited to $Ba^{2+}$, $Sr^{2+}$, $Mg^{2+}$, $Ca^{2+}$, $Mn^{2+}$, $Ni^{2+}$, $Co^{2+}$, salts thereof, and combinations thereof. In some embodiments, the snake or lizard venom is selected from the group consisting of notexin, cardiotoxin, bungarotoxin, and a combination thereof.

In some embodiments, the anesthetic is selected from the group consisting of an amino-amide anesthetic, an amino-ester anesthetic, and a combination thereof. In some cases, the anesthetic is a mild myotoxin. Non-limiting examples of amino-amide anesthetics include bupivacaine, levobupivacaine, articaine, ropivacaine, butanilicaine, carticaine, dibucaine, etidocaine, lidocaine, mepivacaine, prilocaine, and trimecaine. In some embodiments, the composition comprises a combination of amino-amide anesthetics.

In some embodiments, the anesthetic is an amino-ester anesthetic. In particular embodiments, the amino-ester anesthetic is an aminobenzoic acid ester anesthetic, a benzoic acid ester anesthetic, or a combination thereof. Non-limiting examples of aminobenzoic acid ester anesthetics include benzocaine, butacaine, butamben, chloroprocaine, dimethocaine, lucaine, meprylcaine, metabutethamine, metabutoxycaine, nitracaine, orthocaine, propoxycaine, procaine, proxymetacaine, risocaine, and tetracaine. Non-limiting examples of benzoic acid anesthetics include amylocaine, cocaine, cyclomethycaine, α-eucaine, β-eucaine, hexylcaine, isobucaine, and piperocaine. In particular embodiments, the composition comprises a combination of one or more aminobenzoic acid ester anesthetics and/or one or more benzoic acid ester anesthetics.

Other non-limiting examples of anesthetics that may have mild myotoxic effects include benzonatate, diperodon, fomocaine, fotocaine, hydroxyprocaine, oxetacaine, oxybuprocaine, paraethoxycaine, phenacaine, piridocaine, pramocaine, primacaine, procainamide, proparacaine, pyrrocaine, quinisocaine, tolycaine, and tropacocaine.

In some embodiments, the composition for administration according to methods of the present invention comprises a PGE2 compound that comprises PGE2 and/or dmPGE2 and a myotoxin that is an anesthetic (e.g., bupivacaine). In particular embodiments, no anesthetic is administered to the subject. In some embodiments, a myotoxin that is not an anesthetic is administered to the subject.

The methods provided herein can be used to prevent or treat a muscle condition or disease (e.g., a muscle condition or disease associated with muscle damage, injury, or atrophy) in a subject in need thereof. The method can provide prophylactic treatment to a subject who is likely to experience a muscle condition (e.g., muscle damage, injury, or atrophy). In some embodiments, the subject can have a condition or disease with possible secondary symptoms that affect muscle. In other embodiments, the subject has undergone a surgical or therapeutic procedure or intervention to treat the muscle condition or disease, and the method disclosed herein is used to prevent or inhibit recurrence or relapse. In some embodiments, the subject has any one of the conditions or diseases described herein that affects muscle.

As used herein, the term "treatment" or "treating" encompasses administration of compounds and/or cells in an appropriate form prior to the onset of disease symptoms and/or after clinical manifestations, or other manifestations of the condition or disease to reduce disease severity, halt disease progression, or eliminate the disease. The term "prevention of" or "preventing" a disease includes prolonging or delaying the onset of symptoms of the condition or disease, preferably in a subject with increased susceptibility to the condition or disease. In some embodiments, treating the subject produces an improvement in muscle strength and/or muscle coordination.

The methods provided herein may be useful for promoting muscle regeneration in a subject in need thereof, for increasing muscle mass in a subject in need thereof, or both. Regeneration of muscle includes forming new muscle fibers from muscle stem cells, satellite cells, muscle progenitor cells, and any combination thereof. The methods are also useful for enhancing or augmenting muscle repair, maintenance, or both. Furthermore, by promoting muscle regeneration, the methods provided herein also promote neuromuscular junction establishment and restoration of muscle contractile function and volume.

In some embodiments, the methods provided herein comprise administering a composition comprising a PGE2 compound and a myotoxin to a muscle or a muscle cell in vivo. In other embodiments, the methods provided herein comprise providing to a muscle cell a first composition comprising a PGE2 compound ex vivo, and administering the muscle cell to a muscle in vivo. In some cases, the first composition may further comprise a myotoxin. In other cases, the administering the muscle cell to a muscle in vivo further comprises administering a myotoxin to the muscle in vivo.

In some embodiments, the methods provided herein further comprise administering a senolytic drug. A senolytic drug is a drug that induces clearance of senescent cells that produce a senescence-associated secretory phenotype. In some cases, a senolytic drug is a drug that targets a pathway involving BCL-2, BCL-XL, MDM2, p53, p21, serpine (PAI-1&2), HSP-90, PI3Kδ, AKT, HIF1alpha, ephrin, or a combination thereof. Examples of a senolytic drug include dasatinib, alvespimycin, geldanamycin, tanespimycin; fisetin, ABT-263, ABT-767, A1331852, and A1155463. In some cases, administering of a senolytic drug is before, during, after, or a combination, administering a composition comprising a PGE2 compound and a myotoxin.

According to methods of the present invention, compositions and pharmaceutical compositions of the present invention (e.g., comprising a combination of a PGE2 compound and a myotoxin, or comprising a PGE2 receptor agonist and optionally a myotoxin) can be administered to a subject experiencing a muscle condition such as muscle injury, degeneration, damage, atrophy, or any combination thereof. In some instances, the muscle condition is the result of partial or complete denervation. Muscle atrophy can include loss of muscle mass, loss of muscle strength, or both. Muscle atrophy may affect any muscle of a subject. In some cases, the subject in need of the compositions, methods, and kits provided herein may be exhibiting or experiencing muscle loss due to, e.g., age, inactivity, injury, disease, or any combination thereof.

In some embodiments, compounds can activate muscle cell proliferation, muscle cell differentiation, fusion of muscle cells, or any combination thereof. In some cases, the muscle tissue may be regenerated. In other cases, muscle function (e.g., muscle mass, muscle strength, muscle contraction, or any combination thereof) may be restored or enhanced. In some cases, muscle weakness and atrophy may be ameliorated.

The damaged muscle can be any muscle of the body, including but not limited to, musculi pectoralis complex, latissimus dorsi, teres major and subscapularis, brachioradialis, biceps, brachialis, pronator quadratus, pronator teres, flexor carpi radialis, flexor carpi ulnaris, flexor digitorum superficialis, flexor digitorum profundus, flexor pollicis brevis, opponens pollicis, adductor pollicis (e.g., abductor pollicis brevis, abductor pollicis longus), flexor pollicis brevis, iliopsoas, psoas, rectus abdominis, rectus femoris, gluteus maximus, gluteus medius, medial hamstrings, gastrocnemius, lateral hamstring, quadriceps mechanism, adductor longus, adductor brevis, adductor magnus, gastrocnemius medial, gastrocnemius lateral, soleus, tibialis posterior, tibialis anterior, flexor digitorum longus, flexor digitorum brevis, flexor hallucis longus, extensor hallucis longus, hand muscles, arm muscles, foot muscles, leg muscles, chest muscles, stomach muscles, back muscles, buttock muscles, shoulder muscles, head and neck muscles, facial muscles, oculopharyngeal muscles, and the like. In some instances, the muscle may be an abductor pollicis brevis muscle.

Subjects in need of muscle regeneration may have musculoskeletal injuries (e.g., fractures, strains, sprains, acute injuries, overuse injuries, and the like), post-trauma damages to limbs or face, athletic injuries, post-fractures in the aged, soft tissue hand injuries, muscle atrophy (e.g., loss of muscle mass), Duchenne muscular dystrophy (DMD), Becker muscular dystrophy, Fukuyama congenital muscular dystrophy (FCMD), limb-girdle muscular dystrophy (LGMD), congenital muscular dystrophy, facioscapulohumeral muscular dystrophy (FHMD), myotonic muscular dystrophy, oculopharyngeal muscular dystrophy, distal muscular dystrophy, Emery-Dreifuss muscular dystrophy, myotonia congenita, myotonic dystrophy, other muscular dystrophies, muscle wasting disease, such as cachexia due to cancer, end stage renal disease (ESRD), acquired immune deficiency syndrome (AIDS), or chronic obstructive pulmonary disease (COPD), post-surgical muscle weakness, post-traumatic muscle weakness, sarcopenia, inactivity (e.g., muscle disuse or immobility), urethral sphincter deficiency, urethral sphincter deficiency, neuromuscular disease, and the like.

Non-limiting examples of neuromuscular diseases include, but are not limited to, acid maltase deficiency, amyotrophic lateral sclerosis, Andersen-Tawil syndrome, Becker muscular dystrophy, Becker myotonia congenita, Bethlem myopathy, bulbospinal muscular atrophy, carnitine deficiency, carnitine palmityl transferase deficiency, central core disease, centronuclear myopathy, Charcot-Marie-Tooth disease, congenital muscular dystrophy, congenital myasthenic syndromes, congenital myotonic dystrophy, Cori disease, Debrancher enzyme deficiency, Dejerine-Sottas disease, dermatomyositis, distal muscular dystrophy, Duchenne muscular dystrophy, dystrophia myotonica, Emery-Dreifuss muscular dystrophy, endocrine myopathies, Eulenberg disease, facioscapulohumeral muscular dystrophy, tibial distal myopathy, Friedreich's ataxia, Fukuyama congenital muscular dystrophy, glycogenosis type 10, glycogenosis type 11, glycogenosis type 2, glycogenosis type 3, glycogenosis type 5, glycogenosis type 7, glycogenosis type 9, Gowers-Laing distal myopathy, hereditary inclusion-body myositis, hyperthyroid myopathy, hypothyroid myopathy, inclusion-body myositis, inherited myopathies, integrin-deficient congenital muscular dystrophy, spinal-bulbar muscular atrophy, spinal muscular atrophy, lactate dehydrogenase deficiency, Lambert-Eaton myasthenic syndrome, McArdel disease, merosin-deficient congenital muscular dystrophy, metabolic diseases of muscle, mitochondrial myopathy, Miyoshi distal myopathy, motor neuron disease, muscle-eye-brain disease, myasthenia gravis, myoadenylate deaminase deficiency, myofibrillar myopathy, myophosphorylase deficiency, myotonia congenital, myotonic muscular dystrophy, myotubular myopathy, nemaline myopathy, Nonaka distal myopathy, oculopharyngeal muscular dystrophy, paramyotonia congenital, Pearson syndrome, periodic paralysis, phosphofructokinase deficiency, phosphoglycerate kinase deficiency, phosphoglycerate mutase deficiency, phosphorylase deficiency, polymyositis, Pompe disease, progressive external ophthalmoplegia, spinal muscular atrophy, Ullrich congenital muscular dystrophy, Welander distal myopathy, ZASP-related myopathy, and the like.

Muscle atrophy (e.g., muscle wasting) can be caused by or associated with, for example, normal aging (e.g., sarcopenia), genetic abnormalities (e.g., mutations or single nucleotide polymorphisms), poor nourishment, poor circulation, loss of hormonal support, disuse of the muscle due to lack of exercise (e.g., bedrest, immobilization of a limb in a cast, etc.), a surgical procedure (e.g., surgical treatment), trauma (e.g., accidental trauma), injury (e.g., accidental injury), aging, damage to the nerve innervating the muscle, poliomyelitis, amyotrophic lateral sclerosis (ALS or Lou Gehrig's disease), heart failure, liver disease, diabetes, obesity, metabolic syndrome, demyelinating diseases (e.g., multiple sclerosis, Charcot-Marie-Tooth disease, Pelizaeus-Merzbacher disease, encephalomyelitis, neuromyelitis optica, adrenoleukodystrophy, and Guillian-Barre syndrome), denervation, fatigue, exercise-induced muscle fatigue, frailty, neuromuscular disease, weakness, chronic pain, and the like.

In particular embodiments, the muscle condition or disease that is prevented or treated is selected from the group consisting of: traumatic injury (e.g., acute muscle trauma, acute nerve trauma), acute muscle injury, acute nerve injury, chronic nerve injury, soft tissue hand injury, carpal tunnel syndrome (CTS), Duchenne muscular dystrophy (DMD), Becker muscular dystrophy, limb girdle muscular dystrophy, amyotrophic lateral sclerosis (ALS), distal muscular dystrophy (DD), inherited myopathies, myotonic muscular dystrophy (MDD), mitochondrial myopathies, myotubular myopathy (MM), myasthenia gravis (MG), congestive heart failure, periodic paralysis, polymyositis, rhabdomyolysis, dermatomyositis, cancer cachexia, AIDS cachexia, cardiac cachexia, stress induced urinary incontinence, sarcopenia, spinal muscular atrophy, fecal sphincter dysfunction, Bell's palsy, rotator cuff injury, spinal cord injury, hip replacement, knee replacement, wrist fracture, diabetic neuropathy, gastroesophageal reflux disease (GERD), obstructive sleep apnea (OSA), pelvic floor disorders (e.g., stress urinary incontinence, overactive bladder/urinary urgency incontinence, mixed urinary incontinence, pelvic organ prolapse, fecal incontinence), musculoskeletal disorders (e.g., impaired hand function, impaired thumb function, impaired foot function), plantar fasciitis, foot drop, disuse-induced muscle atrophy, impaired eyelid function (e.g., eyelid drooping, impaired blinking, entropion, ectropion), strabismus, nystagmus, and presbyopia. In some instances, the subject has ulnar nerve entrapment (e.g., at the elbow), either with or without muscle wasting. Additional examples of suitable conditions may include muscle disorders that affect small isolated muscles that can be regenerated with localized transplantation of small numbers of cells, including: atrophy and muscle dysfunction in the face or hand after nerve injury or direct trauma that does not recover after reinnervation; extraocular muscle injury causing inability to move the eye and dipoplia seen in Graves' disease, traumatic injury, and progressive external ophthalmoplegia; and urinary and fecal incontinence.

In some embodiments, the subject has received a traumatic injury. In other embodiments, the muscle condition being treated is a traumatic injury. In particular embodiments, the traumatic injury comprises blunt trauma or a crush injury. In some instances, the traumatic injury comprises blunt trauma or a crush injury to a limb (e.g., arm, leg, hand, foot, digit). In some embodiments, the traumatic injury is accidental. In some embodiments, the PGE2 compound (e.g., PGE2 receptor agonist) is administered immediately after the traumatic injury has occurred. In some embodiments, a combination of the PGE2 compound (e.g., PGE2 receptor agonist) and the myotoxin is administered immediately after the traumatic injury has occurred. In some embodiments, the PGE2 compound (e.g., PGE2 receptor agonist) and the myotoxin are administered simultaneously to the subject. In some embodiments, the PGE2 compound or the combination of the PGE2 compound and the myotoxin is administered within about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 minutes after occurrence of the traumatic injury. In other embodiments, the PGE2 compound or the combination of the PGE2 compound and the myotoxin is administered within about 1, 2, 3, 4, 5, 6, 7, 8, 9, 10, 11, 12, 13, 14, 15, 16, 17, 18, 19, 20, 21, 22, 23, or 24 hours of occurrence of the traumatic injury. The PGE2 compound (e.g., PGE2 receptor agonist) or the combination of the PGE2 compound and the myotoxin can be administered, 1, 2, 3, 4, 5, 6, 7, 8, 9, 10, or more times following occurrence of the traumatic injury.

In some embodiments, a subject who is treated (e.g., for a muscle condition or disease, or prophylactically) according to methods of the present invention receives a surgical procedure (e.g., surgical treatment). In some embodiments, the surgical procedure is for the prevention, reduction, or repair of a nerve injury. As a non-limiting example, the nerve injury (e.g., that is surgically treated) can be a peripheral nerve injury. In some instances, a subject who is treated or given prophylactic treatment (e.g., for a muscle condition or disease) according to methods of the present invention undergoes a carpal tunnel release procedure. In some embodiments, the surgical procedure comprises cutting a muscle, repairing a muscle, or both. As a non-limiting example, a PGE2 compound (e.g., a PGE2 receptor agonist), or a combination of a PGE2 compound and a myotoxin can be administered in conjunction with a Caesarean section, a hip replacement, or a knee replacement (e.g., a PGE2 compound, or a combination of a PGE2 compound and a myotoxin can be administered at the same time that a Caesarean section, hip replacement, or knee replacement is performed). In some embodiments, the methods of the present invention enhance post-operative recovery. Methods of the present invention can also be used to enhance the function of small muscles, the strength of small muscles, or both (e.g., hand, facial, oculopharyngeal muscles). When used in conjunction with a surgical procedure, methods of the present invention can be performed, before surgery, during surgery, after surgery, or any combination thereof. In some embodiments, only a PGE2 compound (e.g., a PGE2 receptor agonist) is administered (e.g., before, at the same time, or after a surgical procedure). In particular embodiments, no anesthetic is delivered. As a non-limiting example, in some instances, methods of the present invention may eliminate the need for the administration of marcaine.

The compositions and pharmaceutical compositions (e.g., comprising a PGE2 compound and a myotoxin, or comprising a PGE2 receptor agonist and optionally a myotoxin) can be administered topically, orally, intraperitoneally, intramuscularly, intra-arterially, intradermally, subcutaneously, intravenously, intracranially, intrathecally, intraspinally, intralesionally, intranasally, intracerebroventricularly, by inhalation and/or by intracardiac injection. The compositions can be administered in accordance with an acute regimen (e.g., single or intermittent dosing) or a chronic regimen (e.g., continuous dosing).

When a combination of a PGE2 compound (e.g., a PGE2 receptor agonist) and a myotoxin are administered, the PGE2 compound and the myotoxin can be administered concomitantly or sequentially. When the PGE2 compound and the myotoxin are administered sequentially, the PGE2 compound can be administered first, followed by the myotoxin, or vice versa. In some embodiments, the order of sequential administration alternates or otherwise varies between treatments (e.g., during one treatment, a PGE2 compound is administered first, followed by administration of the myotoxin, then during a subsequent treatment the myotoxin is administered first, followed by the PGE2 compound).

When a PGE2 compound (e.g., a PGE2 receptor agonist) and a myotoxin are administered sequentially, administration of the compounds can be separated by some length of time. In some cases, administration of the compounds is separated by about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, or more minutes. In other cases, administration of the compounds is separated by about 1, 2, 3, 4, 5, 6, 7, 8, 9, 10, 11, 12, 13, 14, 15, 16, 17, 18, 19, 20, 21, 22, 23, 24, or more hours. In other cases, administration of the compounds is separated by about 1, 2, 3, 4, 5, 6, 7, or more days.

In some embodiments, a dose of the PGE2 compound (e.g., PGE2 receptor agonist), the myotoxin, or both, is determined based upon the size of a target muscle. As a non-limiting example, a dose can comprise about 10 µg of the PGE2 compound (e.g., PGE2 receptor agonist), the myotoxin, or both, when the target muscle is an abductor pollicis brevis muscle (e.g., an abductor pollicis brevis muscle that is of about average size). As other non-limiting examples, a dose can comprise about 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19, 20, 25, 30, 25, 40, 45, 50, or more mg of the PGE2 compound (e.g., PGE2 receptor agonist), the myotoxin, or both, per kg of muscle tissue.

In other embodiments, a dose of the PGE2 compound (e.g., PGE2 receptor agonist), the myotoxin, or both, is based on the body weight of the subject. In particular embodiments, a dose of the PGE2 compound (e.g., PGE2 receptor agonist), the myotoxin, or both, is about 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19, 20, 25, 30, 25, 40, 45, 50, or more mg per kg of the subject's body weight.

In some embodiments, the subject is also administered a population of isolated (or isolated and purified) muscle cells that are either autologous or allogeneic to the subject. The cells can be isolated, purified, or both, by any method known to those of skill in the art. The cells can be a homogenous or heterogeneous population of muscle cells.

The isolated muscle cells can be administered by injection or transplantation. In some embodiments, compositions, the pharmaceutical compositions, or both, described herein (e.g., comprising a PGE2 compound and a myotoxin, or comprising a PGE2 receptor agonist and optionally a myotoxin) and the cells may be administered together or concomitantly. In other embodiments, the compositions, the pharmaceutical compositions, or both, and the cells may be administered sequentially. In some cases, the compositions, the pharmaceutical compositions, or both, may be administered before the cells. In other cases, the cells may be administered before the compositions, the pharmaceutical compositions, or both. Furthermore, the cells can be administered before, during, or after a surgical procedure (e.g., surgical treatment, e.g., for treatment of a nerve injury or a muscle condition or disease).

The population of muscle cells administered to the subject can include skeletal muscle cells, smooth muscle cells, cardiac muscle cells, embryonic stem cell-derived muscle cells, induced pluripotent stem cell-derived muscle cells, dedifferentiated muscle cells, or any combinations thereof. Additionally, the muscle cells administered to the subject can be muscle stem cells, satellite cells, myocytes, myoblasts, myotubes, myofibers, or any combination thereof. The compositions and/or pharmaceutical compositions described herein (e.g., comprising a PGE2 compound and a myotoxin, or comprising a PGE2 receptor agonist and optionally a myotoxin) can be administered to the subject by topical, oral, intraperitoneal, intramuscular, intra-arterial, intradermal, subcutaneous, intravenous, or intracardiac administration. In some cases, the compositions and/or pharmaceutical compositions may be administered directly to the dysfunctional, injured, damaged and/or atrophied muscle. The compositions and/or pharmaceutical compositions can be administered in accordance with an acute regimen (e.g., single or intermittent dosing) or a chronic regimen (e.g., continuous dosing).

Satellite cells are small mononuclear progenitor cells that can reside within muscle tissue. These cells can be induced to proliferate and differentiate into muscle cells, and in some instances, fuse to muscle fibers. During muscle damage or injury, quiescent satellite cells (e.g., satellite cells that are not differentiating or undergoing cell division at present) and muscle stem cells can be activated to proliferate, and/or migrate out of the muscle stem cell niche. The satellite cells and muscle stem cells can also differentiate into myocytes, myoblasts, or other muscle cell types.

Methods and protocols for generating muscle cells from embryonic stem cells are described, e.g., in Hwang et al., *PLoS One*, 2013, 8(8):e72023; and Darabi et al., *Cell Stem Cell*, 2012, 10(5):610-9. Methods and protocols for generating muscle cells from induced pluripotent stem cells are described, e.g., in Darabi et al., *Cell Stem Cell*, 2012, 10(5):610-9; Tan et al., PLoS One, 2011; and Mizuno et al., *FASEB J.*, 2010, 24(7):2245-2253.

In some embodiments, muscle cells are obtained by biopsy from a muscle such as a mature or adult muscle, e.g., quadriceps, gluteus maximus, biceps, triceps, or any muscle from an individual. The muscle can be a skeletal muscle, smooth muscle, or cardiac muscle. Detailed descriptions of methods of isolating smooth muscle stem cells can be found, e.g., in U.S. Pat. No. 8,747,838, and U.S. patent application Publ. No. 20070224167. Methods of isolating muscle cells of interest such as muscle stem cells or satellite cells from muscle tissue are described in detail, for example, in Blanco-Bose et al., *Exp. Cell Res.*, 2001, 26592:212-220.

Methods for purifying a population of muscle cells of interest, e.g., muscle stem cells, muscle satellite cells, myocytes, myoblasts, myotubes, and/or myofibers include selecting, isolating or enriching for a cell having a specific cell surface marker or a specific polypeptide that is expressed on the cell surface of the muscle cell of interest. Useful cell surface markers are described in, e.g., Fukada et al., *Front. Physiol.*, 2013, 4:317. Cell sorting methods such as flow cytometry, e.g., fluorescence-activated cell sorting (FACS); magnetic bead cell separation, e.g., magnetic-activated cell sorting (MACS), and other antibody-based cell sorting methods can be performed to isolate or separate the muscle cells of interest from other cell types.

The isolated population of muscle cells of interest can be expanded or multiplied using conventional culture-based methods. Methods for culture muscle cells are found in, e.g., U.S. Pat. No. 5,324,656. In some cases, the cells may be cultured on a scaffold or gel such as a hydrogel.

In some embodiments, the cells may be stimulated to proliferate by culturing the cells with the PGE2 compound (e.g., PGE2 receptor agonist) and/or myotoxin prior to administering them to the subject. The cells can be acutely, intermittently or continuously exposed to the compound during in vitro culturing. In some cases, the population of muscle cells may increase by at least about 1%, at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 100%, at least about 200%, at least about 500%, at least about 1000%, or more after culturing with the PGE2 compound (e.g., PGE2 receptor agonist) and/or myotoxin.

The methods described herein can be used to increase the number of muscle fibers by at least about 1%, at least about 5%, at least about 10%, at least about 15%, at least about 20%, at least about 25%, at least about 30%, at least about 35%, at least about 40%, at least about 45%, at least about 50%, at least about 60%, at least about 70%, at least about 80%, at least about 90%, at least about 100%, at least about 200%, at least about 500%, at least about 1000%, or more. In some embodiments, the methods can increase the growth of a damaged, injured, atrophied, or degenerated muscle.

In some embodiments, a target muscle may be subjected to mechanical injury. As non-limiting examples, mechanical injury can comprise cutting, burning, freezing, needle puncture, exercise (e.g., brief or prolonged exercise), a surgical procedure (e.g., surgical treatment), traumatic injury (e.g., accidental trauma or injury), or a combination thereof. In some instances, the mechanical injury is before, after, or concomitant with administration of a PGE2 compound (e.g., PGE2 receptor agonist). In some embodiments, when performed in conjunction with administration of a PGE2 compound (e.g., PGE2 receptor agonist), mechanical injury acts as a regenerative inducer that stimulates muscle cell proliferation, muscle cell growth, muscle cell survival, muscle regeneration, muscle growth, and/or an increase in muscle mass. In particular embodiments, mechanical injury acts as a regenerative inducer when a myotoxin is not administered to the subject.

In some instances, the mechanical injury is before, after, or concomitant with administration of a PGE2 receptor agonist. In some instances, the mechanical injury is before, after, or concomitant with administration of a myotoxin. In some other instances, the mechanical injury is before, after, or concomitant with administration of a combination of a PGE2 compound (e.g., PGE2 receptor agonist) and a myotoxin.

C. Methods of Treating Ocular Disorders or Diseases

In one aspect, the methods may comprise the administration of a therapeutic composition comprising a PGE2 compound and/or a myotoxin, as described herein, to the ocular system of a subject in need thereof. In some embodiments, the therapeutic composition comprising a PGE2 compound and/or a myotoxin can be administered to a subject in need thereof to treat an ocular disorder or disease. In other embodiments, the therapeutic composition comprising a PGE2 compound and/or a myotoxin can be administered to a subject in need thereof to improve an eye function. In further embodiments, the therapeutic composition comprising a PGE2 compound and/or a myotoxin can be administered to a subject in need thereof to enhance the effectiveness of an existing approach to treat an ocular disorder or disease, such as cataract surgery or retinal surgery.

Eyelid Function

The eyelids protect the eyes. When the eye blinks, the eyelid spreads moisture over the eyes. Blinking also helps move dirt and other particles off the surface of the eye. When something approaches the eye, the eyelid closes to protect the eye against injuries. Eyelid function may be impaired and result in an ocular disorder or disease. In some cases, the eyelid may droop, resulting in a disorder such as ptosis. In other cases, the eyelid may turn in or out, resulting in disorders such as entropion or ectropion. In other cases, the eyelid may have abnormal blinking or twitching, resulting in disorders such as dry eye syndrome or wet eye syndrome (epiphora). In certain aspects, methods are provided herein for the treatment of an ocular disease or disorder due to impaired eyelid function. In some cases, the method comprises administering a therapeutic composition comprising a PGE2 compound and/or a myotoxin to a subject in need thereof to improve an eyelid function. In some cases, an eyelid function may be improved by inducing muscle regeneration in an eye muscle. The eye muscle may be a muscle that impacts an eyelid function. Non-limiting examples of eye muscles include the levator muscle, Muller's muscle or orbicularis. In some cases, the methods may comprise administering a therapeutic composition of the disclosure (e.g., a PGE2 compound and/or a myotoxin) to an eye muscle.

Eyelid Drooping

Eyelid drooping is excess sagging of the upper eyelid. In some cases, the edge of the upper eyelid may be lower than it should, also known as ptosis. In other cases, there may be excess baggy skin in the upper eyelid, also known as dermatochalasis. In other cases, it may be a combination of ptosis and dermatochalasis. Eyelid drooping may be due to the weakness of an eyelid muscle. In some cases, the cause of the weakness of the eyelid muscle may be due to the normal aging process, or a result of an injury or a disease. In some cases, eyelid drooping may be associated with another disorder such as a tumor around or behind the eye, diabetes, Homer syndrome, Myasthenia gravis, stroke, swelling in the eyelid (e.g., stye). In other cases, eyelid drooping may be congenital. In other cases, eyelid drooping may be due to botox administration/exposure.

In some aspects, the methods of the disclosure may involve treating eyelid drooping. In some cases, the methods may comprise administering a therapeutic composition comprising a PGE2 compound and/or a myotoxin to a subject having, suspected of having, or at risk of developing eyelid drooping. In some cases, eyelid drooping may include ptosis, dermatochalasis, or both. In some embodiments, treating eyelid drooping may include treating ptosis, dermatochalasis, or both. In some embodiments, the methods may involve treating eyelid drooping caused by weakness of the eye muscle, such as weakness due to the aging process, or as a result of injury or disease. In some embodiments, the methods may involve treating eyelid drooping caused by a tumor around or behind the eye, Homer syndrome, Myasthenia gravis, stroke, or swelling in the eye (e.g., stye). In some cases, the methods involve administering a therapeutic composition of the disclosure to an eyelid muscle of a subject having eyelid drooping. In some embodiments, the therapeutic composition may treat eyelid drooping by inducing muscle regeneration of an eyelid muscle of a subject. In some cases, the eyelid muscle may be the levator muscle, Muller's muscle, orbicularis, the frontalis muscle, or any one of the facial muscles. In some cases, the methods may involve administering a therapeutic composition of the disclosure to any one of the levator muscle, Muller's muscle, orbicularis, the frontalis muscle, or the facial muscles.

In some embodiments, the therapeutic composition may be administered in combination with eyelift surgery (e.g., blepharoplasty) to treat eyelid drooping. In some cases, the therapeutic composition can be administered before surgery, during surgery, after surgery, or any combination thereof. In other embodiments, the therapeutic composition may be administered without eyelift surgery to treat eyelid drooping.

In some embodiments, the therapeutic composition (e.g., comprising a PGE2 compound and/or a myotoxin) may be administered by topical administration, intradermal administration, intramuscular administration, or a combination thereof. In some cases, the therapeutic composition is administered by intramuscular administration. In some cases, intramuscular administration comprises injection of an eyelid muscle. The eyelid muscle may include any one of the levator muscle, Muller's muscle, the orbicularis muscle, the frontalis muscle, or the facial muscles. In some cases, an anesthetic may be administered to an eye of a subject prior to injection of the therapeutic composition. In some cases, the eyelid muscle may be injected with surgical exposure; in other cases, the eyelid muscle may be injected without surgical exposure. In some embodiments, a 27-, 28-, 29- or 30-gauge needle may be used to inject the eyelid muscle.

In some embodiments, the methods of the disclosure may involve injecting an eyelid muscle of a subject in need thereof with a volume of about 0.01 mL to about 0.15 mL of a therapeutic composition of the disclosure (e.g., comprising a PGE2 compound and/or a myotoxin). In some embodiments, the eyelid muscle may be injected with at least about 0.01 mL of a therapeutic composition. In some embodiments, the eyelid muscle may be injected with at most about 0.15 mL of a therapeutic composition of the disclosure (e.g., comprising a PGE2 compound and/or a myotoxin). In some embodiments, the eyelid muscle may be injected with greater than 0.01 mL, greater than 0.02 mL, greater than 0.03 mL, greater than 0.04 mL, greater than 0.05 mL, greater than 0.06 mL, greater than 0.07 mL, greater than 0.08 mL, greater than 0.09 mL, greater than 0.10 mL, greater than 0.11 mL, greater than 0.12 mL, greater than 0.13 mL, or greater than 0.14 mL of a therapeutic composition of the disclosure (e.g., comprising a PGE2 compound and/or a myotoxin).

In some aspects, the effectiveness of a therapeutic composition of the disclosure to treat eyelid drooping may be determined by conducting tests before administration, after administration, or both. In some cases, the tests may determine how much the eyelid is drooping before administration, after administration, or both. In some cases, the test may be a slit-lamp examination, a tension test, a visual field test, or a combination thereof. In some embodiments, the dose of the therapeutic composition may be adjusted after determining the effectiveness of a prior administration. In some cases, the dose of the PGE2 compound, the myotoxin, or both, may increase. In other cases, the dose of the PGE2 compound, the myotoxin, or both, may decrease. In some cases, the dose of the PGE2 compound, the myotoxin, or both, may not change. In some embodiments, the frequency of administration of a therapeutic composition of the disclosure (e.g., comprising a PGE2 compound, a myotoxin, or both) may be adjusted after determining the effectiveness of an administration of the therapeutic composition. In some cases, only a single administration of the therapeutic composition may be needed to treat eyelid drooping. In some cases, two, three, four, five, or more than five administrations of the therapeutic composition may be needed. In some cases, the frequency of administration may be increased after determining the effectiveness of a prior administration. In other cases, the frequency of administration may be decreased after determining the effectiveness of a prior administration.

In some embodiments, a subject in need of a therapeutic composition of the disclosure may be identified by a test prior to administration of the therapeutic composition. In some cases, the test may be a phenylephrine chemical test. In such cases, a positive reaction to the phenylephrine chemical test may identify the subject as a candidate for regeneration of Muller's muscle. In some cases, a subject may be treated for eyelid drooping by injecting Muller's muscle with a therapeutic composition of the disclosure (e.g., comprising a PGE2 compound, a myotoxin, or both).

In some aspects, methods are provided for treating irregular astigmatism comprising administering a therapeutic composition of the disclosure (e.g., comprising a PGE2 compound, a myotoxin, or both) to a subject in need thereof. Irregular astigmatism may be due to scarring of the cornea as a result of eyelid dropping. In some cases, irregular astigmatism may be treated by treating eyelid drooping as described herein.

Impaired Blinking

Blinking prevents harmful substances from getting into the eye and may be important in the homeostasis of a healthy ocular tear and corneal epithelial surface. The lacrimal gland produces a lubricating fluid for the eye. When the eye blinks, the eyelid moves fluid from the lacrimal gland and across the eye. When the eye becomes irritated, the lacrimal gland produces extra fluid to wash out any impurities. The excess fluid drains through a tear duct and into the nasal cavity. The blinking function of the eye may become impaired, impacting the health of the eye. In some cases, impaired blinking may result in dry eye syndrome, or symptoms similar to dry eye syndrome. In other cases, impaired blinking may result in wet eye syndrome, or symptoms similar to wet eye syndrome. Impaired blinking may be due to many causes including eyelid laxity, lack of eyelid control, and weakness of other eye muscles. Impaired blinking can cause severe damage to the cornea from desiccation and can lead to devastating corneal diseases such as neurotrophic cornea.

In some aspects, methods are provided for treating impaired blinking in a subject in need thereof. In some cases, the methods may comprise administering a therapeutic composition of the disclosure (e.g., comprising a PGE2 compound and/or a myotoxin) to a subject having, suspected of having, or at risk of developing impaired blinking. In some cases, the methods may comprise administering a therapeutic composition of the disclosure to a subject having, suspected of having, or at risk of developing dry eye syndrome. In some embodiments, the therapeutic composition may be administered to treat dry eye syndrome associated with impaired blinking, with lacrimal gland atrophy, with $7^{th}$ nerve palsy, or with repeated styes. In some cases, the methods may comprise administering a therapeutic composition of the disclosure to a subject having, suspected of having, or at risk of developing wet eye syndrome (epiphora or excessive tearing).

In some embodiments, the therapeutic composition may treat impaired blinking, dry eye syndrome, wet eye syndrome, or a combination thereof, by inducing muscle regeneration in an eye muscle of the subject. In some cases, the eye muscle comprises a muscle that impacts blinking. In some cases, the eye muscle may include any one of the orbicularis muscle, the muscle of Riolan, Homer's muscle, the frontalis muscle, or the facial muscles. The facial muscles may include the occipitofrontalis muscle, the temporoparietalis muscle, the procerus muscle, the nasalis muscle, the depressor septi nasi muscle, the orbicularis oculi muscle, the corrugator supercilii muscle, the depressor supercilii muscle, the auricular muscles (anterior, superior and posterior), the orbicularis oris muscle, the depressor anguli oris muscle, the risorius, the zygomaticus major muscle, the zygomaticus minor muscle, the levator labii superioris, the levator labii superioris alaeque nasi muscle, the depressor labii inferioris muscle, the levator anguli oris, the buccinator muscle, or the mentalis. In some cases, impaired blinking, dry eye syndrome, or wet eye syndrome can be treated by administering a therapeutic composition of the disclosure (e.g., comprising a PGE2 compound, a myotoxin, or both) to the orbicularis muscle, the muscle of Riolan, Homer's muscle, the frontalis muscle, any one of the facial muscles, or a combination thereof. Recent studies have shown the importance of muscle stem cells (MuSCs) in stimulating neuromuscular junctions in denervated muscles (Liu et al., 2015), although until recently improving the recovery of muscle function following denervation remained an unsolved problem. A solution to this problem lies in the ability to reverse or prevent denervation atrophy by stimulating and augmenting MuSCs that are already present in the muscles.

In some embodiments, methods of treating impaired blinking, dry eye syndrome, or wet eye syndrome may include administering a therapeutic composition of the disclosure (e.g., comprising a PGE2 compound, and/or a myotoxin) to a subject in need thereof by topical administration, intradermal administration, intramuscular administration, or a combination thereof. In some cases, the therapeutic composition may be administered by intramuscular administration. In some cases, the intramuscular administration may comprise injection of an eye muscle. The eye muscle may include any one of the orbicularis muscle, the muscle of Riolan, Homer's muscle, the frontalis muscle, or the facial muscles. Recent studies have shown the importance of muscle stem cells (MuSCs) in stimulating neuromuscular junctions in denervated muscles, although until recently improving the recovery of muscle function following denervation remained an unsolved problem. A solution to this problem lies in the ability to reverse or prevent denervation atrophy by stimulating and augmenting MuSCs that are already present in the muscles.

In some embodiments, the methods may comprise administering a therapeutic composition of the disclosure to a muscle that impacts a function of the lacrimal gland to treat impaired blinking associated with lacrimal gland dysfunction, such as lacrimal gland atrophy. In some cases, an anesthetic may be administered to an eye of the prior to injection of the therapeutic composition. In some cases, the eyelid muscle may be injected with surgical exposure; in other cases, the eyelid muscle may be injected without surgical exposure. In some embodiments, a 27-, 28-, 29- or 30-gauge needle may be used to inject the eyelid muscle.

In some embodiments, methods of treating impaired blinking, dry eye syndrome, wet eye syndrome, or a combination thereof may include administering (e.g., intramuscular injection) a therapeutic composition of the disclosure to an eye muscle of a subject in need thereof, in a volume of about 0.01 mL to about 0.15 mL. In some embodiments, the eye muscle may be injected with at least about 0.01 mL of a therapeutic composition of the disclosure. In some embodiments, the eye muscle may be injected with at most about 0.15 mL of a therapeutic composition of the disclosure. In some embodiments, the eye muscle may be injected with greater than 0.01 mL, greater than 0.02 mL, greater than 0.03 mL, greater than 0.04 mL, greater than 0.05 mL, greater than 0.06 mL, greater than 0.07 mL, greater than 0.08 mL, greater than 0.09 mL, greater than 0.10 mL, greater than 0.11 mL, greater than 0.12 mL, greater than 0.13 mL, or greater than 0.14 mL of a therapeutic composition of the disclosure.

In some aspects, the effectiveness of an administration of a therapeutic composition may be determined by conducting tests before administration, after administration, or both. For treatment of wet eye syndrome, a fluorescein and Lissamine green staining test, optical coherence tomography of the tear film (OCT), or both, may be conducted. For treatment of dry eye syndrome, a visual acuity measurement, a slit lamp exam, measurement of tear film break-up time (TBUT), measurement of rate of tear production (Schirmer test), measurement of concentration of tears (osmolality), or a combination thereof may be conducted. In some cases, the test may involve measuring levels of inflammatory or growth factor molecules including, without limitation, MMP-9, lactoferrin, and NGF-1.

In some embodiments, a dose of the therapeutic composition may be adjusted after determining the effectiveness of a prior administration. In some cases, the dose of the PGE2 compound, the myotoxin, or both, may increase. In other cases, the dose of the PGE2 compound, the myotoxin, or both may decrease. In some cases, the dose of the PGE2 compound, the myotoxin, or both may not change. In some embodiments, the frequency of administration of a therapeutic composition of the disclosure (e.g., comprising a PGE2 compound and/or a myotoxin) may be adjusted after determining the effectiveness of a prior administration of the therapeutic composition. In some cases, only a single administration of the therapeutic composition may be needed to treat impaired blinking, dry eye syndrome, or wet eye syndrome. In some cases, two, three, four, five, or more than five administrations of the therapeutic composition may be needed to treat impaired blinking, dry eye syndrome, or wet eye syndrome. In some cases, the frequency of administration may be increased after determining the effectiveness of a prior administration. In other cases, the frequency of administration may be decreased after determining the effectiveness of a prior administration.

Entropion and Ectropion

The eyelid protects the eye from foreign objects. In some cases, the eyelid does not lie properly on the eye. For example, entropion is the turning in of an edge of an eyelid. In some cases, it causes the lashes of the eye to rub against the eye. This can result in excessive tearing, eye discomfort, eye pain, eye irritation, eye redness, and in some extreme cases, cornea damage and decreased vision. Causes of entropion may include weakening of eye muscles, especially the muscles in the lower part of the eye. Ectropion is the turning out of the eyelid so that the inner surface is exposed. In some cases, ectropian may cause dry, painful eyes, excessive tearing of the eye (epiphora), chronic conjunctivitis, keratitis, eye redness, or a combination thereof. Causes of ectropion may be due to weakening of the eyelid due to the aging process, facial palsy, and the like.

In some aspects, methods are provided for the treatment of entropion, ectropion, or both. In some cases, the methods may comprise administering a therapeutic composition of the disclosure (e.g., comprising a PGE2 compound and/or a myotoxin) to a subject having, suspected of having, or at risk of developing entropion or ectropion. In some embodiments, the methods of treating entropion or ectropion may involve administering a therapeutic composition of the disclosure to an eye muscle of a subject in need thereof. In some cases, the eyelid muscle may be the orbicularis, the frontalis muscles, or any of the facial muscles. The facial muscles may include the occipitofrontalis muscle, the temporoparietalis muscle, the procerus muscle, the nasalis muscle, the depressor septi nasi muscle, the orbicularis oculi muscle, the corrugator supercilii muscle, the depressor supercilii muscle, the auricular muscles (anterior, superior and posterior), the orbicularis oris muscle, the depressor anguli oris muscle, the risorius, the zygomaticus major muscle, the zygomaticus minor muscle, the levator labii superioris, the levator labii superioris alaeque nasi muscle, the depressor labii inferioris muscle, the levator anguli oris, the buccinator muscle, or the mentalis.

In some embodiments, the therapeutic composition may be administered in combination with eyelid surgery (e.g., lateral tarsal strip procedure). In those embodiments, the therapeutic composition can be administered before surgery, during surgery, after surgery, or any combination thereof. In other embodiments, the therapeutic composition may be administered without eye surgery.

In some embodiments, the methods provided herein may include administering a therapeutic composition of the disclosure (e.g., comprising a PGE2 compound and/or a myotoxin) to a subject in need thereof by topical administration, intradermal administration, intramuscular administration, or a combination thereof. In some cases, the therapeutic composition may be administered by intramuscular administration. In some cases, the intramuscular administration comprises injection of an eye muscle. In some cases, the eye muscle may comprise any of the orbicularis muscle, the frontalis muscle, or the facial muscles. In some cases, an anesthetic may be administered to an eye of a subject in need prior to injection. In some cases, the eye muscle may be injected with surgical exposure; in other cases, the eye muscle may be injected without surgical exposure. In some embodiments, a 27-, 28-, 29- or 30-gauge needle may be used to inject the eye muscle.

In some embodiments, methods of treating ectropion, entropion, or both may include administering (e.g., intramuscular injection) a therapeutic composition of the disclosure to an eye muscle of a subject in need thereof, in a volume of about 0.01 mL to about 0.15 mL. In some embodiments, the eye muscle may be injected with at least about 0.01 mL of a therapeutic composition of the disclosure. In some embodiments, the eye muscle may be injected with at most about 0.15 mL of a therapeutic composition of the disclosure. In some embodiments, the eye muscle is injected with greater than 0.01 mL, greater than 0.02 mL, greater than 0.03 mL, greater than 0.04 mL, greater than 0.05 mL, greater than 0.06 mL, greater than 0.07 mL, greater than 0.08 mL, greater than 0.09 mL, greater than 0.10 mL, greater than 0.11 mL, greater than 0.12 mL, greater than 0.13 mL, or greater than 0.14 mL of a therapeutic composition of the disclosure.

In some aspects, the effectiveness of an administration of a therapeutic composition of the disclosure (e.g., to treat entropion, ectropion, or both) may be determined by conducting tests before administration, after administration, or both. In some cases, the tests may include an examination of the eye, the eyelid, or a combination thereof. In some embodiments, the dose of the therapeutic composition may be adjusted after determining the effectiveness of a prior administration. In some cases, the dose of the PGE2 compound, the myotoxin, or both may be increased. In other cases, the dose of the PGE2 compound, the myotoxin, or both may be decreased. In some cases, the dose of the PGE2 compound, the myotoxin, or both may not change. In some embodiments, the frequency of administration of a therapeutic composition of the disclosure (e.g., comprising a PGE2 compound and/or a myotoxin) may be adjusted after determining the effectiveness of an administration of the therapeutic composition (e.g., to treat ectropion, entropion, or both). In some cases, only a single administration of the therapeutic composition may be needed to treat entropion or ectropion. In some cases, two, three, four, five, or more than five administrations of the therapeutic composition may be needed to treat entropion or ectropion. In some cases, the frequency of administration may be increased after determining the effectiveness of a prior administration. In other cases, the frequency of administration may be decreased after determining the effectiveness of a prior administration.

Extraocular Muscles

The extraocular muscles comprise six muscles that control movement of the eye (lateral rectus, medial rectus, superior rectus, inferior rectus, superior oblique, and inferior oblique) and one muscle (levator palpebrae) that controls eyelid elevation. Damage or injury to, weakening of, or improper innervation of any one of these extraocular muscles can result in an ocular disorder or disease, and reduced visual function. In some aspects, methods are provided for treating an ocular disorder or disease by administering a therapeutic composition of the disclosure (e.g., comprising a PGE2 compound and/or a myotoxin). In some cases, the therapeutic composition may be administered to at least one extraocular muscle, e.g., lateral rectus, medial rectus, superior rectus, inferior rectus, superior oblique, inferior oblique, or levator palpebrae. In some cases, the methods may comprise administering a therapeutic composition of the disclosure to an extraocular muscle of a subject in need thereof to induce muscle regeneration.

Strabismus

Strabismus is an ocular disorder in which both eyes do not line up in the same direction. As a result, the eyes do not look at the same object at the same time. The condition is more commonly known as "crossed eyes". Six different extraocular muscles (lateral rectus, medial rectus, superior rectus, inferior rectus, superior oblique and inferior oblique) surround each eye and work together to allow both eyes to focus on the same object. In a patient having strabismus, these muscles do not work together. As a result, one eye looks at one object and the other eye turns in a different direction to focus on another object. In many cases, the cause of strabismus is unknown. In some cases, eye misalignment is observed at birth or shortly afterwards (congenital strabismus). In some cases, disorders associated with strabismus in children may include, without limitation, Apery Syndrome, Cerebral Palsy, Congenital Rubella, Hemangioma, Incontinentia Pigmenti Syndrome, Noonan Syndrome, Prader-Willi Syndrome, Retinopathy of Prematurity, Retinoblastoma, Traumatic Brain Injury and Trisomy 18. Strabismus can develop in adults and may be due to many different causes including, without limitation, botulism, diabetes, Graves Disease, Guillain-Barre Syndrome, injury to the eye, shellfish poisoning, stroke, traumatic brain injury and vision loss from an eye disease or injury.

In some aspects, methods are provided for treating strabismus or congenital strabismus. In some cases, the methods may comprise administering a therapeutic composition of the disclosure (e.g., a PGE2 compound and/or a myotoxin) to a subject having, suspected of having, or at risk of developing strabismus or congenital strabismus. In some embodiments, the therapeutic composition may treat strabismus or congenital strabismus by inducing muscle regeneration in at least one of the extraocular muscles, e.g., lateral rectus, medial rectus, superior rectus, inferior rectus, superior oblique, and inferior oblique. In some cases, the methods may comprise administering a therapeutic composition of the disclosure to any of the lateral rectus muscle, the medial rectus muscle, the superior rectus muscle, the inferior rectus muscle, the superior oblique muscle, and the inferior oblique muscle. In some cases, each eye muscle may have a width of about 5 mm to about 7 mm, a length of about 10 mm, and a thickness of less than or equal to 1 mm.

In some embodiments, a therapeutic composition of the disclosure may be administered in combination with eye muscle surgery to treat strabismus or congenital strabismus. In some cases, the therapeutic composition can be administered before surgery, during surgery, after surgery, or any combination thereof. In other cases, the therapeutic composition may be administered without eye muscle surgery to treat strabismus or congenital strabismus.

In some embodiments, a therapeutic composition of the disclosure (e.g., comprising a PGE2 compound and/or a myotoxin) may be administered by injection of an extraocular muscle (e.g., lateral rectus, medial rectus, superior rectus, inferior rectus, superior oblique, and inferior oblique) for the treatment of strabismus or congenital strabismus. In other cases, a therapeutic composition of the disclosure may be administered via slow drug release in a drug releasing depot, by gene therapy methods that may include a cell matrix depot that produces a composition of the disclosure (e.g., a PGE2 compound, a myotoxin), or a polymeric implant placed near or adjacent to the muscles. In an exemplary embodiment, a local anesthetic, an ocular decongestant, or both, may be administered to an eye of a subject in need thereof prior to injection of the extraocular muscle. In some cases, the extraocular muscle may be injected with surgical exposure; in other cases, the extraocular muscle may be injected without surgical exposure. In some embodiments, the extraocular muscle may be injected with electromyographic guidance; in other embodiments, the extraocular muscle may be injected without electromyographic guidance. In some embodiments, a 27-, 28-, 29- or 30-gauge needle may be used to inject the extraocular muscle. To correct the misalignment of the eyes, one or more extraocular muscles can be injected as needed. In some embodiments, extraocular muscles in both eyes can be injected to correct the misalignment.

In some embodiments, methods of treating strabismus may include administering (e.g., intramuscular injection) a therapeutic composition of the disclosure to an extraocular eye muscle of a subject in need thereof, in a volume of about 0.05 mL to about 0.15 mL. In some embodiments, the extraocular muscle may be injected with at least about 0.05 mL of the therapeutic composition. In some embodiments, the extraocular muscle may be injected with at most about 0.15 mL of the therapeutic composition. In some embodiments, the extraocular muscle may be injected with greater than 0.05 mL, greater than 0.06 mL, greater than 0.07 mL, greater than 0.08 mL, greater than 0.09 mL, greater than 0.10 mL, greater than 0.11 mL, greater than 0.12 mL, greater than 0.13 mL, or greater than 0.14 mL of the therapeutic composition.

In some aspects, the effectiveness of an administration of a therapeutic composition of the disclosure (e.g., to treat strabismus) may be determined by conducting tests before administration, after administration, or both. In some cases, the tests may determine how much the eyes are out of alignment. In some embodiments, a corneal light reflex test, a cover/uncover test, a retinal exam, an ophthalmic exam, visual acuity, or a combination thereof, may be conducted. In some cases, the effectiveness of an administration of the therapeutic composition can be determined by changes in the alignment of the eyes before administration and after administration. In some embodiments, the dose of the therapeutic composition may be adjusted after determining the effectiveness of a prior administration. In some cases, the dose of the PGE2 compound, the myotoxin, or both, may be increased. In other cases, the dose of the PGE2 compound, the myotoxin, or both may be decreased. In some cases, the dose of the PGE2 compound, the myotoxin, or both, may not be changed.

In some embodiments, the frequency of administration of a therapeutic composition of the disclosure (e.g., comprising a PGE2 compound and/or a myotoxin) may be adjusted after determining the effectiveness of an administration of the therapeutic composition (e.g., to treat strabismus). In some cases, only a single administration of the therapeutic composition may be needed to treat strabismus. In some cases, two, three, four, five, or more than five administrations of the therapeutic composition may be needed. In some cases, the frequency of administration may be increased after determining the effectiveness of a prior administration. In other cases, the frequency of administration may be decreased after determining the effectiveness of a prior administration.

Nystagmus

Nystagmus, or eye tremor, is a term used to describe fast, uncontrollable movement of the eyes. The movement may be from side to side (horizontal nystagmus); up and down (vertical nystagmus), or rotary (rotary or torsional nystagmus). In some cases, the movement may be in one eye. In other cases, the movement may be in both eyes. In some cases, nystagmus may be present at birth (Infantile Nystagmus Syndrome (INS)). In some cases, nystagmus may be caused by a congenital disease of the eye. In other cases, nystagmus may be acquired through a variety of causes including intake of certain drugs or medications (e.g., phenytoin), excessive alcohol, a sedating medicine that can impair a function of the labyrinth, head injury, an inner ear disorder (e.g., labyrinthis or Meniere disease), stroke, and thiamine or vitamin B12 deficiency. In some cases, eye tremors may be secondary to other disorders such as Parkinson's disease.

In some aspects, methods are provided for treating nystagmus. In some cases, nystagmus is horizontal nystagmus, vertical nystagmus, rotary or torsional nystagmus, or any combination thereof. In some cases, nystagmus is Infantile Nystagmus Syndrome. In some cases, the methods comprise a therapeutic composition of the disclosure (e.g., comprising a PGE2 compound and/or a myotoxin) to a subject having, suspected of having, or at risk of developing nystagmus. In some embodiments, the therapeutic composition may treat nystagmus by inducing muscle regeneration in at least one of the extraocular muscles, e.g., lateral rectus, medial rectus, superior rectus, inferior rectus, superior oblique, and inferior oblique. In some cases, the therapeutic composition may be administered to at least one of the extraocular muscles, e.g., lateral rectus, medial rectus, superior rectus, inferior rectus, superior oblique, and inferior oblique, for the treatment of nystagmus.

Iris

Located between the cornea and the lens, the iris comprises a sphincter muscle (sphincter pupillae) and dilator muscles (dilator pupillae). The round, central opening of the iris is called the pupil. The iris modulates the size of the pupil to control how much light comes into the eye. Impairment of the iris can result in impaired visual function.

In some aspects, methods are provided for treating impaired visual function. In some cases, the methods may comprise administering a therapeutic composition of the disclosure (e.g., comprising a PGE2 compound and/or a myotoxin), to a subject having, suspected of having, or at risk of developing impaired visual function. In some embodiments, the therapeutic composition may treat impaired visual function by inducing muscle regeneration of an iris muscle. The iris muscle may be the sphincter muscle, the dilator muscle, or both. In some cases, the therapeutic composition may be administered topically, intradermally, or intraocularly to a subject in need thereof. In some cases, the therapeutic composition may be administered by intramuscular administration to a muscle of the iris (e.g., the sphincter muscle, the dilator muscle). In some aspects, the effectiveness of the treatment may be determined by observing changes in light sensitivity before administration, after administration, or both.

Ciliary Muscle and Other Intraocular Muscles

The ciliary body is a circular structure that contains the ciliary muscle. The ciliary muscle changes the shape of the lens when the eye focuses on a near object in a process called accommodation. Presbyopia is a condition in which the lens of the eye loses its ability to focus, making it hard to see objects up close. Presbyopia is thought to be a natural part of the aging process. One approach to treating presbyopia may be to induce muscle regeneration of the ciliary muscle. Accordingly, provided herein are methods of treating presbyopia. In some cases, the methods may comprise administering a therapeutic composition of the disclosure (e.g., comprising a PGE2 compound and/or a myotoxin) to a subject having, suspected of having, or at risk of developing presbyopia. In some embodiments, the therapeutic composition may treat presbyopia by inducing muscle regeneration of the ciliary muscle. In some aspects, the effectiveness of the treatment can be determined by performing a reading test before administration, after administration, or both.

In some aspects, methods are provided for treating myopia, or to modulate regression of myopia. In some cases, the methods may comprise administering a therapeutic composition of the disclosure (e.g., comprising a PGE2 compound and/or a myotoxin) to a subject having, suspected of having, or at risk of developing myopia, or to a subject to modulate regression of myopia. In some cases, the therapeutic composition may be administered to an eye muscle, such as the ciliary muscle, a muscle in the sclera, a muscle around the sclera, or an intraocular muscle.

Oculopharyngeal Muscular Dystrophy

Oculopharyngeal muscular dystrophy is a genetic disorder characterized by slowly progressing muscle disease (myopathy) affecting the muscles of the upper eyelids and the throat. Onset is typically during adulthood, most often between 40 and 60 years of age. Symptoms may include, without limitation: eyelid drooping (ptosis), arm and leg weakness, and difficulty swallowing (dysphagia).

In some aspects, methods are provided for treating oculopharyngeal muscular dystrophy. In some cases, the methods may comprise administering a therapeutic composition of the disclosure (e.g., comprising a PGE2 compound and/or a myotoxin) to a subject having, suspected of having, or at risk of developing oculopharyngeal muscular dystrophy. In some cases, treating oculopharyngeal muscular dystrophy may involve administering the therapeutic composition to the muscles of the upper eyelid, the muscles of the throat, or both.

D. Methods of Treating Musculoskeletal Disorders

Provided herein are applications of therapeutic compositions of the disclosure (e.g., comprising a PGE2 compound and/or a myotoxin) to the musculoskeletal system. In some embodiments, the therapeutic composition can be administered to a subject in need thereof to treat a musculoskeletal disorder. In some cases, the musculoskeletal disorder is a muscle disorder. In other embodiments, the therapeutic composition can be administered to a subject in need thereof to improve a function of the musculoskeletal system. In further embodiments, the therapeutic composition can be administered to a subject in need thereof to augment effectiveness of an existing treatment of a disorder or disease of the musculoskeletal system such as carpometacarpal arthroplasty.

Impaired function of the musculoskeletal system may be due to different factors. In some cases, the muscle disorder may be due to aging. For example, sarcopenia is the degenerative loss of skeletal muscle mass, varying from 0.5% to 1% muscle loss per year after the age of 50, and is associated with aging. In other cases, the muscle disorder may be due to disuse of the affected muscle. In some cases, disuse may be due to immobilization (e.g., a splint, a cast). In other cases, disuse may be due to pain (e.g., arthritis). In some cases, the muscle disorder may be muscle atrophy as a result of denervation. Diseases that affect lower motor neurons may impair innervation of myofibers resulting in muscle atrophy. In other cases, the muscle disorder may be due to metabolic reasons, such as glucocorticoid-induced muscle atrophy. For example, excess alcohol intake can result in alcoholic myopathy. In another example, chronic diabetes mellitus can damage the nerves that innervate the hands and feet, resulting in diabetic amyotrophy. Other causes of impaired muscle function may include trauma, and muscle-related degenerative diseases. Provided herein are methods of treating a muscle disorder due to any of the causes described herein. In some cases, the methods comprise administering a therapeutic composition of the disclosure (e.g., comprising a PGE2 compound and/or a myotoxin).

Aging Hand

One of the most common changes in aging skeletal muscle in the body is a major reduction in muscle mass ranging from 25% to 45%, which is sometimes described as "sarcopenia of old age". There are 11 intrinsic muscles and 15 extrinsic muscles with direct functional roles in the hand. Extrinsic and intrinsic hand muscles produce the force required for gripping objects (grip force). After 60 years of age there is a rapid decline in hand-grip strength, by as much as 20-25%. This is accompanied by a substantial loss of muscle fibers and decreased muscle-fiber length, particularly in the thenar muscle group, and contributes an important role in reduction of action potential. The thumb intrinsic musculature constitutes approximately 40% of the total intrinsic musculature of the hand. Three of the main muscles, oblique adductor pollicis, opponens pollicis, and flexor pollicis brevis, play important roles in stabilizing the thumb during strong pinch grips of objects, and these movements commonly show age-related dysfunction. The contractile capacity of the thenar muscle in elderly people has been assessed by tetanic stimulation of the median nerve. The higher muscle fatigue resistance in elderly adults has been attributed to differences in both the Peripheral Nervous System and Central Nervous System. There is a significant reduction in both action potentials and in the number of viable motor units associated with the hand muscles in the elderly.

In some aspects, methods are provided for treating impaired hand function. In some cases, the methods may comprise administering a therapeutic composition of the disclosure (e.g., a PGE2 compound and/or a myotoxin) to a subject in need thereof. In some embodiments, the subject is greater than 50 years old, greater than 55 years old, greater than 60 years old, greater than 65 years, or greater than 70 years old. In some embodiments, the impaired hand function may be a result of aging. In some embodiments, the therapeutic composition may treat the impaired hand function by inducing muscle regeneration in a hand muscle of the subject. In some cases, the hand muscle may be an intrinsic muscle. An intrinsic muscle may include any of the following, without limitation: the three thenar muscles, the three hypothenar muscles, the interossei muscles, the lumbrical muscles, the palmaris brevis, and the adductor pollicis. In some cases, the hand muscle is an extrinsic muscle. An extrinsic muscle may include any of the following, without limitation: abductor pollicis longus, extensor pollicis brevis, flexor pollicis longus, flexor carpi radialis, flexor digitorum profundus, four flexor digitorum superficialis, flexor carpi ulnaris, extensor carpi radialis longus, extensor carpi radialis brevis, extensor indicis, extensor digitorum communis, extensor digiti minimi, and extensor carpi ulnaris.

In some embodiments, the therapeutic composition may be administered in combination with hand surgery (e.g., closed reduction and fixation surgery, tendon repair, nerve repair, surgical drainage and/or debridement, or joint replacement). In such cases, the therapeutic composition can be administered before surgery, during surgery, after surgery, or any combination thereof. In other embodiments, the therapeutic composition may be administered without hand surgery.

In some embodiments, a therapeutic composition of the disclosure (e.g., comprising a PGE2 compound and/or a myotoxin) may be administered by topical administration, intradermal administration, intramuscular administration, or a combination thereof. In some cases, the therapeutic composition may be administered by intramuscular administration. In some cases, the intramuscular administration may comprise injection of a hand muscle. The hand muscle may include any one of the following: thenar muscle, a hypothenar muscle, an interossei muscle, a lumbrical muscle, palmaris brevis, adductor pollicis abductor pollicis longus, flexor pollicis longus, flexor carpi radialis, flexor digitorum profundus, four flexor digitorum superficialis, flexor carpi ulnaris, extensor pollicis brevis, extensor carpi radialis longus, extensor carpi radialis brevis, extensor indicis, extensor digitorum communis, extensor digiti minimi, or extensor carpi ulnaris. In some cases, an anesthetic may be administered to a hand of a subject prior to injection of a therapeutic composition. In some cases, the hand muscle may be injected with surgical exposure; in other cases, the hand muscle may be injected without surgical exposure. In some embodiments, a 20-, 21-, 22-, 23-, 24- or 25-gauge needle may be used to inject the hand muscle.

In some embodiments, methods of treating impaired hand function may include administering (e.g., intramuscular injection) a therapeutic composition of the disclosure to a hand muscle of a subject in need thereof, in a volume of about 0.01 mL to about 0.15 mL. In some embodiments, the hand muscle is injected with at least about 0.01 mL of the therapeutic composition. In some embodiments, the hand muscle is injected with at most about 0.15 mL of the therapeutic composition. In some embodiments, the hand muscle is injected with greater than 0.01 mL, greater than 0.02 mL, greater than 0.03 mL, greater than 0.04 mL, greater than 0.05 mL, greater than 0.06 mL, greater than 0.07 mL, greater than 0.08 mL, greater than 0.09 mL, greater than 0.10 mL, greater than 0.11 mL, greater than 0.12 mL, greater than 0.13 mL, or greater than 0.14 mL of the therapeutic composition.

In some aspects, the effectiveness of an administration of a therapeutic composition of the disclosure (e.g., to treat impaired hand function) may be determined by conducting tests before administration, after administration, or both. In some cases, the test may measure a hand function before administration, after administration, or both. In some cases, the test may be a maximum pinch force test, a steadiness pinch force test, a pegboard test, a two-point discrimination test, a precision pinch steadiness test, a handgrip force test, or a combination thereof.

In some embodiments, the dose of a therapeutic composition of the disclosure may be adjusted after determining the effectiveness of a prior administration (e.g., to treat impaired hand function). In some cases, the dose of the PGE2 compound, the myotoxin, or both may be increased. In other cases, the dose of the PGE2 compound, the myotoxin, or both, may be decreased. In some cases, the dose of the PGE2 compound, the myotoxin, or both may not be changed.

In some embodiments, the frequency of administration of a therapeutic composition of the disclosure (e.g., comprising a PGE2 compound and/or a myotoxin) may be adjusted after determining the effectiveness of an administration of the therapeutic composition. In some cases, only a single administration of the therapeutic composition may be needed to treat impaired hand function. In some cases, two, three, four, five, or more than five administrations of the therapeutic composition may be needed to treat impaired hand function. In some cases, the frequency of administration may be increased after determining the effectiveness of a prior administration. In other cases, the frequency of administration may be decreased after determining the effectiveness of a prior administration.

In some embodiments, a subject in need thereof may be identified by a test prior to administration of the therapeutic composition. In some cases, the test may be a maximum pinch force test, a steadiness pinch force test, a pegboard test, a two-point discrimination test, a precision pinch steadiness test, a handgrip force test, or a combination thereof.

Thenar Atrophy

Compression peripheral nerve injuries (PNI) are a category of nerve injury caused by constriction of the nerve. Carpal tunnel syndrome (CTS) is the most common peripheral compression neuropathy, resulting from median nerve compression at the wrist. Symptoms of carpal tunnel syndrome may include sensory impairments (e.g., numbness and paresthesias) and motor deficits in the abductor pollicis brevis (APB), opponens pollicis, and the superficial belly of the flexor pollicis brevis, which are the intrinsic median-innervated thenar muscles. Prolonged compression of the median nerve potentially disturbs motor function of the thenar muscles, and in patients with severe carpal tunnel syndrome, atrophy of the thenar muscles may result. For example, severe CTS results in the denervation and atrophy of the APB muscle. The APB muscle brings the thumb out of the plane of the palm and is integral to many fine motor activities. The surgical treatment of CTS is to release the band constricting the median nerve. This allows for regeneration of the motor nerve and potential recovery of the muscle. Unfortunately, many of those with severe CTS have poor functional recovery even after the nerve has been released. Restoring function to these specific muscle groups that control the hand grip can increase independence and overall quality of life.

In some aspects, methods are provided for the treatment of impaired thumb function. In some cases, the methods comprise administering a therapeutic composition of the disclosure (e.g., comprising a PGE2 compound and/or a myotoxin) to a subject having, suspected of having, or at risk of developing impaired thumb function. In some embodiments, the impaired thumb function is due to thenar atrophy. In some embodiments, the therapeutic composition may treat impaired thumb function by inducing muscle regeneration in a hand muscle of a subject. In some cases, the therapeutic composition in administered to a hand muscle of the subject for the treatment of impaired thumb function. In some cases, the hand muscle is the abductor pollicis brevis (APB), the opponens pollicis, or flexor pollicis brevis. In some cases, the hand muscle is the abductor pollicis brevis.

In some embodiments, a therapeutic composition of the disclosure may administered in combination with hand surgery to treat impaired thumb function. In some cases, the hand surgery may be carpel tunnel syndrome surgery. In some cases, the therapeutic composition can be administered before surgery, during surgery, after surgery, or any combination thereof. In other embodiments, the therapeutic composition may be administered without hand surgery.

In some embodiments, a therapeutic composition of the disclosure (e.g., comprising a PGE2 compound and/or a myotoxin) may be administered by topical administration, intradermal administration, intramuscular administration, or a combination thereof for the treatment of impaired thumb function. In some cases, the therapeutic composition may be administered by intramuscular administration. In some cases, the intramuscular administration comprises injection of a hand muscle. In some cases, the hand muscle may comprise a thenar muscle. In some cases, the hand muscle may comprise the abductor pollicis brevis (APB), the opponens pollicis, or flexor pollicis brevis. In some cases, the hand muscle may be the abductor pollicis brevis. In some cases, an anesthetic may be administered to a hand of a subject in need thereof prior to injection of a therapeutic composition of the disclosure. In some cases, the hand muscle may be injected with surgical exposure; in other cases, the hand muscle may be injected without surgical exposure. In some embodiments, a 20-, 21-, 22-, 23-, 24- or 25-gauge needle may be used to inject the hand muscle.

In some aspects, methods of treating impaired thumb function may include administering (e.g., intramuscular injection) a therapeutic composition of the disclosure to a hand muscle of a subject in need thereof, in a volume of about 0.01 mL to about 0.15 mL. In some embodiments, the hand muscle may be injected with at least about 0.01 mL of the therapeutic composition. In some embodiments, the hand muscle may be injected with at most about 0.15 mL of the therapeutic composition. In some embodiments, the hand muscle may be injected with greater than 0.01 mL, greater than 0.02 mL, greater than 0.03 mL, greater than 0.04 mL, greater than 0.05 mL, greater than 0.06 mL, greater than 0.07 mL, greater than 0.08 mL, greater than 0.09 mL, greater than 0.10 mL, greater than 0.11 mL, greater than 0.12 mL, greater than 0.13 mL, or greater than 0.14 mL of the therapeutic composition.

In some aspects, the effectiveness of an administration of a therapeutic composition of the disclosure may be determined by conducting tests before administration, after administration, or both. In some cases, the test may measure a hand function before administration, after administration, or both. In some cases, the test may be a tip pinch strength test, a Moberg pickup test, or both. In some cases, the test may be a patient-centric overall quality of life measure such as the Canadian Occupational Performance Measure (COPM).

In some aspects, the dose of a therapeutic composition of the disclosure may be adjusted after determining the effectiveness of a prior administration. In some cases, the dose of the PGE2 compound, the myotoxin, or both, may be increased. In other cases, the dose of the PGE2 compound, the myotoxin, or both, may be decreased. In some cases, the dose of the PGE2 compound, the myotoxin, or both, may not be changed.

In some embodiments, the frequency of administration of a therapeutic composition of the disclosure (e.g., comprising a PGE2 compound and/or a myotoxin) may be adjusted after determining the effectiveness of an administration of the therapeutic composition. In some cases, only a single administration of the therapeutic composition may be needed to treat impaired thumb function. In some cases, two, three, four, five, or more than five administrations of the therapeutic composition may be needed to treat impaired thumb function. In some cases, the frequency of administration may be increased after determining the effectiveness of a prior administration. In other cases, the frequency of administration may be decreased after determining the effectiveness of a prior administration.

In some embodiments, a subject having, suspected of having, or at risk of having impaired thumb function may be identified by a test prior to administration of a therapeutic composition of the disclosure. In some cases, the test may be a tip pinch strength test, a Moberg pickup test, or both.

In some aspects, methods are provided for the treatment of muscle impairment caused by compression peripheral nerve injuries. In some cases, the methods comprise administering a therapeutic composition of the disclosure (e.g., comprising a PGE2 compound and/or a myotoxin) to a subject having, suspected of having, or at risk of developing a compression peripheral nerve injury. For example, cubital tunnel syndrome results from ulnar nerve entrapment at the elbow and is the second most common entrapment of the upper limb. Ulnar nerve compression results in pain or parasthesia in the fourth and fifth finger. In addition to the numbness and tingling in the hand and fingers, muscle atrophy is a common result of ulnar nerve compression. In another example, thoracic outlet syndrome results from compression of the nerves between the shoulder and neck, known as the brachial plexus. This can cause pain, weakness, numbness, tingling, a cold sensation, or sometimes a more general type of discomfort in one or both upper limbs. The common symptoms are pain, numbness, and tingling that radiates below the shoulder down towards the hand and usually into the pinky and ring finger. This condition also can lead to muscle atrophy of the intrinsic muscles of the hand.

Plantar Fasciitis

The plantar fascia is the thick tissue on the bottom of the foot. It connects the heel bone to the toes and creates the arch of the foot. When this tissue becomes swollen or inflamed, it is called plantar fasciitis. Plantar fasciitis is one of the most common causes of heel pain and has been estimated to affect about two million people in the US, resulting in more than one million visits to both primary care physicians and foot specialists. Plantar fasciitis affects both sedentary and athletic people and is thought to result from chronic overload either from lifestyle or exercise. Current literature suggests that plantar fasciitis is more correctly termed fasciosis because of the chronicity of the disease and the evidence of degeneration rather than inflammation.

Muscle weakness may be a potential cause of chronic plantar fasciitis. Studies have shown that in a load-bearing limb, there are both passive and active mechanisms that support the medial longitudinal arch. Support is achieved passively by a tensioned plantar fascia, and actively by participation of the plantar intrinsic foot muscles (PIFM) and tibialis posterior (TP) muscle. Plantar fasciitis has been associated with PIFM atrophy at the forefoot. The forefoot volume of a foot with chronic plantar fasciitis was on average 5.2% less than the contralateral healthy foot. The forefoot muscles include flexor hallucis brevis medialis, flexor hallucis brevis lateralis, adductor hallucis transverse, adductor hallucis oblique and the plantar interossei. Patients with abductor digiti minimi atrophy also have a significantly greater frequency of Achilles tendinosis, calcaneal edema, calcaneal spur, plantar fasciitis, and posterior tibialis tendon dysfunction than those without. Additionally, strengthening a weakened or atrophied flexor digitorum brevis could also help stabilize the medial longitudinal arch.

In some aspects, methods are provided for the treatment of impaired foot function. In some cases, the methods comprise administering a therapeutic composition of the disclosure (e.g., comprising a PGE2 compound and/or a myotoxin) to a subject having, suspected of having, or at risk of developing impaired foot function. In some embodiments, the impaired foot function is due to plantar fasciitis. Accordingly, in some embodiments, the therapeutic composition may be suitable to treat plantar fasciitis. In some embodiments, the therapeutic composition may treat the impaired foot function by inducing muscle generation in a foot muscle of a subject in need thereof. In some cases, the foot muscle is a plantar intrinsic foot muscle, flexor hallucis medialis, flexor hallucis brevis lateralis, adductor hallucis transverse, adductor hallucis oblique, dorsal and plantar interossei, abductor digiti minimi, and flexor digitorum brevis.

In some embodiments, a therapeutic composition of the disclosure may be administered in combination with foot surgery. In some cases, the therapeutic composition can be administered before surgery, during surgery, after surgery, or any combination thereof. In other cases, the therapeutic composition may be administered without foot surgery.

In some embodiments, the therapeutic composition may be administered in combination with another treatment. In some cases, the another treatment comprises a nonsteroidal anti-inflammatory medication, stretching, a night splint, custom orthotics, a corticosteroid injection, a platelet-rich plasma injection, extracorporeal shock wave therapy, fasciotomy, or a combination thereof.

In some embodiments, a therapeutic composition of the disclosure may be administered by topical administration, intradermal administration, intramuscular administration, or a combination. In some cases, the therapeutic composition may be administered by intramuscular administration. In some cases, the intramuscular administration may comprise injection of a foot muscle. In some cases, the foot muscle may comprise plantar intrinsic foot muscle, flexor hallucis medialis, flexor hallucis brevis lateralis, adductor hallucis transverse, adductor hallucis oblique, dorsal and plantar interossei, abductor digiti minimi, and flexor digitorum brevis.

In some cases, an anesthetic may be administered to a foot to a subject in need thereof prior to injection of a therapeutic composition of the disclosure. In some cases, the foot muscle may be injected with surgical exposure; in other cases, the foot muscle may be injected without surgical exposure. In some embodiments, a 20-, 21-, 22-, 23-, 24- or 25-gauge needle may be used to inject the foot muscle.

In some embodiments, methods of treating impaired foot function may include administering (e.g., intramuscular injection) a therapeutic composition of the disclosure to a foot muscle of a subject in need thereof, in a volume of about 0.01 mL to about 0.15 mL. In some embodiments, the foot muscle may be injected with at least about 0.01 mL of the therapeutic composition. In some embodiments, the foot muscle may be injected with at most about 0.15 mL of the therapeutic composition. In some embodiments, the foot muscle may be injected with greater than 0.01 mL, greater than 0.02 mL, greater than 0.03 mL, greater than 0.04 mL, greater than 0.05 mL, greater than 0.06 mL, greater than 0.07 mL, greater than 0.08 mL, greater than 0.09 mL, greater than 0.10 mL, greater than 0.11 mL, greater than 0.12 mL, greater than 0.13 mL, or greater than 0.14 mL of the therapeutic composition.

In some aspects, the effectiveness of an administration of a therapeutic composition of the disclosure may be determined by conducting tests before administration, after administration, or both. In some cases, the tests may measure a foot function before administration, after administration, or both. In some cases, the test may be a physical exam to determine pain on the bottom of a foot, pain along the sole of a foot, flat feet, high arches, foot swelling, foot redness, stiffness or tightness of the arch in the bottom of a foot, or a combination thereof.

In some embodiments, the dose of the therapeutic composition may be adjusted after determining the effectiveness of a prior administration. In some cases, the dose of the PGE2 compound, the myotoxin, or both, may be increased. In other cases, the dose of the PGE2 compound, the myotoxin, or both, may be decreased. In some cases, the dose of the PGE2 compound, the myotoxin, or both may not be changed.

In some embodiments, the frequency of administration of a therapeutic composition of the disclosure to treat impaired foot may be adjusted after determining the effectiveness of an administration of the therapeutic composition. In some cases, only a single administration of the therapeutic composition may be needed to treat impaired foot function. In some cases, two, three, four, five, or more than five administrations of the therapeutic composition may be needed to treat impaired foot function. In some cases, the frequency of administration is increased after determining the effectiveness of a prior administration. In other cases, the frequency of administration is decreased after determining the effectiveness of a prior administration.

In some embodiments, a subject in need of treatment for impaired foot function may be identified by a test prior to administration of the therapeutic composition. In some cases, the test may be a physical exam to determine pain on the bottom of a foot, pain along the sole of a foot, flat feet, high arches, foot swelling, foot redness, stiffness or tightness of the arch in the bottom of a foot, or a combination thereof.

Foot Drop

Foot drop, also known as drop foot, is a term for difficulty lifting the front part of the foot. In some case, the front of the foot may drag on the ground during walking. Foot drop impairs ambulation and can result in falls. Foot drop is caused by weakness or paralysis of one or more of the muscles involved in lifting the front part of the foot. There are several causes of foot drop. For example, compression of a nerve in a leg that controls the muscles involved in lifting the foot, the peroneal nerve, is a common cause of foot drop. This nerve may also be injured during hip or knee replacement surgery. A nerve root injury, "pinched nerve", in the spine can also cause foot drop. Diabetes may also make a subject more susceptible to nerve disorders, which are associated with foot drop. Various forms of muscular dystrophy that cause progressive muscle weakness. In addition, disorders that affect the spinal cord or brain, such as amyotrophic lateral sclerosis (ALS), multiple sclerosis or stroke, may cause foot drop.

Described herein are methods of treating foot drop comprising administering a therapeutic composition comprising a PGE2 compound and a myotoxin to a subject in need thereof. In some embodiments, the therapeutic composition treats the impaired foot function by inducing muscle generation in a foot or lower leg muscle of a subject in need thereof. In some cases, the foot or lower leg muscle is the anterior tibialis muscle, fibularis tertius, extensor digitorum longus, extensor hallucis longus, or a combination thereof.

In some embodiments, the therapeutic composition is administered in combination with surgery (e.g., nerve surgery). In those embodiments, the therapeutic composition can be administered before surgery, during surgery, after surgery, or any combination thereof. In other embodiments, the therapeutic composition is administered without foot or lower leg surgery.

In some embodiments, the therapeutic composition is administered in combination with another treatment. In some cases, the another treatment comprises braces or splints, physical therapy, nerve stimulation, nerve surgery, or a combination thereof.

In some embodiments, the therapeutic composition comprising a PGE2 compound and a myotoxin is administered by topical administration, intradermal administration, intramuscular administration, or a combination. In some cases, the therapeutic composition is administered by intramuscular administration. In some cases, the intramuscular administration comprises injection of a foot or lower leg muscle. The foot or lower leg muscle may comprise the anterior tibialis muscle, fibularis tertius, extensor digitorum longus, extensor hallucis longus. In some cases, an anesthetic may be administered to a foot or lower leg of a subject in need prior to injection. In some cases, the foot or lower leg muscle is injected with surgical exposure; in other cases, the foot or lower leg muscle is injected without surgical exposure. In some embodiments, a 20-, 21-, 22-, 23-, 24- or 25-gauge needle is used to inject the foot or lower leg muscle.

In some embodiments, a foot or lower leg muscle of a subject in need is injected with a volume of about 0.01 mL to about 0.15 mL of therapeutic composition comprising a PGE2 compound and a myotoxin. In some embodiments, the foot or lower leg muscle is injected with at least about 0.01 mL of therapeutic composition. In some embodiments, the foot or lower leg muscle is injected with at most about 0.15 mL of therapeutic composition. In some embodiments, the foot or lower leg muscle is injected with greater than 0.01 mL, greater than 0.02 mL, greater than 0.03 mL, greater than 0.04 mL, greater than 0.05 mL, greater than 0.06 mL, greater than 0.07 mL, greater than 0.08 mL, greater than 0.09 mL, greater than 0.10 mL, greater than 0.11 mL, greater than 0.12 mL, greater than 0.13 mL, or greater than 0.14 mL of therapeutic composition comprising a PGE2 compound and a myotoxin.

The effectiveness of an administration of the therapeutic composition may be determined by conducting tests before administration, after administration, or a combination thereof. The tests may measure a foot or lower leg function before and/or after administration. The test may be a physical exam to observe gait, to determine weakness of leg muscles, to determine numbness of shin, foot, and/or toes, or a combination thereof.

In some embodiments, the dose of the therapeutic composition may be adjusted after determining the effectiveness of a prior administration. In some cases, the dose of the PGE2 compound and/or the myotoxin may increase. In other cases, the dose of the PGE2 compound and/or the myotoxin may decrease. In some cases, the dose of the PGE2 compound and/or the myotoxin may stay the same.

In some embodiments, the frequency of administration of the therapeutic composition comprising a PGE2 compound and/or the myotoxin may be adjusted after determining the effectiveness of an administration of the therapeutic composition. In some cases, a single administration of the therapeutic composition is needed to treat impaired foot or lower leg function. In some cases, two or more, three or more, four or more, five or more administrations of the therapeutic composition are needed. In some cases, the frequency of administration is increased after determining the effectiveness of a prior administration. In other cases, the frequency of administration is decreased after determining the effectiveness of a prior administration.

Diabetic Neuropathy

Diabetes is the most common cause of neuropathy in US and neuropathies are the most common complication of diabetes mellitus. Atrophy of the small muscles of the foot is common in diabetes and is related to peripheral motor neuropathy. In long-term diabetic patients, muscle weakness and atrophy in the lower leg muscles, including the foot muscles, is common in neuropathic patients compared to non-neuropathic patients. Volume of the intrinsic foot muscles has been shown to be lower in neuropathic diabetic patients compared to non-neuropathic diabetic patients and non-diabetic controls. Atrophy of the intrinsic muscles of the foot can lead to fixed claw and hammer toe deformities, which are common in neuropathic diabetic patients. Additionally, the intrinsic muscles of the foot stabilize the arches of the foot. High arches are common with the atrophy of plantar intrinsic muscles like Abductor Hallucis, Flexor Hallucis Brevis and Adductor Hallucis.

In some aspects, methods are provided for the treatment of diabetic neuropathy or associated disorders. In some cases, the methods may comprise administering a therapeutic composition of the disclosure (e.g., comprising a PGE2 compound and/or a myotoxin) to a subject having, suspected of having, or at risk of developing a diabetic neuropathy or an associated disorder. In some cases, the disorder associated with a diabetic neuropathy may include, without limitation, atrophy of the small muscles of the foot, muscle weakness and atrophy of the lower leg muscles, and atrophy of the intrinsic muscles of the foot. In some cases, the methods comprise administering the therapeutic composition to the small muscles of the foot, to the lower leg muscles, or to the intrinsic muscles of the foot.

Disuse-Induced Muscle Atrophy

Loss of skeletal muscle mass occurs frequently in clinical settings following limb immobilization, bed rest, spinal cord injury and partial/complete peripheral nerve damage, resulting in significant loss of muscle mass and force production. The extent of muscle atrophy under disuse conditions is variable and can be dependent on a variety of factors including age, the physiological function and fiber type composition of the muscle, and the degree of unloading and inactivity. Disuse-induced atrophy will likely affect every person in his or her lifetime, and can be debilitating especially in the elderly. Currently, there are no good pharmacological strategies to treat disuse-induced muscle atrophy.

Described herein are methods of treating disuse-induced muscle atrophy comprising administering a therapeutic composition comprising a PGE2 compound and a myotoxin to a subject in need thereof. In some embodiments, the affected muscle has experienced unloading, inactivity, or a combination, for greater than 1 day, greater than 5 days, greater than 10 days, greater than 50 days, or greater than 100 days. In some embodiments, the therapeutic composition treats disuse-induced atrophy by inducing muscle generation in a muscle of a subject in need thereof, wherein the muscle has experienced unloading and/or inactivity of a prolonged period of time. In some cases, the muscle is a skeletal muscle. In some embodiments, the therapeutic composition comprising a PGE2 compound and a myotoxin is administered by intramuscular administration. In some cases, the intramuscular administration comprises injection of the affected muscle.

In some embodiments, disuse-induced muscle atrophy is due to a distal radius fracture, also known as Colles fracture. A Colles fracture results in a backward and outward position of the hand in relation to the wrist. It is common in the elderly. Loss of muscle mass can occur due to immobilization. Described herein are methods of treating muscle atrophy due to a distal radius fracture comprising administering a therapeutic composition comprising a PGE2 compound and a myotoxin to a subject in need thereof. In some embodiments, the therapeutic composition treats the muscle atrophy by inducing muscle generation in a muscle of a subject in need thereof. In some cases, the muscle is the flexor carpi radialis, flexor pollicis longus, flexor digitorum superficialis, flexor digitorum profundus, flexor carpi ulnaris, extensor carpi radialis brevis/longus, extensor pollicis longus, extensor digitorum communis, extensor carpi ulnaris or a combination thereof. In some embodiments, the therapeutic composition is administered in combination with surgery (e.g., wrist arthroscopy). In those embodiments, the therapeutic composition can be administered before surgery, during surgery, after surgery, or any combination thereof. In other embodiments, the therapeutic composition is administered without surgery.

In some embodiments, the therapeutic composition is administered in combination with another treatment. In some cases, the another treatment comprises braces or splints, physical therapy, nerve stimulation, nerve surgery, or a combination thereof.

In some embodiments, the therapeutic composition comprising a PGE2 compound and a myotoxin is administered by topical administration, intradermal administration, intramuscular administration, or a combination. In some cases, the therapeutic composition is administered by intramuscular administration. In some cases, the intramuscular administration comprises injection of a hand or lower arm muscle. The hand or lower arm muscle may comprise the flexor carpi radialis, flexor pollicis longus, flexor digitorum superficialis, flexor digitorum profundus, flexor carpi ulnaris, extensor carpi radialis brevis/longus, extensor pollicis longus, extensor digitorum communis, extensor carpi ulnaris, or a combination thereof.

In some cases, an anesthetic may be administered to a hand or lower arm of a subject in need prior to injection. In some cases, the hand or lower arm muscle is injected with surgical exposure; in other cases, the hand or lower arm muscle is injected without surgical exposure. In some embodiments, a 20-, 21-, 22-, 23-, 24- or 25-gauge needle is used to inject the hand or lower arm leg muscle.

In some embodiments, a hand or lower arm muscle of a subject in need is injected with a volume of about 0.01 mL to about 0.15 mL of therapeutic composition comprising a PGE2 compound and a myotoxin. In some embodiments, the hand or lower arm muscle is injected with at least about 0.01 mL of therapeutic composition. In some embodiments, the hand or lower arm muscle is injected with at most about 0.15 mL of therapeutic composition. In some embodiments, the hand or lower arm muscle is injected with greater than 0.01 mL, greater than 0.02 mL, greater than 0.03 mL, greater than 0.04 mL, greater than 0.05 mL, greater than 0.06 mL, greater than 0.07 mL, greater than 0.08 mL, greater than 0.09 mL, greater than 0.10 mL, greater than 0.11 mL, greater than 0.12 mL, greater than 0.13 mL, or greater than 0.14 mL of therapeutic composition comprising a PGE2 compound and a myotoxin.

The effectiveness of an administration of the therapeutic composition may be determined by conducting tests before administration, after administration, or a combination thereof. The tests may measure a hand or lower arm function before and/or after administration. The test may include range of motion of wrist, grip strength, patient reported outcomes such as the Disability of Arm Shoulder and Hand or a combination thereof.

In some embodiments, the dose of the therapeutic composition may be adjusted after determining the effectiveness of a prior administration. In some cases, the dose of the PGE2 compound and/or the myotoxin may increase. In other cases, the dose of the PGE2 compound and/or the myotoxin may decrease. In some cases, the dose of the PGE2 compound and/or the myotoxin may stay the same.

In some embodiments, the frequency of administration of the therapeutic composition comprising a PGE2 compound and/or the myotoxin may be adjusted after determining the effectiveness of an administration of the therapeutic composition. In some cases, a single administration of the therapeutic composition is needed to treat impaired hand or lower arm function. In some cases, two or more, three or more, four or more, five or more administrations of the therapeutic composition are needed. In some cases, the frequency of administration is increased after determining the effectiveness of a prior administration. In other cases, the frequency of administration is decreased after determining the effectiveness of a prior administration.

In some embodiments, disuse-induced muscle atrophy is due to a hip fracture. A hip fracture may be due to major or minor trauma. In elderly people with bones weakened by osteoporosis, relatively little trauma, even walking, may result in a hip fracture. Loss of muscle mass can occur due to joint immobilization, and bed rest. Loss of muscle can be induced by a combination of unloading and inactivity. Weakness of the hip muscle is an often-occurring condition after displaced fractures of the proximal femur in older patients. Described herein are methods of treating muscle atrophy due to a hip fracture comprising administering a therapeutic composition comprising a PGE2 compound and a myotoxin to a subject in need thereof. In some embodiments, the therapeutic composition treats the muscle atrophy by inducing muscle generation in a hip muscle of a subject in need thereof. In some cases, the hip muscle is iliacus, psoas major, gluteus maximus, gluteus medius, gluteus minimus, tensor fasciae latae, superior gemellus, inferior gemellus, obturator intermus, obturator externus, quadratus femoris, piriformis, adductor magnus, adductor longus, adductor brevis, adductor minimus, pectineus, rectus femoris, vastus lateralis, vastus medialis, vastus intermedius, quadriceps femoris, Sartorius, biceps femoris, semitendinosus, semimembranosus, psoas minor, iliopsoas, gracilis, or a combination thereof.

In some embodiments, the therapeutic composition is administered in combination with surgery (e.g., joint arthroplasty). In those embodiments, the therapeutic composition can be administered before surgery, during surgery, after surgery, or any combination thereof. In other embodiments, the therapeutic composition is administered without surgery.

In some embodiments, the therapeutic composition is administered in combination with another treatment regimen. In some cases, the another treatment regimen comprises braces or splints, physical therapy, nerve stimulation, nerve surgery, or a combination thereof.

In some embodiments, the therapeutic composition comprising a PGE2 compound and a myotoxin is administered by topical administration, intradermal administration, intramuscular administration, or a combination. In some cases, the therapeutic composition is administered by intramuscular administration. In some cases, the intramuscular administration comprises injection of a hip muscle. In some cases, the hip muscle is iliacus, psoas major, gluteus maximus, gluteus medius, gluteus minimus, tensor fasciae latae, superior gemellus, inferior gemellus, obturator intermus, obturator externus, quadratus femoris, piriformis, adductor magnus, adductor longus, adductor brevis, adductor minimus, pectineus, rectus femoris, vastus lateralis, vastus medialis, vastus intermedius, quadriceps femoris, Sartorius, biceps femoris, semitendinosus, semimembranosus, psoas minor, iliopsoas, gracilis, or a combination thereof.

In some cases, an anesthetic may be administered to a hip of a subject in need prior to injection. In some cases, the hip muscle is injected with surgical exposure; in other cases, the hip muscle is injected without surgical exposure. In some embodiments, a 20-, 21-, 22-, 23-, 24- or 25-gauge needle is used to inject the hip muscle.

In some embodiments, a hip muscle of a subject in need is injected with a volume of about 0.5 mL to about 5 mL of therapeutic composition comprising a PGE2 compound and a myotoxin. In some embodiments, the hip muscle is injected with at least about 0.5 mL of therapeutic composition. In some embodiments, the hip muscle is injected with at most about 4 mL of therapeutic composition. In some embodiments, the hip muscle is injected with greater than 0.5 mL, greater than 1.0 mL, greater than 1.5 mL, greater than 2.0 mL, greater than 2.5 mL, greater than 3.0 mL, greater than 3.5 mL of therapeutic composition comprising a PGE2 compound and a myotoxin.

The effectiveness of an administration of the therapeutic composition may be determined by conducting tests before administration, after administration, or a combination thereof. The tests may measure a hip-related function before and/or after administration. The test may be strength testing of hip and knee muscles as well as functional tests such as the get up and go test or a combination thereof.

In some embodiments, the dose of the therapeutic composition may be adjusted after determining the effectiveness of a prior administration. In some cases, the dose of the PGE2 compound and/or the myotoxin may increase. In other cases, the dose of the PGE2 compound and/or the myotoxin may decrease. In some cases, the dose of the PGE2 compound and/or the myotoxin may stay the same.

In some embodiments, the frequency of administration of the therapeutic composition comprising a PGE2 compound and/or the myotoxin may be adjusted after determining the effectiveness of an administration of the therapeutic composition. In some cases, a single administration of the therapeutic composition is needed to treat impaired hand or lower arm function. In some cases, two or more, three or more, four or more, five or more administrations of the therapeutic composition are needed. In some cases, the frequency of administration is increased after determining the effectiveness of a prior administration. In other cases, the frequency of administration is decreased after determining the effectiveness of a prior administration.

In some embodiments, disuse-induced muscle atrophy is due to a rotator cuff injury. In some cases, a rotator cuff injury may be due to an acute rotator cuff tear. In some cases, a rotator cuff injury may be due to degenerative and/or chronic rotator cuff tear. A degenerative and/or chronic rotator cuff tear may be due to repetitive stress, lack of blood supply, bone spurs, or a combination thereof. People over 40 years old are at a greater risk for a rotator cuff tear. Loss of muscle mass can occur due to lack of tension on muscle as well as joint stiffness. Loss of muscle can be induced by a combination of unloading and inactivity. Described herein are methods of treating muscle atrophy due to a rotator cuff injury comprising administering a therapeutic composition comprising a PGE2 compound and a myotoxin to a subject in need thereof. In some embodiments, the therapeutic composition treats the muscle atrophy by inducing muscle generation in a rotator cuff muscle of a subject in need thereof. In some cases, the rotator cuff muscle is supraspinatus, infraspinatus, subscapularis, teres minor, or a combination thereof.

In some embodiments, the therapeutic composition is administered in combination with surgery (e.g., rotator cuff arthroscopy). In those embodiments, the therapeutic composition can be administered before surgery, during surgery, after surgery, or any combination thereof. In other embodiments, the therapeutic composition is administered without surgery.

In some embodiments, the therapeutic composition is administered in combination with another treatment regimen. In some cases, the another treatment regimen comprises braces or splints, physical therapy, nerve stimulation, nerve surgery, or a combination thereof.

In some embodiments, the therapeutic composition comprising a PGE2 compound and a myotoxin is administered by topical administration, intradermal administration, intramuscular administration, or a combination. In some cases, the therapeutic composition is administered by intramuscular administration. In some cases, the intramuscular administration comprises injection of a rotator cuff muscle. In some cases, the rotator cuff muscle is supraspinatus, infraspinatus, subscapularis, teres minor, or a combination thereof.

In some cases, an anesthetic may be administered to a rotator cuff muscle of a subject in need prior to injection. In some cases, the rotator cuff muscle is injected with surgical exposure; in other cases, the rotator cuff muscle is injected without surgical exposure. In some embodiments, a 20-, 21-, 22-, 23-, 24- or 25-gauge needle is used to inject the rotator cuff muscle.

In some embodiments, a rotator cuff muscle of a subject in need is injected with a volume of about 0.5 mL to about 5 mL of therapeutic composition comprising a PGE2 compound and a myotoxin. In some embodiments, the rotator cuff muscle is injected with at least about 0.5 mL of therapeutic composition. In some embodiments, the rotator cuff muscle is injected with at most about 4 mL of therapeutic composition. In some embodiments, the rotator cuff muscle is injected with greater than 0.5 mL, greater than 1.0 mL, greater than 1.5 mL, greater than 2.0 mL, greater than 2.5 mL, greater than 3.0 mL, greater than 3.5 mL of therapeutic composition comprising a PGE2 compound and a myotoxin.

The effectiveness of an administration of the therapeutic composition may be determined by conducting tests before administration, after administration, or a combination thereof. The tests may measure a rotator cuff-related function before and/or after administration. The test may be strength testing of shoulder abduction, external rotation and forward flexion, full and empty can test, drop arm test, and The Quality of Life Outcome Measure for Rotator Cuff or a combination thereof.

In some embodiments, the dose of the therapeutic composition may be adjusted after determining the effectiveness of a prior administration. In some cases, the dose of the PGE2 compound and/or the myotoxin may increase. In other cases, the dose of the PGE2 compound and/or the myotoxin may decrease. In some cases, the dose of the PGE2 compound and/or the myotoxin may stay the same.

In some embodiments, the frequency of administration of the therapeutic composition comprising a PGE2 compound and/or the myotoxin may be adjusted after determining the effectiveness of an administration of the therapeutic composition. In some cases, a single administration of the therapeutic composition is needed to treat impaired hand or lower arm function. In some cases, two or more, three or more, four or more, five or more administrations of the therapeutic composition are needed. In some cases, the frequency of administration is increased after determining the effectiveness of a prior administration. In other cases, the frequency of administration is decreased after determining the effectiveness of a prior administration.

E. Methods of Treating Pelvic Floor Disorders

Pelvic floor disorders (PFDs) arise from dysfunction of the pelvic floor muscles. The pelvic floor muscles are often damaged by childbirth and pelvic surgery. Pelvic floor disorders also arise from other trauma, aging, obesity, neurological diseases, and other injuries. The most common pelvic floor disorders are due, at least in part, to decreased function of the pelvic floor muscles. These disorders include stress urinary incontinence, overactive bladder/urinary urgency incontinence, mixed urinary incontinence, pelvic organ prolapse, and fecal incontinence.

Pelvic floor disorders comprise a wide variety of conditions in both men and women, although women are more commonly affected. The pelvic floor provides anatomic support for the pelvic organs (bladder, prostate, rectum, uterus vagina) and is integral to the proper function of the urinary system, to sexual and reproductive function, and to colorectal function. The pelvic floor is comprised of the pelvic floor muscles as well as the relevant connective tissue (ligaments, tendons, and overlying fascia). The pelvic floor muscles include the levator ani and the coccygeus. The levator ani has three parts: the pubococcygeus, the iliococcygeus and the puborectalis.

Strengthening or improving function of the pelvic floor muscles may treat these types of pelvic floor disorders. In addition, strengthening or improving function of the pelvic floor muscles may prevent pelvic floor disorders from developing in patients identified as high risk (e.g., after complicated delivery, after certain types of pelvic surgery). This application may also be used in combination with existing treatments for pelvic floor disorders (e.g., muscle training/biofeedback, neuromodulation, pharmacotherapy, surgery) in order to improve treatment outcomes.

Provided herein are methods of treating or preventing pelvic floor disorders. In some cases, the methods may comprise administering a therapeutic composition of the disclosure (e.g., comprising a PGE2 compound and/or a myotoxin) to a subject having, suspected of having, or at risk of developing a pelvic floor disorder. In some cases, the pelvic floor disorder is selected from the group consisting of stress urinary incontinence, overactive bladder/urinary urgency incontinence, mixed urinary incontinence, pelvic organ prolapse, and fecal incontinence. In some aspects, the methods may comprise administering a therapeutic composition of the disclosure to the pelvic floor muscles of a subject in need thereof. In some cases, the pelvic floor muscles comprise the levator ani, the coccygeus, or both. In some cases, the levator ani includes the pubococcygeus, the iliococcygeus, and the puborectalis.

In one aspect, provided herein are applications of a therapeutic composition comprising a prostaglandin E2 (PGE2) compound and a myotoxin, as described elsewhere herein, the genitourinary system. In some embodiments, the therapeutic composition can be administered to improve a function of the genitourinary system. In further embodiments, the therapeutic composition can be administered to enhance the effectiveness of an existing approach to treat a disease or disorder of the genitourinary system. The disease or disorder of the genitourinary system can be a urological disorder, gynecological disorder, a colorectal disorder, or a combination thereof.

The pelvic floor muscles support the bladder and the urethra. Most adults can hold over 400 mL of urine in the bladder. Urine flows from the bladder through the urethra to the outside. Around the opening of the bladder is the sphincter muscle. It squeezes to prevent urine from leaking through the urethra. Impairment of any of these muscles can result a urological disorder such as stress incontinence. Moreover, strengthening of any of these muscles can be targeted to treat urological disorders such overactive bladder disorder and underactive bladder disorder.

Stress Urinary Incontinence

Stress urinary incontinence occurs when the bladder leaks urine during physical activity or exertion such as coughing, lifting of heavy objects, exercise, or change in positions. It occurs when any of the muscles that control the ability to hold urine in the bladder is weak or impaired in function. When any one of the muscles, such as the skeletal external urethral muscle, the pubic urethral muscle, becomes weak, urine can pass when pressure is place on the bladder. Weakened muscles may be caused by childbirth, injury to the urethra area, medications, surgery in the pelvic area such as prostate surgery, progressive atrophy and diminished contractility of the skeletal muscles, nerve damage. Current treatments include surgical interventions and injection of "bulking agents".

Described herein are methods of treating stress urinary incontinence (SUI) comprising administering a therapeutic composition comprising a PGE2 compound and a myotoxin to a subject in need thereof. In some embodiments, the therapeutic composition treats SUI by inducing muscle regeneration a muscle of a subject in need thereof. In some cases, the muscle is the skeletal external urethral muscle, the pubic urethral muscle, or the external urethral sphincter muscle.

In some embodiments, the therapeutic composition is administered in combination with surgery (e.g., prostate surgery). In those embodiments, the therapeutic composition can be administered before surgery, during surgery, after surgery, or any combination thereof. In other embodiments, the therapeutic composition is administered without surgery.

In some embodiments, the therapeutic composition comprising a PGE2 compound and a myotoxin is administered by intramuscular administration. In some cases the intramuscular administration comprises injection of the skeletal external urethral muscle, the pubic urethral muscle, and the external urethral sphincter muscle. In some cases, an anesthetic may be administered prior to injection. In some cases, the muscle is injected with surgical exposure; in other cases, the muscle is injected without surgical exposure. In some embodiments, an 18-, 19-, 20-, 21-, 22- or 23-gauge needle is used to inject the muscle.

In some embodiments, a muscle of a subject in need is injected with a volume of about 2 mL or less of therapeutic composition comprising a PGE2 compound and a myotoxin. In some embodiments, the muscle is injected with at least about 2 mL of therapeutic composition. In some embodiments, the muscle is injected with less than 2 mL, less than 1.8 mL, less than 1.6 mL, less than 1.4 mL, less than 1.2 mL, less than 1 mL, less than 0.8 mL, less than 0.6 mL, less than 0.4 mL or less than 0.2 mL of therapeutic composition comprising a PGE2 compound and a myotoxin.

The effectiveness of an administration of the therapeutic composition may be determined by conducting tests before administration, after administration, or a combination thereof. The test may be cystoscopy, a pad weight tests, a voiding diary, pelvic or abdominal ultrasound, post-void residual (PVR), urinalysis, urinary stress test, urodynamic studies such as leak point pressure, x-rays with contrast dye, or a combination thereof. In some embodiments, the dose of the therapeutic composition may be adjusted after determining the effectiveness of a prior administration. In some cases, the dose of the PGE2 compound and/or the myotoxin may increase. In other cases, the dose of the PGE2 compound and/or the myotoxin may decrease. In some cases, the dose of the PGE2 compound and/or the myotoxin may stay the same. In some embodiments, the frequency of administration of the therapeutic composition comprising a PGE2 compound and/or the myotoxin may be adjusted after determining the effectiveness of an administration of the therapeutic composition. In some cases, a single administration of the therapeutic composition is needed. In some cases, two or more, three or more, four or more, five or more administrations of the therapeutic composition are needed. In some cases, the frequency of administration is increased after determining the effectiveness of a prior administration. In other cases, the frequency of administration is decreased after determining the effectiveness of a prior administration.

Mixed Incontinence or Overactive Bladder

Overactive bladder (OAB) is a condition in which the bladder squeezes urine out at the wrong time. For example, a person suffering from an overactive bladder may urinate eight or more times a day or two or more times at night; may have a sudden and strong need to urinate immediately; or leak urine after a sudden, strong urge to urinate. Several conditions may contribute to signs and symptoms of overactive bladder including neurological disorders (e.g., stroke, multiple sclerosis), diabetes, diuretics, urinary tract infections, tumors, bladder stones, enlarged prostate, constipation, excess consumption of caffeine or alcohol, declining cognitive function due to aging, and incomplete bladder emptying. Strengthening and improving function of the external urethral sphincter muscle can impact positive and negative reflex actions between the bladder and the urethra. For example, improved contractile action of the urethral sphincter muscle can signal the bladder to inhibit flow of urine.

Described herein are methods of treating overactive bladder (OAB) comprising administering a therapeutic composition comprising a PGE2 compound and a myotoxin to a subject in need thereof. In some embodiments, the therapeutic composition treats OAB by inducing muscle regeneration a muscle of a subject in need thereof. In some cases, the muscle is the skeletal external urethral muscle.

In some embodiments, the therapeutic composition is administered in combination with surgery (e.g., prostate surgery). In those embodiments, the therapeutic composition can be administered before surgery, during surgery, after surgery, or any combination thereof. In other embodiments, the therapeutic composition is administered without surgery.

In some embodiments, the therapeutic composition comprising a PGE2 compound and a myotoxin is administered by intramuscular administration. In some cases the intramuscular administration comprises injection of the skeletal external urethral muscle. In some cases, an anesthetic may be administered prior to injection. In some cases, the muscle is injected with surgical exposure; in other cases, the muscle is injected without surgical exposure. In some embodiments, an 18-, 19-, 20-, 21-, 22- or 23-gauge needle is used to inject the muscle.

In some embodiments, a muscle of a subject in need is injected with a volume of about 2 mL or less of therapeutic composition comprising a PGE2 compound and a myotoxin. In some embodiments, the muscle is injected with at least about 2 mL of therapeutic composition. In some embodiments, the muscle is injected with less than 2 mL, less than 1.8 mL, less than 1.6 mL, less than 1.4 mL, less than 1.2 mL, less than 1 mL, less than 0.8 mL, less than 0.6 mL, less than 0.4 mL or less than 0.2 mL of therapeutic composition comprising a PGE2 compound and a myotoxin.

The effectiveness of an administration of the therapeutic composition may be determined by conducting tests before administration, after administration, or a combination thereof. The test may be post-void residual (PVR) test, urine flow rate test, bladder pressure test, or a combination thereof. In some embodiments, the dose of the therapeutic composition may be adjusted after determining the effectiveness of a prior administration. In some cases, the dose of the PGE2 compound and/or the myotoxin may increase. In other cases, the dose of the PGE2 compound and/or the myotoxin may decrease. In some cases, the dose of the PGE2 compound and/or the myotoxin may stay the same. In some embodiments, the frequency of administration of the therapeutic composition comprising a PGE2 compound and/or the myotoxin may be adjusted after determining the effectiveness of an administration of the therapeutic composition. In some cases, a single administration of the therapeutic composition is needed. In some cases, two or more, three or more, four or more, five or more administrations of the therapeutic composition are needed. In some cases, the frequency of administration is increased after determining the effectiveness of a prior administration. In other cases, the frequency of administration is decreased after determining the effectiveness of a prior administration.

Obstetrical Anal Sphincter Injury (OASIS)

Obstetrical anal sphincter injury (OASIS) is damage to the anal sphincter during childbirth, and can lead to significant comorbidities, including anal incontinence, rectovaginal fistula and pain. They are more commonly associated with force deliveries than vacuum-assisted vaginal deliveries. They are also associated with an increased risk of postpartum urinary retention. Surgical repair of the anal sphincter may not completely restore muscle function.

Described herein are methods of treating obstetrical anal sphincter injury comprising administering a therapeutic composition comprising a PGE2 compound and a myotoxin to a subject in need thereof. In some embodiments, the therapeutic composition treats OAB by inducing muscle regeneration of an anal muscle of a subject in need thereof. In some cases, the anal muscle is the external anal sphincter muscle, or the inner anal sphincter muscle.

In some embodiments, the therapeutic composition is administered in combination with surgery (e.g., external anal sphincter repair, internal anal sphincter repair). In those embodiments, the therapeutic composition can be administered before surgery, during surgery, after surgery, or any combination thereof. In other embodiments, the therapeutic composition is administered without surgery.

In some embodiments, the therapeutic composition comprising a PGE2 compound and a myotoxin is administered by intramuscular administration. In some cases, the intramuscular administration comprises injection of the skeletal external anal sphincter muscle. In some cases, an anesthetic may be administered prior to injection. In some cases, the muscle is injected with surgical exposure; in other cases, the muscle is injected without surgical exposure. In some embodiments, an 18-, 19-, 20-, 21-, 22- or 23-gauge needle is used to inject the muscle.

In some embodiments, an anal sphincter muscle of a subject in need is injected with a volume of about 2 mL or less of therapeutic composition comprising a PGE2 compound and a myotoxin. In some embodiments, the muscle is injected with at least about 2 mL of therapeutic composition. In some embodiments, the muscle is injected with less than 2 mL, less than 1.8 mL, less than 1.6 mL, less than 1.4 mL, less than 1.2 mL, less than 1 mL, less than 0.8 mL, less than 0.6 mL, less than 0.4 mL or less than 0.2 mL of therapeutic composition comprising a PGE2 compound and a myotoxin.

The effectiveness of an administration of the therapeutic composition may be determined by conducting tests before administration, after administration, or a combination thereof. In some embodiments, the dose of the therapeutic composition may be adjusted after determining the effectiveness of a prior administration. In some cases, the dose of the PGE2 compound and/or the myotoxin may increase. In other cases, the dose of the PGE2 compound and/or the myotoxin may decrease. In some cases, the dose of the PGE2 compound and/or the myotoxin may stay the same. In some embodiments, the frequency of administration of the therapeutic composition comprising a PGE2 compound and/or the myotoxin may be adjusted after determining the effectiveness of an administration of the therapeutic composition. In some cases, a single administration of the therapeutic composition is needed. In some cases, two or more, three or more, four or more, five or more administrations of the therapeutic composition are needed. In some cases, the frequency of administration is increased after determining the effectiveness of a prior administration. In other cases, the frequency of administration is decreased after determining the effectiveness of a prior administration.

Fecal Incontinence

Fecal incontinence, also known as bowel incontinence or encopresis, is the inability to control bowel movement, causing stool/feces to leak unexpectedly from the rectum. It ranges from an occasional leakage of stool while passing gas, to a complete loss of bowel control. Causes include diarrhea, constipation, muscle damage or never damage. In some cases, muscle damage is due to childbirth, or is associated with aging.

Described herein are methods of treating fecal incontinence comprising administering a therapeutic composition comprising a PGE2 compound and a myotoxin to a subject in need thereof. In some embodiments, the therapeutic composition treats fetal incontinence by inducing muscle regeneration of an anal muscle of a subject in need thereof. In some cases, the anal muscle is the external anal sphincter muscle, or the inner anal sphincter muscle.

In some embodiments, the therapeutic composition is administered in combination with surgery (e.g., external anal sphincter repair, internal anal sphincter repair). In those embodiments, the therapeutic composition can be administered before surgery, during surgery, after surgery, or any combination thereof. In other embodiments, the therapeutic composition is administered without surgery.

In some embodiments, the therapeutic composition comprising a PGE2 compound and a myotoxin is administered by intramuscular administration. In some cases, the intramuscular administration comprises injection of the skeletal external anal sphincter muscle. In some cases, an anesthetic may be administered prior to injection. In some cases, the muscle is injected with surgical exposure; in other cases, the muscle is injected without surgical exposure. In some embodiments, an 18-, 19-, 20-, 21-, 22- or 23-gauge needle is used to inject the muscle.

In some embodiments, an anal sphincter muscle of a subject in need is injected with a volume of about 2 mL or less of therapeutic composition comprising a PGE2 compound and a myotoxin. In some embodiments, the muscle is injected with at least about 2 mL of therapeutic composition. In some embodiments, the muscle is injected with less than 2 mL, less than 1.8 mL, less than 1.6 mL, less than 1.4 mL, less than 1.2 mL, less than 1 mL, less than 0.8 mL, less than 0.6 mL, less than 0.4 mL or less than 0.2 mL of therapeutic composition comprising a PGE2 compound and a myotoxin.

The effectiveness of an administration of the therapeutic composition may be determined by conducting tests before administration, after administration, or a combination thereof. In some embodiments, the dose of the therapeutic composition may be adjusted after determining the effectiveness of a prior administration. In some cases, the dose of the PGE2 compound and/or the myotoxin may increase. In other cases, the dose of the PGE2 compound and/or the myotoxin may decrease. In some cases, the dose of the PGE2 compound and/or the myotoxin may stay the same. In some embodiments, the frequency of administration of the therapeutic composition comprising a PGE2 compound and/or the myotoxin may be adjusted after determining the effectiveness of an administration of the therapeutic composition. In some cases, a single administration of the therapeutic composition is needed. In some cases, two or more, three or more, four or more, five or more administrations of the therapeutic composition are needed. In some cases, the frequency of administration is increased after determining the effectiveness of a prior administration. In other cases, the frequency of administration is decreased after determining the effectiveness of a prior administration.

F. Methods of Treating Gastroesophageal Reflux Disease

With a prevalence of 10-20% in the adult population, gastroesophageal reflux disease (GERD) is one of the most common diseases of the upper gastrointestinal tract. GERD occurs when the ring of muscles at the bottom of the esophagus is weakened or damaged, allowing gastric acid to enter the distal esophagus. The acid stimulates the chemoreceptors, causing irritation and leads to the onset of symptoms. Esophageal symptoms (e.g., heartburn) and extraesophageal symptoms (e.g., oral, pharyngeal, laryngeal, and pulmonary disorders) of GERD are triggered by mucosal exposure to the gastric acid, and are related to the frequency of reflux events and the duration of mucosal acidification. Other GERD symptoms may include epigastric fullness, pressure or pain, dyspepsia, nausea, bloating, belching, chronic cough, bronchospasm, wheezing, hoarseness, and asthma.

The antireflux barrier includes two sphincters—the lower esophageal sphincter (LES) and the diaphragmatic sphincter at the gastroesophageal junction. The two sphincters maintain tonic closure and augmented reflex closure of the sphincter mechanism. The LES is composed of smooth muscles, and it maintains tonic contraction owing to myogenic as well as neurogenic factors. The diaphragmatic sphincter is composed of striated muscles that also exhibit tone and contracts due to the excitatory nerves. The mammalian diaphragm is primarily a respiratory muscle. However, it consists of two separate muscles: the crural and the costal diaphragms. The costal diaphragm is a respiratory muscle, while the crural diaphragm has two functions: respiratory and gastrointestinal. The crural diaphragm is composed of skeletal muscle. Contraction of the diaphragmatic sphincter provides a powerful sphincter mechanism at the lower end of the esophagus contributing to both tonic (sustained) and phasic pressure increases at the level of the LES. A crural myotomy study has demonstrated that there was a significant increase in spontaneous acid reflux. After removal of the crural diaphragm, intrinsic esophageal muscle cannot fully compensate for the loss of the crural muscle. In humans, the diaphragmatic hiatus is the site of minimum GEJ opening aperture, and hiatal hernia has shown excess reflux indicating that the crural diaphragm has a crucial barrier role. A study has also shown that patients with esophagitis may have a thinner crural diaphragm and a deficient GEJ activity during forced inhalation. The anatomical changes and functional failure of the crural diaphragm is esophagitis patients supports the possibility of a skeletal muscle deficiency in GERD.

The primary treatment of GERD is acid suppression which can be achieved with several classes of mechanisms including antacids, histamine-receptor antagonists or proton-pump inhibitors. Surgical therapy may include laparoscopic fundoplication or bariatric surgery. Complications from anti-reflux surgery may include dysphagia of sufficient severity to require esophageal dilation in about 6% of patients treated with fundoplication surgery as well as a significant increase in flatulence and the inability to belch (gas bloat syndrome).

In some aspects, methods are provided for treating gastroesophageal reflux disease (GERD). In some cases, the methods may comprise administering a therapeutic composition of the disclosure (e.g., a PGE2 compound and/or a myotoxin) to a subject having, suspected of having, or at risk of developing GERD. In some embodiments, the therapeutic composition may treat GERD by inducing muscle regeneration in the crural diaphragm.

In some embodiments, a therapeutic composition of the disclosure may be administered in combination with a surgical procedure to treat GERD. In some cases, the therapeutic composition can be administered before surgery, during surgery, after surgery, or any combination thereof. In some cases, the crural diaphragm may be accessed laparoscopically and injected with a therapeutic composition of the disclosure. In some cases, the location of the crural diaphragm may be identified by locating the esophagus and the diaphragm hiatus, and then injecting the diaphragm adjacent to the esophagus with a therapeutic composition provided herein. In some cases, the injections may be performed circumferentially around the esophagus. In some cases, at least one, two, three, four, five, six, seven, eight, nine, ten, or more than ten circumferential injections around the esophagus may be performed. In some embodiments, a 27-, 28-, 29- or 30-gauge needle may be used to inject the crural diaphragm.

In some embodiments, methods of treating GERD may include administering (e.g., intramuscular injection) a therapeutic composition of the disclosure to the crural diaphragm of a subject in need thereof, in a volume of about 0.05 mL to about 0.15 mL. In some embodiments, the crural diaphragm may be injected with at least about 0.05 mL of the therapeutic composition. In some embodiments, the crural diaphragm may be injected with at most about 0.15 mL of the therapeutic composition. In some embodiments, the crural diaphragm may be injected with greater than 0.05 mL, greater than 0.06 mL, greater than 0.07 mL, greater than 0.08 mL, greater than 0.09 mL, greater than 0.10 mL, greater than 0.11 mL, greater than 0.12 mL, greater than 0.13 mL, or greater than 0.14 mL of the therapeutic composition.

In some aspects, the effectiveness of an administration of a therapeutic composition of the disclosure (e.g., to treat GERD) may be determined by conducting tests before administration, after administration, or both. In some cases, the test may include the Heartburn Specific Quality of Life (HBQQL) questionnaire, the GERD Health-Related Quality of Life (GERD-HRQL) questionnaire, or both. In some cases, the test may include monitoring an increase in thickness of the crural diaphragm using endoscopic ultrasound.

G. Methods of Treating Obstructive Sleep Apnea

Obstructive sleep apnea (OSA), apnea, or hypopnea, is characterized by repetitive episodes of complete or partial obstructions of the upper airway during sleep. The upper airway is divided into three regions: the nasopharynx, the oropharynx, and the hypopharynx. The oropharynx is subdivided into the retropalatal region (the posterior margin of the hard palate to the caudal margin of the soft palate) and the retroglossal region (the caudal margin of the soft palate to the base of the epiglottis). The majority of patients with OSA have upper airway narrowing in the retropalatal region, the retroglossal region, or both.

The skeletal muscles surrounding the pharyngeal airway are phasically activated during inspiration, which may help to dilate the airway and stiffen the airway walls. The pharyngeal muscles help regulate the position of the soft palate, tongue, hyoid apparatus, and posterolateral pharyngeal walls. Contraction of specific muscles within the palatal muscles opens the airway in the retropalatal region. Pharyngeal muscles can have different effects when activated in concert as opposed to when activated individually. Coactivation of the muscles in the anterior pharyngeal wall such as the geniohyoid and sternohyoid act on the hyoid bone to move it ventrally. The tensor palatine moves the soft palate ventrally. The genioglossus acts to displace the tongue ventrally. The extrinsic muscles of the tongue consist of the genioglossus, hyoglossus, and syloglossus and are important for the protrusion and retraction of the tongue. The genioglossus is the primary protruder muscle of the tongue with its contraction playing a seminal role in keeping the pharyngeal airway open, mainly by widening the oropharynx in the anterior-posterior dimension. During respiration, the primary goal of the pharyngeal muscles is to keep the airway open allowing for the flow of air in and out of the lung.

In healthy individuals, the pharyngeal muscles are able to adequately compensate for the increase in airway resistance to maintain a patient airway. However, individuals that have a narrow upper airway, either due to obesity or bony structures crowding the airway, are at an increased risk of pharyngeal collapse during sleep. OSA is characterized by increased collapsibility of the upper airway during sleep, which results in reduced airflow (hypopnea) or blocked airflow (apnea) resulting in intermittent hypoxia. The upper airway may collapse because dilator muscles may be unable to sustain patency during portions of the respiratory cycle. The genioglossus is the major upper airway dilator muscle. In OSA patients, the genioglossus muscles have been shown to be structurally and functionally abnormal. One potential mechanism by which these upper airway dilating muscles fail is by fatigue. Fatigue is the loss in the muscle capacity for developing force resulting from muscle activity under load, and which is reversible by rest. In OSA, the upper airway dilating muscles are subjected to repeated bursts of forceful contraction at the end of each obstructive apnea, which may occur several hundred times each night. The frequency and duration of obstructive apneas are greater in the latter part of the night in OSA potentially implicating genioglossus fatigue as a contributing factor.

Given the importance of upper airway muscles in maintaining patency, decreased muscle function could contribute to pharyngeal closure. In order to adapt to increased contractile demands, skeletal muscle fiber phenotype can under a shift from oxidative slow-twitch, fatigue resistant Type I, to glycolytic fast-twitch Type II fibers, which generate increased force but are more prone to fatigue. Fast-twitch muscle fibers fatigue more rapidly than slow-twitch fibers. An increase in fast-twitch fibers would be expected to increase the fatigueability of the upper airway muscles, leaving the airway susceptible to collapse and leading to a cycle of increasingly severe episodes as the level of fatigue increases following repeated activation during the night. Although the genioglossus is only one of many muscles that act in concert to prevent flow limitation in the pharynx, it may substantially improve pharyngeal patency when activated adequately to obtain optimal anterior displacement of the tongue.

The reduction in tension and strength of the upper airway muscles may be one of the key factors in the etiology of OSA. These muscles may include the genioglossus and the tensor palatine. In some cases, improving the strength of these muscles may improve the patency of the upper airway, and reducing the symptoms of OSA. In addition, other upper airway muscles that may contribute to upper airway patency may include the geniohyoid muscles. Targeting these muscles, either individually or in combination, may improve upper airway patency to treat OSA. Although a number of factors may contribute to OSA, upper airway collapsibility and anatomy is fundamentally important in OSA pathogenesis. Accordingly, OSA patients with upper airway pharyngeal muscle weakness may be potential targets for this therapy.

Continuous positive airway pressure (CPAP) is the standard treatment for moderate-to-severe OSA. However, the nasal mask required for CPAP during sleep leads to poor acceptance and compliance rates. Oral appliance (OA) therapy is also widely used for the treatment of moderate and severe OSA. These consist of a maxillary and mandibular splint which hold the lower jaw forward during sleep. However, the efficacy of OA is inferior to CPAP. Upper airway stimulation augments neural drive of the pharyngeal muscle by unilaterally stimulating the hypoglossal nerve. The main limitations of this approach are the risky surgical procedure to implant the device, a high upfront cost and variable response. Many surgical approaches have been proposed like RF ablation of the tongue base, genioglossus advancement, hyoid suspension, maxillomandibular advancement, and tongue base suspension. As with any surgical intervention, these approaches carry the risk of surgical complications and high upfront cost. Furthermore, drug therapies based on a number of mechanisms have been proposed with limited success. These include an increase in tone in the upper airway dilator muscles, an increase in ventilatory drive, a reduction in the proportion of rapid eye movement (REM) sleep, an increase in cholinergic tone during sleep, an increase in arousal threshold, a reduction in airway resistance, and a reduction in surface tension in the upper airway.

OSA has various pathophysiologic causes including an anatomically compromised or collapsible upper airway, inadequate responsiveness of the upper airway dilator muscles during sleep (minimal increase in EMG activity to negative pharyngeal pressure), waking up prematurely to airway narrowing (a low respiratory arousal threshold), or having an oversensitive ventilatory control system. Hence, effective treatments may require treating a primary cause of OSA or treating a combination of causes.

In some aspects, methods are provided for treating obstructive sleep apnea (OSA). In some cases, the methods may comprise administering a therapeutic composition of the disclosure (e.g., comprising a PGE2 compound and/or a myotoxin) to a subject having, suspected of having, or at risk of developing OSA. In some cases, the methods may comprise administering a therapeutic composition of the disclosure to a subject having, suspected of having, or at risk of developing hypopnea. In some cases, the methods may comprise administering a therapeutic composition of the disclosure to a subject having, suspected of having, or at risk of developing apnea. In some cases, the methods may comprise administering a therapeutic composition of the disclosure to a subject to complement or enhance the efficacy of an additional therapy or intervention to treat OSA.

In some embodiments, the therapeutic composition may treat obstructive sleep apnea, hypopnea, apnea, or a combination thereof, by inducing muscle regeneration in a muscle of the upper airway of a subject. In some cases, the upper airway muscle comprises the genioglossus. In some cases, the upper airway muscle comprises the tensor palatine. In some cases, the upper airway muscle comprises the geniohyoid muscles. In some cases, OSA, hypopnea, or apnea can be treated by administering a therapeutic composition of the disclosure (e.g., comprising a PGE2 compound and/or a myotoxin) to the upper airway muscle (e.g., the genioglossus, the tensor palatine, the geniohyoid muscles, or any combination thereof).

In some embodiments, methods of treating OSA, hypopnea, or apnea may include administering a therapeutic composition of the disclosure (e.g., comprising a PGE2 compound and/or a myotoxin) to a subject in need thereof by topical administration, intradermal administration, intramuscular administration, or a combination thereof. In some cases, the therapeutic composition may be administered by intramuscular administration. In some cases, the intramuscular administration may comprise injection of an upper airway muscle. The upper airway muscle may include the genioglossus, the tensor palatine, the geniohyoid muscles, or a combination thereof. In some cases, an anesthetic may be administered to the upper airway prior to injection of the therapeutic composition. In some cases, the upper airway muscle may be injected with surgical exposure; in other cases, the upper airway muscle may be injected without surgical exposure. In some cases, surgical procedures to alter the anatomy of the upper airway may be enhanced by increasing the strength of upper airway muscles (e.g., by administering a therapeutic composition of the disclosure to the upper airway muscles). In some embodiments, a 27-, 28-, 29- or 30-gauge needle may be used to inject the upper airway muscle.

In some embodiments, methods of treating OSA, hypopnea, apnea, or a combination thereof may include administering (e.g., intramuscular injection) a therapeutic composition of the disclosure to an upper airway muscle of a subject in need thereof, in a volume of about 0.01 mL to about 0.15 mL. In some embodiments, the upper airway muscle may be injected with at least about 0.01 mL of a therapeutic composition of the disclosure. In some embodiments, the upper airway muscle may be injected with at most about 0.15 mL of a therapeutic composition of the disclosure. In some embodiments, the upper airway muscle may be injected with greater than 0.01 mL, greater than 0.02 mL, greater than 0.03 mL, greater than 0.04 mL, greater than 0.05 mL, greater than 0.06 mL, greater than 0.07 mL, greater than 0.08 mL, greater than 0.09 mL, greater than 0.10 mL, greater than 0.11 mL, greater than 0.12 mL, greater than 0.13 mL, or greater than 0.14 mL of a therapeutic composition of the disclosure.

In some aspects, the effectiveness of an administration of a therapeutic composition may be determined by conducting tests before administration, after administration, or both. In some cases, the test may assess clinical benefits for an OSA patient using the apnea/hypopnea index (AHI) and the level of daytime sleepiness associated with OSA, estimated by the Epworth Sleepiness Scale (ESS). In some cases, the test may include polysomnographic parameters (e.g., AI, HI, RERArl, Arl, LSat), Sleep Related Quality of Life (FOSQ), and Reaction Time Testing (PVT).

In some embodiments, a dose of the therapeutic composition may be adjusted after determining the effectiveness of a prior administration. In some cases, the dose of the PGE2 compound, the myotoxin, or both, may be increased. In other cases, the dose of the PGE2 compound, the myotoxin, or both may be decreased. In some cases, the dose of the PGE2 compound, the myotoxin, or both may not be changed. In some embodiments, the frequency of administration of a therapeutic composition of the disclosure (e.g., comprising a PGE2 compound and/or a myotoxin) may be adjusted after determining the effectiveness of a prior administration of the therapeutic composition. In some cases, only a single administration of the therapeutic composition may be needed to treat OSA, hypopnea, or apnea. In some cases, two, three, four, five, or more than five administrations of the therapeutic composition may be needed to treat OSA, hypopnea, or apnea. In some cases, the frequency of administration may be increased after determining the effectiveness of a prior administration. In other cases, the frequency of administration may be decreased after determining the effectiveness of a prior administration.

H. Kits

In yet another aspect of the present invention, provided herein is a kit for promoting muscle regeneration and/or increasing muscle mass in a subject in need thereof, or for preventing or treating a muscle condition in a subject in need thereof. In some embodiments, the kit comprises a composition described herein that comprises a combination of a PGE2 compound (e.g., PGE2 receptor agonist) and a myotoxin. In other embodiments, the kit comprises a pharmaceutical composition described herein. The kit typically contains containers which may be formed from a variety of materials such as glass or plastic, and can include for example, bottles, vials, syringes, and test tubes. A label typically accompanies the kit, and includes any writing or recorded material, which may be electronic or computer readable form providing instructions or other information for use of the kit contents.

Kits of the present invention may be suitable for treating any number of muscle conditions, including but not limited to muscle conditions that are associated with muscle damage, injury, or atrophy. The kits may also be useful for promoting muscle regeneration in a subject in need thereof and/or increasing muscle mass. Non-limiting examples of suitable conditions for prevention or treatment with kits of the present invention include traumatic injury (e.g., acute muscle trauma, acute nerve trauma), acute muscle injury, acute nerve injury, chronic nerve injury, soft tissue hand injury, carpal tunnel syndrome (CTS), Duchenne muscular dystrophy (DMD), Becker muscular dystrophy, limb girdle muscular dystrophy, amyotrophic lateral sclerosis (ALS), distal muscular dystrophy (DD), inherited myopathies, myotonic muscular dystrophy (MDD), mitochondrial myopathies, myotubular myopathy (MM), myasthenia gravis (MG), congestive heart failure, periodic paralysis, polymyositis, rhabdomyolysis, dermatomyositis, cancer cachexia, AIDS cachexia, cardiac cachexia, stress induced urinary incontinence, sarcopenia, spinal muscular atrophy, fecal sphincter dysfunction, Bell's palsy, rotator cuff injury, spinal cord injury, hip replacement, knee replacement, wrist fracture, diabetic neuropathy, gastroesophageal reflux disease (GERD), obstructive sleep apnea (OSA), pelvic floor disorders (e.g., stress urinary incontinence, overactive bladder/urinary urgency incontinence, mixed urinary incontinence, pelvic organ prolapse, fecal incontinence), musculoskeletal disorders (e.g., impaired hand function, impaired thumb function, impaired foot function), plantar fasciitis, foot drop, disuse-induced muscle atrophy, impaired eyelid function (e.g., eyelid drooping, impaired blinking, entropion, ectropion), strabismus, nystagmus, presbyopia. Additional examples of suitable conditions for prevention or treatment with kits of the present invention may include muscle disorders that affect small isolated muscles that can be regenerated with localized transplantation of small numbers of cells, including: atrophy and muscle dysfunction in the face or hand after nerve injury or direct trauma that does not recover after reinnervation; extraocular muscle injury causing inability to move the eye and dipoplia seen in Graves' disease; traumatic injury; progressive external ophthalmoplegia; and urinary and fecal incontinence.

In some embodiments, the kit further comprises isolated muscle cells. In other embodiments, the kit further comprises instructions for use (e.g., to the kit user). In some embodiments, the kit further comprises one or more reagents and/or one or more devices (e.g., a delivery device) that are used, for example, to administer a composition and/or pharmaceutical composition of the present invention, to administer isolated muscle cells (e.g., to a subject in need thereof), or a combination thereof.

IV. Examples

The present invention will be described in greater detail by way of specific examples. The following examples are offered for illustrative purposes only, and are not intended to limit the invention in any manner.

Example 1: Acute Prostaglandin E2 Delivery Augments Skeletal Muscle Regeneration and Strength in Aged Mice This example illustrates that PGE2 signaling is required for muscle stem cell function during regeneration.

The elderly suffer from progressive skeletal muscle wasting and regenerative failure that decreases mobility and quality of life. Crucial to muscle regeneration are adult muscle stem cells (MuSCs) that reside in niches in muscle tissues, poised to respond to damage and repair skeletal muscles throughout life. During aging, the proportion of functional MuSCs markedly decreases, hindering muscle regeneration. To date, no therapeutic agents are in clinical use that target MuSCs to combat this regenerative decline. Here, we identify a natural immunomodulator, prostaglandin E2 (PGE2), as a potent regulator of MuSC function essential to muscle regeneration. We found that the PGE2 receptor, EP4, is essential for MuSC proliferation in vitro and engraftment in vivo in mice. In MuSCs of aged mice, the PGE2 pathway is dysregulated due to a cell intrinsic molecular defect, elevated prostaglandin degrading enzyme (15-PGDH) that renders PGE2 inactive. This defect is overcome by transient acute exposure of MuSCs to a stable degradation-resistant PGE2, 16,16-dimethyl PGE2 (dmPGE2), concomitant with MuSC transplantation into injured muscles. Notably, a single intramuscular injection of dmPGE2 alone suffices to accelerate regeneration, evident by an early increase in endogenous MuSC numbers and myofiber sizes following injury. Furthermore, aged mouse muscle force generating capacity was increased in response to exercise-induced regeneration and an acute dmPGE2 treatment regimen. Our findings reveal a novel therapeutic indication for PGE2 as a potent inducer of muscle regeneration and strength.

Figure 1:
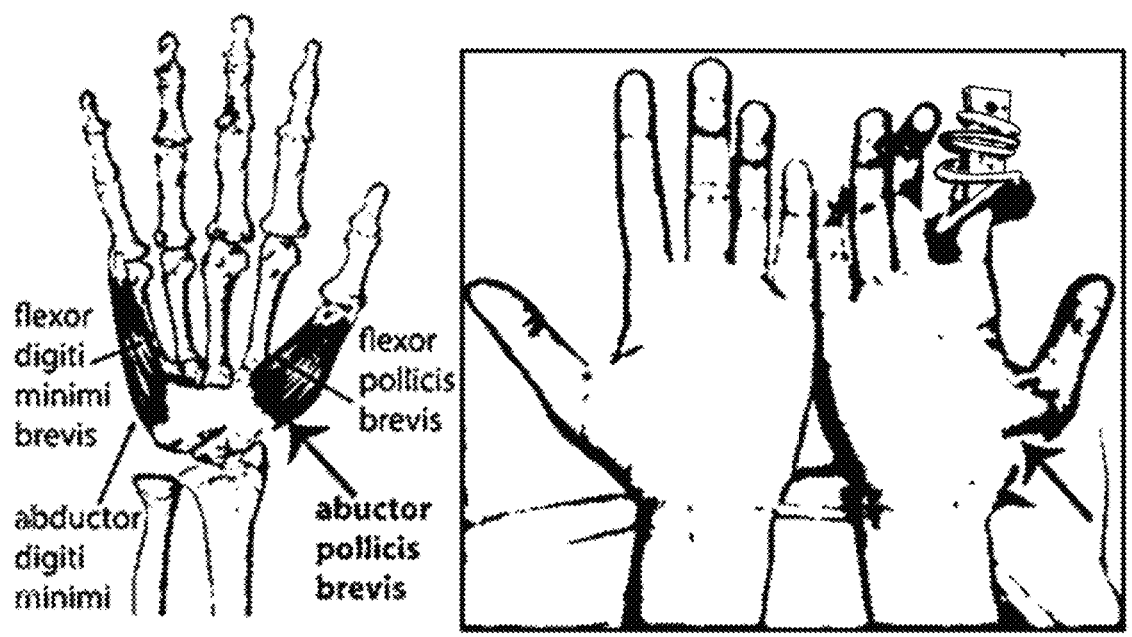
FIG. 1 shows an illustration of the abductor pollicis brevis (APB) muscle (left). The arrows mark the locations of APB atrophy, also shown in the photo on the right.
Figure 2A:
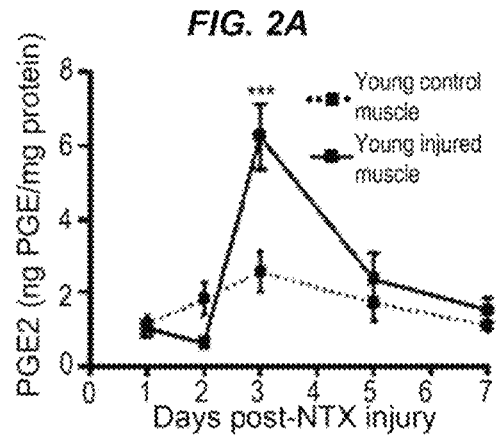
FIGS. 2A-2H show that transient PGE2 treatment promotes young MuSC proliferation in vitro.
Figure 2B:
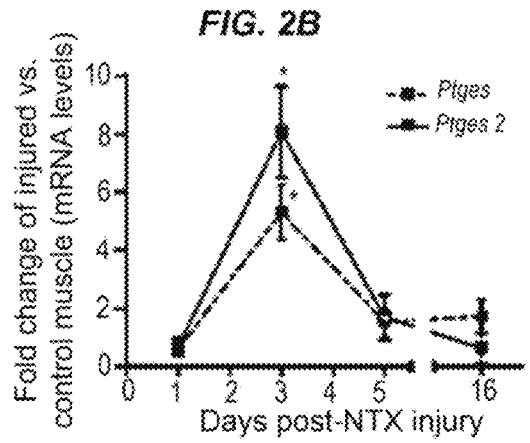
Figure 2C:
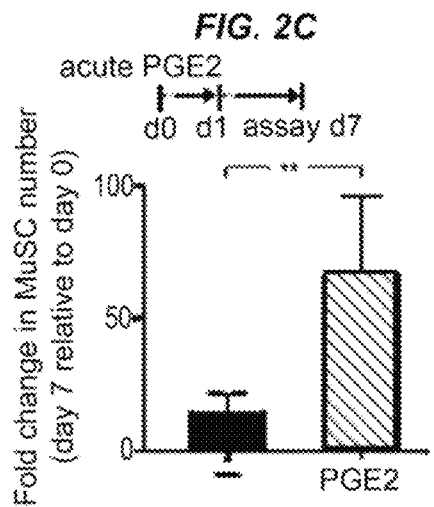

To counter the decline in muscle regenerative potential we sought therapeutic agents that target MuSCs, also known as satellite cells, a stem cell population dedicated to muscle regeneration. Since a transient inflammatory and fibroadipogenic response plays a crucial role in muscle regeneration, we sought to identify inflammatory modulators induced by injury that could overcome the age-related decline in MuSC function. An analysis of our transcriptome database revealed that the Ptger4 receptor for PGE2, a natural and potent lipid mediator during acute inflammation, was expressed at high levels on freshly isolated MuSCs. In muscle tissue lysates, we detected a surge in levels of PGE2 three days after injury to young (2-4 mo) mouse muscles by standard injury paradigms entailing notexin injection or cryoinjury (FIGS. 2A and 6A), and a concomitant upregulation of its synthesizing enzymes, Ptges and Ptges2 (FIG. 2B). This early and transient time window coincides with the well-documented kinetics of MuSC expansion and inflammatory cytokine accumulation post injury. To determine if PGE2 treatment enhanced MuSC behavior, we FACS-purified MuSCs from hindlimb muscles from young mice (2-4 mo) and plated them on hydrogels of 12 kPa stiffness to maintain stem cell function. We found that PGE2 (10 ng/ml) increased cell division assayed by EDU incorporation (FIGS. 2B-2D) and that an acute 1-day exposure to PGE2 induced a 6-fold increase in the number of MuSCs relative to controls one week later (FIG. 2C).

Figure 2D:
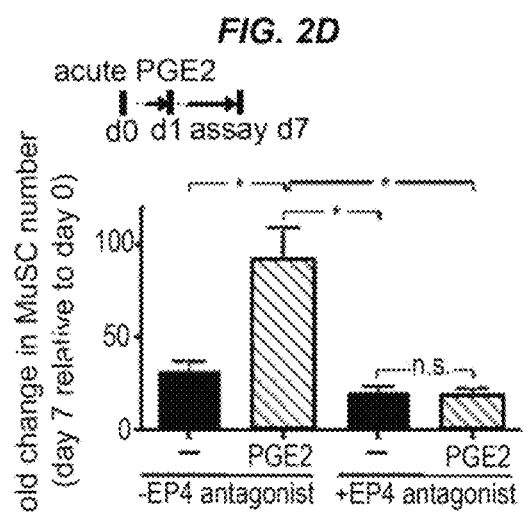
Figure 2E:
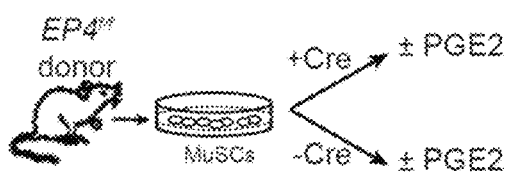
Figure 2F:
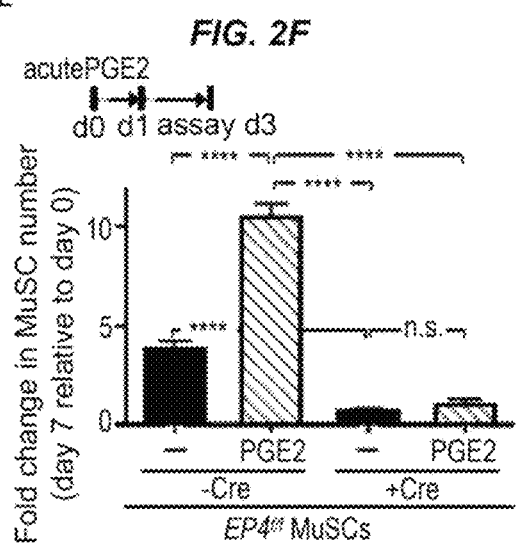
Figure 2G:
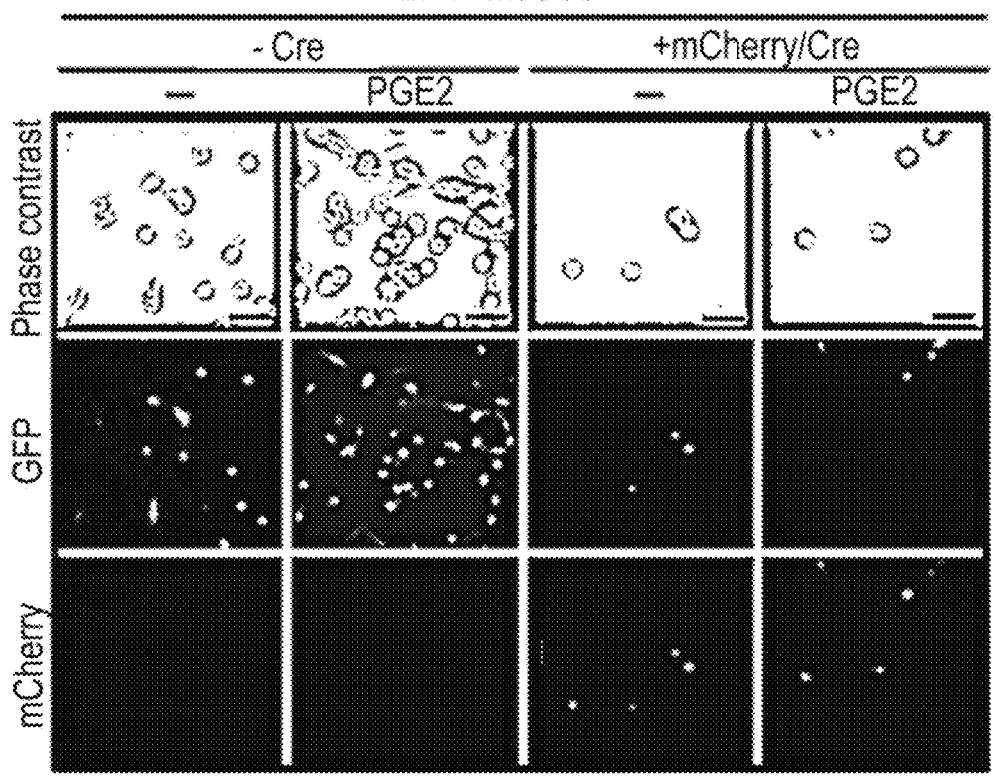
Figure 2H:
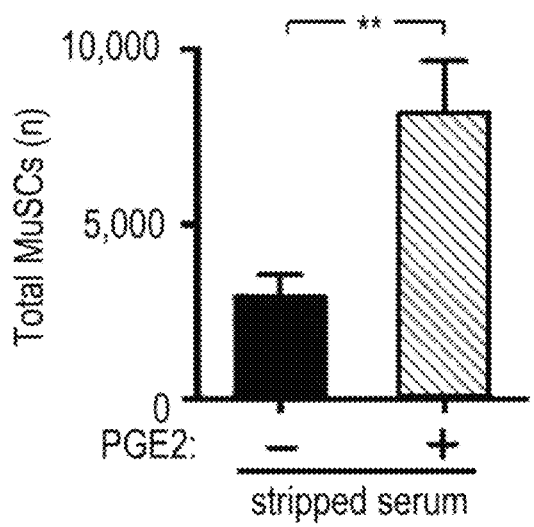

PGE2 is known to signal through four G-protein coupled receptors (Ptger1-4; EP1-4), but the expression of these receptors in MuSCs has not previously been described. An analysis of the transcript levels of the different receptors (Ptger1-4) revealed that the only receptors upregulated after PGE2 treatment of MuSCs are Ptger1 and Ptger4 (FIG. 6E). PGE2 stimulated MuSCs had elevated intracellular cAMP confirming that PGE2 signals through EP4 to promote proliferation and a stem cell transcriptional state (FIGS. 6F-6H). In the presence of an EP4 antagonist, ONO-AE3-208, proliferation induced by PGE2 was blunted (FIG. 2D). However, the specificity of PGE2 for EP4 was most clearly shown in MuSCs lacking the receptor following cre-mediated conditional ablation (FIGS. 2E-2G and 6I-6J). Indeed, even in the presence of growth factor-rich media, these EP4-null MuSCs failed to proliferate. Finally, we found that MuSCs growth arrested by exposure to medium with charcoal stripped serum, divided upon addition of PGE2 (FIGS. 2H and 6K). Thus, PGE2/EP4 stands out as necessary and sufficient for MuSC proliferation.

Figure 3B:
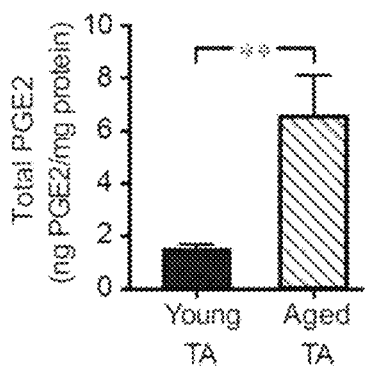
Figure 3C:
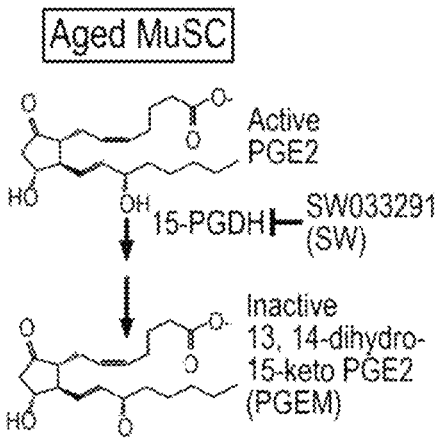
Figure 3D:
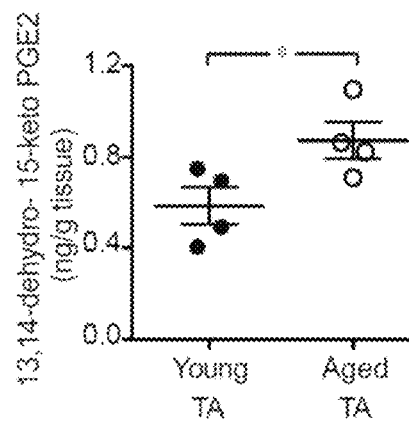
Figure 3E:
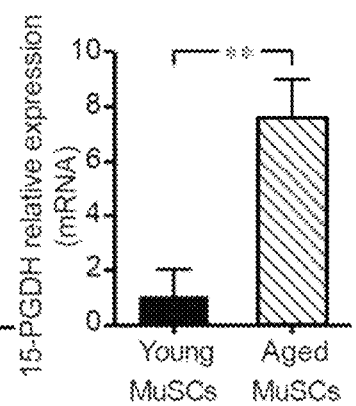

We sought to determine if PGE2 could ameliorate the muscle regenerative defects previously reported for aged MuSCs. By contrast with young mouse muscles (2-4 mo), notexin damage to aged muscles (18-20 mo) did not lead to an increase in PGE2 synthesis. Instead, steady state PGE2 levels in aged muscle remained unchanged post injury (FIG. 3A) and were significantly higher than in young limb tibialis anterior (TA) muscles (FIG. 3B). We hypothesized that the PGE2 in aged muscle might be dysfunctional due to a catabolic defect. Indeed, when we analyzed the PGE2 present in young and aged TA muscle tissues by mass spectrometry, we found that the relative amount of the inactive form, 13,14-dihydro-15-keto PGE2 (PGEM), was significantly increased in the aged (FIGS. 3C-3D and 7A-7C). This proved to be due to a concomitant 7-fold increase in levels of mRNA encoding the PGE2 degrading enzyme (15-PGDH), the initial step in the conversion of PGE2 to its inactive form (FIG. 3E). In contrast, the relative levels of the prostaglandin transporter (PGT), PGE2 synthesizing enzymes, and EP4 receptor did not differ between young and aged MuSCs (FIGS. 8A-8C). Additionally, when aged MuSCs were exposed to a 1-day pulse of PGE2 or to an inhibitor of 15-PGDH (SW033291), the effects of 15-PGDH were overcome and the characteristic increase in proliferation and maintenance of Pax7 expression was observed (FIGS. 3F and 8D). Like young, aged MuSCs failed to proliferate in medium comprised of charcoal stripped serum, but were rescued by addition of PGE2 alone (FIG. 3G). We surmised that in aged MuSCs the PGE2 pathway is dysregulated due to a cell intrinsic molecular defect, elevated 15-PGDH that can be surmounted in culture by acute exposure to PGE2 or SW (FIG. 3H).

Figure 3I:
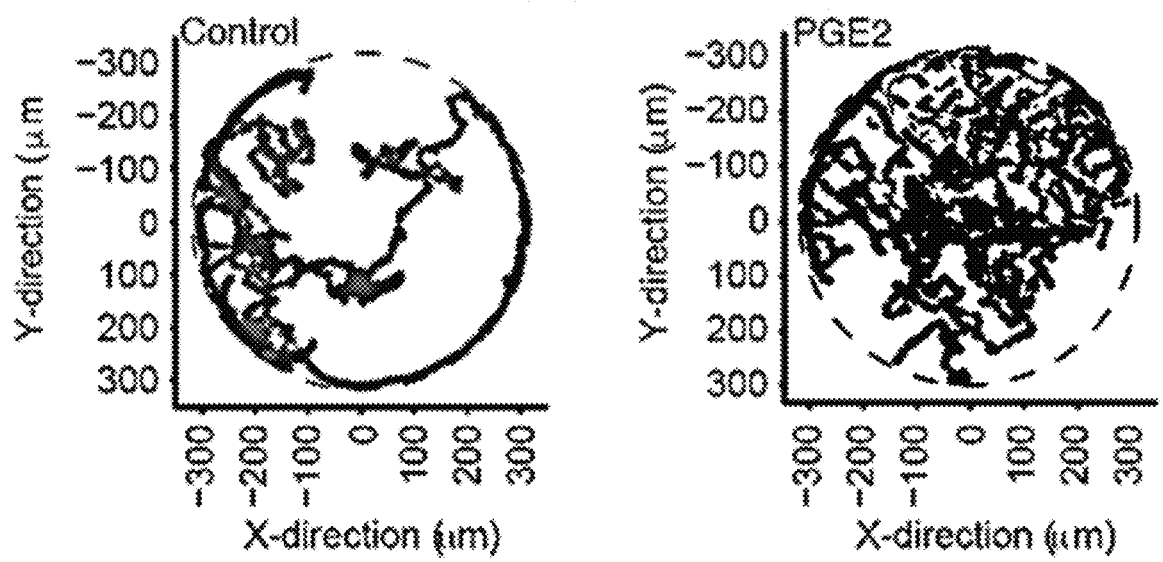
Figure 3J:
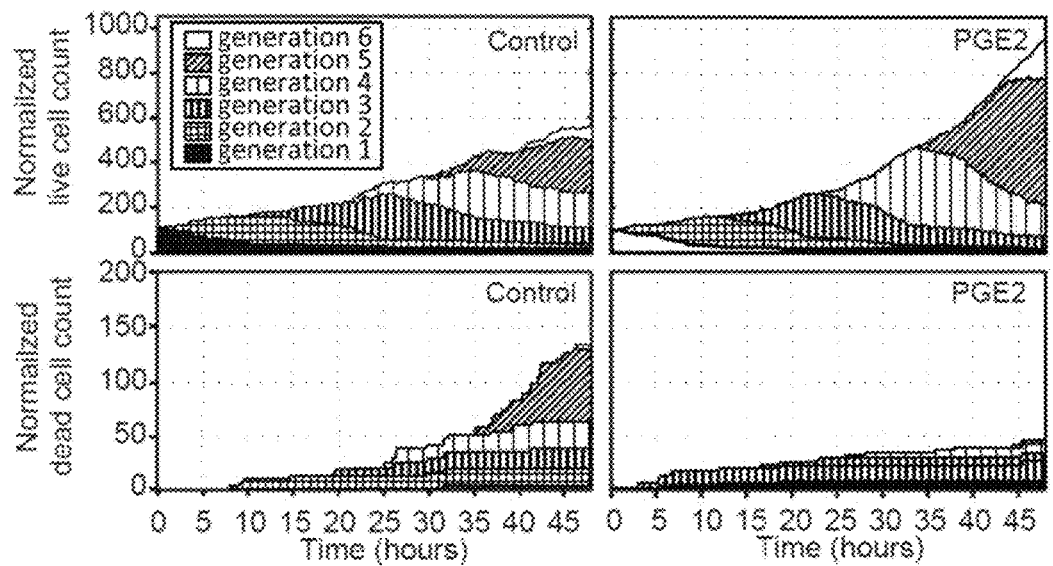

Since aged MuSCs are heterogeneous, we sought to determine the effect of PGE2 at the single cell level. Clonal analysis can reveal differences that are masked by analysis of the population as a whole. Accordingly, we performed long-term time-lapse microscopy in hydrogel 'microwells' of single aged MuSCs transiently exposed to PGE2 for 1 day and untreated control MuSCs. Data were collected over a 48 h time period and then analyzed using our previously described Baxter Algorithms for Cell Tracking and Lineage Reconstruction. We observed a remarkable increase in cumulative cell numbers in response to PGE2, spanning 6 generations for the most robust clones (FIGS. 3I-3J). The numbers of cells per clone following PGE2 treatment were significantly augmented due to a marked increase in proliferation (FIGS. 3I-3J and 8E-8F) that was accompanied by a profound reduction in cell death (FIGS. 3J and 8E-8G). These synergistic effects led to the observed increases in aged MuSC numbers in response to PGE2.

To test whether transient treatment of young MuSCs with PGE2 augments regeneration, we transplanted cultured PGE2 treated MuSCs into injured hindlimb muscles of mice. To monitor the dynamics of regeneration over time in a quantitative manner in vivo, we capitalized on a sensitive and quantitative bioluminescence imaging (BLI) assay we previously developed for monitoring MuSC function post-transplantation. MuSCs were isolated from young transgenic mice (2-4 mo) expressing GFP and luciferase (GFP/Luc mice), exposed to an acute 1-day PGE2 treatment, harvested and transplanted on day 7. Equivalent numbers of dmPGE2 treated and control MuSCs (250 cells) were transplanted into injured hindlimbs of young (2-4 mo) NOD-SCID mice. Following acute treatment with PGE2, young MuSC regenerative capacity was enhanced by an order of magnitude when assessed by BLI (FIG. 4A). In contrast, following transplantation of 4-fold greater numbers of cultured MuSCs that lacked the EP4 receptor due to conditional ablation (FIG. 4B), the BLI signal that was initially detected progressively declined to levels below the threshold of significance (FIG. 4B).

Figure 10G:
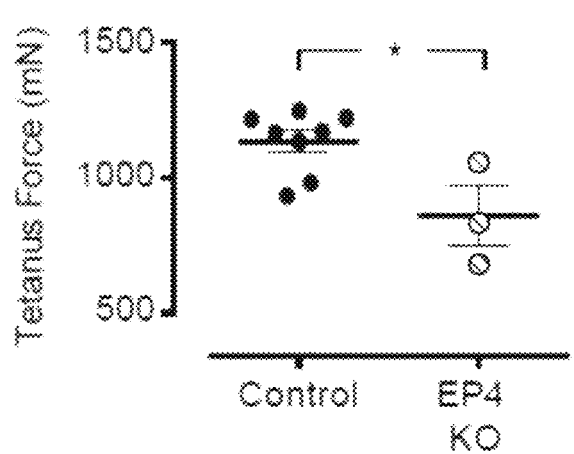

Furthermore, when notexin injury was performed in the mouse model of muscle stem cell specific deletion of EP4 ($Pax7^{CreERT2}$;$EP4^{fl/fl}$) (FIGS. 10A-10B), muscle regeneration was impaired as observed by the elevated number of embryonic myosin heavy chain (eMHC) positive fibers (FIGS. 10C-10D). This was accompanied by the reduction in cross-sectional area of the mouse fibers in the $Pax7^{CreERT2}$;$EP4^{f/f}$ group, assessed at the end of the regeneration time point (day 21) (FIG. 10E). A significant reduction in force output (tetanus) was also detected at day 14 post-injury (FIGS. 10F-10G). Thus, PGE2 signaling via the EP4 receptor is required for MuSC regeneration in vivo.

To test if direct injection of PGE2 without culture could be effective in promoting regeneration in vivo, we coinjected PGE2 together with freshly isolated MuSCs. For all subsequent in vivo injection experiments, we used a modified, more stable form of PGE2, 16,16-dimethyl PGE2 (dmPGE2). We hypothesized that for the aged MuSC experiments, the delivery of the modified 15-PGDH-resistant dmPGE2 was particularly important, as 15-PGDH is significantly elevated in aged MuSCs (FIG. 3E). Using dmPGE2, we observed significantly enhanced engraftment of young and aged MuSCs relative to controls that was further increased in response to notexin injury, a well-accepted stringent test of stem cell function (FIGS. 4C-4D). Thus, the delivery of dmPGE2 together with MuSC cell populations suffices to augment regeneration.

We postulated that delivery of PGE2 alone could stimulate muscle regeneration. To test this, muscles of young mice were injured with cardiotoxin and three days later a bolus of dmPGE2 was injected into the hindlimb muscles of young mice. We observed an increase (60±15%) in endogenous PAX7-expressing MuSCs in the classic satellite cell niche beneath the basal lamina and atop myofibers fourteen days post injury (FIGS. 5A-5B), whereas dmPGE2 had no effect in the absence of injury. Further, at this early time point, the distribution of myofibers shifted toward larger sizes, assessed as cross-sectional area using the Baxter Algorithms for Myofiber Analysis, suggesting that regeneration is accelerated by PGE2 (FIGS. 5C-5D and 9A-9B). In addition, we tracked the response to injury and dmPGE2 of endogenous MuSCs by luciferase expression using a transgenic mouse model, Pax7$^{CreERT2}$;Rosa26-LSL-Luc (FIG. 5E). The BLI data were in agreement with the histological data (FIGS. 5F-5G).

We tested the effects of injecting indomethacin, a non-steroidal anti-inflammatory drug (NSAID) and an inhibitor of COX2 which reduces PGE2 synthesis, on muscle regeneration. Upon indomethacin injection into the hindlimb muscles of the same Pax7$^{CreERT2}$;Rosa26-LSL-Luc mouse model three days post-cardiotoxin injury, we observed a significant decrease in luciferase activity indicative of an impairment in muscle stem cell activation and regeneration (FIGS. 11A-11B). Injection of indomethacin into cardiotoxin-injured muscles also led to a significant loss in Twitch force as compared to the control group assessed at day 14 post-injury (FIG. 11C). In aged mice, we also detected a substantial increase (24±2%) in the number of endogenous MuSCs (FIGS. 5H-5I), and a concomitant increase in myofiber sizes (FIGS. 5J-5K) fourteen days post-injury after a single dmPGE2 injection. Thus, exposure solely to dmPGE2 impacts the magnitude and time course of the endogenous repair.

As the ultimate test, we determined if dmPGE2 enhanced regeneration could lead to increased muscle strength after a natural injury induced by downhill treadmill-running. In this scenario, damage was caused by a daily 10 min run on a downhill treadmill 20 degree decline. During week one, aged mice in the treatment group ran for 5 days in succession and were injected daily with dmPGE2 after exercise. During week two, aged mice in the treatment group ran for 5 consecutive days but received no additional treatment (FIG. 5L). The specific twitch and tetanic force were compared for dmPGE2 treated and untreated gastrocnemius mouse muscles (GA) and both were significantly increased (FIGS. 5M-5P). Thus, an acute exposure to dmPGE2 concurrent with exercise-induced injury can confer a significant increase in aged muscle strength.

We have discovered a new indication for PGE2 in skeletal muscle regeneration. Prior studies of PGE2 effects on skeletal muscle have shown that it alters the proliferation, fusion, protein degradation, and differentiation of myoblasts in tissue culture. Thus, these studies differ from ours as myoblasts are progenitors that have lost stem cell function. Satellite cells (MuSCs) are crucial to development and regeneration and their numbers are increased by running or other high intensity exercise in young and aged mice and humans. Non-steroidal anti-inflammatory agents have been reported to attenuate the exercise-induced increase in MuSCs. Our data provide novel evidence that the beneficial effects of the early transient wave of inflammation that characterizes efficacious muscle regeneration is due in part to PGE2 and its receptor EP4, which are essential and sufficient for MuSC proliferation and engraftment. For hematopoietic, liver, and colon tissues, delivery of the inhibitor of 15-PGDH, SW033291, was recently shown to enhance regeneration. Notably, PGE2 and its analogues have safely been used in human patients for decades, for instance to induce labor and to promote hematopoietic stem cell transplantation paving the way for its clinical use in restoring muscles post-injury. In summary, our findings show that an acute PGE2 regimen suffices to rapidly and robustly enhance regeneration of exercise-induced damage and overcome age-associated limitations leading to increased strength.

Mice: We performed all experiments and protocols in compliance with the institutional guidelines of Stanford University and Administrative Panel on Laboratory Animal Care (APLAC). We obtained wild-type aged C57BL/6 (18-20 mo) mice from the US National Institute on Aging (NIA) for aged muscle studies and young wild-type C57BL/6 mice from Jackson Laboratory. Double-transgenic GFP/luc mice were generated as described previously[1]. Briefly, mice expressing a firefly luciferase (luc) transgene under the regulation of the ubiquitous Actb promoter were maintained in the FVB strain. Mice expressing a green fluorescent protein (GFP) transgene under the regulation of the ubiquitous UBC promoter were maintained in the C57BL/6 strain. We used cells from GFP/luc for allogenic transplantation experiments into NOD-SCID (Jackson Laboratory) recipient mice. EP4$^{flox/flox}$(EP4$^{f/f}$) mice were a kind gift from K. Andreasson (Stanford University)[2]. Double-transgenic Pax7$^{CreERT2}$;Rosa26-LSL-Luc were generated by crossing Pax7$^{CreERT2}$ mice obtained from Jackson Laboratory (Stock #017763)[3] and Rosa26-LSL-Luc obtained from Jackson Laboratory (Stock #005125)[4]. We validated these genotypes by appropriate PCR-based strategies. All mice from transgenic strains were of young age. Young mice were 2-4 months ("mo") of age and aged mice were 18-20 months of age for all strains. All mice used in these studies were females.

Muscle stem cell isolation: We isolated and enriched muscle stem cells as previously described[1,5,6]. Briefly, a gentle collagenase digestion and mincing by the MACs Dissociator enabled numerous single fibers to be dissociated, followed by dispase digestion to release mononucleated cells from their niches. Subsequently, the cell mixture was depleted for hematopoietic lineage expressing and non-muscle cells (CD45$^-$/CD11b$^-$/CD31$^-$) using a magnetic bead column (Miltenyi). The remaining cell mixture was then subjected to FACS analysis to sort for MuSCs co-expressing CD34 and α7-integrin markers. We generated and analyzed flow cytometry scatter plots using FlowJo v10.0. For each sort, we pooled together MuSCs (~5,000 each) from at least three independent donor female mice.

Muscle stem cell transplantation: We transplanted 250 MuSCs (FIGS. 4A, 4C, and 4D) or 1,000 MuSCs (FIG. 4B) immediately following FACS isolation or after collection from cell culture directly into the tibialis anterior (TA) muscles of recipient mice as previously described[1,5,6]. For young MuSC studies, we transplanted cells from GFP/luc mice (2-4 mo of age) into hindlimb-irradiated NOD-SCID mice. For aged MuSCs studies, we transplanted cells from aged C57BL/6 mice (18-20 mo, NIH) that were transduced with a luc-IRES-GFP lentivirus (GFP/luc virus) on day 2 of culture for a period of 24 hr before transplantation, as previously described[5] (see below "Muscle stem cell culture, treatment and lentiviral infection" section for details). Prior to transplantation of muscle stem cells, we anesthetized NOD-SCID recipient mice with ketamine (2.4 mg per mouse) by intraperitoneal injection. We then irradiated hindlimbs with a single 18 Gy dose, with the rest of the body shielded in a lead jig. We performed transplantations within 2 d of irradiation.

Cultured cells were treated as indicated (vehicle or PGE2 treated 10 ng/ml) and collected from hydrogel cultures by incubation with 0.5% trypsin in PBS for 2 min at 37° C. and counted using a hemocytometer. We resuspended cells at desired cell concentrations in 0.1% gelatin/PBS and then transplanted them (250 MuSCs per TA) by intramuscular injection into the TA muscles in a 10 μl volume. For fresh MuSCs transplantation, we coinjected sorted cells with 13 nmol of 16,16-Dimethyl Prostaglandin E2 (dmPGE2) (Tocris, catalog #4027) or vehicle control (PBS). We compared cells from different conditions by transplantation into the TA muscles of contralateral legs in the same mice. One month after transplant, we injected 10 μl of notexin (10 μg ml$^{-1}$; Latoxan, France) to injure recipient muscles and to activate MuSCs in vivo. Eight weeks after transplantation, mice were euthanized and the TAs were collected for analysis.

Bioluminescence imaging: We performed bioluminescence imaging (BLI) using a Xenogen-100 system, as previously described[1,5,6]. Briefly, we anesthetized mice using isofluorane inhalation and administered 120 μL D-luciferin (0.1 mmol kg$^{-1}$, reconstituted in PBS; Caliper LifeSciences) by intraperitoneal injection. We acquired BLI using a 60 s exposure at F-stop=1.0 at 5 minutes after luciferin injection. Digital images were recorded and analyzed using Living Image software (Caliper LifeSciences). We analyzed images with a consistent region-of-interest (ROI) placed over each hindlimb to calculate a bioluminescence signal. We calculated a bioluminescence signal in radiance (p s$^{-1}$ cm$^{-2}$ sr$^{-1}$) value of $10^4$ to define an engraftment threshold. This radiance threshold of $10^4$ is approximately equivalent to the total flux threshold in p/s reported previously. This BLI threshold corresponds to the histological detection of one or more GFP+ myofibers[1,5,6]. We performed BLI imaging every week after transplantation.

Muscle injury: We used an injury model entailing intramuscular injection of 10 μl of notexin (10 μg ml$^{-1}$; Latoxan) or cardiotoxin (10 μM; Latoxan) into the TA muscle. For cryoinjury, an incision was made in the skin overlying the TA muscle and a copper probe, chilled in liquid nitrogen, was applied to the TA muscle for three 10 s intervals, allowing the muscle to thaw between each application of the cryoprobe. When indicated, 48 hr after injury either 16,16-Dimethyl Prostaglandin E2 (dmPGE2) (13 nmol, Tocris, catalog #4027) or vehicle control (PBS) was injected into the TA muscle. The contralateral TA was used as an internal control. We collected tissues 14 days post-injury for analysis.

For Pax7$^{CreERT2}$; Rosa26-LSL-Luc mice experiments, we treated mice with five consecutive daily intraperitoneal injections of tamoxifen to activate luciferase expression under the control of the Pax7 promoter. A week after the last tamoxifen injection, mice were subjected to intramuscular injection of 10 μl of cardiotoxin (10 μM; Latoxan), which we designated as day 0 of the assay. Three days later either 13 nmol dmPGE2 (13 nmol) or vehicle control (PBS) was injected into the TA muscle. The contralateral TA was used as an internal control. Bioluminescence was assayed at days 3, 7, 10 and 14 post-injury.

Tissue histology: We collected and prepared recipient TA muscle tissues for histology as previously described[5,6]. We incubated transverse sections with anti-LAMININ (Millipore, clone A5, catalog #05-206, 1:200), and anti-PAX7 (Santa Cruz Biotechnology, catalog #sc-81648, 1:50) primary antibodies and then with AlexaFluor secondary Antibodies (Jackson ImmunoResearch Laboratories, 1:200). We counterstained nuclei with DAPI (Invitrogen). We acquired images with an AxioPlan2 epifluorescent microscope (Carl Zeiss Microimaging) with Plan NeoFluar 10×/0.30 NA or 20×/0.75 NA objectives (Carl Zeiss) and an ORCA-ER digital camera (Hamamatsu Photonics) controlled by the SlideBook (3i) software. The images were cropped using Adobe Photoshop with consistent contrast adjustments across all images from the same experiment. The image composites were generated using Adobe Illustrator. We analyzed the number of PAX7 positive cells using the MetaMorph Image Analysis software (Molecular Devices), and the fiber area using the Baxter Algorithms for Myofiber Analysis that identified the fibers and segmented the fibers in the image to analyze the area of each fiber. For PAX7 quantification we examined serial sections spanning a depth of at least 2 mm of the TA. For fiber area at least 10 fields of LAMININ-stained myofiber cross-sections encompassing over 400 myofibers were captured for each mouse as above. Data analyses were blinded. The researchers performing the imaging acquisition and scoring were unaware of treatment condition given to sample groups analyzed.

Hydrogel fabrication: We fabricated polyethylene glycol (PEG) hydrogels from PEG precursors, synthesized as described previously[6]. Briefly, we produced hydrogels by using the published formulation to achieve 12-kPa (Young's modulus) stiffness hydrogels in 1 mm thickness which is the optimal condition for culturing MuSCs and maintaining stem cell fate in culture[6]. We fabricated hydrogel microwell arrays of 12-kPa for clonal proliferation experiments, as described previously[6]. We cut and adhered all hydrogels to cover the surface area of 12-well or 24-well culture plates.

Muscle stem cell culture, treatment and lentiviral infection: Following isolation, we resuspended MuSCs in myogenic cell culture medium containing DMEM/F10 (50:50), 15% FBS, 2.5 ng ml$^{-1}$ fibroblast growth factor-2 (FGF-2 also known as bFGF) and 1% penicillin-streptomycin. We seeded MuSC suspensions at a density of 500 cells per cm$^2$ surface area. We maintained cell cultures at 37° C. in 5% $CO_2$ and changed medium daily. For PGE2, 15-PGDH inhibitor and EP4 receptor antagonist treatment studies, we added 1-200 ng/ml Prostaglandin E2 (Cayman Chemical) (unless specified in the figure legends, 10 ng/ml was the standard concentration used), and/or 1 μM EP4 antagonist (ONO-AE3-208, Cayman Chemical), or 1 μM 15-PGDH inhibitor (SW033291, Cayman Chemical) to the MuSCs cultured on collagen coated dishes for the first 24 h. The cells were then trypsinized and cells reseeded onto hydrogels for an additional 6 days of culture. All treatments were compared to their solvent (DMSO) vehicle control. For stripped serum assays, we resuspended isolated MuSCs in medium containing DMEM/F10 (50:50), 15% charcoal stripped FBS (Gibco, cat #12676011), 2.5 ng ml$^{-1}$ bFGF and 1% penicillin-streptomycin. When noted in the figure, we additionally added 1.5 μg/ml insulin (Sigma, 10516) and 0.25 μM dexamethasone (Sigma, D8893) to stripped serum cell medium. For these experiments MuSCs were cultured on hydrogels and vehicle (DMSO) or 10 ng/ml PGE2 (Cayman Chemical) was added to the cultures with every media change (every two days). Proliferation (see below) was assayed 7 days later.

We performed all MuSC culture assays and transplantations after 1 week of culture unless noted otherwise. For aged MuSCs transplant studies, we infected MuSCs with lentivirus encoding elongation factor-1α promoter-driven luc-IRES-GFP (GFP/luc virus) for 24 h in culture as described previously[3]. For EP4$^{f/f}$ MuSCs studies, we isolated MuSCs as described above (Muscle stem cell isolation), and infected all cells with the GFP/luc virus and a subset of them was coinfected with a lentivirus encoding pLM-CMV-R-Cre (mCherry/Cre virus) for 24 h in culture. pLM-CMV-R-Cre was a gift from Michel Sadelain (Addgene plasmid #27546)[7]. We transplanted aged MuSC (250 cells) or EP4$^{f/f}$ MuSCs (1,000 cells) into young (2-4 mo) 18-gy irradiated TAs of NOD-SCID recipient mice. For in vitro proliferation assays, EP4$^{f/f}$ MuSCs were plated on hydrogels post-infection and treated for 24 hr with vehicle (DMSO) or 10 ng/ml PGE2, and proliferation was assayed 3 days later. Cells were assayed for GFP and/or mCherry expression 48 h post-infection using an inverted fluorescence microscope (Carl Zeiss Microimaging). MuSCs are freshly isolated from the mice by FACS and put in culture for a maximum time period of one week, therefore *Mycoplasma* contamination is not assessed.

Proliferation assays: To assay proliferation, we used three different assays (hemocytometer, VisionBlue, and EdU). For each, we seeded MuSCs on flat hydrogels (hemocytometer and VisionBlue) or collagen-coated plates (EdU assay) at a density of 500 cells per cm$^2$ surface area. For hemocytometer cell number count, we collected cells at indicated timepoints by incubation with 0.5% trypsin in PBS for 5 min at 37° C. and quantified them using a hemocytometer at least 3 times. Additionally, we used the VisionBlue Quick Cell Viability Fluorometric Assay Kit (BioVision, catalog #K303) as a readout for cell growth in culture. Briefly, we incubated MuSCs with 10% VisionBlue in culture medium for 3 h, and measured fluorescence intensity on a fluorescence plate reader (Infinite M1000 PRO, Tecan) at Ex=530-570 nm, Em=590-620 nm. We assayed proliferation using the Click-iT EdU Alexa Fluor 555 Imaging kit (Life Technologies). Briefly, we incubated live cells with EdU (20 µM) for 1 hr prior to fixation, and stained nuclei according to the manufacturer's guidelines together with anti-MYOGENIN (Santa Cruz, catalog #sc576, 1:250) to assay differentiation. We counterstained nuclei with DAPI (Invitrogen). We acquired images with an AxioPlan2 epifluorescent microscope (Carl Zeiss Microimaging) with Plan NeoFluar 10×/0.30 NA or 20×/0.75 NA objectives (Carl Zeiss) and an ORCA-ER digital camera (Hamamatsu Photonics) controlled by SlideBook (3i) software. We quantified EdU positive cells using the MetaMorph Image Analysis software (Molecular Devices). Data analyses were blinded, where researchers performing cell scoring were unaware of the treatment condition given to sample groups analyzed.

Clonal muscle stem cell proliferation and fate analyses: We assayed clonal muscle stem cell proliferation by time-lapse microscopy as previously described[56]. Briefly, we treated isolated aged MuSCs with PGE2 (Cayman Chemical) or vehicle (DMSO) for 24 hr. After five days of growth on hydrogels, cells were reseeded at a density of 500 cells per cm$^2$ surface area in hydrogel microwells with 600 µm diameter. For time-lapse microscopy we monitored cell proliferation for those wells with single cells beginning 12 hr (day 0) to two days after seeding and recorded images every 3 min at 10× magnification using a PALM/AxioObserver Z1 system (Carl Zeiss MicroImaging) with a custom environmental control chamber and motorized stage. We changed medium every other day in between the acquisition time intervals. We analyzed time-lapse image sequences using the Baxter Algorithms for Cell Tracking and Lineage Reconstruction to identify and track single cells and generate lineage trees[5,6,8-10].

Viable and dead cells were distinguished in time-lapse sequences based on phase-contrast boundary and motility maintenance or loss, respectively. We found that the rates of proliferation (division) and death in the two conditions varied over time, Therefore, we estimated the rates for the first and the second 24 hour intervals separately. The values were estimated using the equations described in[6], and found in Table 1. We denote the proliferation rates in the two intervals $p_{24}$ and $p_{48}$ and the corresponding death rates $d_{24}$ and $d_{48}$. As an example, the proliferation rate in the treated condition during the second 24 hour interval is 5.38% per hour. Table 1 (below) shows that the rates of proliferation and death in the two conditions are similar in the first time interval, and that the difference in cell numbers at the end of the experiment is due to differences in both the division rates and the death rates during the second time interval. The modeled cell counts in the two time intervals are given by $$c(t) = \begin{cases} c_0 \exp((p_{24} - d_{24})t) & 0 \le t \le 24 \\ c(24) \exp((p_{48} - d_{48})(t-24)) & 24 < t \le 48 \end{cases}$$

where $c_0$ is the number of cells at the onset. The modeled curves are plotted together with the actual cell counts in FIG. 8F.

TABLE 1

Estimated proliferation and death rates per hours.

|  | $p_{24}$ | $p_{48}$ | $d_{24}$ | $d_{48}$ |
|---|---|---|---|---|
| DMSO | 0.0488 | 0.0403 | 0.0045 | 0.0112 |
| E2 | 0.0475 | 0.0538 | 0.0067 | 0.0012 |

The data analysis was blinded. The researchers performing the imaging acquisition and scoring were unaware of the treatment condition given to sample groups analyzed.

Quantitative RT-PCR: We isolated RNA from MuSCs using the RNeasy Micro Kit (Qiagen). For muscle samples, we snap froze the tissue in liquid nitrogen, homogenized the tissues using a mortar and pestle, followed by syringe and needle trituration, and then isolated RNA using Trizol (Invitrogen). We reverse-transcribed cDNA from total mRNA from each sample using the SensiFAST™ cDNA Synthesis Kit (Bioline). We subjected cDNA to RT-PCR using SYBR Green PCR Master Mix (Applied Biosystems) or TaqMan Assays (Applied Biosystems) in an ABI 7900HT Real-Time PCR System (Applied Biosystems). We cycled samples at 95° C. for 10 min and then 40 cycles at 95° C. for 15 s and 60° C. for 1 min. To quantify relative transcript levels, we used 2-ΔΔCt to compare treated and untreated samples and expressed the results relative to Gapdh. For SYBR Green qRT-PCR, we used the following primer sequences: Gapdh, forward 5'-TTCACCACCATGGAGAAGGC-3' (SEQ ID NO: 1), reverse 5'-CCCTTTTGGCTCCACCCT-3' (SEQ ID NO: 2); Hpgd, forward 5'-TCCAGTGT-GATGTGGCTGAC-3' (SEQ ID NO: 3), reverse 5'-AT-TGTTCACGCCTGCATTGT-3' (SEQ ID NO: 4); Ptges, forward 5'-GCTGTCATCACAGGCCAGA-3' (SEQ ID NO: 5), reverse 5'-CTCCACATCTGGGTCACTCC-3' (SEQ ID NO: 6); Ptges2, forward 5'-CTCCTACAG-GAAAGTGCCCA-3' (SEQ ID NO: 7), reverse 5'-ACCAGGTAGGTCTTGAGGGC-3' (SEQ ID NO: 8); Ptger1, forward 5' GTGGTGTCGTGCATCTGCT-3' (SEQ ID NO: 9), reverse, 5' CCGCTGCAGGGAGTTAGAGT-3' (SEQ ID NO: 10), and Ptger2, forward 5'-ACCTTCGC-CATATGCTCCTT-3' (SEQ ID NO: 11), reverse 5'-GGACCGGTGGCCTAAGTATG-3' (SEQ ID NO: 12). TaqMan Assays (Applied Biosystems) were used to quantify Pax7, Myogenin, Slco2a1 (PGT), Ptger3 and Ptger4 in samples according to the manufacturer instructions with the TaqMan Universal PCR Master Mix reagent kit (Applied Biosystems). Transcript levels were expressed relative to Gapdh levels. For SYBR Green qPCR, Gapdh qPCR was used to normalize input cDNA samples. For Taqman qPCR, multiplex qPCR enabled target signals (FAM) to be normalized individually by their internal Gapdh signals (VIC).

PGE2 ELISA: Muscle was harvested, rinsed in ice-cold PBS containing indomethacin (5.6 µg/ml), and snap frozen in liquid nitrogen. Frozen samples were pulverized in liquid nitrogen. The powder was transferred to an Eppendorf tube with 500 µl of lysate buffer (50 mM Tris-HCl pH 7.5, 150 mM NaCl, 4 mM CaCl, 1.5% Triton X-100, protease inhibitors and micrococcal nuclease), and then homogenized using a tissue homogenizer. The PGE2 level of the supernatant was measured using a PGE2 ELISA Kit (R&D Systems, catalog #KGE004B) and expressed relative to total protein measured by BCA assay (BioRad) and expressed as ng of PGE2. Each sample was assayed in duplicate and in each of two independent experiments.

cAMP activity assay: MuSCs were treated with DMSO (vehicle) or PGE2 (10 ng/ml) for 1 h and cyclic AMP levels measured according to the cAMP-Glo Assay protocol optimized by the manufacturer (Promega). Each sample was assayed in triplicate and in two independent experiments.

Flow cytometry: We assayed Annexin V as a readout of apoptosis for MuSCs after 7 days in culture on hydrogels, after an initial acute (24 hr) treatment of vehicle (DMSO) or PGE2 (10 ng/ml). We used the FITC Annexin V Apoptosis Detection Kit (Biolegend, cat #640914) according to the protocol of the manufacturer. We analyzed the cells for Annexin V on a FACS LSR II cytometer using FACSDiva software (BD Biosciences) in the Shared FACS Facility, purchased using an NIH S10 Shared Instrument Grant (S10RR027431-01).

Mass spectrometry—Analytes: All prostaglandin standards—PGF2α; PGE2; PGD2; 15-keto PGE2; 13,14-dihydro 15-keto PGE2; PGE2-D4; and PGF2α-D9-were purchased from Cayman Chemical. For the PGE2-D4 internal standard, positions 3 and 4 were labeled with a total of four deuterium atoms. For PGF2α-D9, positions 17, 18, 19 and 20 were labeled with a total of nine deuterium atoms.

Calibration Curve preparation: Analyte stock solutions (5 mg/mL) were prepared in DMSO. These stock solutions were serially diluted with acetonitrile/water (1:1 v/v) to obtain a series of standard working solutions, which were used to generate the calibration curve. Calibration curves were prepared by spiking 10 uL of each standard working solution into 200 µL of homogenization buffer (acetone/water 1:1 v/v; 0.005% BHT to prevent oxidation) followed by addition of 10 uL internal standard solution (3000 ng/mL each PGF2α-D9 and PGE2-D4). A calibration curve was prepared fresh with each set of samples. Calibration curve ranges: for PGE2 and 13,14-dihydro 15-keto PGE2, from 0.05 ng/mL to 500 ng/mL; for PGD2 and PGF2α, from 0.1 ng/mL to 500 ng/mL; and for 15-keto PGE2, from 0.025 ng/mL to 500 ng/mL.

Extraction procedure: The extraction procedure was modified from that of Prasain et al.[11] and included acetone protein precipitation followed by 2-step liquid-liquid extraction; the latter step enhances LC-MS/MS sensitivity. Butylated hydroxytoluene (BHT) and evaporation under nitrogen (N2) gas were used to prevent oxidation.

Solid tissues were harvested, weighed, and snap-frozen with liquid nitrogen. Muscle tissue was combined with homogenization beads and 200 µL homogenization buffer in a polypropylene tube and processed in a FastPrep 24 homogenizer (MP Biomedicals) for 40 seconds at a speed of 6 m/s. After homogenization, 10 µL internal standard solution (3000 ng/mL) was added to tissue homogenate followed by sonication and shaking for 10 minutes. Samples were centrifuged and the supernatant was transferred to a clean eppendorf tube. 200 µL hexane was added to the sample, followed by shaking for 15 minutes, then centrifugation. Samples were frozen at −80° C. for 40 minutes. The hexane layer was poured off from the frozen lower aqueous layer, and discarded. After thawing, 25 µL of 1 N formic acid was added to the bottom aqueous layer, and the samples were vortexed. For the second extraction, 200 µL chloroform was added to the aqueous phase. Samples were shaken for 15 minutes to ensure full extraction. Centrifugation was performed to separate the layers. The lower chloroform layer was transferred to a new eppendorf tube and evaporated to dryness under nitrogen at 40° C. The dry residue was reconstituted in 100 µL acetonitrile/10 mM ammonium acetate (2:8 v/v) and analyzed by LC-MS/MS.

LC-MS/MS: Since many prostaglandins are positional isomers with identical masses and have similar fragmentation patterns, chromatographic separation is critical. Two SRM transitions—one quantifier and one qualifier—were carefully selected for each analyte. Distinctive qualifier ion intensity ratios and retention times were essential to authenticate the target analytes. All analyses were carried out by negative electrospray LC-MS/MS using an LC-20AD$_{XR}$ prominence liquid chromatograph and 8030 triple quadrupole mass spectrometer (Shimadzu). HPLC conditions: Acquity UPLC BEH C18 2.1×100 mm, 1.7 um particle size column was operated at 50° C. with a flow rate of 0.25 mL/min. Mobile phases consisted of A: 0.1% acetic acid in water and B: 0.1% acetic acid in acetonitrile. Elution profile: initial hold at 35% B for 5 minutes, followed by a gradient of 35%-40% in 3 minutes, then 40%-95% in 3 minutes; total run time was 14 minutes. Injection volume was 20 uL. Using these HPLC conditions, we achieved baseline separation of the analytes of interest.

Selected reaction monitoring (SRM) was used for quantification. The mass transitions were as follows: PGD2: m/z 351.10→m/z 315.15 (quantifier) and m/z 351.10→m/z 233.05 (qualifier); PGE2: m/z 351.10→m/z 271.25 (quantifier) and m/z 351.10→m/z 315.20 (qualifier); PGF2α: m/z 353.10→m/z 309.20 (quantifier) and m/z 353.10→m/z 193.20 (qualifier); 15 keto-PGE2: m/z 349.30→m/z 331.20 (quantifier) and m/z 349.30→m/z 113.00 (qualifier); 13,14-dihydro 15-keto PGE2: m/z 351.20→m/z 333.30 (quantifier) and m/z 351.20→m/z 113.05 (qualifier); PGE2-D4: m/z 355.40→m/z 275.20; and PGF2α-D9: m/z 362.20→m/z 318.30. Dwell time was 20-30 ms.

Quantitative analysis was done using LabSolutions LCMS (Shimadzu). An internal standard method was used for quantification: PGE2-D4 was used as an internal standard for quantification of PGE2, 15-keto PGE2, and 13, 14-dihydro 15-keto PGE2. PGF2α-D9 was the internal standard for quantification of PGD2 and PGF2α. Calibration curves were linear (R>0.99) over the concentration range using a weighting factor of $1/X^2$ where X is the concentration. The back-calculated standard concentrations were ±15% from nominal values, and ±20% at the lower limit of quantitation (LLOQ).

In vivo muscle force measurement: Aged mice (18 mo.) were subjected to downhill treadmill run for 2 consecutive weeks. During week 1, mice ran daily for 5 days and rested on days 6 and 7. Two hours after each treadmill run during week 1, each (lateral and medial) gastrocnemius (GA) muscle from both legs of each mouse was injected with a dose of either PBS (vehicle control) or 13 nM dmPGE2 (experimental group). During week 2, mice were subjected to 5 days treadmill run only. The treadmill run was performed using the Exer3/6 (Columbus Instruments). Mice ran for 10 minutes on the treadmill at 20 degrees downhill, starting at a speed of 7 meters/min. After 3 min, the speed was increased by 1 meter/min to a final speed of 14 meter/min. 10 minutes run time was chosen, as exhaustion defined as the inability of the animal to remain on the treadmill despite electrical prodding, was observed at a median of 12 minute in an independent control aged mouse group. Force measurements were on the GA muscles at week 5 based on a protocol published previously[5]. Briefly, for each mouse, an incision was made to expose the GA. We severed the calcaneus bone with intact achilles tendon and attached the tendon-bone complex to a 300C-LR force transducer (Aurora Scientific) with a thin metal hook. The muscles and tendons were kept moist by periodic wetting with saline (0.9% sodium chloride) solution. The lower limb was immobilized below the knee by a metal clamp without compromising the blood supply to the leg. The mouse was under inhaled anesthetic (2% isoflurane) during the entire force measuring procedure and body temperature was maintained by a heat lamp. In all measurements, we used 0.1-ms pulses at a predetermined supramaximal stimulation voltage. The GA muscles were stimulated via the proximal sciatic nerve using a bipolar electrical stimulation cuff delivering a constant current of 2 mA (square pulse width 0.1 ms). GA muscles were stimulated with a single 0.1-ms pulse for twitch force measurements, and a train of 150 Hz for 0.3 s pulses for tetanic force measurements. We performed five twitch and then five tetanic measurements on each muscle, with 2-3 min recovery between each measurement with n=5 mice per group. Data were collected with a PCI-6251 acquisition card (National Instruments) and analyzed in Matlab. We calculated specific force values by normalizing the force measurements by the muscle physiological cross-sectional areas (PCSAs), which were similar between the control and the experimental PGE2 treated group (Table 2). PCSA (measured in mm$^2$) was calculated according to the following equation[12]:

$$PCSA\ (mm^2) = [mass\ (g) \times Cos\ \theta] \div [\rho\ (g/mm^3) \times fiber\ length\ (mm)],$$

where $\theta$ is pennation angle of the fiber and $\rho$ is muscle density (0.001056 g/mm$^3$).

Statistical analyses: We performed cell culture experiments in at least three independent experiments where three biological replicates were pooled in each. In general, we performed MuSC transplant experiments in at least two independent experiments, with at least 3-5 total transplants per condition. We used a paired t-test for experiments where control samples were from the same experiment in vitro or from contralateral limb muscles in vivo. A non-parametric Mann-Whitney test was used to determine the significance difference between untreated (−) vs treated (PGE or dmPGE2) groups using $\alpha=0.05$. ANOVA or multiple t-test was performed for multiple comparisons with significance level determined using Bonferroni correction or with Fisher's test as indicated in the figure legends. Unless otherwise described, data are shown as the mean±s.e.m.

Methods references: Sacco, A., Doyonnas, R., Kraft, P., Vitorovic, S. & Blau, H. M. Self-renewal and expansion of single transplanted muscle stem cells. *Nature* 456, 502-506, doi:10.1038/nature07384 (2008); Schneider, A. et al. Generation of a conditional allele of the mouse prostaglandin EP4 receptor. *Genesis* 40, 7-14, doi:10.1002/gene.20048 (2004); Murphy, M. M., Lawson, J. A., Mathew, S. J., Hutcheson, D. A. & Kardon, G. Satellite cells, connective tissue fibroblasts and their interactions are crucial for muscle regeneration. *Development* 138, 3625-3637, doi:10.1242/dev.064162 (2011); Safran, M. et al. Mouse reporter strain for noninvasive bioluminescent imaging of cells that have undergone Cre-mediated recombination. *Molecular imaging* 2, 297-302 (2003); Cosgrove, B. D. et al. Rejuvenation of the muscle stem cell population restores strength to injured aged muscles. *Nature medicine* 20, 255-264, doi:10.1038/nm.3464 (2014); Gilbert, P. M. et al. Substrate elasticity regulates skeletal muscle stem cell self-renewal in culture. *Science* 329, 1078-1081, doi:10.1126/science.1191035 (2010); Papapetrou, E. P. et al. Genomic safe harbors permit high beta-globin transgene expression in thalassemia induced pluripotent stem cells. *Nature biotechnology* 29, 73-78, doi:10.1038/nbt.1717 (2011); Chenouard, N. et al. Objective comparison of particle tracking methods. *Nature methods* 11, 281-289, doi:10.1038/nmeth.2808 (2014); Magnusson, K. E., Jalden, J., Gilbert, P. M. & Blau, H. M. Global linking of cell tracks using the Viterbi algorithm. *IEEE transactions on medical imaging* 34, 911-929, doi:10.1109/TMI.2014.2370951 (2015); Maska, M. et al. A benchmark for comparison of cell tracking algorithms. *Bioinformatics* 30, 1609-1617, doi:10.1093/bioinformatics/btu080 (2014); Prasain, J. K., Hoang, H. D., Edmonds, J. W. & Miller, M. A. Prostaglandin extraction and analysis in Caenorhabditis elegans. *Journal of visualized experiments: JoVE*, doi:10.3791/50447 (2013); Burkholder, T. J., Fingado, B., Baron, S. & Lieber, R. L. Relationship between muscle fiber types and sizes and muscle architectural properties in the mouse hindlimb. *J Morphol* 221, 177-190, doi:10.1002/jmor.1052210207 (1994).

TABLE 2

Physiological cross-sectional area (PCSA) of aged gastrocnemius week 5 post-exercise.

| Mouse ID | Leg | Pennation angle θ (degree) | Cosine (θ) | Fiber length (mm) | GA Mass (g) | PCSA (medial + lateral) (mm$^2$) |
|---|---|---|---|---|---|---|
| Control-1 | Left | 21 | 0.93 | 6.88 | 0.18 | 23.13 |
| | Right | 21 | 0.93 | 6.64 | 0.18 | 23.82 |
| Control-2 | Left | 26 | 0.90 | 4.03 | 0.16 | 33.79 |
| | Right | 22 | 0.93 | 5.34 | 0.16 | 26.31 |
| Control-3 | Left | 21 | 0.93 | 4.52 | 0.15 | 29.34 |
| | Right | 23 | 0.92 | 4.59 | 0.17 | 32.28 |
| Control-4 | Left | 24 | 0.91 | 5.07 | 0.14 | 23.89 |
| | Right | 23 | 0.92 | 4.75 | 0.13 | 23.86 |
| Control-5 | Left | 19 | 0.95 | 6.07 | 0.16 | 17.75 |
| | Right | 18 | 0.95 | 6.05 | 0.15 | 10.25 |
| dmPGE2-1 | Left | 12 | 0.98 | 7.60 | 0.25 | 30.47 |
| | Right | Tendon damage | — | — | — | — |
| dmPGE2-2 | Left | 12 | 0.96 | 4.85 | 0.16 | 30.56 |
| | Right | 16 | 0.91 | 4.80 | 0.14 | 26.55 |
| dmPGE2-3 | Left | 14 | 0.97 | 5.89 | 0.17 | 26.52 |
| | Right | 13 | 0.94 | 5.63 | 0.14 | 22.94 |

TABLE 2-continued

Physiological cross-sectional area (PCSA)
of aged gastrocnemius week 5 post-exercise.

| Mouse ID | Leg | Pennation angle θ (degree) | Cosine (θ) | Fiber length (mm) | GA Mass (g) | PCSA (medial + lateral) (mm²) |
|---|---|---|---|---|---|---|
| dmPGE2-4 | Left | 14 | 0.97 | 6.67 | 0.14 | 19.29 |
|  | Right | 13 | 0.97 | 7.74 | 0.16 | 19.07 |
| dmPGE2-5 | Left | 11 | 0.98 | 5.56 | 0.17 | 28.42 |
|  | Right | 11 | 0.98 | 5.54 | 0.16 | 26.85 |
| Avg. Control |  |  |  |  |  | 25.09 |
| Avg. dmPGE2 |  |  |  |  |  | 25.63 |

Example 2: Increased Muscle Forces after Prostaglandin E2 (PGE2) Injection

This example shows an increase in specific twitch force of gastrocnemius muscles in aged mice injected with PGE2. The aged mice (18 months old) were subject to treadmill run to exhaustion daily for 10 days. The treadmill run was performed using the Exer3/6 (Columbus Instruments). Mice ran on the treadmill at 20 degrees downhill, starting at a speed of 10 meters/min. After 3 min, the speed was increased 1 meter/min to a final speed of 20 meters/min. Exhaustion was defined as the inability of the animal to remain on the treadmill despite electrical prodding. 2 h after each treadmill run, both gastrocnemius muscles of each mouse were injected with either PBS (control group) or 3 nM PGE2 (experimental group). The force measurement was performed 4 weeks after the last treadmill run using a 300C-LR force transducer (Aurora Scientific) with a single 0.1 ms pulse at predetermined supramaximal stimulation intensity.

Representative raw muscle force traces of single gastrocnemius muscles are provided in FIGS. 5M-5N. The muscle force and synchronization pulses were recorded via a PCI-6251 acquisition card (National Instruments) and analyzed using Matlab. FIGS. 5O-5P show the specific muscle force values that were calculated by normalizing the force measurements with the muscle physiological cross-sectional area. The specific twitch force values ($kN/m^2$) are represented by the Box and Whiskers plot that shows the minimum, maximum, and median values. Five repetitive measurements were made from each muscle. N=4 for the control group and n=5 for the PGE2 injected group. ** represents a statistical significant value of $p<0.005$ by 2-tailed Mann Whitney test.

FIGS. 5Q and 5R show twitch force and tetanic force data, respectively, from a separate experiment in which mice were treated with PGE2 or vehicle only. Importantly, we observed an increase in isometric force in aged (18-22 mo) mice injected with PGE2 and subjected to downhill treadmill exercise. Briefly, aged mice ran daily (at 20 degrees downhill and 14 meter/min maximum speed for 10 min) for 5 days and rested on days 6 and 7. This eccentric exercise regime leads to MuSC expansion due to a cycle of muscle degeneration and regeneration. Two hours after each treadmill run during week 1, TA muscles of both legs of each mouse were injected with either PBS (vehicle control group) or 10 μg PGE2 (experimental group). During week 2, mice were subjected to 5 days treadmill run only. Force measurements (twitch and tetanic) were performed on the TA muscles at week 5 using our previously published protocols. The PGE2 treated group exhibited a significant increase in force compared to the control group.

Example 3: Prostaglandin E2 is Essential for Efficacious Skeletal Muscle Stem Cell Function, Augmenting Regeneration and Strength Skeletal muscles harbor quiescent muscle-specific stem cells (MuSCs) capable of tissue regeneration throughout life. Muscle injury precipitates a complex inflammatory response in which a multiplicity of cell types, cytokines and growth factors participate, including prostaglandins. Here we show that Prostaglandin E2 (PGE2) directly targets MuSCs via the EP4 receptor leading to MuSC expansion. An acute treatment with PGE2 suffices to robustly augment muscle regeneration by either endogenous or transplanted MuSCs. Loss of PGE2 signaling by specific genetic ablation of the EP4 receptor in MuSCs impairs regeneration leading to decreased muscle force. Inhibition of PGE2 production through NSAID administration just after injury similarly hinders regeneration and compromises muscle strength. Mechanistically, the PGE2 EP4 interaction causes MuSC expansion by triggering a cyclic AMP/phosphoCREB pathway that activates the proliferation-inducing transcription factor, Nurr1. Our findings reveal that loss of PGE2 signaling to MuSCs during recovery from injury impedes muscle repair and strength. Through such gain or loss of function experiments, we found that PGE2 signaling acts as a rheostat for muscle stem cell function. Decreased PGE2 signaling due to NSAIDs or increased PGE2 due to exogenous delivery dictates MuSC function which determines the outcome of regeneration. The markedly enhanced and accelerated repair of damaged muscles following intramuscular delivery of PGE2 suggests a new indication for this therapeutic agent.

Muscle repair after injury entails an immune response that orchestrates efficacious regeneration. Here we identify Prostaglandin E2 (PGE2) as a crucial inflammatory mediator of muscle stem cells (MuSCs), the building blocks of muscle regeneration. PGE2 is synthesized and secreted into the stem cell niche in response to injury leading to robust MuSC proliferation, key to myofiber repair. EP4 is the receptor that mediates PGE2 signaling in MuSCs and genetically engineered mice that lack EP4 in MuSCs have impaired regeneration. Non-steroidal anti-inflammatory drugs (NSAIDs), commonly used to treat pain after muscle injury, inhibit PGE2 synthesis, hinder muscle regeneration, and lead to weakened muscles. Importantly, a single treatment of injured muscles with PGE2 dramatically accelerates muscle repair and recovery of strength.

Satellite cells, also known as muscle stem cells (MuSCs) are crucial to muscle regeneration. They reside in a quiescent state in niches juxtaposed to myofibers in muscle tissues, poised to respond to damage and repair skeletal muscles throughout life (1-4). Muscle injury precipitates an inflammatory response that is marked by the sequential infiltration of multiple cell types including neutrophils, monocytes, macrophages, T-cells and fibroadipocytes, and is accompanied by muscle stem cell activation. During this inflammatory phase, concurrent waves of cytokine and growth factor release, including CC-chemokine ligand 2 (CCL2), IL-10, IL-1β, tumor necrosis factor-α (TNFα), transforming growth factor-β1 (TGFβ1) (3, 5-10). In addition, prostaglandins, potent lipid mediators of inflammation, are synthesized and secreted by immune and myogenic cells (6, 11). Prostaglandins derive from arachidonic acid, which is released from membrane phospholipids by phospholipase A2 and converted by cyclooxygenase enzymes (COX-1 and -2) into prostaglandin H2 (PGH2), and subsequently into the different prostaglandin subtypes, PGD2, PGE2, PGF2α, PGI2 or thromboxane (TXA2). Specific to the generation of PGE2 are the prostaglandin synthases (PGES: mPGES-1, mPGES-2 and cPGES) (11-13).

While PGE2 has been associated with muscle regeneration, it was not known to have a direct beneficial effect on muscle regeneration and strength until this benefit was discovered by the inventors of the present invention. Conflicting reports suggest that PGE2 can either promote myoblast proliferation or differentiation in culture (14-18). In the COX2-knockout mouse model, which lacks PGE2, regeneration is delayed. However, the mechanism by which PGE2 acts could not be established in these studies due to the systemic constitutive loss of COX2 and consequent nonspecific effects on many cell types (15, 19). Similarly, muscle recovery after injury was impaired in mice given a COX-2 inhibitor (15). Additionally, mice treated with non-steroidal anti-inflammatory drugs (NSAIDs), which block the production of prostaglandins through inhibition of COX1 and COX2, exhibited regeneration deficits (20, 21). Moreover, NSAIDS lead to an attenuation of exercise-induced expansion of human satellite cells in biopsies (20). Likewise, glucocorticoids, which reduce prostaglandin synthesis by suppressing phospholipase A2, COX-2 and mPGES-1 expression, adversely affect the recovery of muscle strength in polymyositis patients (22). However, since the target of NSAIDs and glucocorticoids are the COX enzymes, this effect could entail a number of prostaglandin subtypes in addition to PGE2 and therefore have pleiotropic effects. Thus, to date the spatiotemporal effects of PGE2 in muscle regeneration remain unresolved. Moreover, although inhibition of PGE2 synthesis and activity was shown to be detrimental to the recovery of muscle function, the studies referenced here do not provide any suggestion that administration of PGE2 could be directly beneficial for muscle regeneration and the recovery of muscle function.

The inventors have discovered that in response to injury, PGE2 is transiently induced in muscle tissues. To establish if PGE2 acts directly on MuSCs, the building blocks of muscle regeneration, we generated mice in which the PGE2 receptor, EP4, could be conditionally ablated in MuSCs. In addition, we established transgenic reporter mice that enabled specific tracking of MuSC contribution to regeneration dynamically and sensitively over time by bioluminescence imaging after PGE2 delivery. We coupled these models with assays of muscle force and found a direct link between the ability of MuSCs to respond to PGE2 and regeneration, leading to restoration of force. Gain and loss of function experiments revealed that PGE2 signaling acts as a rheostat for muscle stem cell function. We provide evidence that although PGE2 is normally synthesized after injury, by transiently increasing PGE2 levels above normal endogenous levels, regeneration is augmented. Our data indicate that PGE2 impacts regeneration and has therapeutic applications.

A surge of PGE2 in damaged muscle tissues accelerates MuSC proliferation: We sought to identify an activator of MuSC function by capitalizing on an inflammatory response that mediates muscle regeneration. Since muscle injury triggers an immediate inflammatory response (5, 7, 8, 23), we hypothesized that a transiently induced inflammatory modulator could regulate MuSC function and play a crucial role in regeneration. We performed qRT-PCR and detected increased levels of the Ptger4 receptor (EP4) for PGE2, a potent lipid mediator during acute inflammation (11), on isolated MuSCs obtained by dissociating muscle tissue followed by fluorescence activated cell sorting (FACS) (FIG. 12A). In accordance with receptor expression, we detected a surge in the levels of PGE2 in mouse muscle lysates three days after injury by standard paradigms entailing notexin injection or cryoinjury (FIGS. 12B, 12C, and 18A). The concomitant transient upregulation of its synthesizing enzymes, Ptges and Ptges2 was also detected (FIG. 12D). Although other cell types within muscles may also produce PGE2 in response to injury such as endothelial cells, inflammatory cells and FAPs, the myofibers that circumscribe MuSCs are a source of PGE2, as observed in conditioned medium from dissociated myofibers (FIG. 12E). Moreover, upon treatment of myofibers with indomethacin, a NSAID that inhibits COX2, PGE2 synthesis is markedly reduced (FIG. 12E). The peak in PGE2 levels coincides temporally with the expansion of MuSCs and the well documented accumulation of inflammatory cytokines such as TGFβ1, CCL2, IL-10, IL-1β and TNFα post-injury, where MuSC activation and expansion takes place (3, 5, 7, 8). Although PGE2 has previously been implicated in the inflammatory damage response, the cellular and molecular mechanism by which it acts in muscle regeneration has yet to be resolved.

To determine whether PGE2 has a direct effect on MuSC expansion, we assessed the proliferation potential of FACS isolated MuSCs (24) treated with PGE2 (10 ng/ml) in culture. This concentration of PGE2 was selected based on a dose-response assay, which resolved the lowest drug concentration that promotes a robust MuSC proliferation response (FIG. 18B). We found that a 1-day exposure to PGE2 in culture induced a 6-fold increase in the number of MuSCs relative to controls one week later (FIG. 12F). This increase in cell division after PGE2 treatment was also evident by EdU incorporation (FIGS. 18C and 18D). Culture of MuSCs in media with charcoal stripped serum, which is depleted of lipid components including prostaglandins (25), markedly impeded cell proliferation. Addition of PGE2 rescued this block in proliferation (FIG. 18E). Notably, whereas freshly isolated MuSCs expressed relatively high levels of EP4 receptor mRNA, expression progressively declined to negligible levels was as the cells gave rise to increasingly differentiated muscle cells in culture. This result suggests that MuSCs are the myogenic cell type most responsive to PGE2 (FIG. 12A). We further analyzed the effect of PGE2 at the single cell level by tracking individual MuSCs by time-lapse microscopy analysis in a hydrogel 'microwell' platform as previously described (26, 27) (FIGS. 12G-K and 18F-H). Clonal assays can reveal differences that are obscured by analysis of the population as a whole. Data were collected over a 38 h time period and then analyzed using the Baxter Algorithms for Cell Tracking and Lineage Reconstruction (26-28). We observed a marked increase in cumulative cell divisions and cell numbers in response to PGE2, spanning 6 generations for the most robust clones (FIGS. 12G and 12H). The basis for the difference between PGE2-treated cells and vehicle-treated controls is that immediately following PGE2 addition post-plating, entry into mitosis is accelerated which is the cause of the subsequent increased expansion (FIGS. 12I, 12J, 18G, and 18H). The subsequent exponential increase in cells in both conditions exacerbates the difference at the onset, culminating in almost twice the number of total cells at the end of the 38 h timespan (FIGS. 18G and 18H). The concomitant increase in the incidence of larger cell sizes observed after PGE2 treatment (FIG. 12K), support its role in mitotic events (29).

PGE2 treatment augments muscle regeneration: To determine if PGE2 impacted the function of MuSCs in regeneration, we performed in vivo experiments. To monitor the dynamics of regeneration over time in a quantitative manner, we capitalized on a sensitive and quantitative bioluminescence imaging (BLI) assay we previously developed for monitoring MuSC function post-transplantation (24, 26, 27, 30). MuSCs were isolated from transgenic mice expressing both GFP and luciferase (GFP/Luc mice) and equivalent numbers of MuSCs (250 cells) were coinjected with either PGE2 or vehicle only into injured TAs of NOD-SCID gamma (NSG) mice. PGE2 coinjection enhanced the regenerative capacity of MuSCs by nearly two orders of magnitude compared to controls assessed by BLI. Histological analysis reveals GFP$^+$ MuSC engraftment in the niche and GFP$^+$ fibers resulting from fusion over the time course (FIGS. 13A, 19A, and 19B). Moreover, following engraftment, a secondary injury elicited a spike in BLI signals of PGE2-treated MuSCs relative to controls, suggesting enhanced stem cell repopulation (FIG. 13A). Notably PGE2 is known to have a relatively short half-life in vivo (31). Thus these experiments demonstrate that transient exposure of MuSCs to PGE2 at the time of co-delivery to injured muscle suffices to significantly enhance muscle regeneration.

We postulated that delivery of PGE2 alone could increase endogenous MuSC numbers and enhance regeneration, circumventing the need for a cell therapeutic. We reasoned that PGE2 delivered during the early time window immediately post-injury could augment the beneficial effects of the innate inflammatory response and PGE2 surge. To test this possibility, muscles of young mice were injured and three days later we injected a bolus of PGE2 (FIG. 13B). We observed a striking increase (65±7%) in endogenous PAX7-expressing MuSCs in the classic satellite cell niche beneath the basal lamina and atop myofibers 14 days post-injury (FIGS. 13B and 13C). PGE2 is only effective after injury, as no difference from vehicle-injected controls was observed in the absence of tissue damage (data not shown). A striking shift in the distribution of myofibers from smaller toward larger sizes, assessed as cross-sectional-area was evident over the time course of regeneration (FIGS. 13D, 13E, 19A, and 19B). This change reflects the remodeling of myofiber architecture that accompanies the observed accelerated regeneration, as muscle mass did not increase during this time period (FIG. 19C). In addition, we tracked the response to injury and PGE2 of endogenous MuSCs by luciferase expression using a transgenic mouse model, Pax7$^{CreERT2}$; Rosa26-LSL-Luc (FIGS. 13F and 13G). The BLI data were in agreement with the histological data (FIGS. 13B and 13C). That a single injection of PGE2 post-injury could suffice to boost endogenous MuSC numbers and regenerative function leading to this degree of accelerated regeneration was quite unexpected.

EP4 receptor mediates PGE2 signaling to promote MuSC proliferation and engraftment: PGE2 is known to signal through four G-protein coupled receptors (Ptger1-4; EP1-4) (6, 11), but the expression of these receptors in MuSCs has not previously been reported. An analysis of the transcript levels of the different receptors (Ptger1-4) revealed that 24 h after PGE2 treatment, the most highly expressed receptor in MuSCs is Ptger4 (FIG. 14A). PGE2 treated MuSCs showed elevated downstream intracellular cyclic AMP (cAMP) levels (FIG. 14B), a response associated to EP4 signaling (11), and in the presence of an EP4 antagonist, ONO-AE3-208, the increased proliferation response induced by PGE2 was blunted (FIG. 14C). This data confirms that PGE2 signals through the EP4 receptor to promote proliferation. The specificity of PGE2 for EP4 was most clearly shown by the marked reduction in proliferation of MuSCs lacking the receptor following Cre-mediated conditional ablation of EP4 in MuSCs isolated from EP4$^{f/f}$ mice (FIGS. 14D and 20A-D). A requirement for EP4 in the proliferative response to PGE2 was confirmed by tamoxifen treatment of MuSCs isolated from Pax7$^{CreERT2}$:EP4$^{f/f}$ mice in which Cre-mediated EP4 ablation is under the control of the MuSC-specific Pax7 promoter (FIGS. 20E and 20F). Notably, compensation by other PGE2 receptors does not occur in MuSCs lacking EP4 as expression of EP1, EP2 and EP3 receptors (Ptger1-3) remains low in MuSCs (FIG. 20G). Together, these data show that PGE2 and its receptor EP4 are crucial for MuSC proliferation. To determine if EP4 plays a role in MuSC function in vivo, we transplanted luciferase-expressing MuSCs that lacked the EP4 receptor following conditional ablation in culture into injured TAs of NSG mice. The BLI signal that was initially detected progressively declined to levels below the threshold of significance (FIGS. 14E and 20A-D). Thus, in the absence of PGE2 signaling via the EP4 receptor regeneration is impaired.

Transcription factor Nurr1 is a downstream mediator of PGE2/EP4 signaling in MuSCs: To perform an unbiased search for mediators of signaling downstream of PGE2 that mediate the enhanced effect of MuSC functions, we performed an RNA-seq analysis comparing isolated MuSCs treated with vehicle (control) or PGE2 for 24 h (FIG. 21A). Bioinformatics analyses using Ingenuity Pathway Analysis (IPA) and Metacore software packages revealed that in addition to regulators of PGE2 metabolism, PGE2 treatment of MuSCs led to an increase in molecular and cellular functions consistent with stem cell expansion, including cAMP signaling, and cell cycle regulation (FIGS. 21B and 21C). Among the top 200 differentially expressed genes with a non-adjusted p-value <0.05, only 11 transcription factors were identified (FIG. 15A). Nurr1 was among the few that were differentially expressed. Nurr1 had also previously been shown to mediate PGE2 signaling through cAMP and phospho-CREB to induce cell proliferation in colorectal cancer and neuronal cells (32, 33). To investigate its putative role as a downstream effector of EP4 signaling in MuSCs, we examined its expression in vivo. Remarkably, the time window of Nurr1 expression mirrored that of PGE2 in muscle tissue, peaking at day 3 post-injury (FIGS. 15B and 12B). In culture, PGE2 treatment increased Nurr1 mRNA and protein expression (FIGS. 15C and 15D) and Nurr1 knockdown blunted the effect of PGE2 in inducing MuSC proliferation (FIGS. 4E and 21D). To determine the specificity of Nurr1 transcriptional regulation to PGE2 mediated-EP4 receptor signaling we ablated the EP4 receptor in Pax7$^{CreERT2}$:EP4$^{f/f}$ MuSCs by tamoxifen treatment (FIG. 21E). Nurr1 was not upregulated after PGE2 treatment in EP4 knockout MuSCs (FIG. 15F). Expression of Nurr1 was highest in MuSCs and declined at the onset of differentiation of myogenic cells, in accordance with the expression pattern of EP4 (FIG. 15G). Together, these data implicate the Nurr1 transcription factor as a mediator of PGE2/EP4 signaling that triggers MuSC expansion.

Loss of PGE2 signaling impairs muscle regeneration and strength: To determine if EP4 is required for regeneration in vivo, we used the Pax7$^{CreERT2}$:EP4$^{f/f}$ mouse model in which EP4 is specifically and conditionally ablated in MuSCs by sequential intraperitoneal tamoxifen injection into mice (FIG. 16A). Induction of EP4 ablation was highly efficient in Pax7$^+$ cells in vivo following tamoxifen treatment and injury. Ptger4 mRNA levels detected in sorted MuSCs was 96% lower than in the control (FIGS. 16A and 16B). In the absence of EP4 signaling in MuSCs, we observed an aberrant persistence of immature centrally nucleated regenerating myofibers that express embryonic myosin heavy chain (eMyHC) at day 7 post-injury (FIGS. 16C and 16E). This evidence of impaired regeneration was corroborated by a shift toward myofibers with diminished myofiber cross sectional area relative to controls at day 21 post-injury (FIGS. 16D and 16E). In these experiments, PGE2 can act on other cell types in muscle tissue in the course of regeneration, such as mature myofibers, fibroadipogenic progenitors (FAPs) and immune cells; however, these cells were not sufficient to restore the EP4-deficient MuSC functions. These features provide strong evidence that in the absence of EP4 signaling efficacious muscle regeneration is impeded.

We further tested whether the defects in muscle repair stemming from specific loss of EP4 in MuSCs impacted muscle strength. Strikingly, eliminating signaling through EP4 on MuSCs alone led to a 35±6% and 31±4% decrease in twitch and tetanus force, respectively (FIGS. 16F-H), without apparent loss of muscle mass (FIG. 22A). To determine if the absence of PGE2 altered muscle regeneration and strength after injury, we subjected mice to treatment with a non-steroidal anti-inflammatory drug (NSAID, indomethacin). A single indomethacin injection into TA muscles of a Pax7$^{CreERT2}$;Rosa26-LSL-Luc mouse model three days after injury led to a decline in BLI relative to controls, indicative of an impairment in muscle stem cell expansion and regeneration (FIGS. 16I and 16J). This loss of regenerative capacity after NSAID treatment was accompanied by a substantial 33±7% reduction in twitch force compared to controls (FIGS. 16K, 16L, and 22B). The diminished strength seen upon global muscle inhibition of PGE2 synthesis mirrored that observed in regenerating muscle with MuSC-EP4 specific knockout, suggesting that MuSC expansion accounts for the majority of the PGE2 mediated effects on muscle regeneration.

We have discovered that a major effect of PGE2 during muscle regeneration is to target MuSCs directly. PGE2 has been implicated as an immunomodulator that acts on neutrophils, mast cells, and macrophages that are crucial to the early inflammatory response after injury. The ensuing cytokine storm is thought to induce muscle stem cell function in regeneration (3, 6, 7, 11). Studies in whole body COX2 KO mice, in which all prostaglandin synthesis was ablated, supported this conclusion (15, 19). Myoblasts have been proposed as the cell type responsive to PGE2 in culture (14, 16-18, 34, 35), but these cells perform poorly in regeneration (24) and cannot account for the observed effects. Moreover, other studies implicating PGE2 in regeneration all suffered from pleiotropic effects on a multiplicity of cell types.

MuSCs are crucial to development and regeneration (1-3, 24, 36-38) and their numbers dramatically increase in response to insults that damage the muscles in mice and humans (5, 20, 39-42). Injections of MuSCs into injured muscles leads to their exponential increase, whereas injection of their myoblast derivatives results in a decline in numbers, revealing a remarkable distinction in regenerative capacity of these two cell types (24). Here we show that the major effect of PGE2 during muscle regeneration is on MuSCs and that this effect is direct and mediated by the EP4 receptor. Notably, EP4 is robustly expressed on MuSCs and progressively diminishes to negligible levels on differentiating myoblasts suggesting that the most responsive myogenic cell type to PGE2 is the MuSC. Mechanistically, once PGE2 engages the EP4 receptor, it activates cAMP and the downstream proliferation-inducing transcription factor Nurr1 leading to accelerated MuSC proliferation (FIG. 17). Although Nurr1 has been associated in intestinal epithelial cells with induction of proliferation and regeneration by directly blocking the cell cycle inhibitor p21 (Waf1/Cip1) in intestinal epithelial cells (43), its role in the expansion of stem cells, and particularly muscle stem cells, has not previously been described. The finding that further substantiates that Nurr1 mediates the onset of MuSC proliferation in vivo is that its levels transiently peak in muscle tissues three days post injury, concomitant with the observed surge in PGE2.

We show that MuSC function and engraftment are strictly dependent on PGE2 signaling through its receptor by its conditional and specific ablation of EP4 using two approaches. Ablation of EP4 on MuSCs in vitro followed by transplantation in vivo leads to diminished engraftment evident by BLI. The most striking evidence of a crucial role for EP4 derives from its in vivo ablation of EP4 specifically on endogenous MuSCs which causes a marked reduction in muscle strength post-injury accompanied by a shift toward smaller and more immature myofibers relative to controls (FIG. 17). Thus, in the absence of the EP4 receptor, regeneration by both transplanted and endogenous MuSCs is severely impaired.

The surge in PGE2 post-injury is transient. Similarly, acute PGE2 treatment enhances and accelerates muscle regeneration long-term. When freshly isolated MuSCs were coinjected with PGE2 into injured muscles, a boost in muscle repair was evident by BLI. A single ex vivo exposure of hematopoietic stem cells to PGE2 had a similarly pronounced effect on subsequent stem cell expansion and reconstitution of the blood post-transplant (44). Indeed, a single injection of PGE2 alone (without MuSCs) directly into injured muscles led to a striking increase in endogenous MuSC numbers and myofiber sizes that was apparent within 2 weeks. The beneficial effects of delivery of the inhibitor of the PGE2-degrading enzyme (15-PGDH), SW033291, on hematopoietic, liver, and colon regeneration are likely due to a similar augmentation of endogenous PGE2 levels (45). Notably, PGE2 and its analogues have safely been used in patients for more than a decade, for instance to induce labor (46) and to promote hematopoietic stem cell transplantation (44). Together with our findings, these studies pave the way for its clinical use in boosting muscle repair post-injury.

We show that PGE2 levels act as a rheostat that controls the efficacy of regeneration. Augmentation of the innate pro-inflammatory PGE2 response to injury leads to accelerated MuSC expansion and muscle regeneration. By contrast, NSAID administration at the time of injury to control pain, a common practice, abrogates that effect, suggesting that PGE2 signaling during this early temporal window is crucial to its beneficial effects. Most striking is our finding that a single PGE2 treatment suffices to rapidly and robustly invoke a muscle stem cell response to enhance regeneration of damaged muscle and restore strength.

We performed all experiments and protocols in compliance with the institutional guidelines of Stanford University and Administrative Panel on Laboratory Animal Care (APLAC). We obtained young wild-type C57BL/6 mice from Jackson Laboratory. Double-transgenic GFP/luc mice were obtained as described previously (Jackson Laboratory, Stock #008450) (24). NOD-scid gamma (NSG) were obtained from Jackson Laboratory (Stock #0055570). EP4$^{flox/flox}$ (EP4$^{f/f}$) mice were a kind gift from K. Andreasson (Stanford University) (Jackson Laboratories, Stock #028102) (47). Double-transgenic Pax7$^{CreERT2}$;EP4$^{f/f}$ were generated by crossing Pax7$^{CreERT2}$ mice obtained from Jackson Laboratory (Stock #017763) (48) and EP4$^{f/f}$ mice. Double-transgenic Pax7$^{CreERT2}$;Rosa26-LSL-Luc were generated by crossing Pax7$^{CreERT2}$ mice and Rosa26-LSL-Luc obtained from Jackson Laboratory (Stock #005125) (49). We validated these genotypes by appropriate PCR-based strategies. All mice from transgenic and wild-type strains were of young age (2-4 months). All experiments were conducted using age and gender-matched controls, and littermates randomly assigned to experimental groups.

We used an injury model entailing intramuscular injection of 10 µl of notexin (10 µg ml$^{-1}$; Latoxan, catalog #L8104) or cardiotoxin (10 µM; Latoxan, catalog #L8102) into the Tibialis anterior (TA) muscle. For cryoinjury, an incision was made in the skin overlying the TA muscle and a copper probe, chilled in liquid nitrogen, was applied to the TA muscle for three 10 s intervals, allowing the muscle to thaw between each application of the cryoprobe. When indicated, 48 hr after injury either 16,16-Dimethyl Prostaglandin E2 (dmPGE2) (13 nmol, Tocris, catalog #4027), Indomethacin (35 µg, Sigma, catalog #17378) or vehicle control (PBS) was injected into the TA muscle. The contralateral TA was used as an internal control, except for the force measurement experiments where each mouse had both legs injured with the same condition and independent mice were used for each condition.

For Pax7$^{CreERT2}$;Rosa26-LSL-Luc mice experiments, we treated mice with five consecutive daily intraperitoneal injections of tamoxifen to activate luciferase expression under the control of the Pax7 promoter. A week after the last tamoxifen injection, mice were subjected to intramuscular injection of 10 µl of cardiotoxin (10 µM; Latoxan), which we designated as day 0 of the assay. Three days later either 13 nmol dmPGE2 or vehicle control (PBS) was injected into the TA muscle. The contralateral TA was used as an internal control. Bioluminescence was assayed at days 3, 7, 10 and 14 post-injury.

For Pax7$^{CreERT2}$; EP4$^{flox/flox}$ mice experiments, we treated mice with five consecutive daily intraperitoneal injections of tamoxifen to excise the EP4 allele in Pax7 expressing cells. A week after the last tamoxifen injection, mice were subjected to intramuscular injection of 10 µl of notexin (10 µg ml$^{-1}$; Latoxan), which we designated as day 0 of the assay. As control mice, Pax7$^{+/+}$; EP4$^{flox/+}$ littermates of the same sex were used.

We isolated and enriched muscle stem cells as previously described (24, 26, 27). Briefly, mouse hind-limb muscles were isolated and dissociated using the gentleMACS Octo Dissociator with a modified manufacturer protocol (Miltenyi Biotech). Dissociated muscle was digested with 0.2% collagenase (Roche) for 60 min, followed by collagenase/dispase (0.04 U ml$^{-1}$; Roche) digestion for 30 minutes. Mononucleated cells were liberated by syringe dissociation with an 18 G needle. For mouse muscle stem cells, single cell suspension were incubated with biotinylated antibodies against CD11b (1:800), CD45 (1:500), Sca1 (1:200) and CD31 (1:200), followed by incubation with streptavidin magnetic beads (Miltenyi Biotech), streptavidin-APC-Cy7, integrin-$\alpha_7$-PE (1:500) and CD34-eFluor660 (1:67). The cell mixture was depleted for hematopoietic lineage expressing and non-muscle cells on a magnetic based selection column (Miltenyi) for biotin-positive cells. The remaining cell mixture was then subjected to FACS analysis to sort for CD45$^-$CD11b$^-$CD31$^-$Sca1$^-$CD34$^+$integrin-$\alpha_7^+$ MuSCs with >95% purity (DIVA-Van, Becton-Dickinson). We generated and analyzed flow cytometry scatter plots using FlowJo v10.0. For wild-type MuSC sorts, we pooled together MuSCs (~5,000 each) from at least three independent age- and sex-matched donor mice.

We analyzed NURR1 levels by flow cytometry using myogenic progenitors after a 24 hr treatment of vehicle (DMSO) or PGE2 (10 ng/ml), or from MuSCs transfected with shSCR or shNurr1 (see Knockdown assays section). We collected cells by incubation with 0.5% trypsin in PBS for 2 min at 37° C. We fixed the cells using 1.6% paraformaldehyde in PBS and then permeabilized them in ice-cold methanol. We then blocked them in staining buffer (0.5% BSA in PBS) for 30 min at room temperature and stained them with a Mouse monoclonal anti-Nurr1 (Abcam, catalog #ab41917, 1:75) primary antibody or anti-mouse IgG control (Jackson ImmunoResearch Laboratories). Then, we stained cells with Pacific Blue-conjugated goat anti-mouse secondary antibody (Thermo Fisher Scientific, catalog #P-10994, 1:500). We analyzed the cells on a FACS LSR II cytometer using FACSDiva software (BD Biosciences) in the Stanford Shared FACS Facility, purchased using an NIH S10 Shared Instrument Grant (S10RR027431-01).

We transplanted 250 MuSCs (FIG. 13A) or 1,000 MuSCs (FIG. 14E) from cell culture directly into the TA muscles of recipient mice as previously described (24, 26, 27). For wild-type MuSC studies, we transplanted cells from GFP/luc mice (2-4 mo of age) into hindlimb-irradiated NSG mice. For EP4$^{flox/flox}$ MuSCs studies, we transplanted cells from EP4$^{flox/flox}$ mice (2-4 mo) that were transduced with a luc-IRES-GFP lentivirus (GFP/luc virus) and a subgroup received either a mCherry/Cre lentivirus or a mock infection on day 2 of culture for a period of 24 hr before transplantation, as previously described (26) (see below "Muscle stem cell culture, treatment and lentiviral infection" section for details). Prior to transplantation of muscle stem cells, we anesthetized NSG recipient mice with ketamine (2.4 mg per mouse) by intraperitoneal injection. We then irradiated hindlimbs with a single 18 Gy dose, with the rest of the body shielded in a lead jig. We performed transplantations within 2 days of irradiation. We resuspended MuSCs at desired cell concentrations in 0.1% gelatin/PBS and then transplanted them (250 or 100 mouse MuSCs per TA) by intramuscular injection into the TA muscles in a 15 µl volume. For fresh MuSCs transplantation, we coinjected sorted cells with 13 nmol of 16,16-Dimethyl Prostaglandin E2 (dmPGE2) (Tocris, catalog #4027) or vehicle control (PBS). One month after transplant, we injected 10 µl of notexin (10 µg ml-1; Latoxan, France) to injure recipient muscles and to re-activate MuSCs in vivo. We compared cells from different conditions by transplantation into the TA muscles of contralateral legs in the same mice. Three or eight weeks after transplantation as indicated in the figure legends, mice were euthanized and the TAs were collected for analysis.

We performed bioluminescence imaging (BLI) using a Xenogen-100 system, as previously described (24, 26, 27, 30). Briefly, we anesthetized mice using isofluorane inhalation and administered 120 µL D-luciferin (0.1 mmol kg$^{-1}$, reconstituted in PBS; Caliper LifeSciences) by intraperitoneal injection. We acquired BLI using a 60 s exposure at F-stop=1.0 at 5 minutes after luciferin injection. Digital images were recorded and analyzed using Living Image software (Caliper LifeSciences). We analyzed images with a consistent region-of-interest (ROI) placed over each hindlimb to calculate a bioluminescence signal. We calculated a bioluminescence signal in radiance (p s$^{-1}$ cm$^{-2}$ sr$^{-1}$) value of $10^4$ to define an engraftment threshold. This radiance threshold of $10^4$ is approximately equivalent to the total flux threshold of $10^5$ p/s defined by the region of interest of similar size as reported previously. This BLI threshold corresponds to the histological detection of one or more GFP+ myofibers (24, 26, 27). We performed BLI imaging every week after transplantation.

We fabricated polyethylene glycol (PEG) hydrogels from PEG precursors, synthesized as described previously (27). Briefly, we produced hydrogels by using the published formulation to achieve 12-kPa (Young's modulus) stiffness hydrogels in 1 mm thickness, which is the optimal condition for culturing MuSCs and maintaining stem cell fate in culture (27). We fabricated hydrogel microwell arrays of 12-kPa for clonal proliferation experiments, as described previously (27). We cut and adhered all hydrogels to cover the surface area of 12-well or 24-well culture plates.

Following isolation, we resuspended MuSCs in myogenic cell culture medium containing DMEM/F10 (50:50), 20% FBS, 2.5 ng ml$^{-1}$ fibroblast growth factor-2 (FGF-2 also known as bFGF) and 1% penicillin-streptomycin. We seeded MuSC suspensions at a density of 500 cells per cm$^2$ surface area. We maintained cell cultures at 37° C. in 5% $CO_2$ and changed medium every other day. For PGE2, EP4 receptor antagonist treatment studies, we added 1-200 ng/ml Prostaglandin E2 (Cayman Chemical) (unless specified in the figure legends, 10 ng/ml was the standard concentration used), and/or 1 μM EP4 antagonist (ONO-AE3-208, Cayman Chemical), to the MuSCs cultured on collagen coated dishes for the first 24 h. The cells were then trypsinized and cells reseeded onto hydrogels for an additional 6 days of culture. All treatments were compared to their solvent (DMSO) vehicle control. For stripped serum assays, we resuspended isolated MuSCs in stripped serum medium containing DMEM/F10 (50:50), 20% charcoal stripped FBS (Gibco, cat #12676011), 2.5 ng ml$^{-1}$ bFGF and 1% penicillin-streptomycin. For these experiments MuSCs were cultured on hydrogels and vehicle (DMSO) or 10 ng/ml PGE2 (Cayman Chemical) was added to the cultures with every media change (every two days). Proliferation (see below) was assayed 7 days later. We performed all MuSC culture assays and transplantations after 1 week of culture unless noted otherwise.

For EP4$^{f/f}$ MuSCs studies, we isolated MuSCs as described above (Muscle stem cell isolation), and infected all cells with lentivirus encoding EF1α-luc-IRES-GFP (GFP/luc virus) for 24 h in culture as described previously (26) and a subset of them was coinfected with a lentivirus encoding pLM-CMV-R-Cre (mCherry/Cre virus) for 24 h in culture. pLM-CMV-R-Cre was a gift from Michel Sadelain (Addgene plasmid #27546) (50). We transplanted EP4$^{f/f}$ MuSCs (1,000 cells) into young (2-4 mo) 18-gy irradiated TAs of NSG recipient mice. For in vitro proliferation assays, EP4$^{f/f}$ MuSCs were plated on hydrogels post-infection and treated for 24 hr with vehicle (DMSO) or 10 ng/ml PGE2, and proliferation was assayed 3 days later. Cells were assayed for GFP and/or mCherry expression 48 h post-infection using an inverted fluorescence microscope (Carl Zeiss Microimaging). Additionally, we also performed experiments with MuSCs isolated from Pax7$^{CreERT2}$; EP4$^{flox/flox}$ or control Pax7$^{+/+}$; EP4$^{flox/+}$ littermates. MuSCs were plated on collagen-coated plates and treated with 1 μM 4-hydroxy tamoxifen or vehicle (95% Ethanol) during 48 h and then either passed onto hydrogels to assess proliferation 7 days later or treated with PGE2 or vehicle and collected for analysis. MuSCs are freshly isolated from the mice by FACS and put in culture for a maximum time period of one week, therefore *Mycoplasma* contamination is not assessed.

We assayed clonal muscle stem cell proliferation by time-lapse microscopy as previously described (26, 27). Briefly, we sorted MuSCs from C57Bl/6 mice (2-4 months), plated them on collagen-coated plates and treated them PGE2 (Cayman Chemical) or vehicle (DMSO) for 24 hr. Cells were then trypsinized and reseeded at a density of 500 cells per cm$^2$ surface area in hydrogel microwells with 600 μm diameter. For time-lapse microscopy we monitored cell proliferation for those wells with single cells for 38 h days after seeding and recorded images every 3 min at 10× magnification using a PALM/AxioObserver Z1 system (Carl Zeiss MicroImaging) with a custom environmental control chamber and motorized stage. We analyzed time-lapse image sequences using the Baxter Algorithms for Cell Tracking and Lineage Reconstruction to identify and track single cells and generate lineage trees (26-28, 51, 52).

Viable and dead cells were distinguished in time-lapse sequences based on phase-contrast boundary and motility maintenance or loss, respectively. The proportion of live cells in each generation (G1-G6) at all timepoints is shown as cell number normalized to a starting population of 100 single MuSCs. The data analysis was blinded. The researchers performing the imaging acquisition and scoring were unaware of the treatment condition given to sample groups analyzed.

To assay proliferation, we used three different assays (hemocytometer, VisionBlue, and EdU). For each, we seeded MuSCs on flat hydrogels (hemocytometer and VisionBlue) or collagen-coated plates (EdU assay) at a density of 500 cells per cm$^2$ surface area. For hemocytometer cell number count, we collected cells at indicated timepoints by incubation with 0.5% trypsin in PBS for 5 min at 37° C. and quantified them using a hemocytometer at least 3 times. Additionally, we used the VisionBlue Quick Cell Viability Fluorometric Assay Kit (BioVision, catalog #K303) as a readout for cell growth in culture. Briefly, we incubated MuSCs with 10% VisionBlue in culture medium for 3 h, and measured fluorescence intensity on a fluorescence plate reader (Infinite M1000 PRO, Tecan) at Ex=530-570 nm, Em=590-620 nm. We assayed proliferation using the Click-iT EdU Alexa Fluor 555 Imaging kit (Life Technologies). Briefly, we incubated live cells with EdU (20 μM) for 1 hr prior to fixation, and stained nuclei according to the manufacturer's guidelines together with anti-MYOGENIN (Santa Cruz, catalog #sc576, 1:250) to assay differentiation. We counterstained nuclei with DAPI (Invitrogen). We acquired images with an AxioPlan2 epifluorescent microscope (Carl Zeiss Microimaging) with Plan NeoFluar 10×/0.30 NA or 20×/0.75 NA objectives (Carl Zeiss) and an ORCA-ER digital camera (Hamamatsu Photonics) controlled by SlideBook (3i) software. We quantified EdU positive cells using the MetaMorph Image Analysis software (Molecular Devices). Data analyses were blinded, where researchers performing cell scoring were unaware of the treatment condition given to sample groups analyzed.

For Nurr1 silencing in MuSCs, lentiviruses containing pLKO.1-scramble shRNA (shSCR) and pLKO.1-Nurr1 shRNA (Mission shRNA, TRCN0000026029, Sigma) were produced in 293T cells using the packaging plasmids pLP1, pLP2 and pLP/VSVG (Invitrogen), by cotransfecting all plasmids using FuGENE-6 (Promega) according to the manufacturer's protocol. Cells were plated the day prior to infection, and supernatants were collected every 12 hours for two days from 293T cells. Freshly sorted MuSCs were seeded on collagen-coated plates for 24 hrs and were then infected with the lentiviruses. 48 hrs after, cells were passed onto hydrogels and treated with PGE2 or vehicle (DMSO) for 24 hrs. Proliferation was assayed 7 days later.

We isolated RNA from MuSCs using the RNeasy Micro Kit (Qiagen). For muscle samples, we snap froze the tissue in liquid nitrogen, homogenized the tissues using a mortar and pestle, followed by syringe and needle trituration, and then isolated RNA using Trizol (Invitrogen). We reverse-transcribed cDNA from total mRNA from each sample using the SensiFAST™ cDNA Synthesis Kit (Bioline). We subjected cDNA to RT-PCR using SYBR Green PCR Master Mix (Applied Biosystems) or TaqMan Assays (Applied Biosystems) in an ABI 7900HT Real-Time PCR System (Applied Biosystems). We amplified samples at 95° C. for 10 min and then 40 cycles at 95° C. for 15 s and 60° C. for 1 min. To quantify relative transcript levels, we used $2^{\Delta\Delta Ct}$ to compare treated and untreated samples and expressed the results relative to Gapdh. For SYBR Green qRT-PCR, we used the following primer sequences: Gapdh, forward 5'-TTCACCACCATGGAGAAGGC-3' (SEQ ID NO: 1), reverse 5'-CCCTTTTGGCTCCACCCT-3' (SEQ ID NO: 2); Ptges, forward 5'-GCTGTCATCACAGGCCAGA-3' (SEQ ID NO: 5), reverse 5'-CTCCACATCTGGGTCACTCC-3' (SEQ ID NO: 6); Ptges2, forward 5'-CTCCTACAGGAAAGTGCCCA-3' (SEQ ID NO: 7), reverse 5'-ACCAGGTAGGTCTTGAGGGC-3' (SEQ ID NO: 8); Ptger1, forward 5' GTGGTGTCGTGCATCTGCT-3' (SEQ ID NO: 9), reverse, 5' CCGCTGCAGGGAGTTAGAGT-3' (SEQ ID NO: 10), and Ptger2, forward 5'-ACCTTCGCCATATGCTCCTT-3' (SEQ ID NO: 11), reverse 5'-GGACCGGTGGCCTAAGTATG-3' (SEQ ID NO: 12). TaqMan Assays (Applied Biosystems) were used to quantify Pax7, Myogenin, Nurr1, Ptger3 and Ptger4 in samples according to the manufacturer instructions with the TaqMan Universal PCR Master Mix reagent kit (Applied Biosystems). Transcript levels were expressed relative to Gapdh levels. For SYBR Green qPCR, Gapdh qPCR was used to normalize input cDNA samples. For Taqman qPCR, multiplex qPCR enabled target signals (FAM) to be normalized individually by their internal Gapdh signals (VIC).

Muscle was harvested, rinsed in ice-cold PBS containing indomethacin (5.6 μg/ml), and snap frozen in liquid nitrogen. Frozen samples were pulverized in liquid nitrogen. The powder was transferred to an Eppendorf tube with 500 μl of lysate buffer (50 mM Tris-HCl pH 7.5, 150 mM NaCl, 4 mM CaCl, 1.5% Triton X-100, protease inhibitors and micrococcal nuclease), and then homogenized using a tissue homogenizer. The PGE2 level of the supernatant was measured using a PGE2 ELISA Kit (R&D Systems, catalog #KGE004B) and expressed relative to total protein measured by BCA assay (BioRad) and expressed as ng of PGE2. Each sample was assayed in duplicate and in each of two independent experiments.

For conditioned medium assays, muscle fibers from the extensor digitorum longus (EDL) were isolated as previously described (53). Fibers were cultured in stripped serum medium in the presence or absence of indomethacin (1 μM, Sigma) for 24 hours. Conditioned medium was collected and measured using the PGE2 ELISA Kit (R&D Systems, catalog #KGE004B) and expressed relative to the collected volume (ml). Each sample was assayed in triplicate and in two independent experiments.

MuSCs were treated with DMSO (vehicle) or PGE2 (10 ng/ml) for 1 h and cyclic AMP levels measured according to the cAMP-Glo Assay protocol optimized by the manufacturer (Promega). Each sample was assayed in triplicate and in two independent experiments.

Mice were injured as described in the Muscle injury section. Force measurements were on the TA muscles at day 14 post-injury based on protocols published previously (26, 54). Briefly, mice were anesthetized with 2-5% vaporized Isoflurane mixed with $O_2$. Mice were positioned under a heat lamp in order to maintain the body and muscle temperature at 30° C. The distal tendon of the TA muscle was dissected and tied to a 300C-LR force transducer (Aurora Scientific) by surgical suture. Knees of the animals were secured to a fixed steel post and their feet were taped to the platform to prevent movement from the contraction of other muscle groups. Electrical stimulations were applied across two needle electrodes, placed through the skin just above the knee and beneath the TA muscle to stimulate the tibial nerve. In all measurements, we used 0.1-ms pulses at a predetermined supramaximal stimulation voltage. TA muscles were stimulated with a single 0.1-ms pulse for twitch force measurements, and a train of 150 Hz for 0.3 s pulses for tetanic force measurements. We performed five twitch and then five tetanic measurements on each muscle, with 2-3 min recovery between each measurement. Data were collected with a PCI-6251 acquisition card (National Instruments) and analyzed in Matlab. We calculated specific force values by normalizing the force measurements by the muscle physiological cross-sectional areas (PCSAs), which were similar between groups. PCSA (measured in $mm^2$) was calculated according to the following equation (55):

$$PCSA\ (mm^2) = [mass\ (g) \times Cos\ \theta] \div [\rho\ (g/mm^3) \times fiber\ length\ (mm)],$$

where θ is pennation angle of the fiber and ρ is muscle density (0.001056 $g/mm^3$).

For RNA sequencing, α7-integrin⁺CD34⁺ muscle stem cells were isolated as described above, seeded on collagen-coated plates, treated a day later with PGE2 or vehicle (DMSO) and processed after 24 hours of treatment. RNA was isolated using Qiagen RNAEasy Micro kit from 5,000-10,000 cells, and cDNA generated and amplified using NuGEN Ovation RNA-Seq System v2 kit. Libraries were constructed from cDNA with the TruSEQ RNA Library Preparation Kit v2 (Illumina), and sequenced to 30-40×106 1×75 bp reads per sample on a HiSEQ 2500 from the Stanford Functional Genomics Facility, purchased using an NIH S10 Shared Instrument Grant (S10OD018220).

For the RNA-Seq analysis, RNA sequences were aligned against the *Mus musculus* genome using STAR (56). RSEM (57) was used for calling transcripts and calculating transcripts per million (TPM) values, as well as total counts. A counts matrix containing the number of counts for each gene and each sample was obtained. This matrix was analyzed by DESeq to calculate statistical analysis of significance (58) of genes between samples.

We collected and prepared recipient TA muscle tissues for histology as previously described (26, 27). For mouse injury assays we incubated transverse sections with Rabbit polyclonal anti-PGE2 (abcam, Catalog #ab2318, 1:100) Rat polyclonal anti-Laminin (Clone A5) (EMD Millipore, Catalog #05-206, 1:200), Mouse monoclonal anti-Pax7 (Santa Cruz, Catalog #sc-81648, 1:50), AlexaFluor 647-conjugated wheat germ agglutinin (WGA) antibody (W32466, Thermo Fisher Scientific), Rabbit polyclonal anti-GFP (A11122, Thermo Fisher Scientific, 1:500) and Mouse monoclonal anti-Embryonic Myosin Heavy Chain (DSHB, Catalog #F1.652, 1:10) primary antibodies and then with AlexaFluor secondary Antibodies (Jackson ImmunoResearch Laboratories, 1:500). We counterstained nuclei with DAPI (Invitrogen).

We acquired images with an AxioPlan2 epifluorescent microscope (Carl Zeiss Microimaging) with Plan NeoFluar 10×/0.30 NA or 20×/0.75 NA objectives (Carl Zeiss) and an ORCA-ER digital camera (Hamamatsu Photonics) controlled by the SlideBook (3i) software or with a KEYENCE BZ-X700 all-in-one fluorescence microscope (Keyence, Osaka, Japan) with a 20×/0.75 NA objectives. The images were cropped using Adobe Photoshop with consistent contrast adjustments across all images from the same experiment. The image composites were generated using Adobe Illustrator. We analyzed the number of PAX7 positive cells using the MetaMorph Image Analysis software (Molecular Devices), and the fiber area using the Baxter Algorithms for Myofiber Analysis that identified the fibers and segmented the fibers in the image to analyze the area of each fiber. For PAX7 quantification we examined serial sections spanning a depth of at least 2 mm of the TA. For fiber area the entire cross-section of the TA with the largest injured area was captured and stitched using the Keyence Analysis Software. Data capture and analyses were blinded. The researchers performing the imaging acquisition and scoring were unaware of treatment condition given to sample groups analyzed.

We performed cell culture experiments in at least three independent experiments where three biological replicates were pooled in each. In general, we performed MuSC transplant experiments in at least two independent experiments, with at least 3-5 total transplants per condition. We used a paired t-test for experiments where control samples were from the same experiment in vitro or from contralateral limb muscles in vivo. A non-parametric Mann-Whitney test was used to determine the significance difference between vehicle-treated vs PGE2-treated groups using $\alpha=0.05$. ANOVA or multiple t-test was performed for multiple comparisons with significance level determined using Bonferroni correction or Fisher's test as indicated in the figure legends. Unless otherwise described, data are shown as the mean±s.e.m. Differences with p value <0.05 were considered significant (*$p<0.05$, $p<0.01$, *$p<0.001$, ****$p<0.0001$).

RNASeq data have been submitted in MIME-compliant format to GEO, accession number GSE97375.

References: Chakkalakal J V, Jones K M, Basson M A, & Brack A S (2012) The aged niche disrupts muscle stem cell quiescence. *Nature* 490(7420):355-360; Kuang S, Gillespie M A, & Rudnicki M A (2008) Niche regulation of muscle satellite cell self-renewal and differentiation. *Cell Stem Cell* 2(1):22-31; Shi X & Garry D J (2006) Muscle stem cells in development, regeneration, and disease. *Genes Dev* 20(13): 1692-1708; Tierney M T, et al. (2014) STAT3 signaling controls satellite cell expansion and skeletal muscle repair. *Nat Med* 20(10):1182-1186; Chazaud B (2016) Inflammation during skeletal muscle regeneration and tissue remodeling: application to exercise-induced muscle damage management. *Immunol Cell Biol* 94(2):140-145; Korotkova M & Lundberg I E (2014) The skeletal muscle arachidonic acid cascade in health and inflammatory disease. *Nat Rev Rheumatol* 10(5):295-303; Tidball J G (2017) Regulation of muscle growth and regeneration by the immune system. *Nat Rev Immunol* 17(3):165-178; Joe A W, et al. (2010) Muscle injury activates resident fibro/adipogenic progenitors that facilitate myogenesis. *Nat Cell Biol* 12(2):153-163; Uezumi A, Fukada S, Yamamoto N, Takeda S, & Tsuchida K (2010) Mesenchymal progenitors distinct from satellite cells contribute to ectopic fat cell formation in skeletal muscle. *Nat Cell Biol* 12(2):143-152; Tidball J G (2011) Mechanisms of muscle injury, repair, and regeneration. *Compr Physiol* 1(4):2029-2062; Ricciotti E & FitzGerald G A (2011) Prostaglandins and Inflammation. *Arteriosclerosis, Thrombosis, and Vascular Biology* 31(5):986-1000; Funk C D (2001) Prostaglandins and leukotrienes: advances in eicosanoid biology. *Science* 294(5548):1871-1875; Simmons D L, Botting R M, & Hla T (2004) Cyclooxygenase isozymes: the biology of prostaglandin synthesis and inhibition. *Pharmacol Rev* 56(3):387-437; Beaulieu D, et al. (2012) Abnormal prostaglandin E2 production blocks myogenic differentiation in myotonic dystrophy. *Neurobiol Dis* 45(1):122-129; Bondesen B A, Mills S T, Kegley K M, & Pavlath G K (2004) The COX-2 pathway is essential during early stages of skeletal muscle regeneration. *Am J Physiol Cell Physiol* 287(2):C475-483; Mo C, Romero-Suarez S, Bonewald L, Johnson M, & Brotto M (2012) Prostaglandin E2: from clinical applications to its potential role in bone-muscle crosstalk and myogenic differentiation. *Recent Pat Biotechnol* 6(3):223-229; Mo C, et al. (2015) Prostaglandin E2 promotes proliferation of skeletal muscle myoblasts via EP4 receptor activation. *Cell Cycle* 14(10):1507-1516; Otis J S, Burkholder T J, & Pavlath G K (2005) Stretch-induced myoblast proliferation is dependent on the COX2 pathway. *Exp Cell Res* 310(2):417-425; Shen W, Prisk V, Li Y, Foster W, & Huard J (2006) Inhibited skeletal muscle healing in cyclooxygenase-2 gene-deficient mice: the role of PGE2 and PGF2alpha. *J Appl Physiol* (1985) 101(4):1215-1221; Mackey A L, et al. (2007) The influence of anti-inflammatory medication on exercise-induced myogenic precursor cell responses in humans. *J Appl Physiol* (1985) 103(2):425-431; Schoenfeld B J (2012) The use of nonsteroidal anti-inflammatory drugs for exercise-induced muscle damage: implications for skeletal muscle development. *Sports Med* 42(12):1017-1028; Lundberg I, Kratz A K, Alexanderson H, & Patarroyo M (2000) Decreased expression of interleukin-1alpha, interleukin-1beta, and cell adhesion molecules in muscle tissue following corticosteroid treatment in patients with polymyositis and dermatomyositis. *Arthritis Rheum* 43(2):336-348; Arnold L, et al. (2007) Inflammatory monocytes recruited after skeletal muscle injury switch into antiinflammatory macrophages to support myogenesis. *J Exp Med* 204(5):1057-1069; Sacco A, Doyonnas R, Kraft P, Vitorovic S, & Blau H M (2008) Self-renewal and expansion of single transplanted muscle stem cells. *Nature* 456(7221): 502-506; Smethurst M & Williams D C (1977) Levels of prostaglandin E and prostaglandin F in samples of commercial serum used for tissue culture. *Prostaglandins* 13(4):719-722; Cosgrove B D, et al. (2014) Rejuvenation of the muscle stem cell population restores strength to injured aged muscles. *Nat Med* 20(3):255-264; Gilbert P M, et al. (2010) Substrate elasticity regulates skeletal muscle stem cell self-renewal in culture. *Science* 329(5995):1078-1081; Magnusson K E, Jalden J, Gilbert P M, & Blau H M (2015) Global linking of cell tracks using the Viterbi algorithm. *IEEE Trans Med Imaging* 34(4):911-929; Rodgers J T, et al. (2014) mTORC1 controls the adaptive transition of quiescent stem cells from G0 to G(Alert). *Nature* 510(7505):393-396; Ho A T & Blau H M (2016) Noninvasive Tracking of Quiescent and Activated Muscle Stem Cell (MuSC) Engraftment Dynamics In Vivo. *Methods Mol Biol* 1460:181-189; Bygdeman M (2003) Pharmacokinetics of prostaglandins. *Best Pract Res Clin Obstet Gynaecol* 17(5):707-716; Holla V R, Mann J R, Shi Q, & DuBois R N (2006) Prostaglandin E2 regulates the nuclear receptor NR4A2 in colorectal cancer. *J Biol Chem* 281(5):2676-2682; Volakakis N, et al. (2010) NR4A orphan nuclear receptors as mediators of CREB-dependent neuroprotection. *Proc Natl Acad Sci USA* 107(27):12317-12322; Baracos V, Rodemann H P, Dinarello C A, & Goldberg A L (1983) Stimulation of muscle protein degradation and prostaglandin E2 release by leukocytic pyrogen (interleukin-1). A mechanism for the increased degradation of muscle proteins during fever. *N Engl J Med* 308(10):553-558; Rodemann H P & Goldberg A L (1982) Arachidonic acid, prostaglandin E2 and F2 alpha influence rates of protein turnover in skeletal and cardiac muscle. *J Biol Chem* 257(4):1632-1638; Mauro A (1961) Satellite cell of skeletal muscle fibers. *J Biophys Biochem Cytol* 9:493-495; Montarras D, et al. (2005) Direct isolation of satellite cells for skeletal muscle regeneration. *Science* 309(5743):2064-2067; Pawlikowski B, Pulliam C, Betta N D, Kardon G, & Olwin B B (2015) Pervasive satellite cell contribution to uninjured adult muscle fibers. *Skelet Muscle* 5:42; Crameri R M, et al. (2004) Changes in satellite cells in human skeletal muscle after a single bout of high intensity exercise. *J Physiol* 558 (Pt 1):333-340; Darr K C & Schultz E (1987) Exercise-induced satellite cell activation in growing and mature skeletal muscle. *J Appl Physiol* (1985) 63(5):1816-1821; Dreyer H C, Blanco C E, Sattler F R, Schroeder E T, & Wiswell R A (2006) Satellite cell numbers in young and older men 24 hours after eccentric exercise. *Muscle Nerve* 33(2):242-253; Paulsen G, Mikkelsen U R, Raastad T, & Peake J M (2012) Leucocytes, cytokines and satellite cells: what role do they play in muscle damage and regeneration following eccentric exercise? *Exerc Immunol Rev* 18:42-97; Zu G, et al. (2017) Nurr1 promotes intestinal regeneration after ischemia/reperfusion injury by inhibiting the expression of p21 (Waf1/Cip1). *J Mol Med (Berl)* 95(1):83-95; North T E, et al. (2007) Prostaglandin E2 regulates vertebrate haematopoietic stem cell homeostasis. *Nature* 447 (7147):1007-1011; Zhang Y, et al. (2015) Inhibition of the prostaglandin-degrading enzyme 15-PGDH potentiates tissue regeneration. *Science* 348(6240):aaa2340; Thomas J, Fairclough A, Kavanagh J, & Kelly A J (2014) Vaginal prostaglandin (PGE2 and PGF2α) for induction of labour at term. *Cochrane Database Syst Rev* 6:CD003101; Schneider A, et al. (2004) Generation of a conditional allele of the mouse prostaglandin EP4 receptor. *Genesis* 40(1):7-14; Murphy M M, Lawson J A, Mathew S J, Hutcheson D A, & Kardon G (2011) Satellite cells, connective tissue fibroblasts and their interactions are crucial for muscle regeneration. *Development* 138(17):3625-3637; Safran M, et al. (2003) Mouse reporter strain for noninvasive bioluminescent imaging of cells that have undergone Cre-mediated recombination. *Mol Imaging* 2(4):297-302; Papapetrou E P, et al. (2011) Genomic safe harbors permit high beta-globin transgene expression in thalassemia induced pluripotent stem cells. *Nat Biotechnol* 29(1):73-78; Chenouard N, et al. (2014) Objective comparison of particle tracking methods. *Nat Methods* 11(3):281-289; Maska M, et al. (2014) A benchmark for comparison of cell tracking algorithms. *Bioinformatics* 30(11):1609-1617; Moyle L A & Zammit P S (2014) Isolation, culture and immunostaining of skeletal muscle fibres to study myogenic progression in satellite cells. *Methods Mol Biol* 1210:63-78; Hakim C H, Wasala N B, & Duan D (2013) Evaluation of muscle function of the extensor digitorum longus muscle ex vivo and tibialis anterior muscle in situ in mice. *J Vis Exp* (72); Burkholder T J, Fingado B, Baron S, & Lieber R L (1994) Relationship between muscle fiber types and sizes and muscle architectural properties in the mouse hindlimb. *J Morphol* 221(2):177-190; Dobin A, et al. (2013) STAR: ultrafast universal RNA-seq aligner. *Bioinformatics* 29(1):15-21; Li B & Dewey C N (2011) RSEM: accurate transcript quantification from RNA-Seq data with or without a reference genome. *BMC Bioinformatics* 12:323; Anders S & Huber W (2010) Differential expression analysis for sequence count data. *Genome Biol* 11(10):R106.

Muscle injury: We used an injury model entailing intramuscular injection of 10 µl of notexin (10 µg ml$^{-1}$; Latoxan, catalog #L8104) or cardiotoxin (10 µM; Latoxan, catalog #L8102) into the Tibialis anterior (TA) muscle. For cryoinjury, an incision was made in the skin overlying the TA muscle and a copper probe, chilled in liquid nitrogen, was applied to the TA muscle for three 10 s intervals, allowing the muscle to thaw between each application of the cryoprobe. When indicated, 48 hr after injury either 16,16-Dimethyl Prostaglandin E2 (dmPGE2) (13 nmol, Tocris, catalog #4027), Indomethacin (35 µg, Sigma, catalog #17378) or vehicle control (PBS) was injected into the TA muscle. The contralateral TA was used as an internal control, except for the force measurement experiments where each mouse had both legs injured with the same condition and independent mice were used for each condition.

For Pax7$^{CreERT2}$;Rosa26-LSL-Luc mice experiments, we treated mice with five consecutive daily intraperitoneal injections of tamoxifen to activate luciferase expression under the control of the Pax7 promoter. A week after the last tamoxifen injection, mice were subjected to intramuscular injection of 10 µl of cardiotoxin (10 µM; Latoxan), which we designated as day 0 of the assay. Three days later either 13 nmol dmPGE2 or vehicle control (PBS) was injected into the TA muscle. The contralateral TA was used as an internal control. Bioluminescence was assayed at days 3, 7, 10 and 14 post-injury.

For Pax7$^{CreERT2}$; EP4$^{flox/flox}$ mice experiments, we treated mice with five consecutive daily intraperitoneal injections of tamoxifen to excise the EP4 allele in Pax7 expressing cells. A week after the last tamoxifen injection, mice were subjected to intramuscular injection of 10 µl of notexin (10 µg ml$^{-1}$; Latoxan), which we designated as day 0 of the assay. As control mice, Pax7$^{+/+}$; EP4$^{flox/+}$ littermates of the same sex were used.

Fluorescence activated cell sorting for mouse muscle stem cells: For muscle stem cell isolation, mouse hind-limb muscles were dissociated using the gentleMACS Octo Dissociator with a modified manufacturer protocol (Miltenyi Biotech). Dissociated muscle was digested with 0.2% collagenase (Roche) for 60 min, followed by collagenase/dispase (0.04 U ml$^{-1}$; Roche) digestion for 30 minutes. Mononucleated cells were liberated by syringe dissociation with an 18 G needle. For mouse muscle stem cells, single cell suspension were incubated with biotinylated antibodies against CD11b (1:800), CD45 (1:500), Sca1 (1:200) and CD31 (1:200), followed by incubation with streptavidin magnetic beads (Miltenyi Biotech), streptavidin-APC-Cy7, integrin-α$_7$-PE (1:500) and CD34-eFluor660 (1:67). The cell mixture was depleted for hematopoietic lineage expressing and non-muscle cells on a magnetic based selection column (Miltenyi) for biotin-positive cells. The remaining cell mixture was then subjected to FACS analysis to sort for CD45$^-$CD11b$^-$CD31$^-$Sca1$^-$CD34$^+$ integrin-α$_7^+$ MuSCs with >95% purity (DIVA-Van, Becton-Dickinson). We generated and analyzed flow cytometry scatter plots using FlowJo v10.0. For wild-type MuSC sorts, we pooled together MuSCs (~5,000 each) from at least three independent age- and sex-matched donor mice.

Muscle stem cell transplantation: For wild-type MuSC studies, we transplanted cells from GFP/luc mice (2-4 mo of age) into hindlimb-irradiated NSG mice. For EP4$^{flox/flox}$ MuSCs studies, we transplanted cells from EP4$^{flox/flox}$ mice (2-4 mo) that were transduced with a luc-IRES-GFP lentivirus (GFP/luc virus) and a subgroup received either a mCherry/Cre lentivirus or a mock infection on day 2 of culture for a period of 24 hr before transplantation, as previously described (26) (see "Muscle stem cell culture, treatment and lentiviral infection" section for details). Prior to transplantation of muscle stem cells, we anesthetized NSG recipient mice with ketamine (2.4 mg per mouse) by intraperitoneal injection. We then irradiated hindlimbs with a single 18 Gy dose, with the rest of the body shielded in a lead jig. We performed transplantations within 2 days of irradiation. We resuspended MuSCs at desired cell concentrations in 0.1% gelatin/PBS and then transplanted them (250 or 100 mouse MuSCs per TA) by intramuscular injection into the TA muscles in a 15 µl volume. For fresh MuSCs transplantation, we coinjected sorted cells with 13 nmol of 16,16-Dimethyl Prostaglandin E2 (dmPGE2) (Tocris, catalog #4027) or vehicle control (PBS). One month after transplant, we injected 10 µl of notexin (10 µg ml$^{-1}$; Latoxan, France) to injure recipient muscles and to re-activate MuSCs in vivo. We compared cells from different conditions by transplantation into the TA muscles of contralateral legs in the same mice. Three or eight weeks after transplantation as indicated in the figure legends, mice were euthanized and the TAs were collected for analysis.

Bioluminescent Imaging: For bioluminescence imaging (BLI), we anesthetized mice using isofluorane inhalation and administered 120 µL D-luciferin (0.1 mmol kg$^{-1}$, reconstituted in PBS; Caliper LifeSciences) by intraperitoneal injection. We acquired BLI using a 60 s exposure at F-stop=1.0 at 5 minutes after luciferin injection. Digital images were recorded and analyzed using Living Image software (Caliper LifeSciences). We analyzed images with a consistent region-of-interest (ROI) placed over each hindlimb to calculate a bioluminescence signal. We calculated a bioluminescence signal in radiance (p s$^{-1}$ cm$^{-2}$ sr$^{-1}$) value of $10^4$ to define an engraftment threshold. This radiance threshold of $10^4$ is approximately equivalent to the total flux threshold of $10^5$ p/s defined by the region of interest of similar size as reported previously. This BLI threshold corresponds to the histological detection of one or more GFP$^+$ myofibers (24, 26, 27). We performed BLI imaging every week after transplantation.

Hydrogel fabrication: We produced hydrogels by using the published formulation to achieve 12-kPa (Young's modulus) stiffness hydrogels in 1 mm thickness, which is the optimal condition for culturing MuSCs and maintaining stem cell fate in culture (27). We fabricated hydrogel microwell arrays of 12-kPa for clonal proliferation experiments, as described previously (27). We cut and adhered all hydrogels to cover the surface area of 12-well or 24-well culture plates.

Clonal muscle stem cell proliferation and fate analyses: To perform time lapse-analysis, we sorted MuSCs from C57Bl/6 mice (2-4 months), plated them on collagen-coated plates and treated them PGE2 (Cayman Chemical) or vehicle (DMSO) for 24 hr. Cells were then trypsinized and reseeded at a density of 500 cells per cm$^2$ surface area in hydrogel microwells with 600 µm diameter. For time-lapse microscopy we monitored cell proliferation for those wells with single cells for 38 h days after seeding and recorded images every 3 min at 10× magnification using a PALM/AxioObserver Z1 system (Carl Zeiss MicroImaging) with a custom environmental control chamber and motorized stage. We analyzed time-lapse image sequences using the Baxter Algorithms for Cell Tracking and Lineage Reconstruction to identify and track single cells and generate lineage trees (26-28, 51, 52).

Viable and dead cells were distinguished in time-lapse sequences based on phase-contrast boundary and motility maintenance or loss, respectively. The proportion of live cells in each generation (G1-G6) at all timepoints is shown as cell number normalized to a starting population of 100 single MuSCs. The data analysis was blinded. The researchers performing the imaging acquisition and scoring were unaware of the treatment condition given to sample groups analyzed.

Proliferation assays: To assay proliferation, we used three different assays (hemocytometer, VisionBlue, and EdU). For each, we seeded MuSCs on flat hydrogels (hemocytometer and VisionBlue) or collagen-coated plates (EdU assay) at a density of 500 cells per cm$^2$ surface area. For hemocytometer cell number count, we collected cells at indicated timepoints by incubation with 0.5% trypsin in PBS for 5 min at 37° C. and quantified them using a hemocytometer at least 3 times. Additionally, we used the VisionBlue Quick Cell Viability Fluorometric Assay Kit (BioVision, catalog #K303) as a readout for cell growth in culture. Briefly, we incubated MuSCs with 10% VisionBlue in culture medium for 3 h, and measured fluorescence intensity on a fluorescence plate reader (Infinite M1000 PRO, Tecan) at Ex=530-570 nm, Em=590-620 nm. We assayed proliferation using the Click-iT EdU Alexa Fluor 555 Imaging kit (Life Technologies). Briefly, we incubated live cells with EdU (20 µM) for 1 hr prior to fixation, and stained nuclei according to the manufacturer's guidelines together with anti-MYOGENIN (Santa Cruz, catalog #sc576, 1:250) to assay differentiation. We counterstained nuclei with DAPI (Invitrogen). We acquired images with an AxioPlan2 epifluorescent microscope (Carl Zeiss Microimaging) with Plan NeoFluar 10×/0.30 NA or 20×/0.75 NA objectives (Carl Zeiss) and an ORCA-ER digital camera (Hamamatsu Photonics) controlled by SlideBook (3i) software. We quantified EdU positive cells using the MetaMorph Image Analysis software (Molecular Devices). Data analyses were blinded, where researchers performing cell scoring were unaware of the treatment condition given to sample groups analyzed.

PGE2 ELISA: Muscle was harvested, rinsed in ice-cold PBS containing indomethacin (5.6 µg/ml), and snap frozen in liquid nitrogen. Frozen samples were pulverized in liquid nitrogen. The powder was transferred to an Eppendorf tube with 500 µl of lysate buffer (50 mM Tris-HCl pH 7.5, 150 mM NaCl, 4 mM CaCl, 1.5% Triton X-100, protease inhibitors and micrococcal nuclease), and then homogenized using a tissue homogenizer. The PGE2 level of the supernatant was measured using a PGE2 ELISA Kit (R&D Systems, catalog #KGE004B) and expressed relative to total protein measured by BCA assay (BioRad) and expressed as ng of PGE2. Each sample was assayed in duplicate and in each of two independent experiments.

For conditioned medium assays, muscle fibers from the extensor digitorum longus (EDL) were isolated as previously described (53). Fibers were cultured in stripped serum medium in the presence or absence of indomethacin (1 µM, Sigma) for 24 hours. Conditioned medium was collected and measured using the PGE2 ELISA Kit (R&D Systems, catalog #KGE004B) and expressed relative to the collected volume (ml). Each sample was assayed in triplicate and in two independent experiments.

In vivo muscle force measurement: To perform force measurements, mice were first anesthetized with 2-5% vaporized Isoflurane mixed with $O_2$. Mice were positioned under a heat lamp in order to maintain the body and muscle temperature at 30° C. The distal tendon of the TA muscle was dissected and tied to a 300C-LR force transducer (Aurora Scientific) by surgical suture. Knees of the animals were secured to a fixed steel post and their feet were taped to the platform to prevent movement from the contraction of other muscle groups. Electrical stimulations were applied across two needle electrodes, placed through the skin just above the knee and beneath the TA muscle to stimulate the tibial nerve. In all measurements, we used 0.1-ms pulses at a predetermined supramaximal stimulation voltage. TA muscles were stimulated with a single 0.1-ms pulse for twitch force measurements, and a train of 150 Hz for 0.3 s pulses for tetanic force measurements. We performed five twitch and then five tetanic measurements on each muscle, with 2-3 min recovery between each measurement. Data were collected with a PCI-6251 acquisition card (National Instruments) and analyzed in Matlab. We calculated specific force values by normalizing the force measurements by the muscle physiological cross-sectional areas (PCSAs), which were similar between groups. PCSA (measured in mm$^2$) was calculated according to the following equation (55):

PCSA (mm$^2$)=[mass (g)×Cos θ]÷[ρ (g/mm$^3$)×fiber length (mm)], where θ is pennation angle of the fiber and ρ is muscle density (0.001056 g/mm$^3$).

Example 4: Study to Establish an Optimal PGE2 Dosage for Use in Combination with Bupivacaine and Monitor MuSC Numbers and Muscle Regeneration in Mice This example describes the use of a double-transgenic mouse model and bioluminescent imaging to examine the effects of compositions of the present invention on muscle regeneration and to establish an optimal dose of PGE2 or a PGE2 derivative (16,16-dimethyl prostaglandin E2) for use in conjunction with bupivacaine.

Double-transgenic Pax7$^{CreERT2}$;Rosa26-LSL-Luc mice were generated by crossing Pax7$^{CreERT2}$ mice and Rosa26-LSL-Luc mice obtained from Jackson Laboratory (Stock #005125). These genotypes were validated by appropriate PCR-based strategies. All mice from transgenic and wild-type strains were of young age (2-4 months). All experiments were conducted using age and gender-matched controls. As depicted in the experimental scheme shown in FIG. 23A, mice were treated with five consecutive daily intraperitoneal injections of tamoxifen to activate luciferase expression under the control of the Pax7 promoter. A week after the last tamoxifen injection, the tibialis anterior (TA) muscles were injected intramuscularly with 50 μL of a drug mixture containing 0.125%, 0.25%, or 0.5% bupivacaine (BPV) (Cayman Chemical Cat #16618) and 10 μg 16,16-dimethyl prostaglandin E2 (dmPGE2; Tocris, Catalog #4027) using a 30 gauge needle on a Hamilton syringe. The contralateral TA received 50 μL of a mixture containing 0.5% bupivacaine (BPV) and DMSO vehicle as baseline sham control. Bioluminescence was assayed at days 3, 7, 10 and 14 post-injury.

Bioluminescence imaging (BLI) was performed using a Xenogen-100 system, as previously described. Briefly, mice were anesthetized using isofluorane inhalation and administered 120 μL D-luciferin (0.1 mmol/kg, reconstituted in PBS; Caliper LifeSciences) by intraperitoneal injection. BLI was acquired with between 5-60 second exposure at F-stop=1.0 at 5 minutes after luciferin injection. Digital images were recorded and analyzed using Living Image software (Caliper LifeSciences). Images were analyzed with a consistent region-of-interest (ROI) placed over each hindlimb to calculate a bioluminescence signal. A bioluminescence signal was calculated in radiance (p s$^{-1}$ cm$^{-2}$ sr$^{-1}$) value of 10$^4$ to define a positive threshold signal over background. BLI imaging was performed bi-weekly for 2 weeks after coinjection of BPV with dmPGE2 or vehicle.

The data in FIGS. 23A-C and 24 are shown as the mean±s.e.m. with n=6 mice. Multiple t-test for each time point or one-way ANOVA was performed to compare between treatment (BPV/dmPGE2) and control (BPV/vehicle) group. Differences with p value <0.05, denoted as * (asterisk), were considered significant.

FIG. 23B shows examples of BLI signals, which were higher in muscles that were treated with a combination of BPV and dmPGE2 than muscles that were treated with BPV alone. The BLI images were obtained two weeks after injection. As shown in FIG. 23C, the log fold change in BLI two weeks after injection was significantly higher (p<0.05) in the BPV/dmPGE2 group compared to the BPV/vehicle group, indicating that muscle regeneration was more pronounced when a combination of BPV and dmPGE2 was used. No detectable change was noted in the negative control (DMSO vehicle only) and dmPGE2 only groups.

As shown in FIG. 24, when given in combination with dmPGE2, BPV produced a dose-dependent increase in muscle regeneration (as evidenced by larger fold changes in BLI signals), with statistically significant changes apparent two weeks after injection.

Together, these data show that a combination of dmPGE2 and BPV is more effective at promoting muscle regeneration than either dmPGE2 or BPV alone, and that higher doses of dmPGE2 result in more pronounced muscle regeneration.

References: Safran, M. et al. Mouse reporter strain for noninvasive bioluminescent imaging of cells that have undergone Cre-mediated recombination. *Molecular imaging* 2, 297-302 (2003); Cosgrove, B. D. et al. Rejuvenation of the muscle stem cell population restores strength to injured aged muscles. *Nature medicine* 20, 255-264 (2014); Gilbert, P. M. et al. Substrate elasticity regulates skeletal muscle stem cell self-renewal in culture. *Science* 329, 1078-1081 (2010); Sacco, A., Doyonnas, R., Kraft, P., Vitorovic, S. & Blau, H. M. Self-renewal and expansion of single transplanted muscle stem cells. *Nature* 456, 502-506 (2008); Ho, A. T. & Blau, H. M. Noninvasive Tracking of Quiescent and Activated Muscle Stem Cell (MuSC) Engraftment Dynamics In Vivo. *Methods in molecular biology* 1460, 181-189 (2016).

Example 5: Study to Establish an Optimal PGE2 Dosage for Use in Combination with Bupivacaine and Monitor MuSC Numbers and Muscle Regeneration in Mice This example illustrates a study that can be performed to optimize the effective dose of PGE2 together with bupivacaine. The bupivacaine component serves two purposes: it provides anesthesia for the injection and also stimulates muscle stem cell function in regeneration. The dosages to be tested comprise ranges that have been used previously in patients for each drug alone. In each case, the total PGE2-bupivacaine dosage is delivered in four injections in order to maximize muscle stem cell activation due to the needle and the mildly myotoxic anesthetic. To test muscle regenerative capacity non-invasively by BLI, the Pax7-Luciferase transgenic mouse model is used, which provides a bioluminescence readout for increased endogenous stem cell function non-invasively over time. A model of sciatica nerve transection is employed, which is a well-tolerated, validated, and reproducible model of denervation-induced skeletal muscle atrophy in rodents. This technique leads to a loss of muscle mass mimicking the atrophic abductor pollicis brevis (APB) muscles seen in patients with CTS. Then a bolus of PGE2-bupivacaine is delivered into four randomized groups of mice to test the range of three PGE2 dosages that are compared to a control untreated group. These experiments can be used to define the optimal dosage of an injected combination of PGE2 and bupivacaine for use in a clinical trial.

Both PGE2 and bupivacaine have previously been used for other indications in human clinical trials (see, NCT01861665 and, but not together in muscle. For the studies described in this example, the published efficacious and FDA approved dose range that is at the NOAEL of 0.5% Bupivacaine can be used. The purpose is to test for the optimal PGE2 dose that maximally augments endogenous murine MuSC function in atrophied hindlimb muscles. In these experiments, assessment of endogenous MuSC expansion entails a series of rapid sensitive and non-invasive BLI measurements over a time course. Finally, histology is especially useful in analyses of the atrophied muscle cohort, to determine the degree of denervation and early muscle damage response induced by a combination of PGET2 and bupivacaine injection and subsequent muscle regeneration and re-innervation, which may be attributed to restoration of muscle functions at the treatment endpoint.

Establishing the Effective Dose of PGE2 in Stimulating Endogenous MuSC Numbers In Vivo A bioluminescence imaging (BLI) assay is employed as a convenient non-invasive method to quickly assess MuSC expansion in vivo, and provide a sensitive measure of regeneration potential, by using a muscle stem cell reporter mouse model (i.e., Pax7$^{CreERT2}$; Rosa26-LSL-Luc) after inducing nerve transection induced atrophy and GA injection of a combination of PGE2 and bupivacaine. The PGE-bupivacaine total dosage in each case is delivered in 4 injections to maximize exposure of the entire muscle and enhance muscle stem cell activation and regeneration due to the needle and the mild myotoxin anesthetic.

BLI affords extraordinary sensitivity due to its high signal-to-noise ratio, as excitation light used in fluorescence imaging (which generates background noise) is not required. The BLI signal emitted from the luciferin catalytic reaction by the luciferase expressed in the expanded endogenous muscle stem cells is directly recorded by a cooled charge-coupled device (CCD) camera. This dynamic readout allows longitudinal studies of MuSC functions in vivo to be conducted in the same mouse over time, and therefore constitutes a useful adjunct to endstage serial sectioning and immunofluorescence analyses of regenerated muscles.

Muscle regeneration is induced by using bupivacaine as a myotoxin. Bupivacaine has been found to be efficacious in muscle injury/regeneration models in prior studies of muscle stem cells. A dosage of 0.5% bupivacaine, which is well documented to induce robust regeneration in mouse muscles, is used. This dose is comparable to the dose used clinically in patients for local anesthesia and peripheral nerve blocks.

A combined formulation of a fixed dose of bupivacaine is tested with a range of PGE2 concentrations, all of which are below the maximum FDA approved dose of PGE2 (see, NCT00602095). An FDA-approved GMP-grade PGE2 is used, which can be obtained, for example, from Pfizer Pharmaceuticals, UK.

The formulation comprising PGE2 and bupivacaine is delivered to the induced atrophied gastrocnemius (GA) muscles of both legs, as the mixed fast and slow fiber type composition and size of the GA mouse muscles (135±22.6 mg) more closely approximates the human ABP muscle (261±119 mg) than the tibialis anterior muscles studied previously. The mouse GA muscle also has a similar fiber length/muscle length ratio (45.5%±4.5%) to the human APB muscle (69%±9%). Previous studies have shown that transplanted MuSCs can restore strength to injured GA muscles of dystrophic mice.

Mouse hindlimb muscle atrophy is induced using the established sciatic nerve transection model to mimic the atrophic APB muscles seen in patients with CTS. This model causes a period of denervation of the posterior hindlimb muscles (i.e., after nerve transection) which results in atrophy, and is followed by reinnervation of the muscle (after the nerve axons have regenerated back to their motor endplates).

Using a MuSC reporter mouse model and the BLI technique, the dose most effective in enhancing endogenous MuSC regenerative function assayed by BLI is determined. Specifically, mice are treated with five consecutive daily intraperitoneal injections of tamoxifen to activate luciferase expression. A week after the last tamoxifen injection, mice are subjected to sciatic nerve transection. After two weeks, a time point when muscle atrophy is evident, intramuscular injection of 50 μL of the PGE2-bupivacaine mixture is performed. Previous reports have shown that the proposed maximum dose of PGE2 20 μg (or 4 mg/kg) can be administered to rodents without deleterious effects. Therefore a range of PGE2 doses from 5, 10, and 20 μg are delivered to the GA. Delivery entails four 12.5 μL injections, two into each GA muscle per leg (0.5 cc total). As controls, GA muscles are injected with vehicle alone (i.e., PBS), 0.5% Bupivacaine alone, or PGE2 alone (5, 10, or 20 μg). In vivo MuSC activity is assessed by bioluminescence imaging (BLI) every 2 days for 2 weeks post-injury, and biweekly afterward for 3 months. The optimal PGE2-bupivacaine dose is the lowest effective dose with a saturating effect on muscle regeneration, as assessed by BLI. Endogenous MuSC populations are believed to be initially activated and then rapidly proliferate, yielding an exponential increase in BLI signal that peaks and then plateaus when regeneration reaches homeostasis. 6 mice per condition (total 48 mice) are analyzed, to achieve 95% statistical power, based on a two-sided alpha of 0.05 and a standard deviation of 6.24× $10^5$ p/s/cm$^2$/sr in BLI intensity (based upon prior data).

In summary, the experiments described in this section determine the formulation, or optimal dose of PGE2, that enhances expansion of endogenous MuSC numbers in regeneration. The optimal dose is then used in experiments described in the following section of this example.

Assessing long-term effects of a PGE2-bupivacaine formulation on muscle regeneration by immunohistology: The improvement of muscle regeneration measured by MuSC numbers and BLI is corroborated with histological analysis of myofiber size, architecture and stem cell numbers in an independent transgenic mouse line Pax7$^{CreERT2}$ Rosa26-LSL-dtTOMATO. Using this line, MuSC activity is assessed, as is regeneration based on lineage tracing and assessment of the number of dtTOMATO+ myofibers post-injury. The optimal dose of PGE2 established as described above is used in atrophic Pax7$^{CreERT2}$; Rosa26-LSL-dtTOMATO mouse muscles. TOMATO signal is used to trace activated stem cells and their differentiated progeny histologically in muscle fibers tissue sections.

Whereas the bioluminescence and TOMATO assays track expansion of endogenous stem cells, they do not distinguish stem cells, subsets which include progenitors, and differentiating myoblasts. To address this need, histological analysis and immunostaining is performed with antibodies to myogenic transcription factors that mark stem cells (e.g., Pax7), progenitors (e.g., Myf5) and differentiated cells (e.g., MyoD) at the end of each experiment. Also quantified is the contribution of MuSCs to myofibers and self-renewal to yield stem cells in niches in the satellite cell position along the myofiber. Myofibers are identified by immunostaining with antibodies to laminin and myosin heavy chain (MHC). Based on previous work, it is expected that soon after PGE2 treatment there will be a boost the proportion of stem cells relative to more differentiated cells in the GA muscle.

To analyze muscle reinnervation, the "reinnervation ratio" is scored as the frequency of reinnervated neuromuscular junctions (NMJs). This ratio derives from the total NMJs labeled by neurofilament and synaptic vessel protein (SV2) immunoreactivity (new NMJs) as a function of the frequency of neuromuscular junctions labeled by α-bungarotoxin and Schwann cell GAP-43 immunoreactivity (total NMJs).

For a more quantitative assessment of the total GA muscle, FACS analysis of dissociated wildtype muscle tissue is performed to determine the ratio of muscle stem cells ($Pax7^+$) to activated ($Pax7^+/Myf5^+$) and committed ($MyoD^+/Myogenin^+$) myogenic cells. This is critical for establishing that PGE2 is enhancing stem cell activity.

For these experiments, 6 mice per group are used: vehicle alone, bupivacaine alone, optimal PGE2 dose alone, and bupivacaine and optimal PGE2 dose together, for histological (n=24 mice) and for FACs analysis (n=24 mice), to achieve 95% statistical power. A non-parametric t-test (e.g., Mann-Whitney test) is used to assess the statistical significance of all proposed animal experiments.

Example 6: Assessing Mouse Muscle Response to PGE2 by Assessing Strength, Architecture, and Muscle Volume This example illustrates a study which can be used to evaluate muscle function improvement in mice using multiple technologies. A novel handheld microendoscope built by the Delp laboratory at Stanford (FIG. 25) is employed that allows measurement of the contractile dynamics from a single motor unit in mice or humans. Force generation dynamics are calculated based on the time course of sarcomere displacement. In parallel, in vivo force measurements are made using an independent technique developed by the Blau and Delp labs at Stanford to evaluate strength and assesses twitch and tetanic muscle force. Additionally, increases in muscle volume are measured by ultrasound to determine the extent of injured muscle recovery of muscle mass. These measurements assess the efficacy of the PGE2-bupivacaine formulation in promoting muscle regeneration in the atrophic GA mouse model. Histological assessment of the fiber sizes and extent of reinnervation is performed to cross-validate the outcomes based on endoscopy and ultrasound studies. Importantly, the microendoscopy and ultrasound assessment methodologies can be directly translated and applied to evaluate the human hand muscles of patients to assess baseline function and post-intervention recovery.

Following the experiments described above in Example 5, as described herein mice are assessed using ultrasound, microendoscopy, and force assays to evaluate increases in muscle volume, architecture, and strength. Using a novel handheld microendoscope, non-invasive measurements of the contractile dynamics of a single motor unit are performed. Force generation is calculated based on the time course of sarcomere displacement. In some instances, this assay is conducted weekly over an 8-week time-course. The aim is to assess the functional improvement of muscles that have received a combination of PGE2 and bupivacaine treatment compared to a control group. The volume of the treated muscles is also evaluated by ultrasound analysis.

Evaluation of muscle function with measurements of strength using microendoscopy: The ultimate test of the effects of a combination of PGE2 and bupivacaine on muscle regeneration is to perform a functional assay for muscle force increase. Using microendoscopes as small as 350 micrometers, individual sarcomeres can be imaged in passive and activated muscle, allowing for direct visualization of individual sarcomeres and length changes in a dynamic manner, a technology developed in the Delp lab. As described herein, measurement is made of the contractile dynamics and force generating capacity of muscle tissue produced by endogenous MuSCs after injection of the optimal PGE2-bupivacaine dose determined above in Example 5. Sarcomere length is also assessed using minimally invasive optical microendoscopy in order to observe second-harmonic frequencies of light generated in the muscle fibers in mice after treatment. Striated skeletal muscles are comprised of sarcomeres, the basic contractile units. Useful instruments for performing these measurements include a laser-scanning microscope, adapted to allow the addition of a microendoscope for deep-tissue imaging, and an ultrashort-pulsed titanium-sapphire laser to generate second-harmonic signals. This minimally invasive technology can be readily translated to the clinic for assessing parameters of muscle function and can used to evaluate the efficacy of PGE2-bupivacaine treated abductor pollicis brevis (APB) in patients (see, Example 7 below). Force is assessed 6 weeks post PGE2-bupivacaine treatment in mice treated as described above in Example 5. Accordingly, the optimal PGE2-bupivacaine dose not only yields the highest BLI signal but also yields the strongest force output compared to that of a PBS control. As an alternative to the microendoscope, strength can be assessed in vivo by a force transducer technique established by the Blau laboratory previously. 6 independent mice per condition are analyzed to obtain 95% statistical power.

Evaluation of muscle volume by ultrasound imaging. Ultrasound imaging is a non-invasive method that can be used to assess muscle regeneration based on muscle volume. Furthermore, ultrasound is a fast and noninvasive method, allowing repeated measurements to be made over time to evaluate the effects of compositions and methods of the present invention on muscle mass. Ultrasound imaging of the muscle is based on the different acoustical impedance produced when the ultrasound beam encounters tissue. Atrophy and increased muscle mass due to regeneration can be readily quantified by measuring muscle thickness, as the sonographic appearance of muscle is quite distinct from the surrounding fat, fibrous tissue, nerves, blood vessels and bone.

Neuromuscular atrophy due to CTS causes structural muscle changes that can be visualized with ultrasound. Atrophy can be objectified by measuring muscle thickness (i.e., the muscles become whiter on the ultrasound image). Ultrasound is more sensitive in detecting fasciculations compared to electromyography (EMG) and clinical observations, because ultrasound can visualize a large muscle area and deeper muscles, especially in the hand. With improving resolution and frame, smaller scale spontaneous muscle activity such as fibrillations can be detected by ultrasound.

Example 7: Clinical Trial for the Treatment of Carpal Tunnel Syndrome

This example illustrates a clinical trial designed to determine the benefit of compositions and methods of the present invention for the treatment of patients with severe carpal tunnel syndrome (CTS). The intervention for this trial tests the therapeutic strategy by injecting a PGE2-bupivacaine formulation into denervated abductor pollicis brevis (APB) muscles 2 months post carpal tunnel release. The following outcomes are assessed: 1) upper extremity function using the upper limb PROMIS assessment; 2) patient outcomes as assessed by a self-evaluation questionnaire standardized by The Canadian Occupational Performance; 3) Moberg pickup test; 4) ultrasound volume measurements; 5) functional strength using pinch strength using the "digital Pinch Dynamometer" device; and 6) determination of muscle mass by ultrasound and muscle architecture by microendoscopy. Assessments are performed at 1, 3, and 6 months post intervention. The studies described in this example can serve as a phase II clinical trial for the treatment of CTS muscle atrophy and provide a platform for the treatment of other nerve-related muscle atrophies, which are a major problem for both combat casualties as well as the aging population.

Design: The study is a randomized placebo-controlled trial to assess whether intramuscular PGE2 administration improves muscle recovery after denervation. This clinical trial that will yield two deliverables: (1) It will reveal if PGE2 improves denervated muscle regenerative capacity; (2) it will also test if PGE2 improves muscle function after denervation/re-innervation.

Study Population

Inclusion Criteria: Subjects who meet the following criteria are included in the trial:
 Patient is scheduled for open carpal tunnel release at the Palo Alto V A
 Nerve conduction studies showing motor impact of the APB muscle with distal motor latency to APB<6.5 ms
 Persistent weakness of APB muscle 2 months after carpal tunnel release as tested by tip pinch measurement Exclusion criteria: subjects having one or more of the following are excluded from participating in the trial:
 Diagnosis of glaucoma
 Inability to complete study forms (education, cognitive ability, mental status, medical status).
 Previous adverse reactions to prostaglandins.
 Asthma
 Systolic blood pressure greater than 170 mm/hg at time of administration of intervention
 Pregnancy
 Unable to remain off NSAIDS for two days before and after intervention
 Persistent surgical site pain greater than 3 on 0-10 pain scale Withdrawal: All patients approached for screening, the number agreeing to participate, the number providing informed consent, the number completing the baseline evaluation measures, the number undergoing randomization, and the number completing the trial in their assigned group are recorded. Patients choosing not to undergo randomization are asked if they will participate in the observational study identical to the proposed clinical trial but without any active intervention. In this manner an attempt is made to collect follow-up data from those not participating as well as those undergoing randomization to identify if the trial population differs significantly from those not participating. Patients may withdraw at any time.

Surgery: Surgery is an open carpal tunnel release. These procedures are performed under local anesthetic with 1% lidocaine with epinephrine. This procedure uses a longitudinal incision on the palmar aspect of the hand. The patients are wrapped in light gauze without splint immobilization and return 12 days for suture removal. At the 12-day visit the patients are taught scar massage and only follow up again if they are having difficulties.

Medications/Randomization: PGE2 (dinoprostone) that is in solution at a 10 mg/ml dilution that comes in 0.5 ml ampule (Pfizer, UK) is used for the intervention arm. Dinoprostone has been used for many years in pregnant women as a drug for induction of labor. This study repurposes this clinically available medication. The most common side effects in humans are largely pregnancy related: uterine rupture, and amniotic embolism. Other side effects reported include anaphylaxis, pyrexia, chest pain, arrhythmias, nausea as well as others. The half-life of the drug is less than 5 minutes.

This medication is diluted with bupivacaine to the optimal dose as directed by one or more preceding animal trials for optimal dosage. Matching placebo injections that are identical in appearance are mixed within a pharmacy. The randomization (i.e., assignment of subjects to treatment or control groups) is prepared using an R-program written by the Stanford department of biostatistics. This program utilizes a "biased-coin" methodology that progressively alters the probability of randomization assignment to correct any imbalances in the groups of previously randomized subjects. This "biased-coin" approach reduces the likelihood of significant imbalances between treatment groups in all strata while maintaining unpredictability in every treatment assignment. Randomization is done in a 1:1 ratio of treatment to placebo.

Recruitment: Subjects with APB weakness on physical exam are approached for recruitment and enrolled and pre-operative assessments completed. APB strength is assessed using tip pinch strength using dynamometry. Tip pinch is a recommended measure for assessing APB strength in CTS. Tip pinch is also the first pinch/grip test that shows improvement after carpal tunnel release. For inclusion in the trial, the APB strength needs to be 15% less than normative data or 3.84 kg in women and 5.78 kg in men.

Two months after surgery, subjects are re-evaluated. Those who have persistent weakness then proceed with the intervention. This allows for treatment of those who have failed to recover from nerve release alone. Persistent weakness is defined by using a force measure of the APB with the patient having 15% less force than the contralateral side. Patients with continued pain greater than 3 at the surgical site are then excluded. Pain greater than three is moderate pain and may interfere with force generation. Previous work suggests (minocycline trial) that 6% will still have moderate pain at 3 months.

About 50% of the subjects have APB denervation. Of those 50% are expected to have persistent weakness at 2 months.

Pre-operative Data Acquisition: After recruitment participants complete a baseline assessment. This is accomplished prior to the carpal tunnel release. This assessment includes the measures listed below:

Demographic data: Ethnic origin, race, age, gender and medical comorbidities.

TABLE 3

Nerve conduction severity scoring

| Grade | Definition |
|---|---|
| 0 | No abnormality |
| 1 | CTS demonstrable only with most sensitive tests |

TABLE 3-continued

Nerve conduction severity scoring

| Grade | Definition |
|---|---|
| 2 | Sensory conduction slow but normal terminal motor latency |
| 3 | SNAP preserved with motor slowing, distal motor latency to APB < 6.5 ms |
| 4 | SNAP absent but motor response preserved, distal motor latency to APB < 6.5 ms |
| 5 | Terminal latency to APB > 6.5 ms |
| 6 | Sensory and motor potentials effectively unrecordable |

This is a score that categorizes severity of the carpal tunnel using nerve conduction studies. Nerve conduction studies are operator dependent and values can vary between sites. This assessment eliminates this problem by using values that are abnormal for that test for that testing site instead of a precise value.

Upper Extremity PROMIS instrument: The PROMIS Upper extremity instrument is a computer adaptive test, which draws items from the PROMIS item Bank (v1.0: PF) that has a collection of calibrated questions that define and quantify a particular symptom or functional problem. It uses an item selection algorithm that enables the assessment program to choose a respondent's next item based on the response given to the respondent's current item, thereby avoiding the presentation of redundant, irrelevant, or otherwise poorly targeted items. PROMIS scores are reported as T-scores, with a mean of 50 and a SD of 10; higher scores represent higher levels of PF. This test has been evaluated and showed to have a reliability >0.95 for a representative US sample.

Canadian Occupational Performance Measure (COPM): This patient-centric exam measures the patient's perceived occupational performance in the area of self-care, leisure and productivity. It is carried out in a 5-step process nested within a semi-structured interview conducted by a provider which typically takes 10-20 minutes to administer. The patient identifies areas of difficulty and prioritizes them. The patient's performance and satisfaction are rated in the areas important to the patient. The performance and satisfaction scores are measured for change over time. The COPM has been shown to be responsive to change, with a two-point improvement on performance scores recognized as clinically significant.

Moberg pickup test: In this test, the thumb, index finger, and middle finger are used to pick up 12 different objects, one at a time, at random. The patient puts them in an open box as quickly as possible. The time (in seconds) required to complete the task is measured and recorded as the end point. The is performed twice until all objects are picked up, or until 30 seconds has been spent unsuccessfully attempting to pick up an identified object. The test is repeated with and without a blindfold. The same procedure will be done for the uninjured hand. This will be scored as an index between the injured hand and the other hand. This test provides information on fine motor and sensory function of the hand.

Tip Pinch strength: Tip pinch strength is measured using a digital pinch dynamometer, used for measuring a patient's hand strength to evaluate the degree of patient's APB muscle dysfunction. This tip pinch applies force of the thumb pulp to index pulp. The patient is seated with the test arm at his/her side and the elbow flexed 90°. The palm faces down and pinch strength is measured between the pad of the thumb and the pad and the index finger. The patient squeezes, holds, and releases. This test is performed in three consecutive measurements within 2 minutes inter-measurement interval.

Ultrasound volume measure of the APB: Ultrasound has been used to assess the volume of the APB and the other small muscles in the hand. Ultrasound can detect several aspects of muscle. First, the ultrasound can identify the size of the muscle. This is routinely done by measuring the cross sectional area (CSA). CSA of the APB is strongly correlated with muscle strength. The APB muscle is measured by placing the probe at the proximal third of the first metacarpal bone. The images of the CSA are saved as bitmap image files and transferred to a personal computer. The analysis of the images is performed using Adobe Photoshop CS6 Extended. The lasso tool is used to identify the muscle in question. The CSA is computed using the analysis option. The fascia delineates the margins of APB muscles and allows separation of the APB from the opponens pollicis (an adjacent thenar muscle).

The muscle's echo intensity is also measured and is a sign of denervation. Indeed the echo intensity and homogeneity of the muscle correlate with severity of CTS. The APB muscle is measured by ultrasound using B-mode with a 5-10 MHz transducer and the following equipment settings: 50 dB gain, 56 dB dynamic range, and 3 cm depth. The subject sits with hands fully supinated. CSA is measured. All measures are repeated three times and the mean is taken as the final measure.

The ten test: The ten test is an efficient method to assess sensation and is a marker of severity of the carpal tunnel syndrome. This test is performed with the patient seated palm up. The patient is advised of the 0-10 score of the test. The examiner uses the pulp of the index fingertip and strokes lightly an area of normal sensation (often the contralateral digit). The participant is instructed that this represents a score of 10 on the scale. Subsequently, the abnormal area and normal area are stimulated simultaneously using identical pressure and the participant scores the stimulus on the affected limb (0-10) in comparison to the normal anchor area. From these measurements, a sensory ratio is derived.

Intervention: At 2 months after surgical release, patients are re-evaluated for persistent weakness of the APB on tip pinch strength. Those who continue to have weakness participate in the trial and are randomized to placebo vs. combination of PGE2 and bupivacaine. The dose is extrapolated from the optimal dose determined in mice as described above in Examples 5 and 6. In preclinical preliminary studies, 10 µg PGE2 was administered per average GA muscle mass (135 mg). The dose in humans can be extrapolated from the dosage used in mice since the drug is not being delivered systemically. The dose for use in the APB muscle is well below the dose clinically used as a drug to induce labor in pregnant women (i.e., 1-5 mg per treatment).

For the intervention, antiseptic technique is used and the skin is anesthetized with a weal of 1% lidocaine. Then 0.5 cc of either a combination of PGE2 and bupivacaine or a combination of saline and bupivacaine is injected in 4 aliquots into the APB muscle using a 30 gauge needle. Patients are monitored for half an hour post-injection. The half-life of PGE2 is 5 minutes, thus 30 minutes is sufficient to monitor for any acute reaction to the medication.

Exercise is an important component to muscle regeneration. All patients are given an exercise program to strengthen their APB muscles with instructions to perform exercises at least 10 minutes/day. Theraputty is provided to each patient to assist with their home therapy program. Patients are contacted weekly to encourage them to perform the activities every day.

Post-Surgery Data Acquisition: Patients are assessed at 4 months and 6 months after surgery (2 and 4 months post-intervention). Post-operative assessments will include:
1. Upper Extremity PROMIS
2. COPM
3. Moberg pickup test
4. Ultrasound volume measure
5. Tip Pinch strength
6. Participation in formal physical therapy: each patient is asked if they have worked with a physical therapist on their hand. Formal physical therapy could potentially impact the results. Thus those who receive physical therapy are excluded.
7. Exercise compliance: each participant is asked how often they did their exercises: daily, a few times per week, weekly or not at all.
8. Adverse events: subjects are asked if they have had any health issues since the last visit.

An exemplary subject timeline is shown in FIG. 26.

Microendoscopy: Two groups are selected to undergo microendoscopy. This is performed on 5 healthy volunteers at the beginning of the trial to understand healthy muscle architecture. Microendoscopy is also performed on 20 subjects pre-intervention and 4 months post-intervention to assess improvement. Since this is a double-blind study, subjects will be included from both groups by random selection. Thus, it is expected that at least 5 of each group (PGE2 vs. placebo) will be represented. In previous studies, this number has sufficed to yield significant findings. The technique is the same for all. Subjects are seated comfortably with the hand at rest in supination. Antiseptic technique is used and ultrasound guidance is used to place the microendoscope into the APB muscle. The ultrasound helps determine the muscle location and fiber orientation. The microendoscope is extracted slowly at 1 mm increments. At least 3 different fibers are imaged.

Analysis

Endpoints and Measurements: The trial has three types of endpoints: feasibility endpoints, safety endpoints, and efficacy endpoints.

Primary Feasibility Endpoint: Feasibility endpoints are designed to provide reliable measures of efficacy at completing study processes. The primary feasibility endpoint is the percentage of people screened that complete the study in the group to which they were randomized.

Safety and Adverse Events Endpoint: Active capture of side effects is accomplished during the administration of the medication and with a follow up phone call on post intervention day 2 specifically asking for edema, bruising or increased pain. Adverse events are recorded and reviewed bimonthly during the trial.

Efficacy Endpoints: The primary efficacy endpoint is force measure of APB using tip pinch strength in kg measured by dynamometry. The secondary endpoint includes changes in APB muscle cross sectional area. This is recorded using ultrasound and is measured in $cm^2$.

Analysis Populations: All randomized patients are included in an intention-to-treat analysis. Patients with 100% compliance are included in a per-protocol analysis.

Background and Demographic Characteristics: Demographic and background information is summarized with descriptive statistics (e.g., mean, standard deviation, percentages, and the like)

Analysis of Feasibility: A formal analysis of factors leading to failure to complete the study protocol is undertaken based on baseline variables obtained at the time of consent. Patients are dichotomized according to the primary feasibility endpoint (i.e., did they complete the study in a group to which they were randomized). Logistic regression is used to identify factors associated with failure to complete the study.

Analysis of Efficacy: Primary and secondary efficacy endpoints are analyzed using linear regression models. Patient factors such as age, diabetes status, and NCS score will be controlled for. Study sample size and power are derived from this comparison (see below). Secondary analysis of the primary endpoint is corrected for multiple comparisons. Exploratory subgroup analysis is not corrected for multiple comparisons.

Analysis of Safety: Descriptive statistics and counts of the adverse events associated with intervention are performed. Rates between placebo and intervention group are compared.

Methods for handling missing data and non-adherence to protocol: Primary analysis is intent-to-treat. Separate efficacy analysis on those with complete protocol adherence is also performed.

Evaluation of Conduct of trial (including accrual rates, data quality): The conduct of the trial is reviewed every 20 primary endpoint events. Feasibility endpoints are reviewed to ensure likelihood of trial completion. For these reviews accrual rates and cumulative statistics on protocol violations will be prepared.

Subgroup Analyses: Subgroup analysis examines the treatment efficacy in pre-defined high risk subgroups defined by age greater than 70 and severe entrapment score for nerve conduction studies.

Sample Size

Accrual estimates: Sixty subjects are enrolled over a 30-month period. This equates to approximately 2 patients per month.

Sample size justification: 60 patients are recruited for the study. The basis for the sample size is as follows. The Null hypothesis is no change in force measurements of the APB between treatment groups. The alternative hypothesis is that the combination of PGE2 and bupivacaine significantly changes the force measurements of the APB.

A two-sample t-test with equal variance is used to test for differences in force measurement of the APB between the placebo and PGE2-bupivacaine groups. A difference in total effect size is sought for primary outcome with 80% power, based upon data from a previous study in mice with a 10.0 N difference in tetanic force measurement. Therefore, the power is calculated for testing the hypothesis using the Proc Power calculation using the statistical analysis software (SAS version 9.4) with the following parameters: Group Assignment=1:1, Pooled Standard Deviation=7.62 N, and a one-sided alpha of 0.05. The number of subjects needed per group to have 80% power with a one-sided alpha of 0.05 is determined to be 25 patients per group. If a 15% drop out is planned for, 29 patients are needed per group, or a total of 58 patients. Based upon preclinical data, it is anticipated that the magnitude of the increase in force in the treatment group will make a significant difference to subjects when translated to the lateral pinch force reported for CTS patients. Per published results, the anticipated force increase will allow subjects to perform certain daily basic tasks not previously possible, such as the ability to hold a fork or to pull up a zipper (Smaby et al, 2004).

Additional Analyses: Several other outcomes can be assessed, including changes in COPM scores and time of Moberg pick up test. Both of these are continuous variables and are compared using the Mann Whitney U test. Statistical analyses of APB function based on microendoscopy measurements can also be performed.

Potential Pitfalls

Inadequate Recruitment: If difficulties are met in recruiting an adequate number of subjects, the recruitment pool can be expanded to include those with entrapment of the ulnar nerve at the elbow with intrinsic muscle wasting. This disease process is similar to carpal tunnel syndrome with wasting of multiple small muscles of the hand. If recruitment is altered in this manner, changes to the protocol are made, as follows.

1) The timing of injection is 4 months after release to provide more time for nerve regeneration.
2) The muscle to undergo assessment is the first dorsal interossei. The first dorsal interossei has also been measured with ultrasound, with size being correlated with strength.
3) The analysis plan still includes the assessments described above. Of the ulnar nerve releases that are performed, about 50% have atrophy.

Veteran population: In some instances, the study population may not be representative of the general population. For example, military veterans are older and have a higher male population. However, intervention with PGE2 appears to be particularly effective for the lack of regeneration in older mice. Thus, having an older population may be best suited for seeing the benefits of this intervention.

Military Benefit and Impact

PNI is a common combat injury that prevents many soldiers from returning to active duty. In addition, many older veterans have PNI from compression injuries that result in loss of ability to perform activities of daily living. Loss of muscle function after PNI continues to be a difficult and unsolved question. Research to improve nerve regeneration continues but less has been done to improve muscle regeneration with re-innervation. A medication treatment to improve the amount of muscle recovery after nerve injury and repair is needed. The potential applications beyond this focused CTS trial are broad and would allow treatment of both the nerve and the muscle.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference.

References Abe, T., Counts, B. R., Barnett, B. E., Dankel, S. J., Lee, K., and Loenneke, J. P. (2015). Associations between Handgrip Strength and Ultrasound-Measured Muscle Thickness of the Hand and Forearm in Young Men and Women. Ultrasound Med Biol 41, 2125-2130; Anderson, K. D. (2004). Targeting Recovery: Priorities of the Spinal Cord-Injured Population. Journal of Neurotrauma 21, 1371-1383; Armand, A. S., Launay, T., Gaspera, B. D., Charbonnier, F., Gallien, C. L., and Chanoine, C. (2003). Effects of eccentric treadmill running on mouse soleus: degeneration/regeneration studied with Myf-5 and MyoD probes. Acta physiologica Scandinavica 179, 75-84; Badr, C. E. (2014). Bioluminescence imaging: basics and practical limitations. Methods Mol Biol 1098, 1-18; Barr, C., Suarez, P., Ota, D., and Curtin, C. M. (2011). Is carpal tunnel release under-utilized in veterans with spinal cord injury? J Spinal Cord Med 34, 563-568; Bauder, A. R., and Ferguson, T. A. (2012). Reproducible mouse sciatic nerve crush and subsequent assessment of regeneration by whole mount muscle analysis. J Vis Exp; Berger, M. J., Regan, W. R., Seal, A., and Bristol, S. G. (2016). Reliability of the "Ten Test" for assessment of discriminative sensation in hand trauma. J Plast Reconstr Aesthet Surg 69, 1411-1416; Birch, R., Misra, P., Stewart, M. P., Eardley, W. G., Ramasamy, A., Brown, K., Shenoy, R., Anand, P., Clasper, J., Dunn, R., and Etherington, J. (2012a). Nerve injuries sustained during warfare: part II: Outcomes. J Bone Joint Surg Br 94, 529-535; Birch, R., Misra, P., Stewart, M. P. M., Eardley, W. G. P., Ramasamy, A., Brown, K., Shenoy, R., Anand, P., Clasper, J., Dunn, R., and Etherington, J. (2012b). Nerve injuries sustained during warfare: Part I—Epidemiology. The Bone & Joint Journal 94-B, 523-528; Blaauw, B., Canato, M., Agatea, L., Toniolo, L., Mammucari, C., Masiero, E., Abraham, R., Sandri, M., Schiaffino, S., and Reggiani, C. (2009). Inducible activation of Akt increases skeletal muscle mass and force without satellite cell activation. FASEB J 23, 3896-3905; Bland, J. D. (2000). A neurophysiological grading scale for carpal tunnel syndrome. Muscle Nerve 23, 1280-1283; Blau, H. M., Cosgrove, B. D., and Ho, A. T. (2015). The central role of muscle stem cells in regenerative failure with aging. Nature medicine 21, 854-862; Bondesen, B. A., Mills, S. T., and Pavlath, G. K. (2006). The COX-2 pathway regulates growth of atrophied muscle via multiple mechanisms. American journal of physiology Cell physiology 290, C1651-1659; Chambers, J. A., Hiles, C. L., and Keene, B. P. (2014). Brachial Plexus Injury Management in Military Casualties: Who, What, When, Why, and How. Military Medicine 179, 640-644; Champion, H. R., Holcomb, J. B., Lawnick, M. M., Kelliher, T., Spott, M. A., Galarneau, M. R., Jenkins, D. H., West, S. A., Dye, J., Wade, C. E., et al. (2010). Improved characterization of combat injury. J Trauma 68, 1139-1150; Chen, X., Sanchez, G. N., Schnitzer, M. J., and Delp, S. L. (2016). Changes in sarcomere lengths of the human vastus lateralis muscle with knee flexion measured using in vivo microendoscopy. Journal of Biomechanics 49, 2989-2994; Cooney, D. S., Wimmers, E. G., Ibrahim, Z., Grahammer, J., Christensen, J. M., Brat, G. A., Wu, L. W., Sarhane, K. A., Lopez, J., Wallner, C., et al. (2016). Mesenchymal Stem Cells Enhance Nerve Regeneration in a Rat Sciatic Nerve Repair and Hindlimb Transplant Model. Scientific Reports 6, 31306; Cosgrove, B. D., Gilbert, P. M., Porpiglia, E., Mourkioti, F., Lee, S. P., Corbel, S. Y., Llewellyn, M. E., Delp, S. L., and Blau, H. M. (2014). Rejuvenation of the muscle stem cell population restores strength to injured aged muscles. Nature medicine 20, 255-264; Cox, C. R., Faccenda, K. A., Gilhooly, C., Bannister, J., Scott, N. B., and Morrison, L. M. (1998). Extradural S(−)-bupivacaine: comparison with racemic RS-bupivacaine. Br J Anaesth 80, 289-293; FDA (2005). Guidance for Industry: Estimating the Maximum Safe Starting Dose in Adult Healthy Volunteer, (Rockville, Md.: U. S. Food and Drug Administration); Funk, C. D. (2001). Prostaglandins and leukotrienes: advances in eicosanoid biology. Science 294, 1871-1875; Geere, J., Chester, R., Kale, S., and Jerosch-Herold, C. (2007). Power grip, pinch grip, manual muscle testing or thenar atrophy—which should be assessed as a motor outcome after carpal tunnel decompression? A systematic review. BMC Musculoskelet Disord 8, 114; Gilbert, P. M., Havenstrite, K. L., Magnusson, K. E., Sacco, A., Leonardi, N. A., Kraft, P., Nguyen, N. K., Thrun, S., Lutolf, M. P., and Blau, H. M. (2010). Substrate elasticity regulates skeletal muscle stem cell self-renewal in culture. Science 329, 1078-1081; Gilbertson, L., and Barber-Lomax, S. (1994). Power and Pinch Grip Strength Recorded Using the Hand-Held Jamar® Dynamometer and B+L Hydraulic Pinch Gauge: British Normative Data for Adults. The British Journal of Occupational Therapy 57, 483-488; Hansen, M.

O., Polly, D. W., McHale, K. A., and Asplund, L. M. (1994). A prospective evaluation of orthopedic patients evacuated from Operations Desert Shield and Desert Storm: the Walter Reed experience. Military medicine 159, 376-380; Jackman, M., Novak, I., and Lannin, N. (2014). Effectiveness of functional hand splinting and the cognitive orientation to occupational performance (CO-OP) approach in children with cerebral palsy and brain injury: two randomised controlled trial protocols. BMC Neurol 14, 144; Kamiya, H., Kimura, M., Hoshino, S., Kobayashi, M., and Sonoo, M. (2016). Prognosis of severe carpal tunnel syndrome with absent compound muscle action potential. Muscle Nerve 54, 427-431; Kim, J. S., Seok, H. Y., and Kim, B. J. (2016). The significance of muscle echo intensity on ultrasound for focal neuropathy: The median- to ulnar-innervated muscle echo intensity ratio in carpal tunnel syndrome. Clinical Neurophysiology 127, 880-885; Korotkova, M., and Lundberg, I. E. (2014). The skeletal muscle arachidonic acid cascade in health and inflammatory disease. In Nature Publishing Group, (Nature Publishing Group), pp. 295-303; Lavasani, M., Thompson, S. D., Pollett, J. B., Usas, A., Lu, A., Stolz, D. B., Clark, K. A., Sun, B., Peault, B., and Huard, J. (2014). Human muscle-derived stem/progenitor cells promote functional murine peripheral nerve regeneration. J Clin Invest 124, 1745-1756; Liu, W., Wei-LaPierre, L., Klose, A., Dirksen, R. T., and Chakkalakal, J. V. (2015). Inducible depletion of adult skeletal muscle stem cells impairs the regeneration of neuromuscular junctions. eLife 4; Llewellyn, M. E., Thompson, K. R., Deisseroth, K., and Delp, S. L. (2010). Orderly recruitment of motor units under optical control in vivo. Nature medicine 16, 1161-1165; Magown, P., Shettar, B., Zhang, Y., and Rafuse, V. F. (2015). Direct optical activation of skeletal muscle fibres efficiently controls muscle contraction and attenuates denervation atrophy. Nature Communications 6, 8506; Marti, A., and Fernandez-Otero, M. P. (1994). Prostaglandin E2 accelerates enzymatic and morphological maturation of the small intestine in suckling rats. Biol Neonate 65, 119-125; Masini, B. D., Waterman, S. M., Wenke, J. C., Owens, B. D., Hsu, J. R., and Ficke, J. R. (2009). Resource utilization and disability outcome assessment of combat casualties from Operation Iraqi Freedom and Operation Enduring Freedom. J Orthop Trauma 23, 261-266; McColl, M. A., Law, M., Baptiste, S., Pollock, N., Carswell, A., and Polatajko, H. J. (2005). Targeted applications of the Canadian Occupational Performance Measure. Can J Occup Ther 72, 298-300; Mele, A., Fonzino, A., Rana, F., Camerino, G. M., De Bellis, M., Conte, E., Giustino, A., Conte Camerino, D., and Desaphy, J. F. (2016). In vivo longitudinal study of rodent skeletal muscle atrophy using ultrasonography. Sci Rep 6, 20061; Mo, C., Zhao, R., Vallejo, J., Igwe, O., Bonewald, L., Wetmore, L., and Brotto, M. (2015). Prostaglandin E2 promotes proliferation of skeletal muscle myoblasts via EP4 receptor activation. Cell cycle 14, 1507-1516; Moberg, E. (1958). Objective methods for determining the functional value of sensibility in the hand. J Bone Joint Surg Br 40-B, 454-476; Mohseny, B., Nijhuis, T. H., Hundepool, C. A., Janssen, W. G., Selles, R. W., and Coert, J. H. (2015). Ultrasonographic quantification of intrinsic hand muscle cross-sectional area; reliability and validity for predicting muscle strength. Arch Phys Med Rehabil 96, 845-853; Murphy, M. M., Lawson, J. A., Mathew, S. J., Hutcheson, D. A., and Kardon, G. (2011). Satellite cells, connective tissue fibroblasts and their interactions are crucial for muscle regeneration. Development 138, 3625-3637; NCT01861665. Weill Medical College of Cornell University. Marcaine Use in Laparoscopic Gynecological Surgery (Marcaine). In: ClinicalTrials.gov [Internet]. Bethesda (Md.): National Library of Medicine (US). 2000-[cited Nov. 14, 2016]. Available from: https://clinicaltrials.gov/ct2/show/NCT01861665 NLM Identifier: NCT01861665; NCT02051296. VA Palo Alto Health Care System. Minocycline to Reduce Pain After Carpal Tunnel Release. In: ClinicalTrials.gov [Internet]. Bethesda (Md.): National Library of Medicine (US). 2000-[cited Nov. 14, 2016]. Available from: https://clinicaltrials.gov/ct2/show/NCT02051296 NLM Identifier: NCT02051296; NCT00602095. Karolinska University Hospital. Labour Induction With Misoprostol, Dinoprostone and Bard Catheter (LI). In: ClinicalTrials.gov [Internet]. Bethesda (Md.): National Library of Medicine (US). 2000-[cited Nov. 14, 2016]. Available from: https://clinicaltrials.gov/ct2/show/NCT00602095 NLM Identifier: NCT00602095; Omer, G. E. (1974). Injuries to Nerves of the Upper Extremity. The Journal of Bone & amp; amp; Joint Surgery 56, 1615; Overbeek, C. L., Nota, S. P., Jayakumar, P., Hageman, M. G., and Ring, D. (2015). The PROMIS physical function correlates with the QuickDASH in patients with upper extremity illness. Clin Orthop Relat Res 473, 311-317; Owens, B. D., Kragh, J. F., Jr., Macaitis, J., Svoboda, S. J., and Wenke, J. C. (2007a). Characterization of extremity wounds in Operation Iraqi Freedom and Operation Enduring Freedom. J Orthop Trauma 21, 254-257; Owens, B. D., Kragh, J. F., Macaitis, J., Svoboda, S. J., and Wenke, J. C. (2007b). Characterization of Extremity Wounds in Operation Iraqi Freedom and Operation Enduring Freedom. Journal of Orthopaedic Trauma 21, 254-257; Palmer, B. N. (2011). Carpal tunnel syndrome, active component, U.S. Armed Forces, 2000-2010. MSMR 18, 12-15; Pillen, S., and van Alfen, N. (2011). Skeletal muscle ultrasound. Neurol Res 33, 1016-1024; Plant, D. R., Colarossi, F. E., and Lynch, G. S. (2006). Notexin causes greater myotoxic damage and slower functional repair in mouse skeletal muscles than bupivacaine. Muscle Nerve 34, 577-585; Powell, P. L., Roy, R. R., Kanim, P., Bello, M. A., and Edgerton, V. R. (1984). Predictability of skeletal muscle tension from architectural determinations in guinea pig hindlimbs. J Appl Physiol Respir Environ Exerc Physiol 57, 1715-1721; Reigner, B. G., and Blesch, K. S. (2002). Estimating the starting dose for entry into humans: principles and practice. Eur J Clin Pharmacol 57, 835-845; Rivera, J. C., Glebus, G. P., and Cho, M. S. (2014). Disability following combat-sustained nerve injury of the upper limb. The Bone & Joint Journal 96-B, 254-258; Sacco, A., Doyonnas, R., Kraft, P., Vitorovic, S., and Blau, H. M. (2008). Self-renewal and expansion of single transplanted muscle stem cells. Nature 456, 502-506; Sacco, A., Mourkioti, F., Tran, R., Choi, J., Llewellyn, M., Kraft, P., Shkreli, M., Delp, S., Pomerantz, J. H., Artandi, S. E., and Blau, H. M. (2010). Short telomeres and stem cell exhaustion model Duchenne muscular dystrophy in mdx/mTR mice. Cell 143, 1059-1071; Safran, M., Kim, W. Y., Kung, A. L., Homer, J. W., DePinho, R. A., and Kaelin, W. G., Jr. (2003). Mouse reporter strain for noninvasive bioluminescent imaging of cells that have undergone Cre-mediated recombination. Mol Imaging 2, 297-302; Sanchez, G. N., Sinha, S., Liske, H., Chen, X., Nguyen, V., Delp, S. L., and Schnitzer, M. J. (2015). In Vivo Imaging of Human Sarcomere Twitch Dynamics in Individual Motor Units. Neuron 88, 1109-1120; Shen, W., Prisk, V., Li, Y., Foster, W., and Huard, J. (2006). Inhibited skeletal muscle healing in cyclooxygenase-2 gene-deficient mice: the role of PGE2 and PGF2alpha. Journal of applied physiology 101, 1215-1221; Simmons, D. L., Botting, R. M., and Hla, T. (2004). Cyclooxygenase isozymes: the biology of prostaglandin synthesis and inhibition. Pharmacol Rev 56, 387-437; Smaby, N., Johanson, M. E., Baker, B., Kenney, D. E., Murray, W. M., and Hentz, V. R. (2004). Identification of key pinch forces required to complete functional tasks. J Rehabil Res Dev 41, 215-224; Spring, K. R. (2013). Cameras for digital microscopy. Methods Cell Biol 114, 163-178; Strauch, B., Lang, A., Ferder, M., Keyes-Ford, M., Freeman, K., and Newstein, D. (1997). The ten test. Plast Reconstr Surg 99, 1074-1078; Thomas, J., Fairclough, A., Kavanagh, J., and Kelly, A. J. (2014). Vaginal prostaglandin (PGE2 and PGF2α) for induction of labour at term. The Cochrane database of systematic reviews 6, CD003101; Toomey, M., Nicholson, D., and Carswell, A. (1995). The clinical utility of the Canadian Occupational Performance Measure. Can J Occup Ther 62, 242-249; Trombly, C. (1995). Clinical practice guidelines for post-stroke rehabilitation and occupational therapy practice. Am J Occup Ther 49, 711-714; Tyser, A. R., Beckmann, J., Franklin, J. D., Cheng, C., Hon, S. D., Wang, A., and Hung, M. (2014). Evaluation of the PROMIS physical function computer adaptive test in the upper extremity. J Hand Surg Am 39, 2047-2051 e2044; Valero-Cuevas, F. J., Smaby, N., Venkadesan, M., Peterson, M., and Wright, T. (2003). The strength-dexterity test as a measure of dynamic pinch performance. J Biomech 36, 265-270; Ward, S. R., and Lieber, R. L. (2005). Density and hydration of fresh and fixed human skeletal muscle. J Biomech 38, 2317-2320; Weinreb, M., Suponitzky, I., and Keila, S. (1997). Systemic administration of an anabolic dose of PGE2 in young rats increases the osteogenic capacity of bone marrow. Bone 20, 521-526; Whiteside, J. B., and Wildsmith, J. A. (2001). Developments in local anaesthetic drugs. Br J Anaesth 87, 27-35; Xu, X., Wilschut, K. J., Kouklis, G., Tian, H., Hesse, R., Garland, C., Sbitany, H., Hansen, S., Seth, R., Knott, P. D., et al. (2015). Human Satellite Cell Transplantation and Regeneration from Diverse Skeletal Muscles. Stem Cell Reports 5, 419-434; Zealear, D. L., Mainthia, R., Li, Y., Kunibe, I., Katada, A., Billante, C., and Nomura, K. (2014). Stimulation of denervated muscle promotes selective reinnervation, prevents synkinesis, and restores function. Laryngoscope 124, E180-187.

Example 8. Synergistic Effect of PGE2 Compound and Myotoxin Combination in Muscle Regeneration Pax7-CreERT2; Rosa-LSL-Luciferase mice (2-4 months old) were treated with tamoxifen for five consecutive days in order to obtain Pax7 promoter expressing luciferase mice in vivo. One week later, baseline tetanic force of the tibialis anterior was measured using a foot plate force measurement instrument before injection of drugs (timepoint day 0). Mice were subsequently injected with 50 µl of vehicle (saline), the muscle stem cell activator prostaglandin E2 (PGE2, 20 µg), the muscle stem cell expansion agent bupivacaine (BPV, 0.25%) or the combination drug (bupivacaine 0.25% together with PGE2 20 µg) into the Tibialis anterior (TA) muscle. FIG. 27A shows bioluminescence (BLI, measured as radiance) measured every 3 days for 2 weeks to measure muscle stem cell expansion. FIG. 27B shows the resulting tetanic force measured at week 4 from the same mice, where the percent difference to baseline force was calculated. FIG. 27C: at 4 weeks (endpoint) the TA was isolated, and the specific force ($mN/mm^2$) was obtained based on the physiological cross-sectional area (PCSA) calculated by the muscle length, weight and pennation angle. The specific force and the percent difference of tetanic force were significantly increased for the combination drug compared to the vehicle and both of the small molecules injected alone. *P<0.05, **P<0.001. ANOVA test for group comparisons and significant difference for endpoint by Fisher's test (FIG. 27A). ANOVA test with Bonferroni correction for multiple comparisons (FIG. 27B, FIG. 27C). Data are shown as means±SEM.

The results reveal that a combination of a PGE2 compound with a myotoxin such as bupivacaine has a synergistic effect on muscle regeneration. As shown in FIG. 27A, the combination of PGE2 and bupivacaine induces muscle stem cell expansion that is greater than that of PGE2 alone or bupivacaine alone. Importantly, the observed muscle stem cell expansion is greater than the sum of muscle stem cell expansion for PGE2 alone, and bupivacaine alone. The synergistic effect on muscle regeneration is also confirmed with another assay. As shown in FIG. 27B, the increase in tetanic force for muscles treated with PGE2 and bupivacaine combined is greater than the sum of the increase in tetanic force for muscles treated with PGE2.

What is claimed is:

1. A pharmaceutical composition comprising:
   (a) a myotoxin that is an amino-amide anesthetic; and
   (b) a prostaglandin E2 (PGE2) compound, wherein the myotoxin and the PGE2 compound are present in the pharmaceutical composition in amounts effective for regenerating a population of muscle stem cells in a muscle of a subject having muscle injury, muscle damage, or muscle atrophy.

2. The pharmaceutical composition of claim 1, wherein the PGE2 compound is selected from the group consisting of: PGE2, a PGE2 derivative, a PGE2 prodrug, a derivative thereof, and an analog thereof.

3. The pharmaceutical composition of claim 1, wherein the PGE2 compound is PGE2.

4. The pharmaceutical composition of claim 1, wherein the PGE2 compound is a PGE2 derivative, and the PGE2 derivative comprises 16,16-dimethyl prostaglandin E2.

5. The pharmaceutical composition of claim 1, wherein the amino-amide anesthetic is selected from the group consisting of: bupivacaine, levobupivacaine, articaine, ropivacaine, butanilicaine, carticaine, dibucaine, etidocaine, lidocaine, mepivacaine, prilocaine, trimecaine, and a combination thereof.

6. The pharmaceutical composition of claim 1, wherein the PGE2 compound is PGE2 and/or 16,16-dimethyl prostaglandin E2, and the myotoxin is bupivacaine.

7. The pharmaceutical composition of claim 1, wherein the pharmaceutical composition is formulated for intramuscular injection.

8. The pharmaceutical composition of claim 1, wherein the pharmaceutical composition further comprises a pharmaceutically acceptable excipient.

9. The pharmaceutical composition of claim 1, wherein the muscle injury, muscle damage, or muscle atrophy is or is associated with traumatic injury, acute muscle injury, acute nerve injury, chronic nerve injury, soft tissue hand injury, carpal tunnel syndrome (CTS), Duchenne muscular dystrophy (DMD), Becker muscular dystrophy, limb girdle muscular dystrophy, amyotrophic lateral sclerosis (ALS), distal muscular dystrophy (DD), inherited myopathies, myotonic muscular dystrophy (MDD), mitochondrial myopathies, myotubular myopathy (MM), myasthenia gravis (MG), congestive heart failure, periodic paralysis, polymyositis, rhabdomyolysis, dermatomyositis, cancer cachexia, AIDS cachexia, cardiac cachexia, stress induced urinary incontinence, sarcopenia, spinal muscular atrophy, fecal sphincter dysfunction, Bell's palsy, rotator cuff injury, spinal cord injury, hip replacement, knee replacement, wrist fracture, diabetic neuropathy, gastroesophageal reflux disease (GERD), obstructive sleep apnea (OSA), pelvic floor disorders, musculoskeletal disorders, plantar fasciitis, foot drop, disuse-induced muscle atrophy, impaired eyelid function, strabismus, nystagmus, or presbyopia.

* * * * *